(12) United States Patent
Armstrong et al.

(10) Patent No.: US 8,801,685 B2
(45) Date of Patent: Aug. 12, 2014

(54) APPARATUSES AND METHODS FOR NEGATIVE PRESSURE WOUND THERAPY

(75) Inventors: Ed Armstrong, Palm Harbor, FL (US); Iain Michael Blackburn, Cottingham (GB); Robert Emmerson, Beverly (GB); Steven Gianelis, Abington, MA (US); Joseph Gordon, Mansfield, MA (US); Mark Guarraia, Providence, RI (US); Andrew Linton, Woodthorpe (GB); Dan Nelsen, Warwick, RI (US); Michael Salame, Norwich, CT (US); Tim Stern, Belper (GB); Mark White, Norton (GB)

(73) Assignee: Smith & Nephew, Inc., Memphis, TN (US)

( * ) Notice: Subject to any disclaimer, the term of this patent is extended or adjusted under 35 U.S.C. 154(b) by 5 days.

(21) Appl. No.: 13/381,885

(22) PCT Filed: Dec. 22, 2010

(86) PCT No.: PCT/US2010/061938
§ 371 (c)(1),
(2), (4) Date: Dec. 30, 2011

(87) PCT Pub. No.: WO2011/087871
PCT Pub. Date: Jul. 21, 2011

(65) Prior Publication Data
US 2012/0116334 A1 May 10, 2012

Related U.S. Application Data

(60) Provisional application No. 61/289,358, filed on Dec. 22, 2009, provisional application No. 61/332,440, filed on May 7, 2010, provisional application No. 61/369,008, filed on Jul. 29, 2010.

(51) Int. Cl.
*A61M 1/00* (2006.01)

(52) U.S. Cl.
USPC .......................................... 604/319

(58) Field of Classification Search
USPC .................... 604/313–324; 602/44
See application file for complete search history.

(56) References Cited

U.S. PATENT DOCUMENTS

| 1,585,104 A | 5/1926 | Montgomery |
|---|---|---|
| 2,736,317 A | 2/1956 | Alexander |

(Continued)

FOREIGN PATENT DOCUMENTS

| DE | 3907007 | 9/1990 |
|---|---|---|
| DE | 20 2010 009 1 | 10/2010 |

(Continued)

OTHER PUBLICATIONS

U.S. Appl. No. 13/201,611, filed Aug. 15, 2011, Bannister et al.

(Continued)

*Primary Examiner* — Philip R Wiest
(74) *Attorney, Agent, or Firm* — Knobbe Martens Olson & Bear LLP

(57) ABSTRACT

Disclosed herein are several embodiments of a negative pressure appliance and methods of using the same in the treatment of wounds. Some embodiments are directed to improved fluidic connectors or suction adapters for connecting to a wound site, for example using softer, kink-free conformable suction adapters.

16 Claims, 92 Drawing Sheets

(56) References Cited

U.S. PATENT DOCUMENTS

| | | |
|---|---|---|
| 3,042,041 A | 7/1962 | Jascalevich |
| 3,568,675 A | 3/1971 | Harvey |
| 3,572,340 A | 3/1971 | Lloyd et al. |
| 3,874,387 A | 4/1975 | Barbieri |
| 3,880,164 A | 4/1975 | Stepno |
| 4,080,970 A | 3/1978 | Miller |
| 4,164,027 A | 8/1979 | Bonnie et al. |
| 4,231,357 A | 11/1980 | Hessner |
| 4,261,363 A | 4/1981 | Russo |
| 4,360,015 A | 11/1982 | Mayer |
| 4,382,441 A | 5/1983 | Svedman |
| 4,392,853 A | 7/1983 | Muto |
| 4,468,219 A | 8/1984 | George et al. |
| 4,540,412 A | 9/1985 | Van Overloop |
| 4,553,967 A | 11/1985 | Ferguson et al. |
| 4,561,435 A | 12/1985 | McKnight et al. |
| 4,569,674 A | 2/1986 | Phillips et al. |
| 4,579,120 A | 4/1986 | MacGregor |
| 4,614,183 A | 9/1986 | McCracken et al. |
| 4,906,240 A | 3/1990 | Reed et al. |
| 4,921,492 A | 5/1990 | Schultz et al. |
| 4,941,882 A | 7/1990 | Ward et al. |
| 4,969,880 A | 11/1990 | Zamierowski |
| 4,980,226 A | 12/1990 | Hellgren et al. |
| 5,009,224 A | 4/1991 | Cole |
| 5,056,510 A | 10/1991 | Gilman |
| 5,060,642 A | 10/1991 | Gilman |
| 5,088,483 A | 2/1992 | Heinecke |
| 5,106,362 A | 4/1992 | Gilman |
| 5,112,323 A | 5/1992 | Winkler et al. |
| 5,134,007 A | 7/1992 | Reising et al. |
| 5,147,698 A | 9/1992 | Cole |
| 5,149,331 A | 9/1992 | Ferdman et al. |
| 5,152,757 A | 10/1992 | Eriksson |
| 5,160,315 A | 11/1992 | Heinecke et al. |
| 5,160,334 A | 11/1992 | Billings et al. |
| 5,176,663 A | 1/1993 | Svedman et al. |
| 5,230,496 A | 7/1993 | Shillington et al. |
| 5,244,457 A | 9/1993 | Karami et al. |
| 5,263,922 A | 11/1993 | Sova et al. |
| 5,300,054 A | 4/1994 | Feist et al. |
| 5,304,161 A | 4/1994 | Noel et al. |
| 5,308,313 A | 5/1994 | Karami et al. |
| 5,366,451 A | 11/1994 | Levesque |
| 5,391,161 A | 2/1995 | Hellgren et al. |
| 5,437,651 A | 8/1995 | Todd et al. |
| 5,439,458 A | 8/1995 | Noel et al. |
| 5,447,492 A | 9/1995 | Cartmell et al. |
| 5,486,167 A | 1/1996 | Dragoo et al. |
| 5,520,629 A | 5/1996 | Heinecke et al. |
| 5,525,407 A | 6/1996 | Yang |
| 5,527,293 A | 6/1996 | Zamierowski |
| 5,527,923 A | 6/1996 | Klingler et al. |
| 5,531,855 A | 7/1996 | Heinecke et al. |
| 5,549,584 A | 8/1996 | Gross |
| 5,593,750 A | 1/1997 | Rothrum et al. |
| 5,599,289 A | 2/1997 | Castellana |
| 5,613,942 A | 3/1997 | Lucast et al. |
| 5,618,278 A | 4/1997 | Rothrum |
| 5,624,423 A | 4/1997 | Anjur et al. |
| 5,636,643 A | 6/1997 | Argenta et al. |
| 5,637,093 A | 6/1997 | Hyman et al. |
| 5,645,081 A | 7/1997 | Argenta et al. |
| 5,678,564 A | 10/1997 | Lawrence et al. |
| 5,695,846 A | 12/1997 | Lange et al. |
| 5,738,642 A | 4/1998 | Heinecke et al. |
| 5,797,844 A | 8/1998 | Yoshioka et al. |
| 5,797,894 A | 8/1998 | Cadieux et al. |
| 5,894,608 A | 4/1999 | Birbara |
| 5,914,282 A | 6/1999 | Dunshee et al. |
| 6,071,267 A | 6/2000 | Zamierowski |
| 6,117,111 A | 9/2000 | Fleischmann |
| 6,121,508 A | 9/2000 | Bischof et al. |
| 6,142,982 A | 11/2000 | Hunt et al. |
| 6,169,224 B1 | 1/2001 | Heinecke et al. |
| 6,264,976 B1 | 7/2001 | Heinecke et al. |
| 6,291,050 B1 | 9/2001 | Cree et al. |
| 6,345,623 B1 | 2/2002 | Heaton et al. |
| 6,406,447 B1 | 6/2002 | Thrash et al. |
| 6,420,622 B1 | 7/2002 | Johnston et al. |
| 6,436,432 B2 | 8/2002 | Heinecke et al. |
| 6,461,467 B2 | 10/2002 | Blatchford et al. |
| 6,479,073 B1 | 11/2002 | Lucast et al. |
| 6,553,998 B2 | 4/2003 | Heaton et al. |
| 6,566,575 B1 | 5/2003 | Stickels et al. |
| 6,607,799 B1 | 8/2003 | Heinecke et al. |
| 6,648,862 B2 | 11/2003 | Watson |
| 6,685,681 B2 | 2/2004 | Lockwood et al. |
| 6,685,682 B1 | 2/2004 | Heinecke et al. |
| 6,752,794 B2 | 6/2004 | Lockwood et al. |
| 6,755,807 B2 | 6/2004 | Risk, Jr. et al. |
| 6,814,079 B2 | 11/2004 | Heaton et al. |
| 6,838,589 B2 | 1/2005 | Liedtke et al. |
| 6,855,135 B2 | 2/2005 | Lockwood et al. |
| 6,867,342 B2 | 3/2005 | Johnston et al. |
| 6,878,857 B1 | 4/2005 | Chihani et al. |
| 6,903,243 B1 | 6/2005 | Burton |
| 6,936,037 B2 | 8/2005 | Bubb et al. |
| 6,951,553 B2 | 10/2005 | Bubb et al. |
| 6,994,702 B1 | 2/2006 | Johnson |
| 6,994,904 B2 | 2/2006 | Joseph et al. |
| 7,004,915 B2 | 2/2006 | Boynton et al. |
| 7,005,143 B2 | 2/2006 | Abuelyaman et al. |
| 7,070,580 B2 | 7/2006 | Nielsen |
| 7,070,584 B2 | 7/2006 | Johnson et al. |
| 7,108,683 B2 | 9/2006 | Zamierowski |
| 7,117,869 B2 | 10/2006 | Heaton |
| 7,128,735 B2 | 10/2006 | Weston |
| 7,183,454 B1 | 2/2007 | Rosenberg |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,273,054 B2 | 9/2007 | Heaton et al. |
| 7,276,247 B2 | 10/2007 | Fansler et al. |
| 7,279,612 B1 | 10/2007 | Heaton et al. |
| 7,285,576 B2 | 10/2007 | Hyde et al. |
| 7,316,672 B1 | 1/2008 | Hunt et al. |
| 7,338,482 B2 | 3/2008 | Lockwood et al. |
| 7,438,705 B2 | 10/2008 | Karpowicz et al. |
| 7,442,849 B2 | 10/2008 | Heinecke |
| 7,485,112 B2 | 2/2009 | Karpowicz et al. |
| 7,503,910 B2 | 3/2009 | Adahan |
| 7,534,927 B2 | 5/2009 | Lockwood et al. |
| 7,585,554 B2 | 9/2009 | Johnson et al. |
| 7,586,019 B2 | 9/2009 | Oelund et al. |
| 7,625,362 B2 | 12/2009 | Boehringer et al. |
| 7,645,269 B2 | 1/2010 | Zamierowski |
| 7,670,323 B2 | 3/2010 | Hunt et al. |
| 7,678,102 B1 | 3/2010 | Heaton |
| 7,686,785 B2 | 3/2010 | Boehringer et al. |
| 7,723,560 B2 | 5/2010 | Lockwood et al. |
| 7,745,681 B1 | 6/2010 | Ferguson |
| 7,754,937 B2 | 7/2010 | Boehringer et al. |
| 7,758,554 B2 | 7/2010 | Lina et al. |
| 7,759,537 B2 | 7/2010 | Bishop et al. |
| 7,759,539 B2 | 7/2010 | Shaw et al. |
| 7,779,625 B2 | 8/2010 | Joshi et al. |
| 7,781,639 B2 | 8/2010 | Johnston et al. |
| 7,794,438 B2 | 9/2010 | Henley et al. |
| 7,815,616 B2 | 10/2010 | Boehringer et al. |
| 7,862,718 B2 | 1/2011 | Doyen et al. |
| 7,880,050 B2 | 2/2011 | Robinson et al. |
| 7,896,864 B2 | 3/2011 | Lockwood et al. |
| 7,942,866 B2 | 5/2011 | Radl et al. |
| 7,951,124 B2 | 5/2011 | Boehringer et al. |
| 7,976,533 B2 | 7/2011 | Larsson |
| 7,981,098 B2 | 7/2011 | Boehringer et al. |
| 8,002,313 B2 | 8/2011 | Singh et al. |
| 8,021,347 B2 | 9/2011 | Vitaris et al. |
| 8,057,449 B2 | 11/2011 | Sanders et al. |
| 8,083,712 B2 | 12/2011 | Biggie et al. |
| 2001/0034223 A1 | 10/2001 | Rieser et al. |
| 2002/0002209 A1 | 1/2002 | Mork |
| 2002/0115952 A1 | 8/2002 | Johnson et al. |

(56) References Cited

U.S. PATENT DOCUMENTS

| | | |
|---|---|---|
| 2002/0182246 A1 | 12/2002 | Oyaski |
| 2004/0039415 A1 | 2/2004 | Zamierowski |
| 2004/0064132 A1 | 4/2004 | Boehringer et al. |
| 2004/0073151 A1 | 4/2004 | Weston |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0065484 A1 | 3/2005 | Watson, Jr. |
| 2005/0070858 A1 | 3/2005 | Lockwood et al. |
| 2005/0085795 A1 | 4/2005 | Lockwood et al. |
| 2005/0137539 A1 | 6/2005 | Biggie et al. |
| 2005/0203452 A1 | 9/2005 | Weston et al. |
| 2005/0222527 A1 | 10/2005 | Miller et al. |
| 2005/0273066 A1 | 12/2005 | Wittmann |
| 2006/0009744 A1 | 1/2006 | Erdman et al. |
| 2006/0036221 A1 | 2/2006 | Watson, Jr. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2007/0038172 A1 | 2/2007 | Zamierowski |
| 2007/0156104 A1 | 7/2007 | Lockwood et al. |
| 2007/0167927 A1 | 7/2007 | Hunt et al. |
| 2007/0219497 A1 | 9/2007 | Johnson et al. |
| 2007/0233022 A1 | 10/2007 | Henley et al. |
| 2007/0265585 A1 | 11/2007 | Joshi et al. |
| 2008/0103489 A1 | 5/2008 | Dahners |
| 2008/0108977 A1 | 5/2008 | Heaton et al. |
| 2008/0119802 A1 | 5/2008 | Riesinger |
| 2008/0161778 A1 | 7/2008 | Steward |
| 2008/0167593 A1 | 7/2008 | Fleischmann |
| 2008/0195017 A1* | 8/2008 | Robinson et al. ............... 602/44 |
| 2008/0200906 A1 | 8/2008 | Sanders et al. |
| 2008/0208147 A1 | 8/2008 | Argenta et al. |
| 2008/0243096 A1 | 10/2008 | Svedman |
| 2008/0281281 A1 | 11/2008 | Meyer et al. |
| 2008/0300578 A1 | 12/2008 | Freedman |
| 2008/0306456 A1 | 12/2008 | Riesinger |
| 2009/0005744 A1 | 1/2009 | Karpowicz et al. |
| 2009/0093778 A1 | 4/2009 | Svedman |
| 2009/0099519 A1 | 4/2009 | Kaplan |
| 2009/0124988 A1 | 5/2009 | Coulthard |
| 2009/0131892 A1 | 5/2009 | Karpowicz et al. |
| 2009/0137973 A1 | 5/2009 | Karpowicz et al. |
| 2009/0157016 A1 | 6/2009 | Adahan |
| 2009/0171288 A1 | 7/2009 | Wheeler |
| 2009/0192467 A1 | 7/2009 | Hansen et al. |
| 2009/0192499 A1 | 7/2009 | Weston et al. |
| 2009/0227968 A1 | 9/2009 | Vess |
| 2009/0234307 A1 | 9/2009 | Vitaris |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala et al. |
| 2009/0299256 A1 | 12/2009 | Barta et al. |
| 2009/0299257 A1 | 12/2009 | Long et al. |
| 2009/0299303 A1 | 12/2009 | Seegert |
| 2009/0299307 A1 | 12/2009 | Barta et al. |
| 2009/0299308 A1 | 12/2009 | Kazala et al. |
| 2009/0299340 A1 | 12/2009 | Kazala et al. |
| 2009/0299341 A1 | 12/2009 | Kazala et al. |
| 2009/0299342 A1 | 12/2009 | Cavanaugh et al. |
| 2009/0312728 A1 | 12/2009 | Randolph et al. |
| 2010/0016767 A1 | 1/2010 | Jones et al. |
| 2010/0069850 A1 | 3/2010 | Fabo |
| 2010/0069858 A1 | 3/2010 | Olson |
| 2010/0069863 A1 | 3/2010 | Olson |
| 2010/0069885 A1 | 3/2010 | Stevenson et al. |
| 2010/0069886 A1 | 3/2010 | Wilkes |
| 2010/0087767 A1 | 4/2010 | McNeil |
| 2010/0094234 A1 | 4/2010 | Ramella et al. |
| 2010/0106106 A1 | 4/2010 | Heaton et al. |
| 2010/0106188 A1 | 4/2010 | Heaton et al. |
| 2010/0125258 A1 | 5/2010 | Coulthard et al. |
| 2010/0125259 A1 | 5/2010 | Olson |
| 2010/0152639 A1 | 6/2010 | Miau et al. |
| 2010/0160878 A1 | 6/2010 | Hunt et al. |
| 2010/0185163 A1 | 7/2010 | Heagle |
| 2010/0191198 A1 | 7/2010 | Heagle |
| 2010/0210986 A1 | 8/2010 | Sanders |
| 2010/0262091 A1 | 10/2010 | Larsson |
| 2010/0262095 A1 | 10/2010 | Hall et al. |
| 2010/0268128 A1 | 10/2010 | Randolph |
| 2010/0305524 A1* | 12/2010 | Vess et al. ..................... 604/313 |
| 2010/0324510 A1 | 12/2010 | Andresen et al. |
| 2010/0324516 A1 | 12/2010 | Braga et al. |
| 2011/0028290 A1 | 2/2011 | Ozawa |
| 2011/0028919 A1 | 2/2011 | Johnnison et al. |
| 2011/0028920 A1 | 2/2011 | Johannison |
| 2011/0125066 A1 | 5/2011 | Robinson et al. |
| 2011/0125110 A1 | 5/2011 | Cotton |
| 2011/0230849 A1 | 9/2011 | Coulthard et al. |

FOREIGN PATENT DOCUMENTS

| | | |
|---|---|---|
| EP | 0325771 B1 | 9/1993 |
| EP | 0392640 B1 | 6/1995 |
| EP | 0441418 B1 | 7/1995 |
| EP | 0692987 B1 | 10/1997 |
| EP | 0651983 B1 | 9/1998 |
| EP | 0777504 B1 | 10/1998 |
| EP | 0782421 B1 | 7/1999 |
| EP | 1018967 A1 | 7/2000 |
| EP | 0690706 B1 | 11/2000 |
| EP | 1088569 A2 | 4/2001 |
| EP | 1129734 A2 | 9/2001 |
| EP | 0921775 B1 | 12/2001 |
| EP | 1169071 A1 | 1/2002 |
| EP | 0853950 B1 | 10/2002 |
| EP | 1283702 A1 | 2/2003 |
| EP | 0708620 B1 | 5/2003 |
| EP | 1014905 B1 | 5/2003 |
| EP | 0993317 B1 | 9/2003 |
| EP | 0880953 B1 | 10/2003 |
| EP | 1219311 B1 | 7/2004 |
| EP | 1440667 A1 | 7/2004 |
| EP | 1448261 A1 | 8/2004 |
| EP | 1476217 A2 | 11/2004 |
| EP | 1478313 A2 | 11/2004 |
| EP | 1487389 A1 | 12/2004 |
| EP | 1100574 B1 | 2/2005 |
| EP | 1513478 A2 | 3/2005 |
| EP | 1517660 A2 | 3/2005 |
| EP | 1556120 A2 | 7/2005 |
| EP | 1565219 A2 | 8/2005 |
| EP | 1637088 A2 | 3/2006 |
| EP | 1284777 B1 | 4/2006 |
| EP | 1660000 A2 | 5/2006 |
| EP | 1663062 A2 | 6/2006 |
| EP | 0982015 B1 | 8/2006 |
| EP | 0620720 B2 | 11/2006 |
| EP | 1772160 A1 | 4/2007 |
| EP | 1809350 A2 | 7/2007 |
| EP | 1824533 A2 | 8/2007 |
| EP | 1227853 B1 | 1/2008 |
| EP | 1904137 A2 | 4/2008 |
| EP | 1906903 A2 | 4/2008 |
| EP | 2218431 A2 | 4/2008 |
| EP | 1919533 A1 | 5/2008 |
| EP | 1920791 A2 | 5/2008 |
| EP | 1940485 A2 | 7/2008 |
| EP | 1957018 A2 | 8/2008 |
| EP | 1976477 A2 | 10/2008 |
| EP | 1977776 A2 | 10/2008 |
| EP | 1986584 A2 | 11/2008 |
| EP | 1993491 A2 | 11/2008 |
| EP | 1827561 B1 | 1/2009 |
| EP | 2010065 A1 | 1/2009 |
| EP | 2037852 A1 | 3/2009 |
| EP | 2052750 A1 | 4/2009 |
| EP | 2063952 A1 | 6/2009 |
| EP | 2068798 A2 | 6/2009 |

(56) References Cited

FOREIGN PATENT DOCUMENTS

| | | |
|---|---|---|
| EP | 2079507 A2 | 7/2009 |
| EP | 2081629 A2 | 7/2009 |
| EP | 2098257 A1 | 9/2009 |
| EP | 2103290 A2 | 9/2009 |
| EP | 2109473 A2 | 10/2009 |
| EP | 2129409 A1 | 12/2009 |
| EP | 2138139 A2 | 12/2009 |
| EP | 1652549 B1 | 1/2010 |
| EP | 1905465 B1 | 1/2010 |
| EP | 2146759 A1 | 1/2010 |
| EP | 2152196 A1 | 2/2010 |
| EP | 2127690 A2 | 3/2010 |
| EP | 2167157 A1 | 3/2010 |
| EP | 2172164 A1 | 4/2010 |
| EP | 2203137 A1 | 7/2010 |
| EP | 2244217 A1 | 10/2010 |
| EP | 2244746 A2 | 11/2010 |
| EP | 2252247 A2 | 11/2010 |
| EP | 2254537 A2 | 12/2010 |
| EP | 2268348 A1 | 1/2011 |
| EP | 2279017 A1 | 2/2011 |
| EP | 2279018 A1 | 2/2011 |
| EP | 2285430 A2 | 2/2011 |
| EP | 2306951 A1 | 4/2011 |
| EP | 1703922 B1 | 5/2011 |
| EP | 1578477 B1 | 9/2011 |
| GB | 2356148 B2 | 6/2004 |
| GB | 2431351 A1 | 4/2007 |
| WO | WO 94/03214 | 2/1994 |
| WO | WO 94/21207 | 9/1994 |
| WO | WO 94/23678 | 10/1994 |
| WO | WO 99/01173 | 1/1999 |
| WO | WO 00/07653 | 2/2000 |
| WO | WO 00/61206 | 10/2000 |
| WO | WO 01/85228 | 11/2001 |
| WO | WO 01/85248 | 11/2001 |
| WO | WO 02/43634 | 6/2002 |
| WO | WO 02/070040 | 9/2002 |
| WO | WO 03/086232 | 10/2003 |
| WO | WO 03/101508 | 12/2003 |
| WO | WO 2004/018020 | 3/2004 |
| WO | WO 2004/037334 | 5/2004 |
| WO | WO 2004/041064 | 5/2004 |
| WO | WO 2004/060148 | 7/2004 |
| WO | WO 2005/009488 | 2/2005 |
| WO | WO 2005/016179 | 2/2005 |
| WO | WO 2005/025447 | 3/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/061025 | 7/2005 |
| WO | WO 2005/072789 | 8/2005 |
| WO | WO 2005/079718 | 9/2005 |
| WO | WO 2005/102415 | 11/2005 |
| WO | WO 2005/105174 | 11/2005 |
| WO | WO 2005/105175 | 11/2005 |
| WO | WO 2005/105176 | 11/2005 |
| WO | WO 2005/105179 | 11/2005 |
| WO | WO 2005/105180 | 11/2005 |
| WO | WO 2005/115497 | 12/2005 |
| WO | WO 2005/115523 | 12/2005 |
| WO | WO 2005/123170 | 12/2005 |
| WO | WO 2006/046060 | 5/2006 |
| WO | WO 2006/052338 | 5/2006 |
| WO | WO 2006/052745 | 5/2006 |
| WO | WO 2006/114637 | 11/2006 |
| WO | WO 2006/114638 | 11/2006 |
| WO | WO 2006/114648 | 11/2006 |
| WO | WO 2007/006306 | 1/2007 |
| WO | WO 2007/013049 | 2/2007 |
| WO | WO 2007/015964 | 2/2007 |
| WO | WO 2007/019038 | 2/2007 |
| WO | WO 2007/030598 | 3/2007 |
| WO | WO 2007/030599 | 3/2007 |
| WO | WO 2007/030601 A2 | 3/2007 |
| WO | WO 2007/030601 A3 | 3/2007 |
| WO | WO 2007/031757 | 3/2007 |
| WO | WO 2007/031762 | 3/2007 |
| WO | WO 2007/031765 | 3/2007 |
| WO | WO 2007/041642 | 4/2007 |
| WO | WO 2007/062024 | 5/2007 |
| WO | WO 2007/067685 | 6/2007 |
| WO | WO 2007/085396 | 8/2007 |
| WO | WO 2007/087808 | 8/2007 |
| WO | WO 2007/087809 | 8/2007 |
| WO | WO 2007/087811 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2007/133618 | 11/2007 |
| WO | WO 2007/143060 | 12/2007 |
| WO | WO 2008/008032 | 1/2008 |
| WO | WO 2008/010094 | 1/2008 |
| WO | WO 2008/011774 | 1/2008 |
| WO | WO 2008/012278 | 1/2008 |
| WO | WO 2008/013896 | 1/2008 |
| WO | WO 2008/014358 | 1/2008 |
| WO | WO 2008/016304 | 2/2008 |
| WO | WO 2008/027449 | 3/2008 |
| WO | WO 2008/027449 A2 | 3/2008 |
| WO | WO 2008/036162 | 3/2008 |
| WO | WO 2008/040020 | 4/2008 |
| WO | WO 2008/041926 | 4/2008 |
| WO | WO 2008/043067 | 4/2008 |
| WO | WO 2008/048527 | 4/2008 |
| WO | WO 2008/064502 | 6/2008 |
| WO | WO 2008/086397 | 7/2008 |
| WO | WO 2008/100437 | 8/2008 |
| WO | WO 2008/100440 | 8/2008 |
| WO | WO 2008/100446 | 8/2008 |
| WO | WO 2008/112304 | 9/2008 |
| WO | WO 2008/131895 | 11/2008 |
| WO | WO 2008/132215 | 11/2008 |
| WO | WO 2008/135997 | 11/2008 |
| WO | WO 2008/141470 | 11/2008 |
| WO | WO 2008/154158 | 12/2008 |
| WO | WO 2009/002260 | 12/2008 |
| WO | WO 2009/004370 | 1/2009 |
| WO | WO 2009/016603 | 2/2009 |
| WO | WO 2009/016605 | 2/2009 |
| WO | WO 2009/019229 | 2/2009 |
| WO | WO 2009/021047 | 2/2009 |
| WO | WO 2009/021353 | 2/2009 |
| WO | WO 2009/034322 | 3/2009 |
| WO | WO 2009/062327 | 5/2009 |
| WO | WO 2009/066104 | 5/2009 |
| WO | WO 2009/066106 | 5/2009 |
| WO | WO 2009/067711 | 5/2009 |
| WO | WO 2009/068665 | 6/2009 |
| WO | WO 2009/071926 | 6/2009 |
| WO | WO 2009/071929 | 6/2009 |
| WO | WO 2009/071932 | 6/2009 |
| WO | WO 2009/071933 | 6/2009 |
| WO | WO 2009/071935 | 6/2009 |
| WO | WO 2009/071948 | 6/2009 |
| WO | WO 2009/078790 | 6/2009 |
| WO | WO 2009/086580 | 7/2009 |
| WO | WO 2009/088925 | 7/2009 |
| WO | WO 2009/111655 | 9/2009 |
| WO | WO 2009/114624 | 9/2009 |
| WO | WO 2009/114760 | 9/2009 |
| WO | WO 2009/114790 | 9/2009 |
| WO | WO 2009/124473 | 10/2009 |
| WO | WO 2009/124548 | 10/2009 |
| WO | WO 2009/126102 | 10/2009 |
| WO | WO 2009/126103 | 10/2009 |
| WO | WO 2009/137194 | 11/2009 |
| WO | WO 2009/145703 | 12/2009 |
| WO | WO 2009/145894 | 12/2009 |
| WO | WO 2009/158125 | 12/2009 |
| WO | WO 2009/158126 | 12/2009 |
| WO | WO 2009/158127 | 12/2009 |

(56) References Cited

FOREIGN PATENT DOCUMENTS

| WO | WO 2009/158129 | 12/2009 |
|---|---|---|
| WO | WO 2010/033271 | 3/2010 |
| WO | WO 2010/033574 A1 | 3/2010 |
| WO | WO 2010/033769 A1 | 3/2010 |
| WO | WO 2010/035017 | 4/2010 |
| WO | WO 2010/042240 | 4/2010 |
| WO | WO 2010/051073 A1 | 5/2010 |
| WO | WO 2010/056977 | 5/2010 |
| WO | WO 2010/059712 | 5/2010 |
| WO | WO 2010/059712 A2 | 5/2010 |
| WO | WO 2010/059730 A2 | 5/2010 |
| WO | WO 2010/072395 | 7/2010 |
| WO | WO 2010/085270 A1 | 7/2010 |
| WO | WO 2010/094957 | 8/2010 |
| WO | WO 2010/147533 | 12/2010 |
| WO | WO 2010/147592 A1 | 12/2010 |

OTHER PUBLICATIONS

Fleischmann et al., Vacuum Sealing: Indication, Technique, and Results, Eur J Orthop Surg Traumatol, (1995) 5:37-40.

Greer, et al., Techniques for Applying Subatmospheric Pressure Dressing to Wounds in Difficult Regions of Anatomy, JWOCN, vol. 26, No. 5, 1999 pp. 250-253.

International Search Report and Written Opinion for PCT/US2010/061938 mailed Sep. 8, 2011 in 21 pages.

International Search Report and Written Opinion for PCT/US2011/041521 mailed Oct. 7, 2011 in 15 pages.

K.F. Jeter, T.E. Tintle, and M. Chariker "Managing Draining Wounds and Fistulae: New and Established Methods" (1990) 240-246.

KCI V.A.C. GranuFoam Bridge Dressing Product Brochure (2009) in 2 pages.

\* cited by examiner

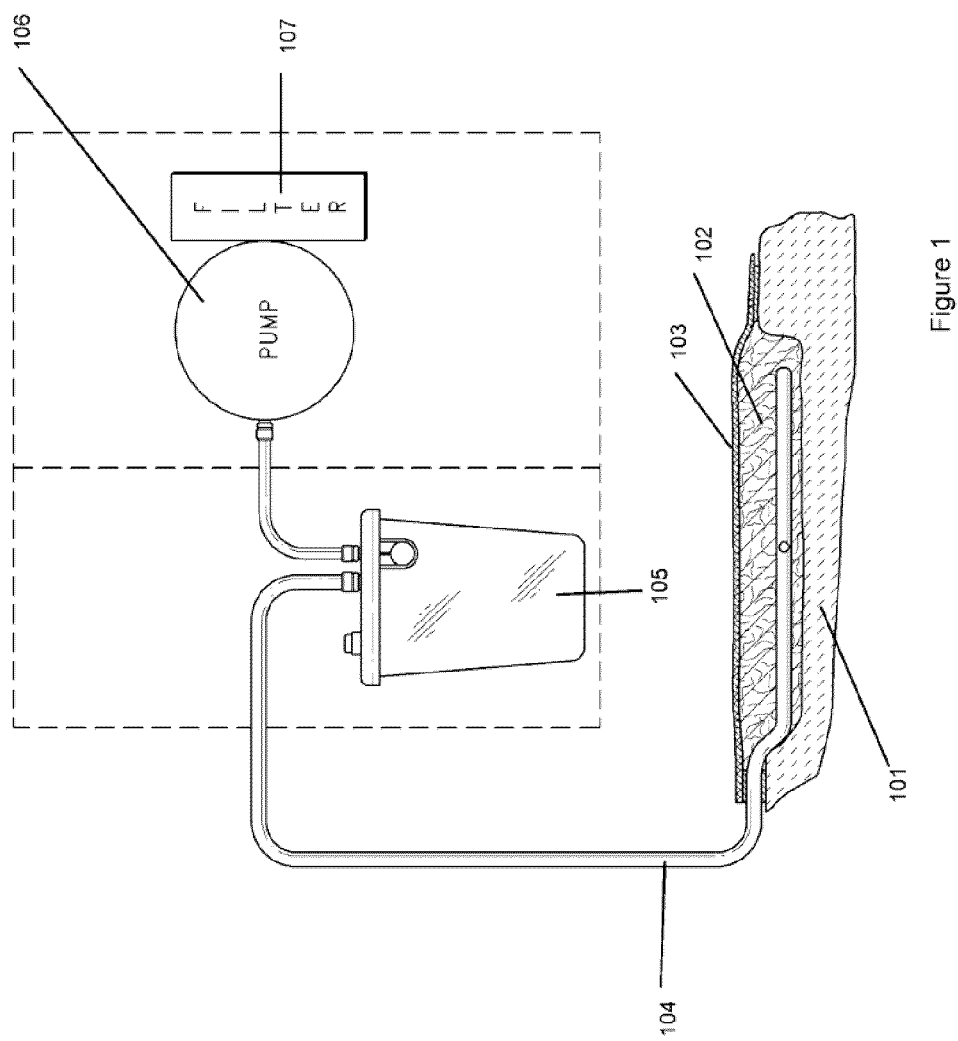

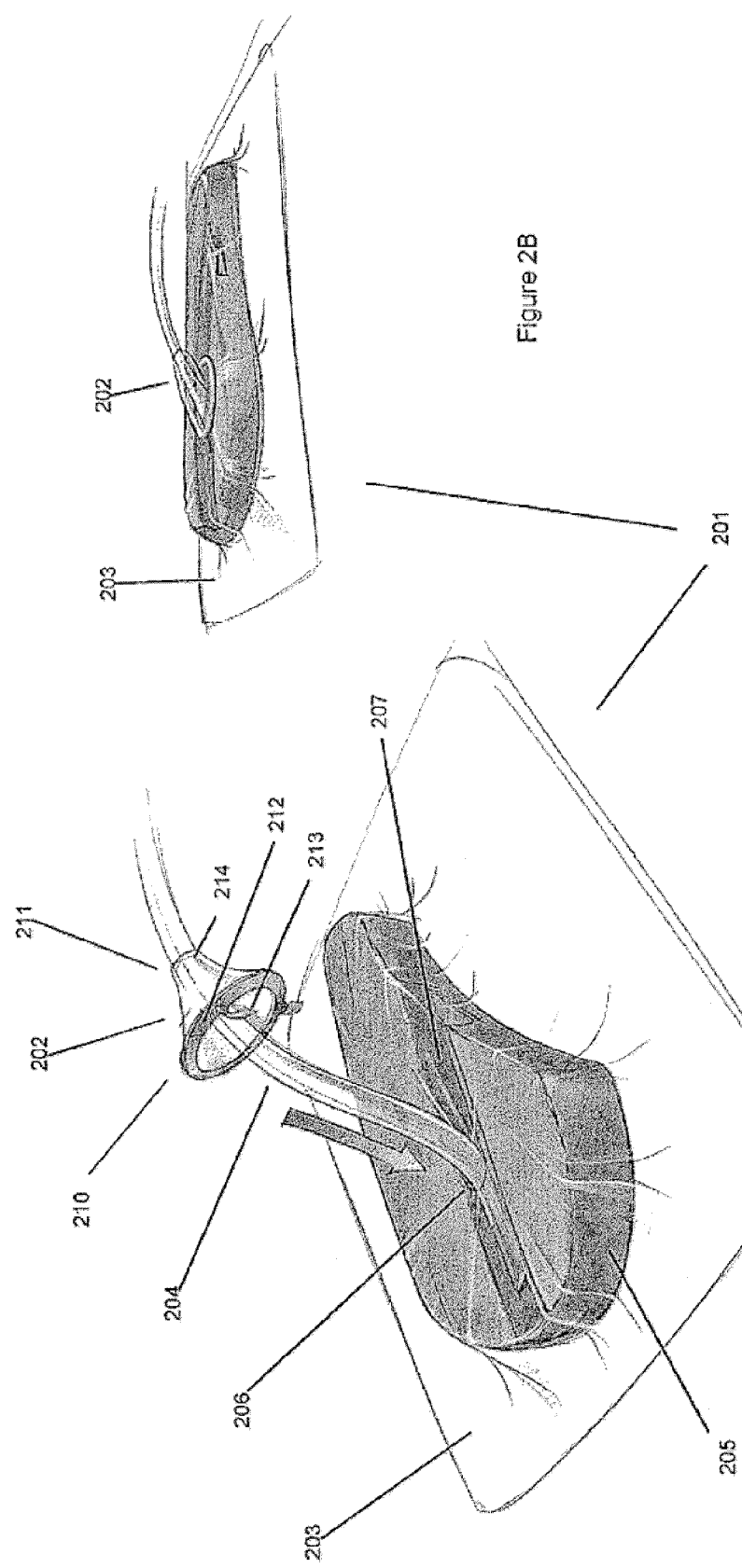

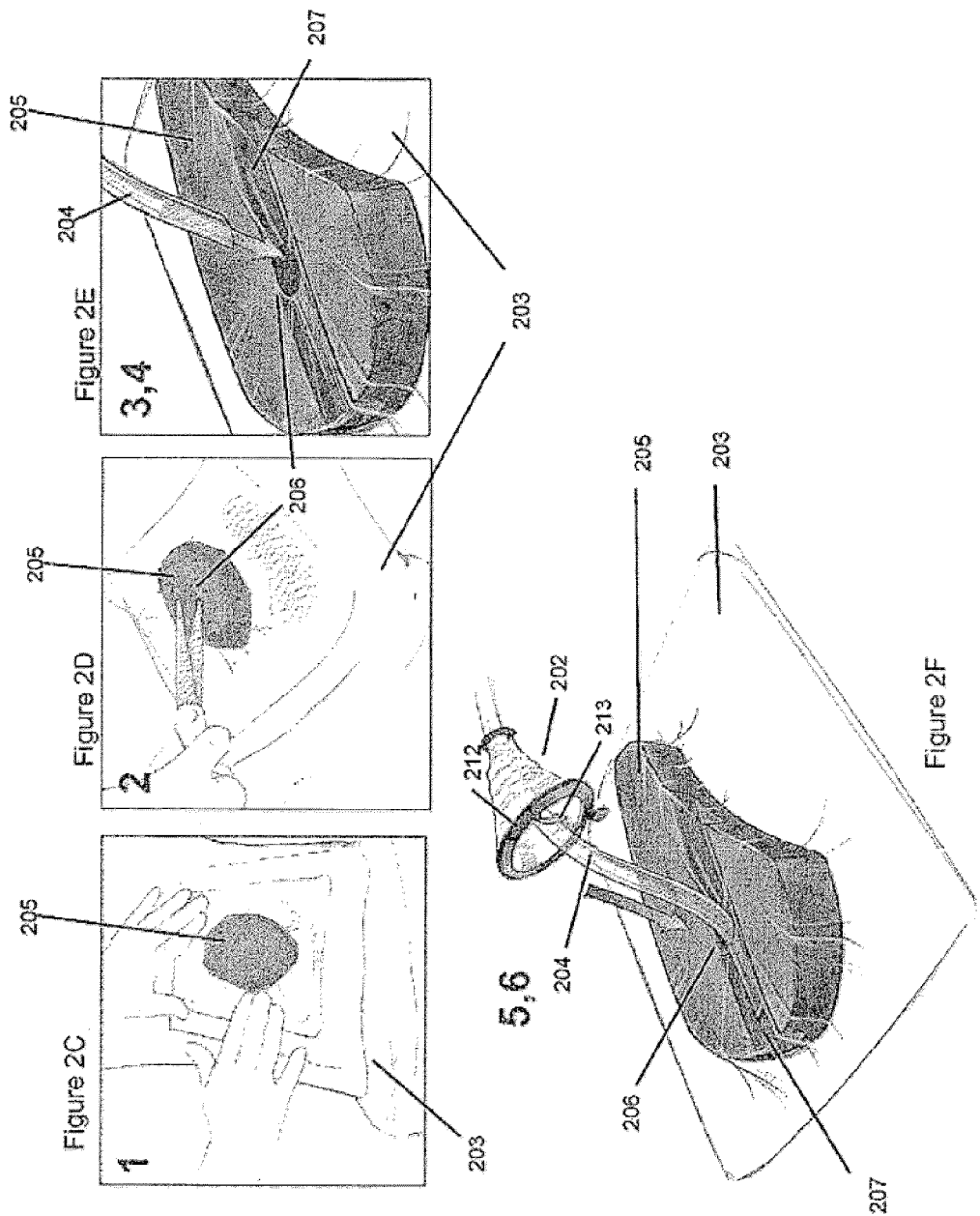

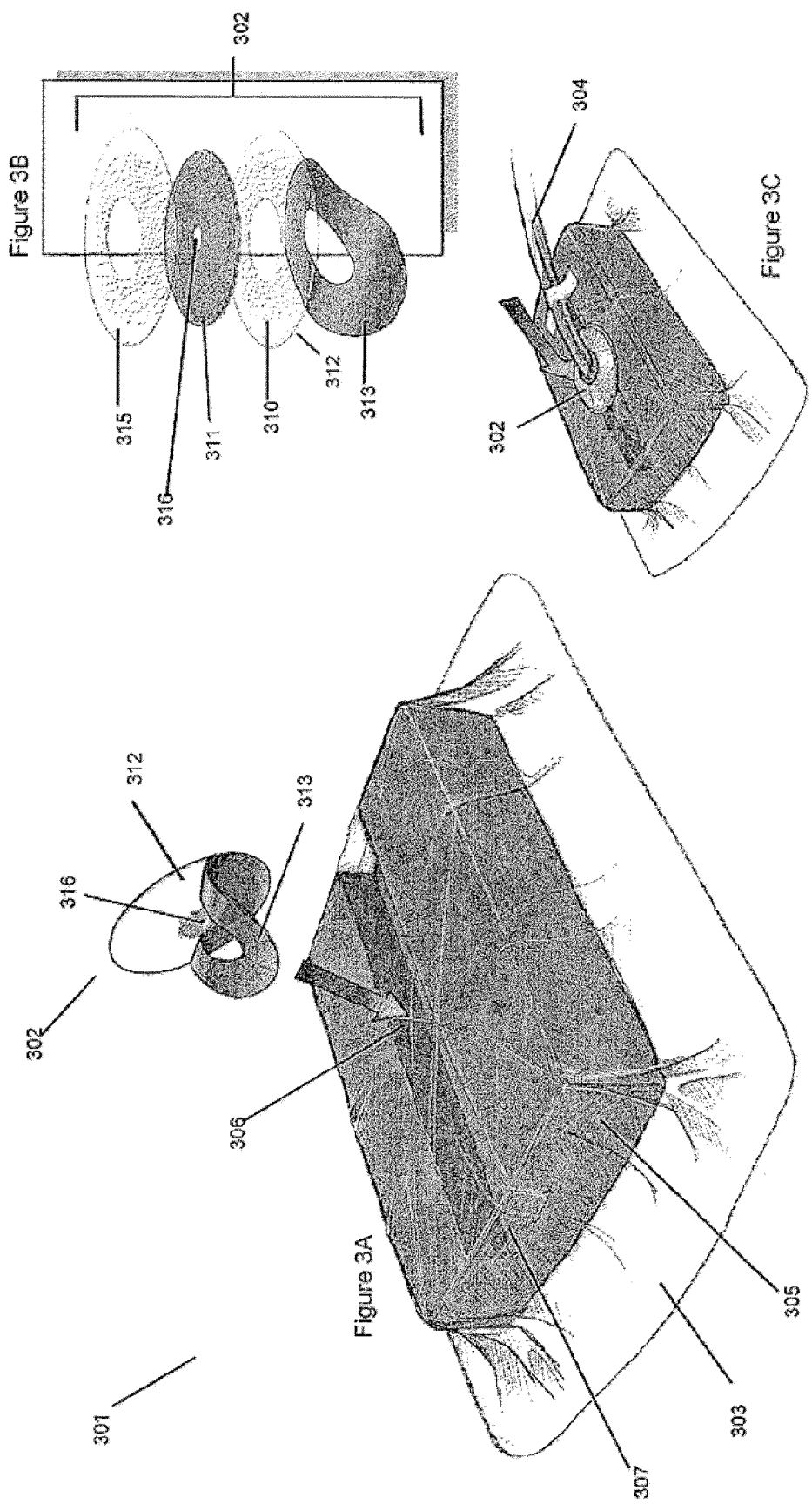

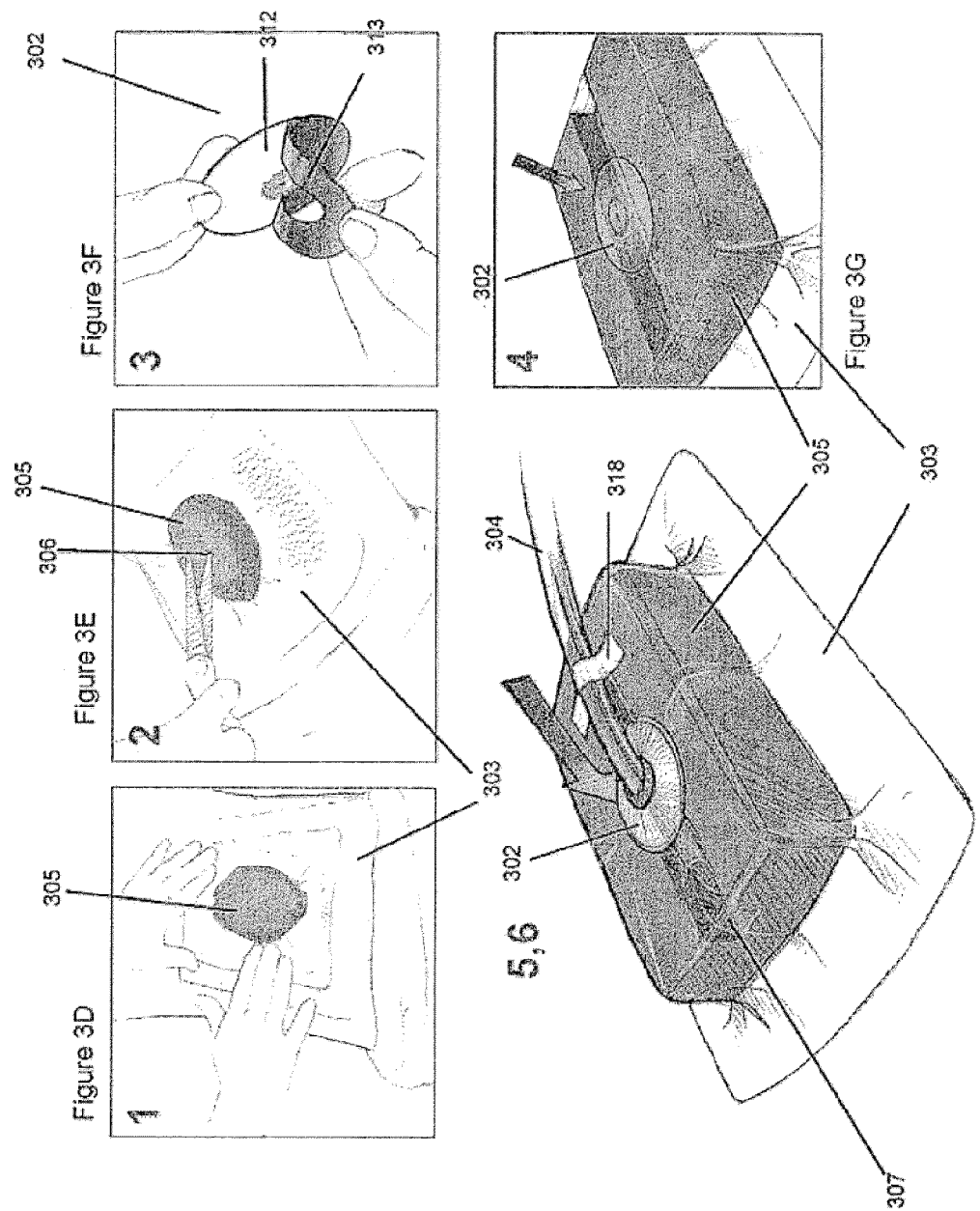

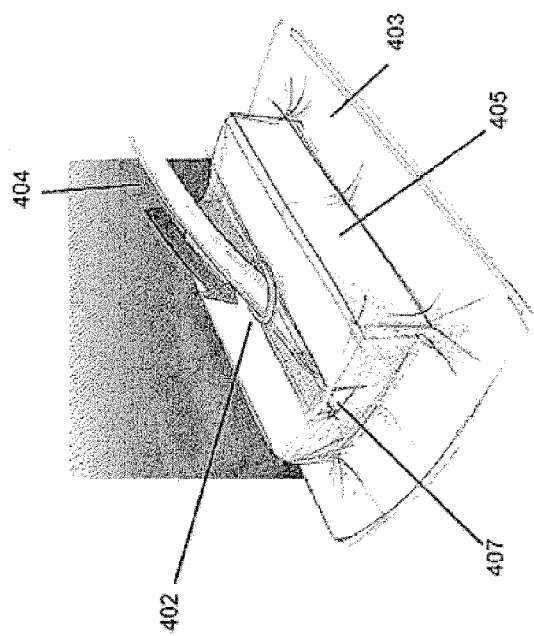
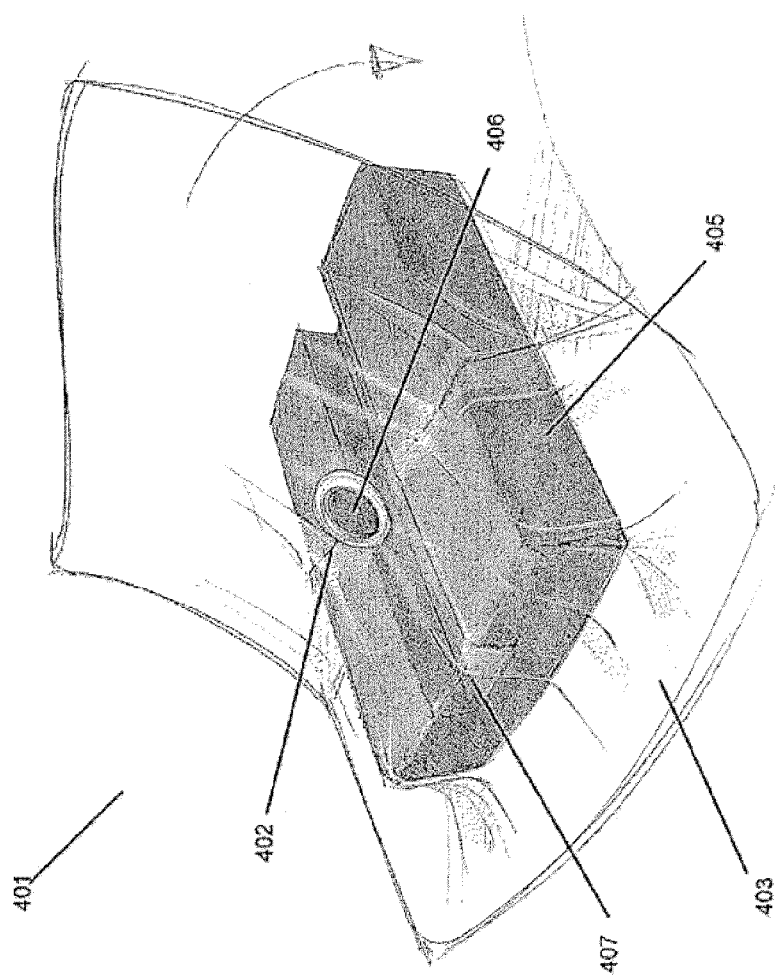
Figure 4B
Figure 4A

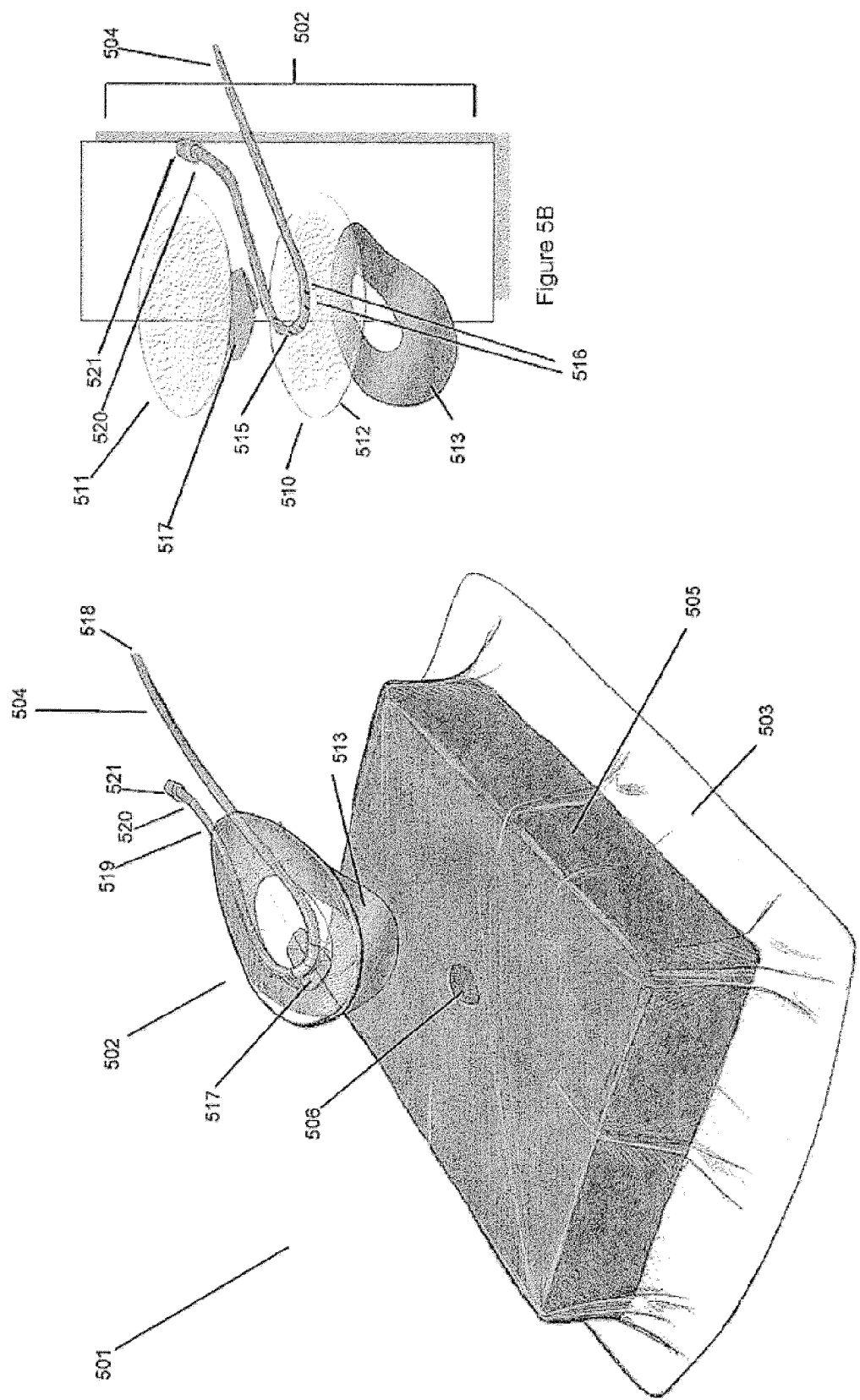

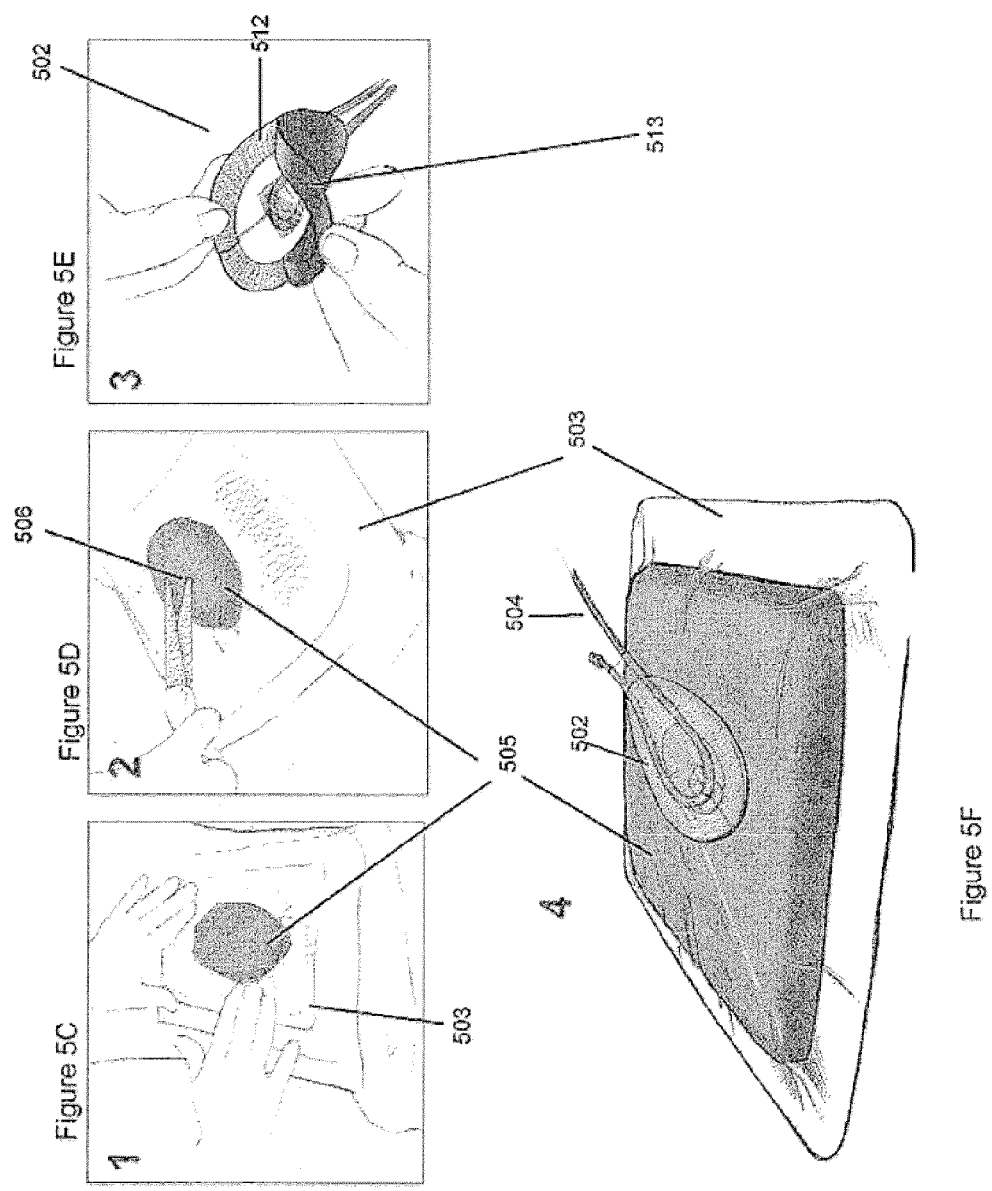

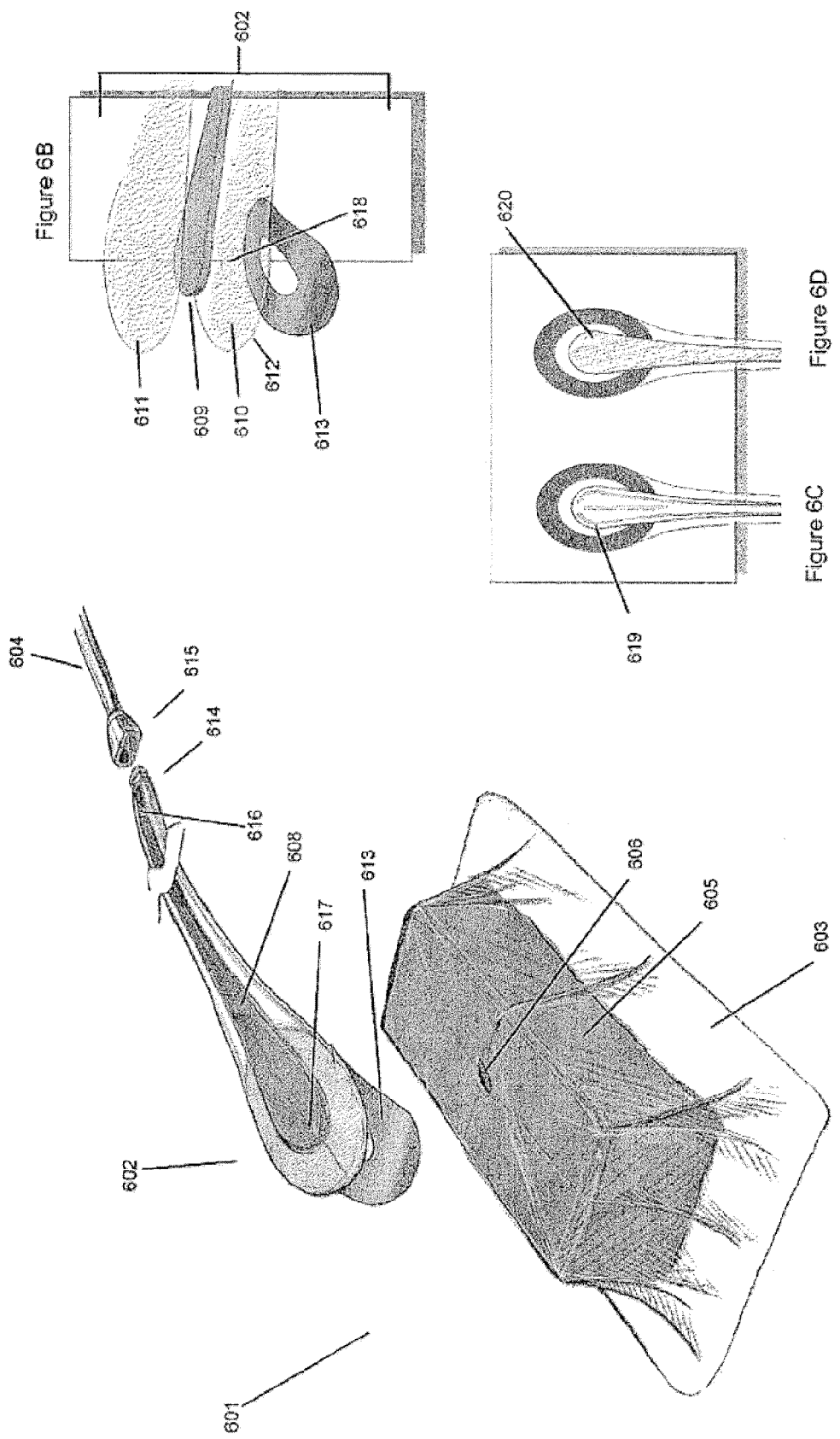

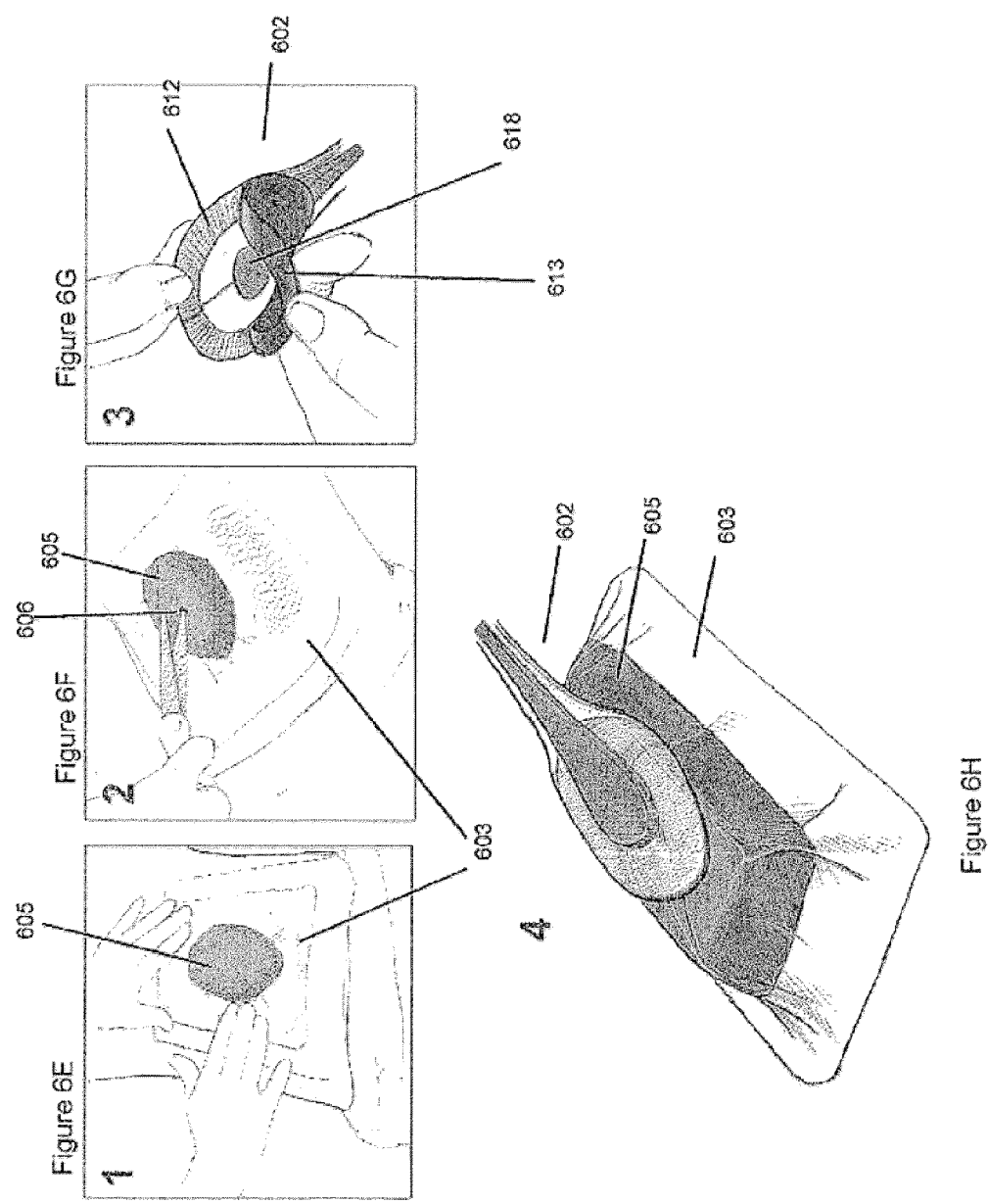

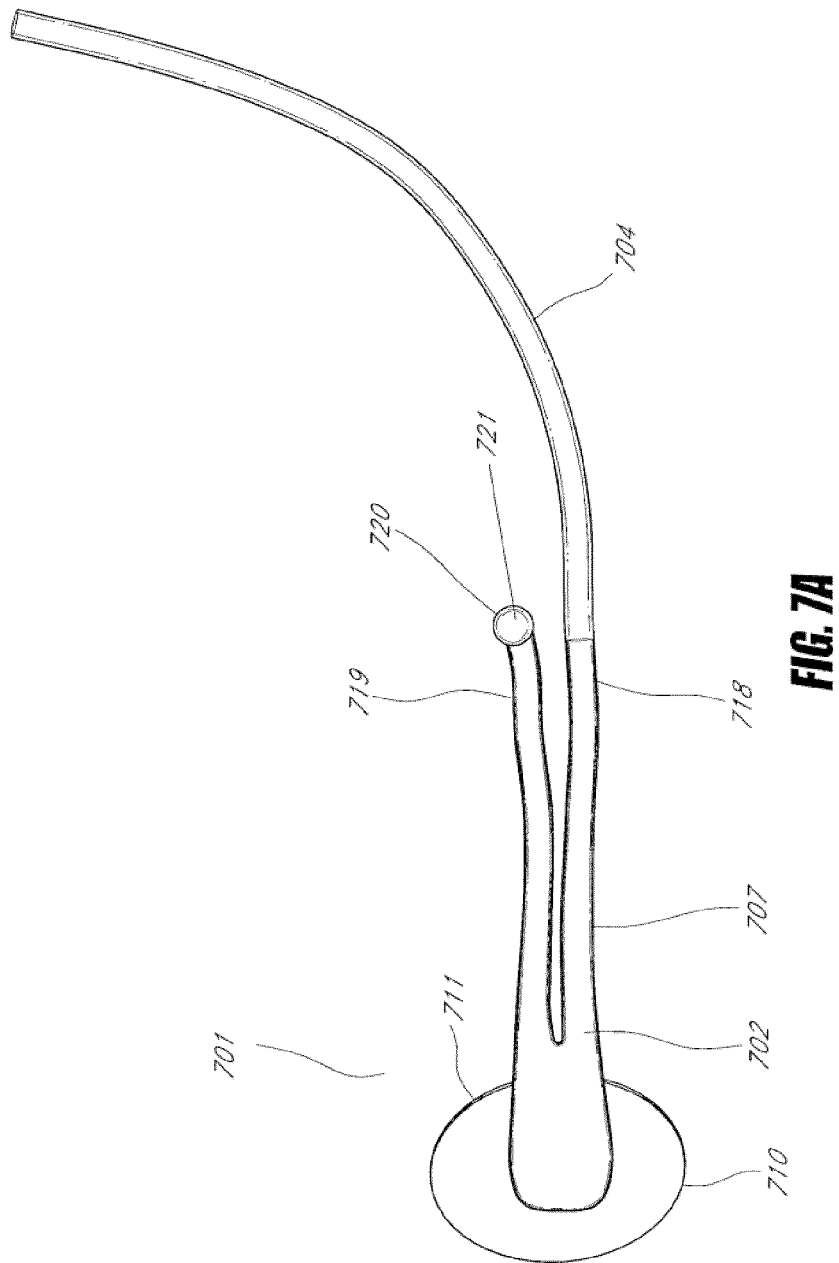

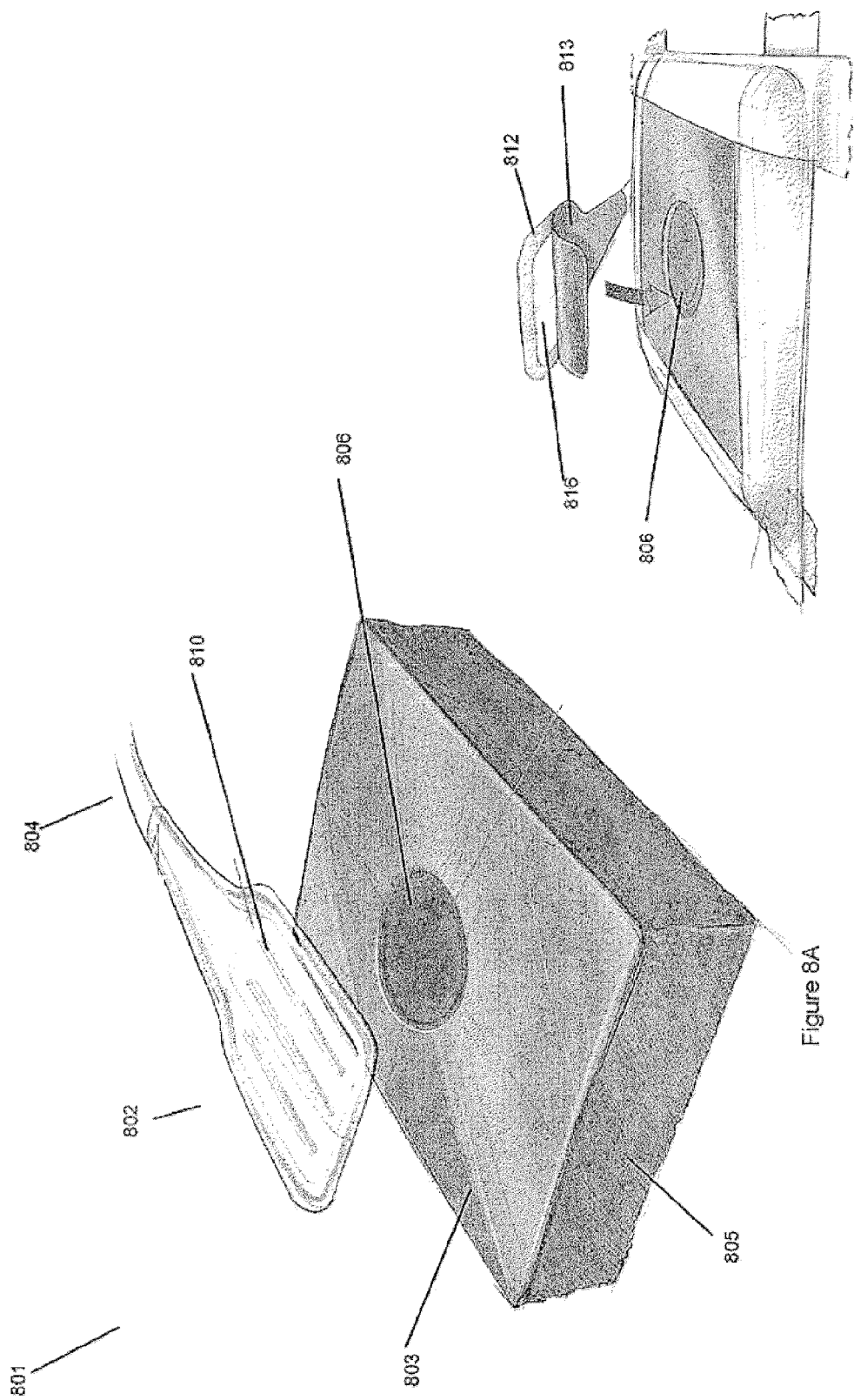

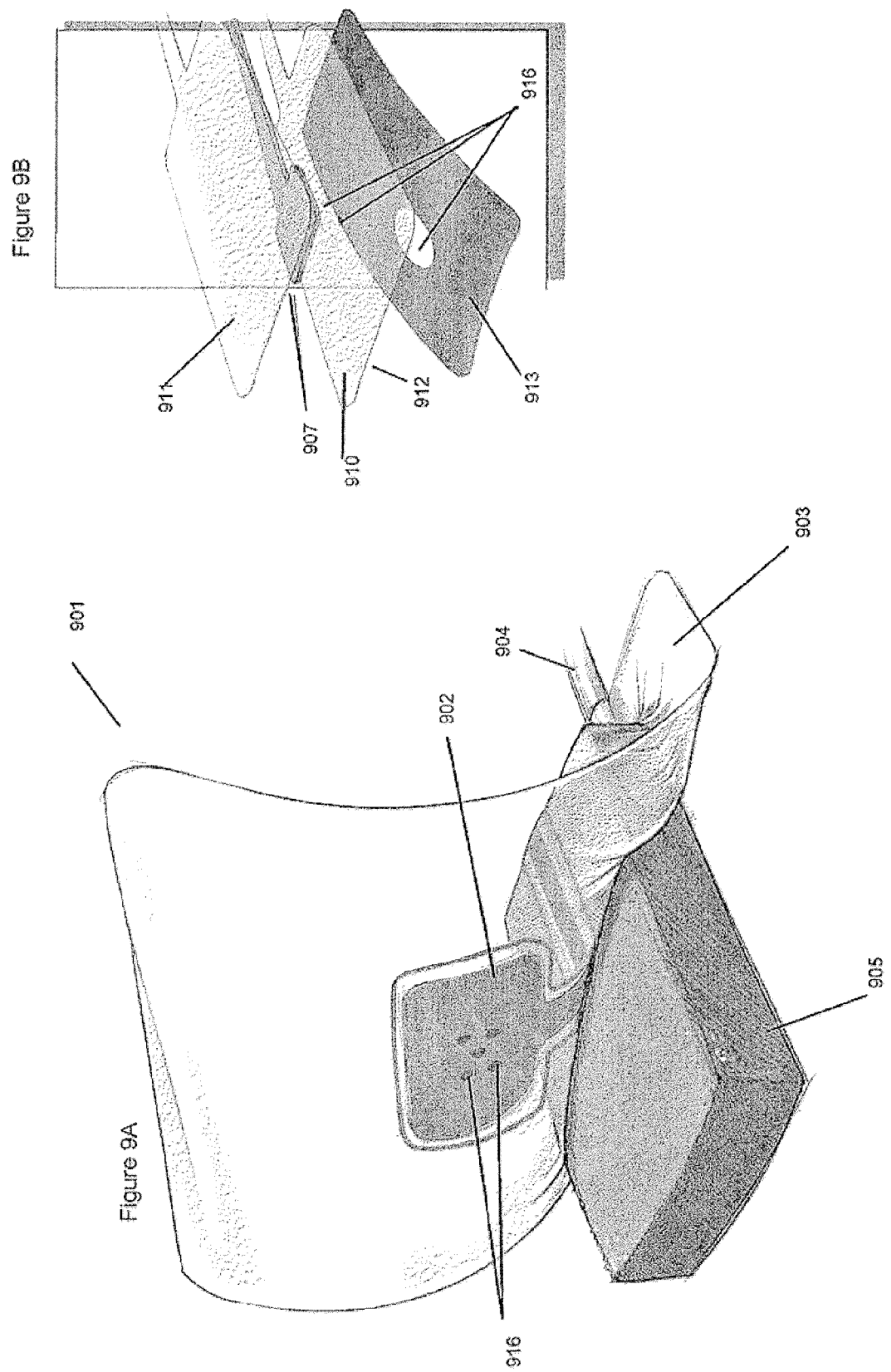

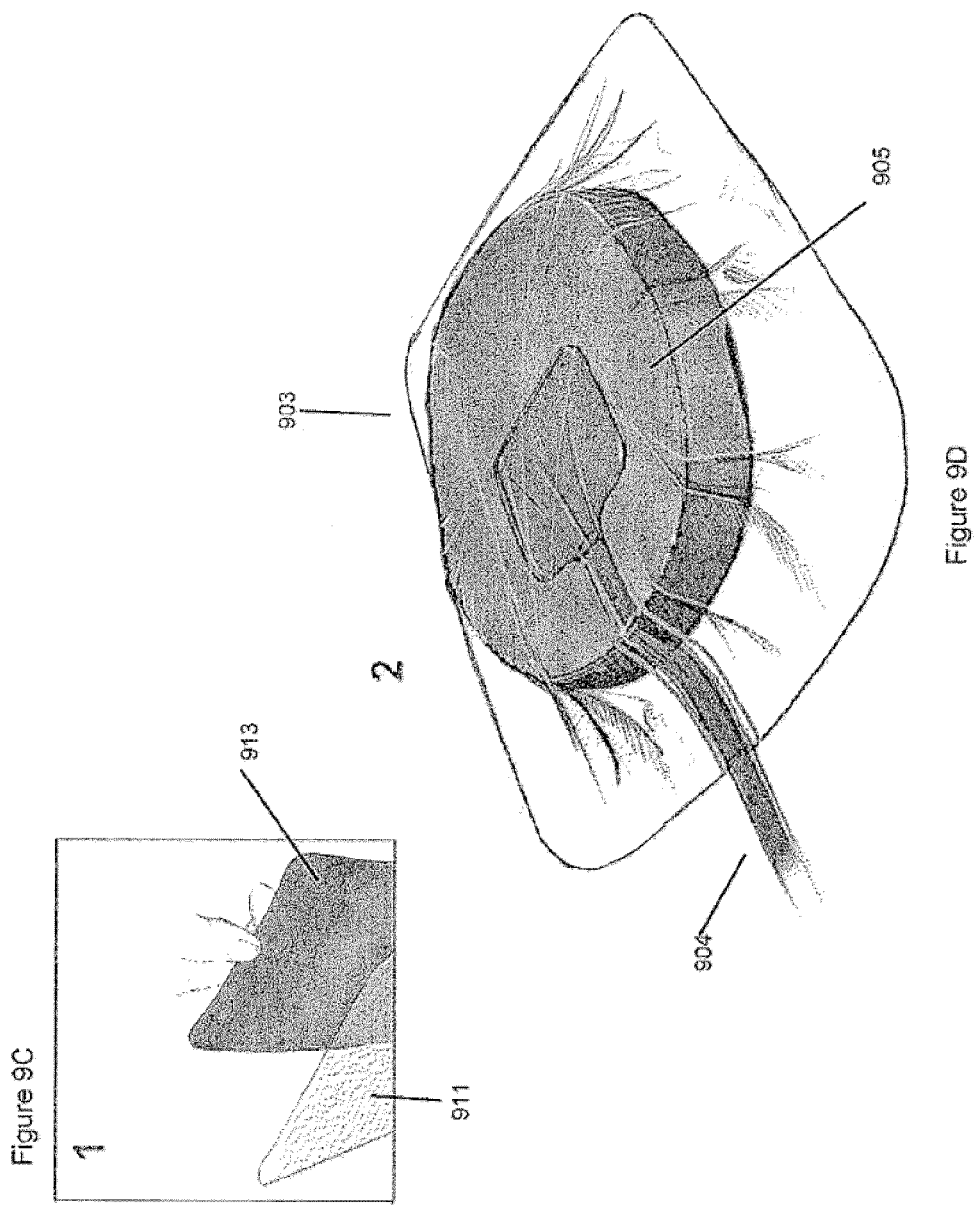

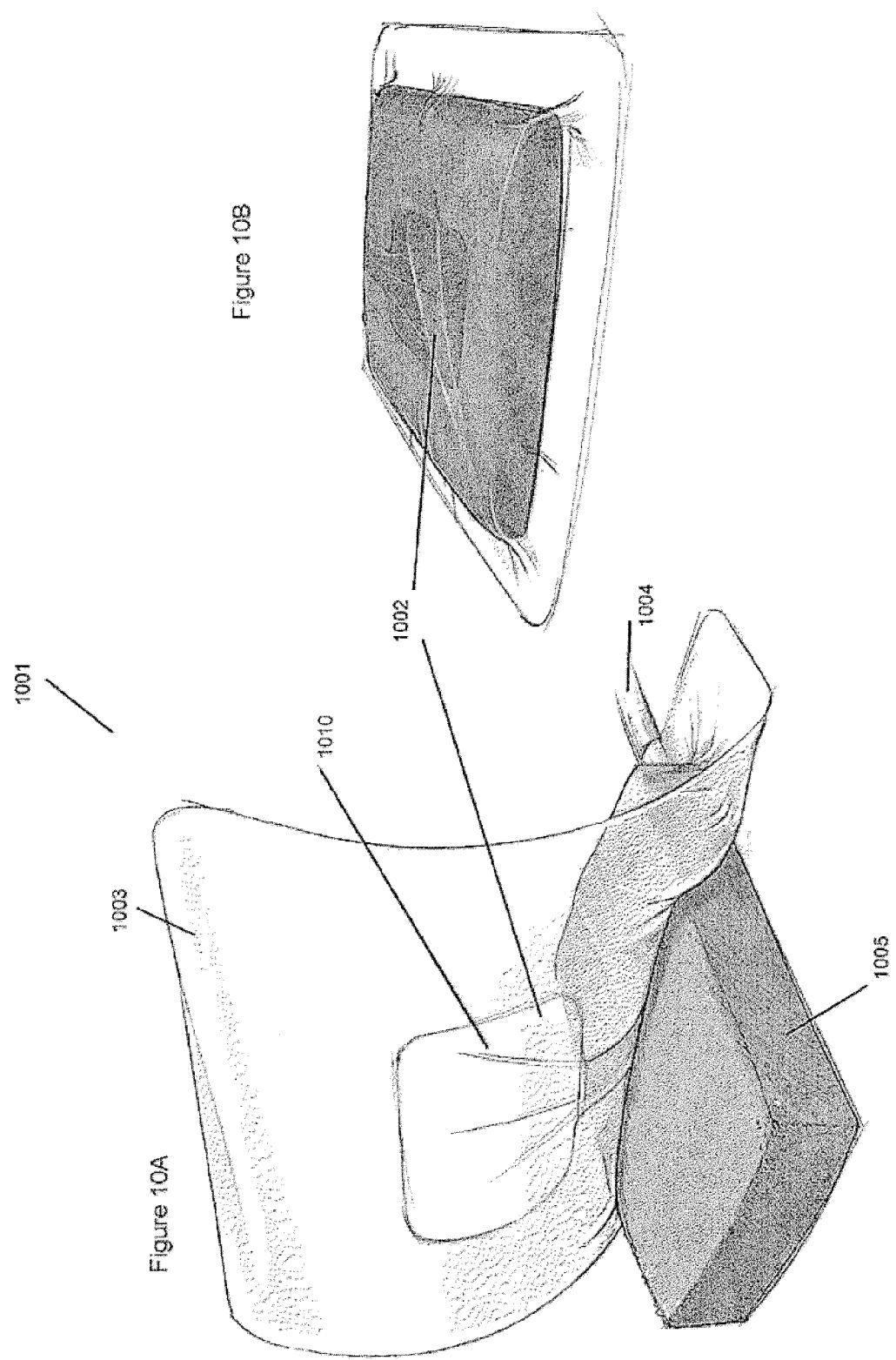

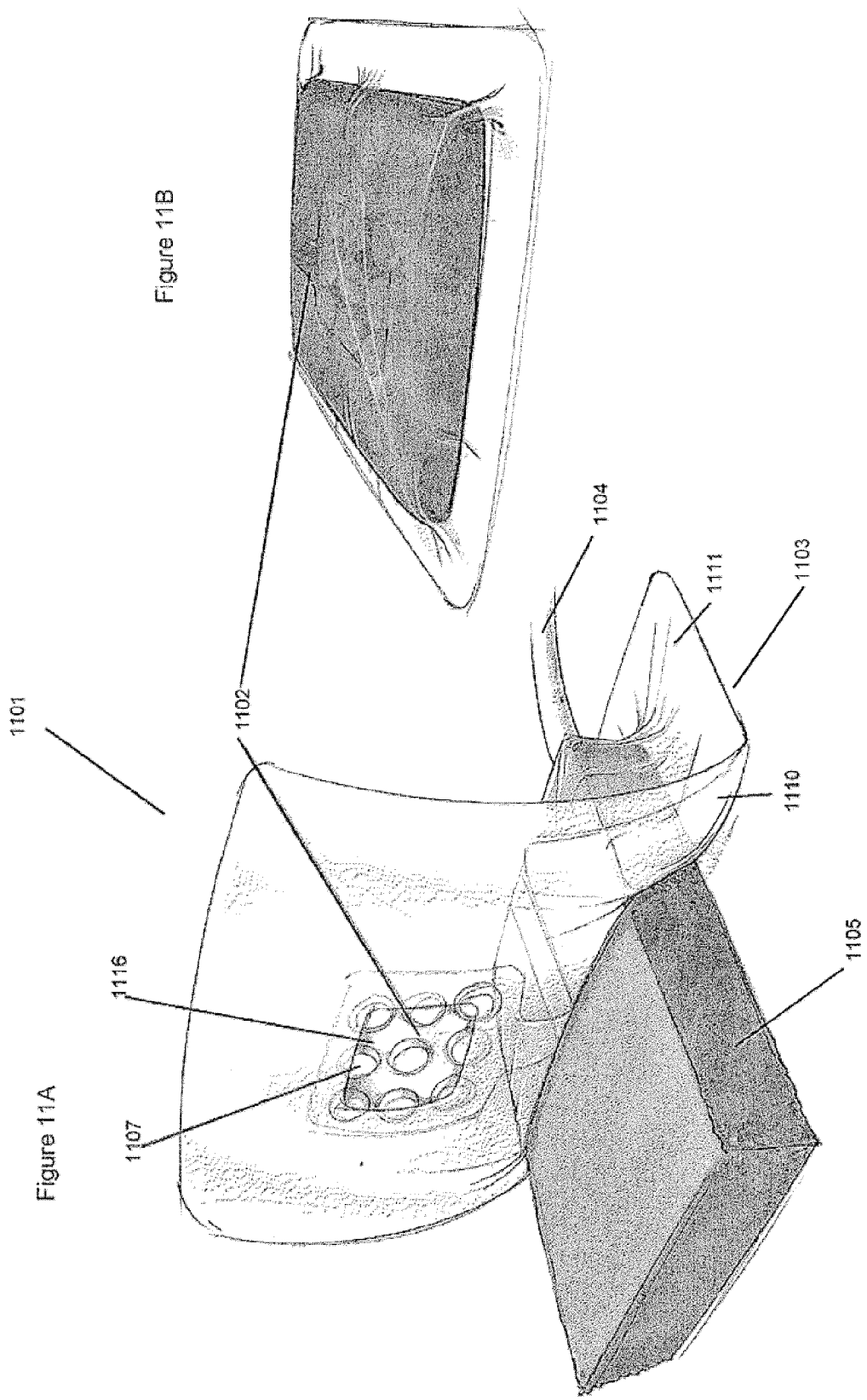

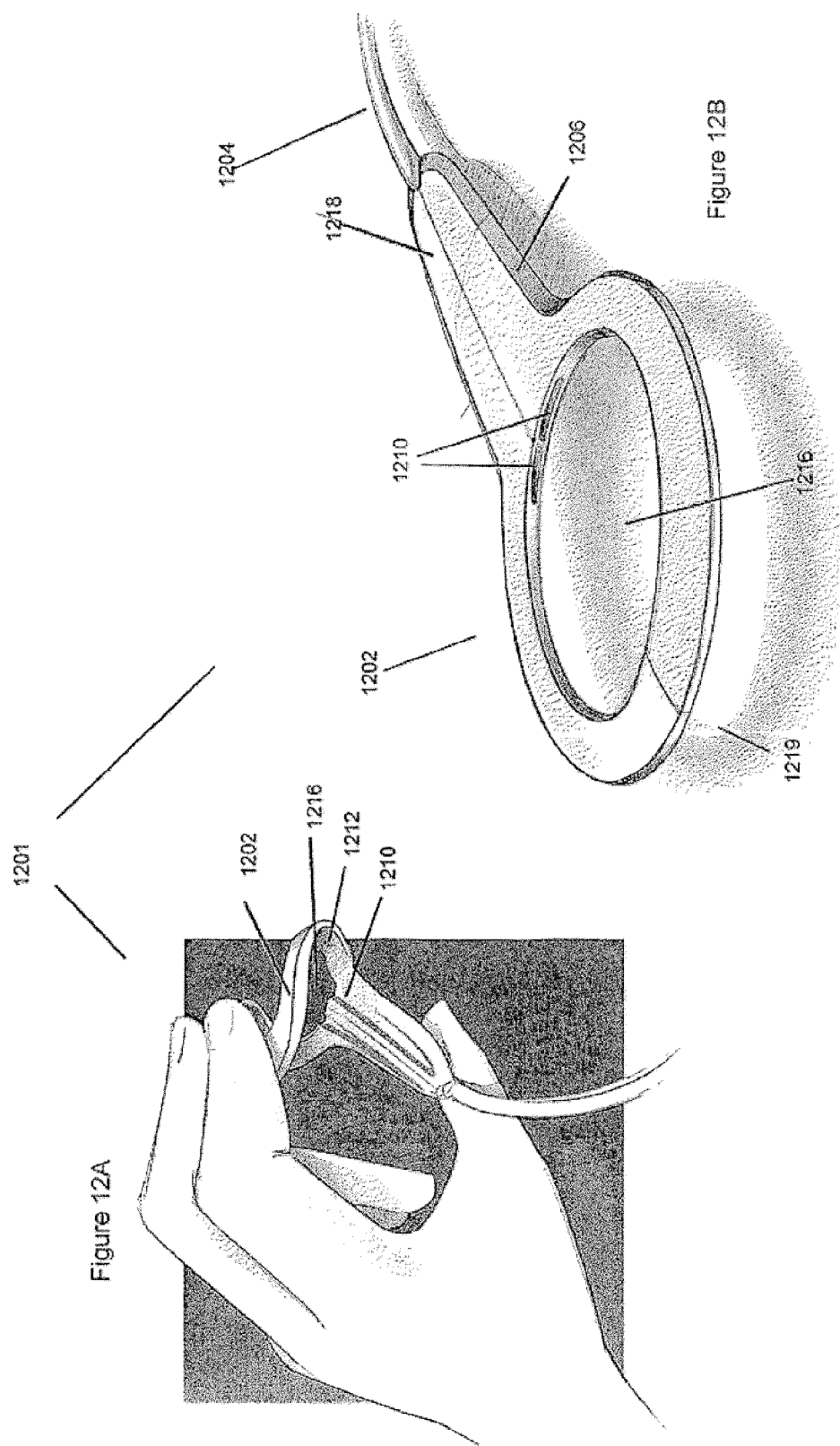

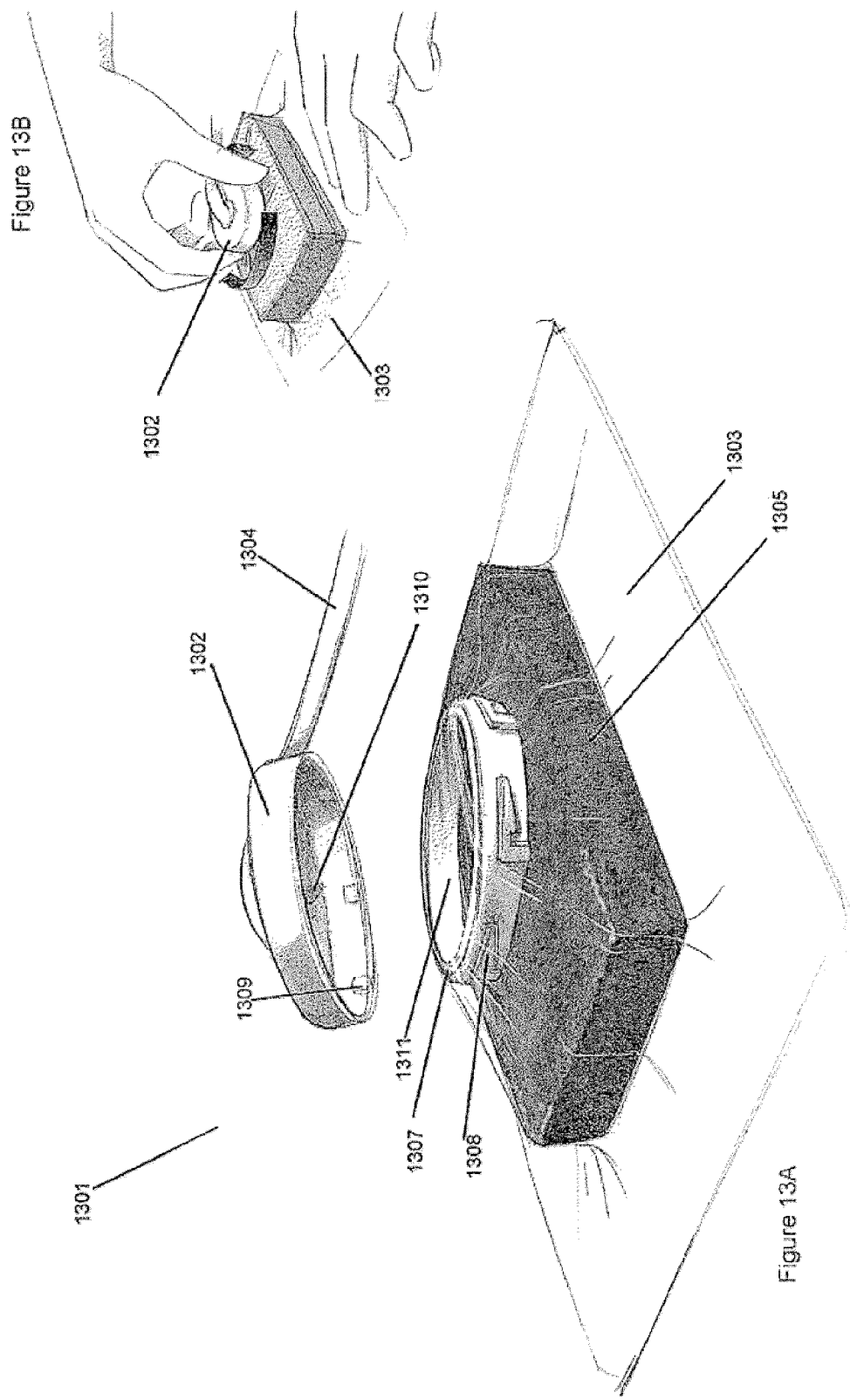

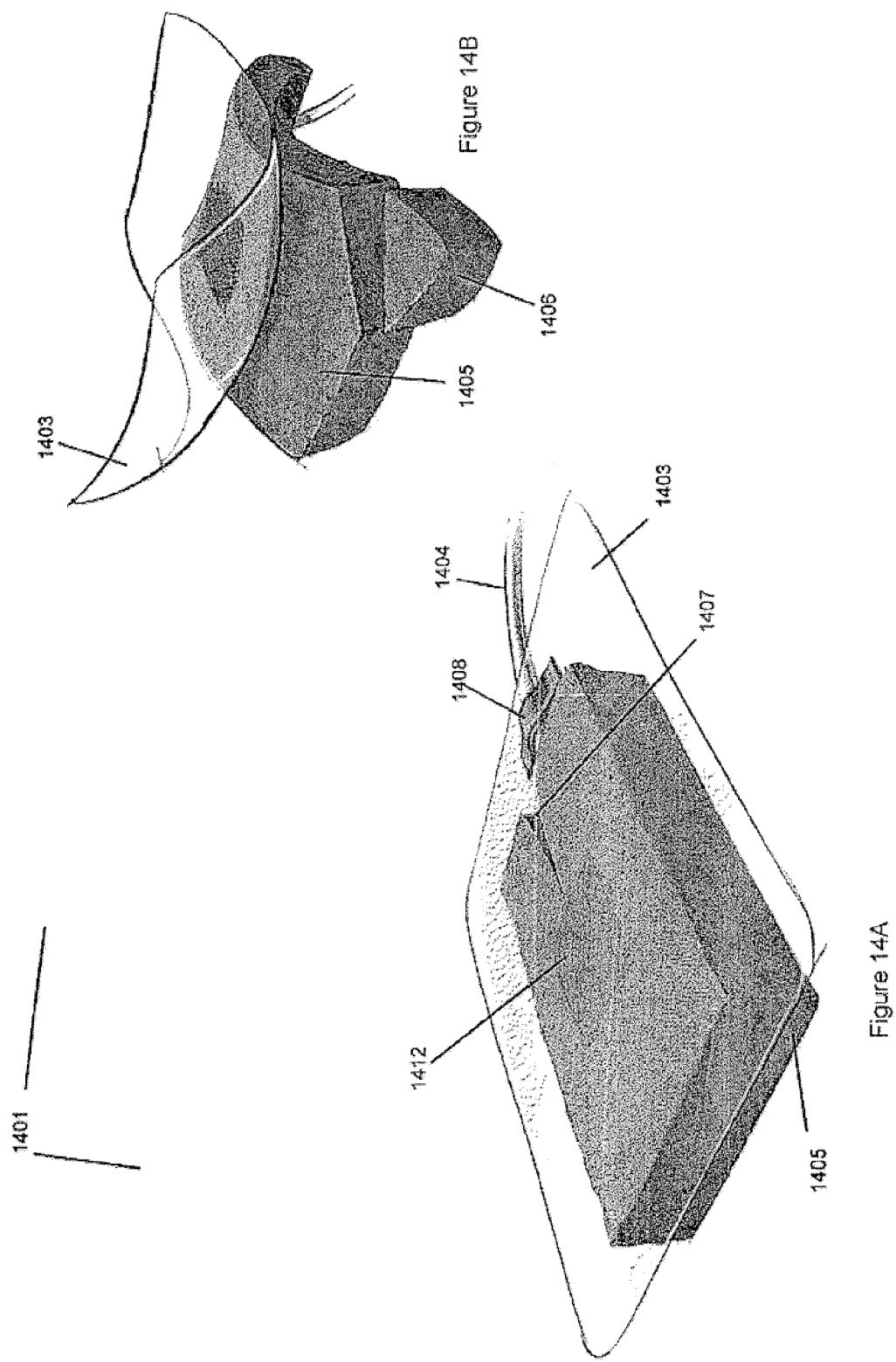

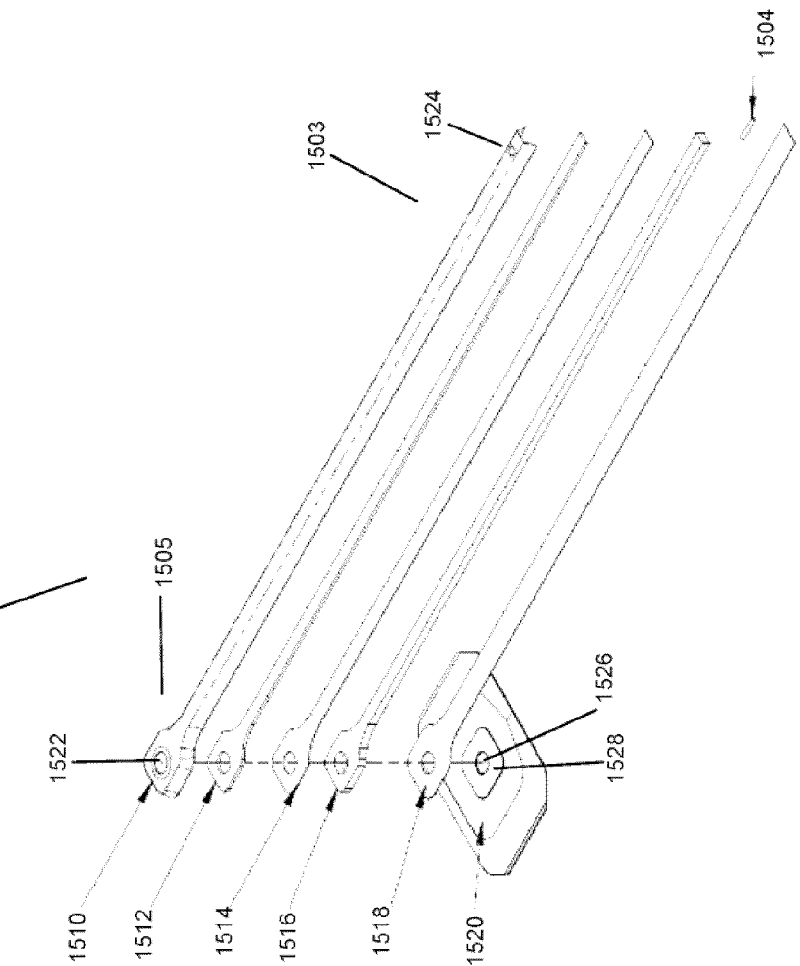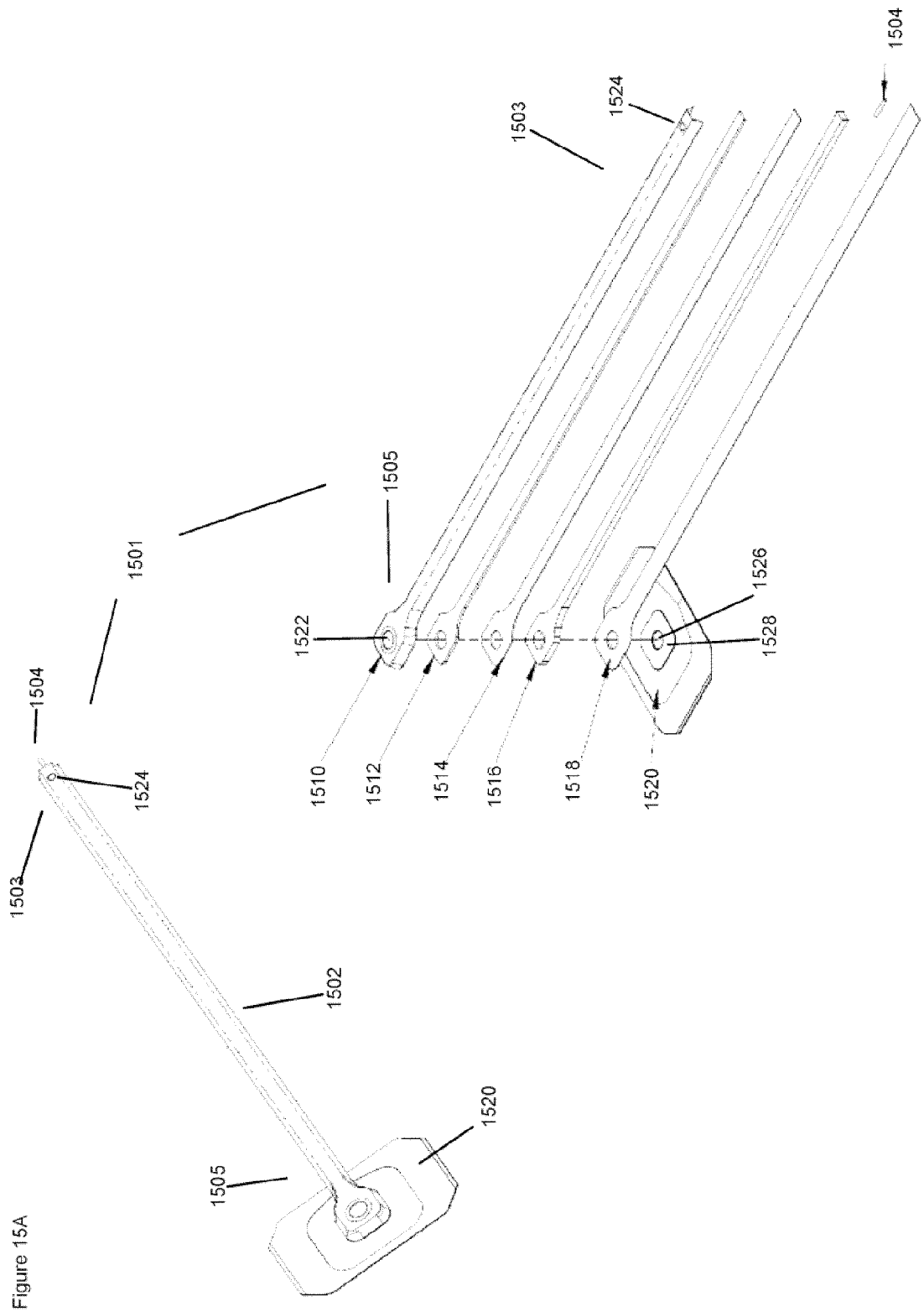
Figure 15A
Figure 15B

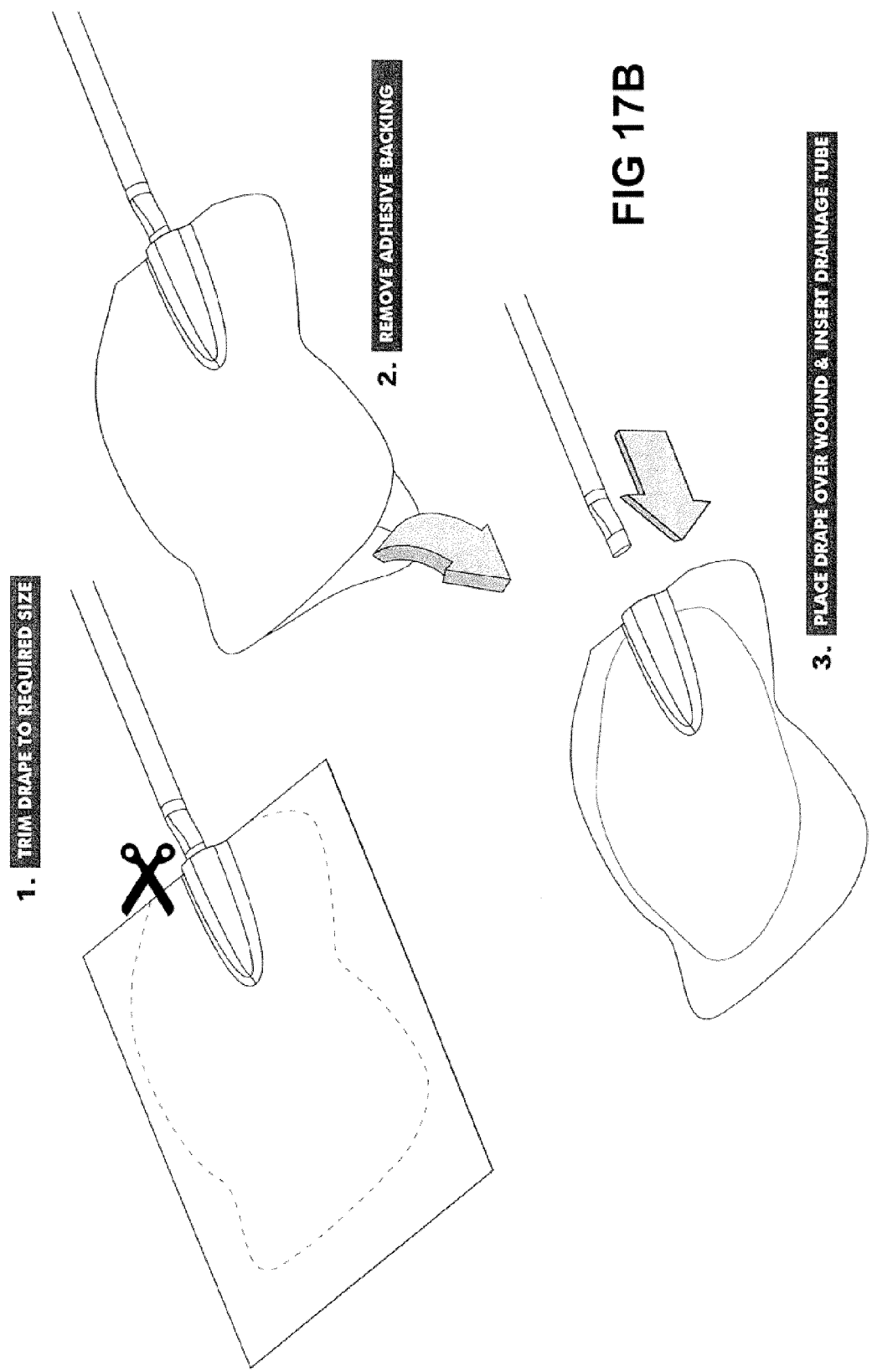

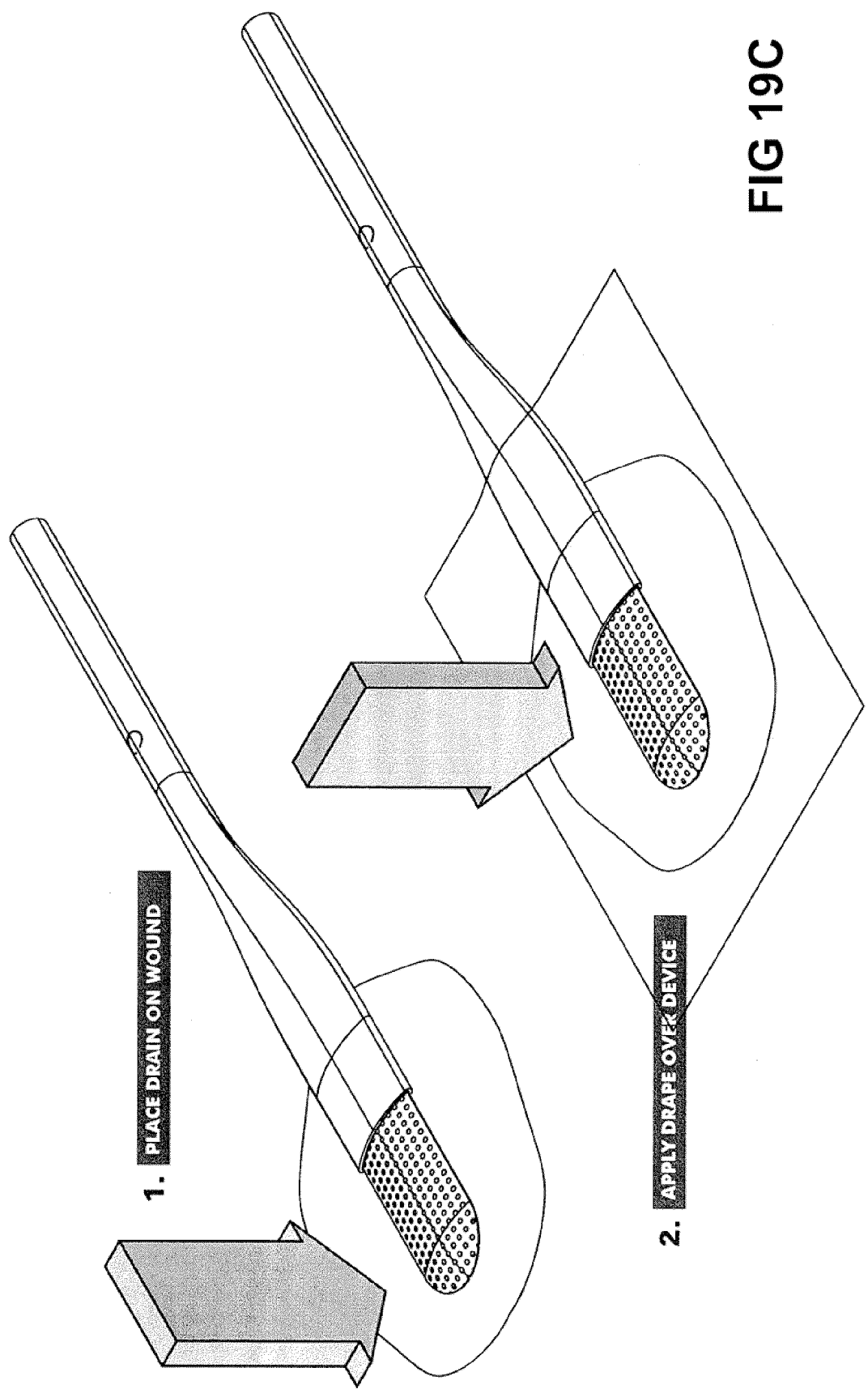

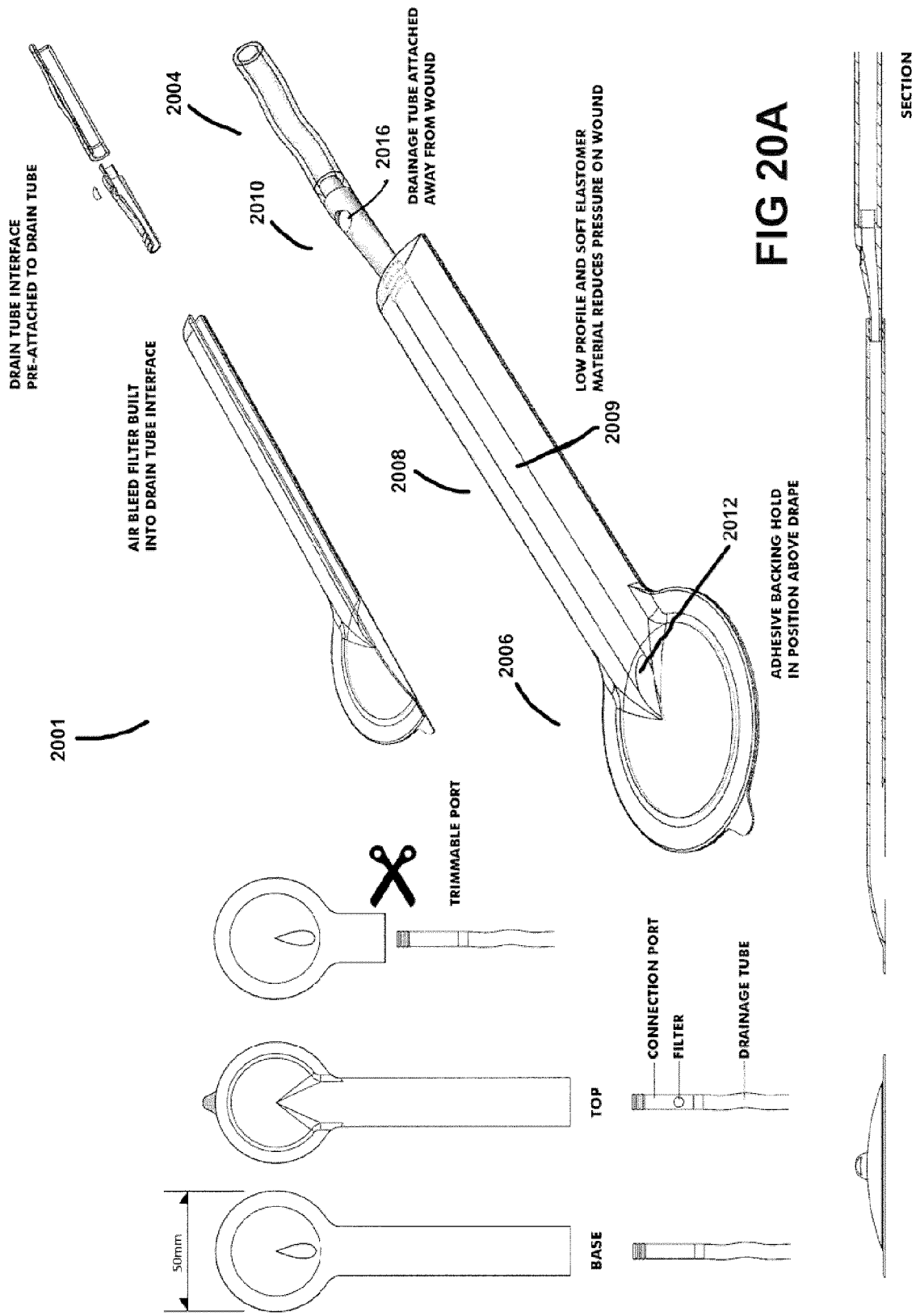

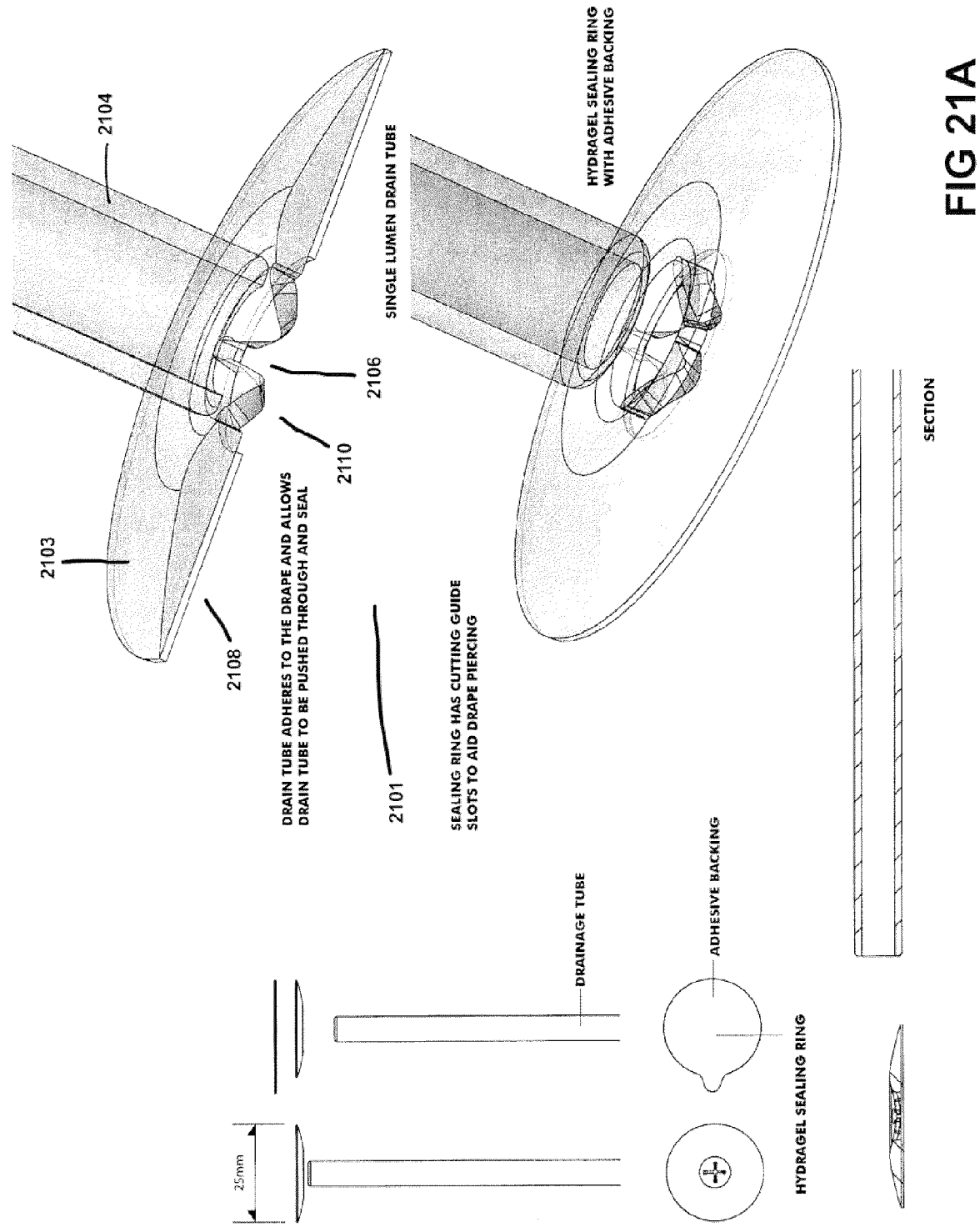

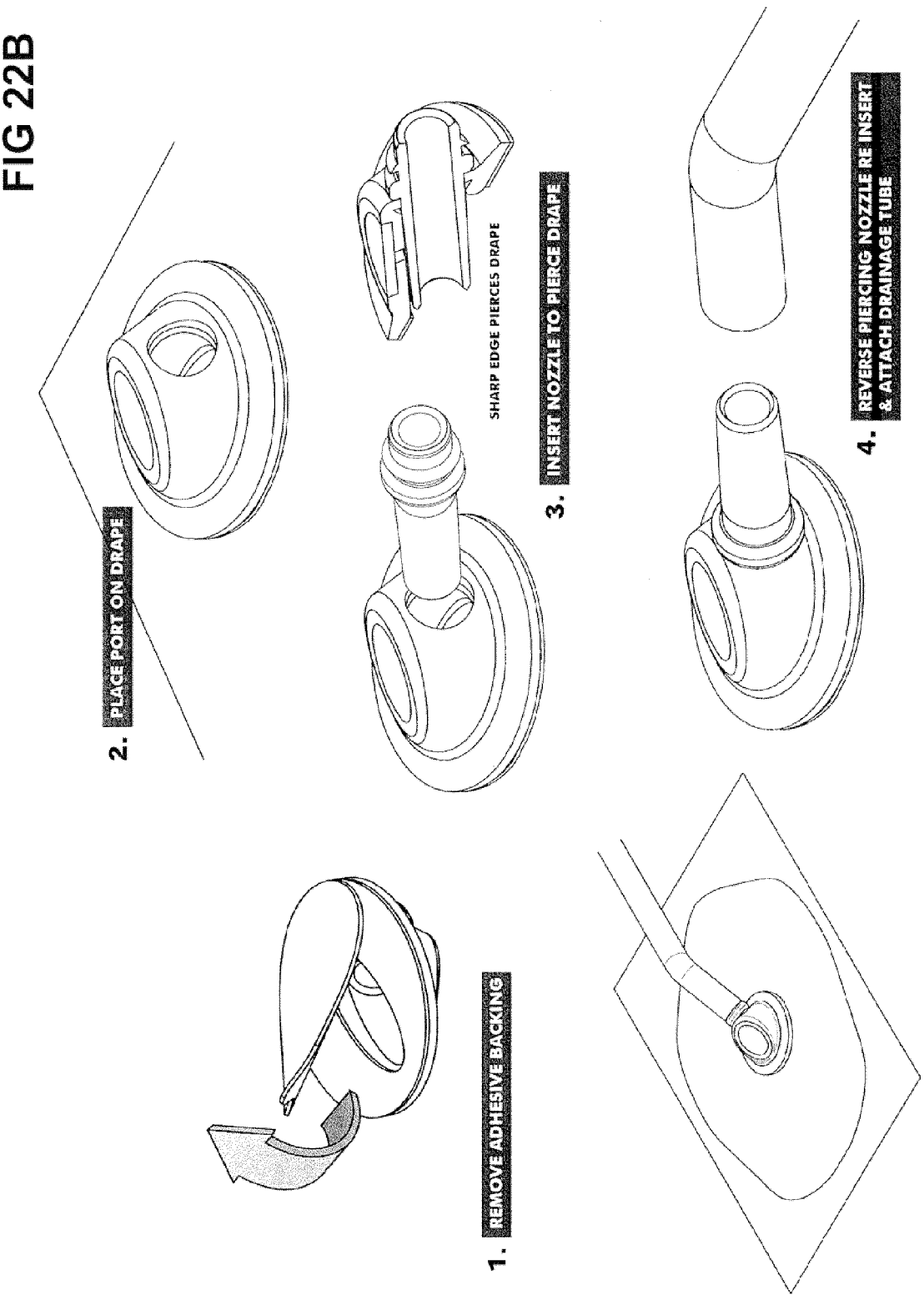

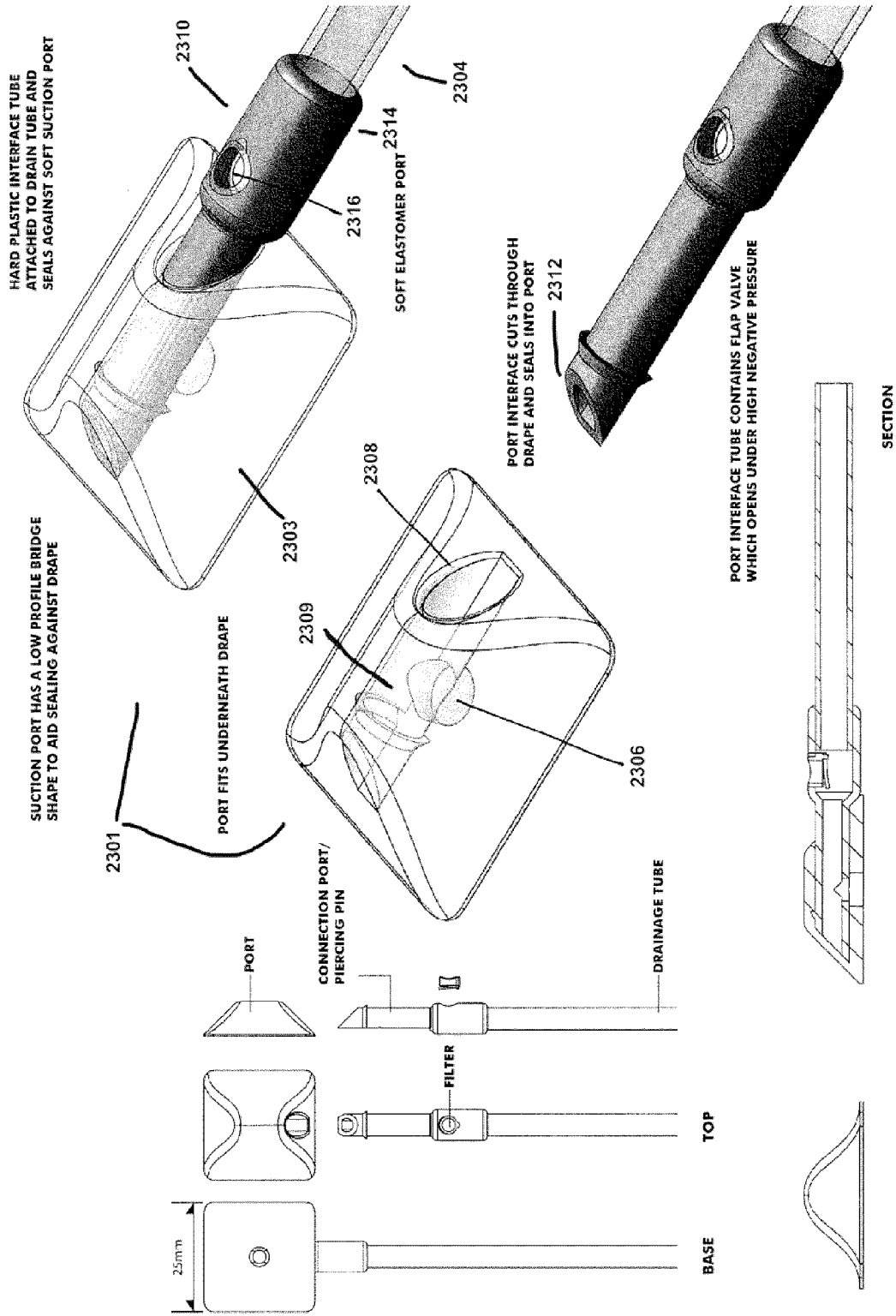

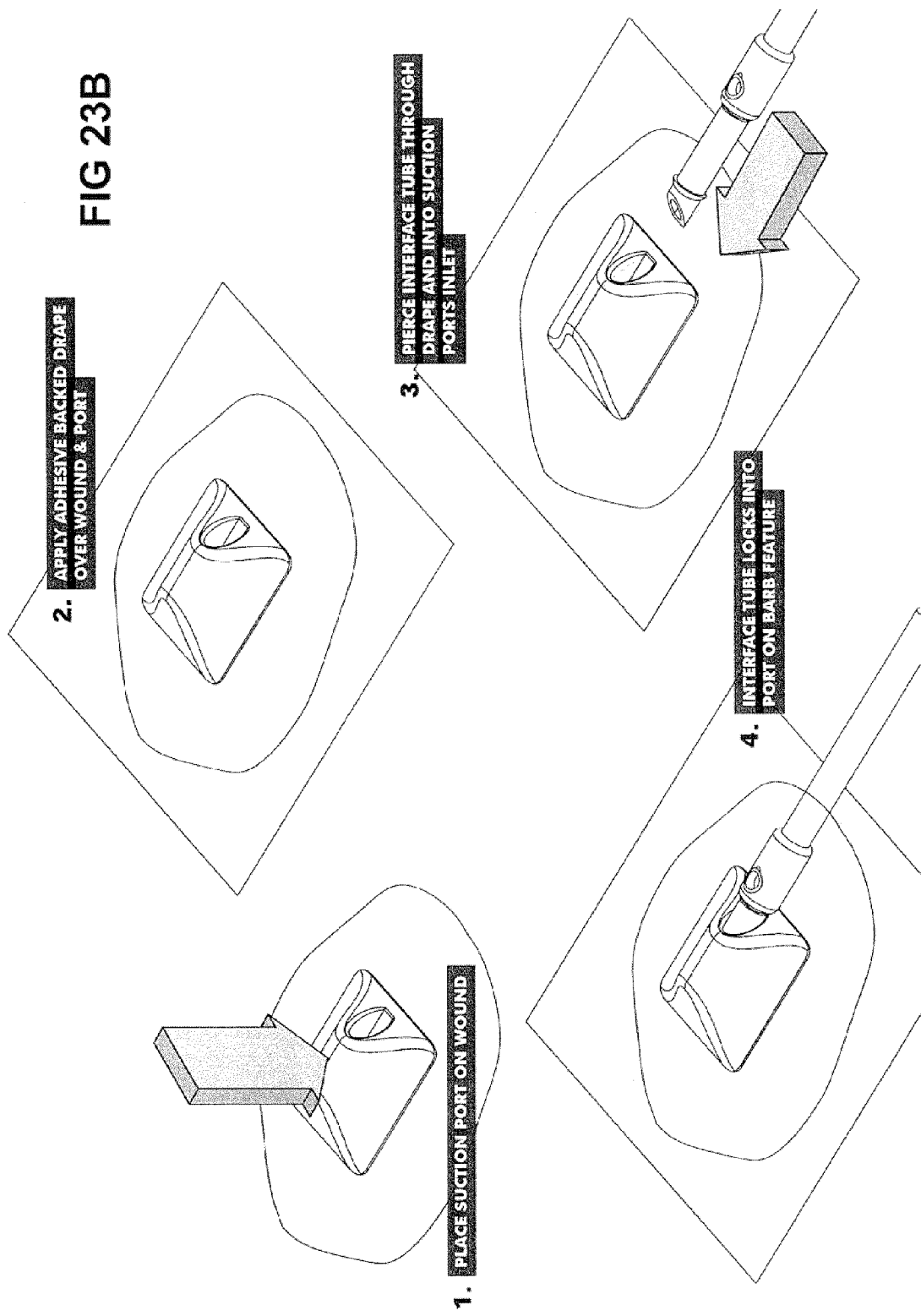

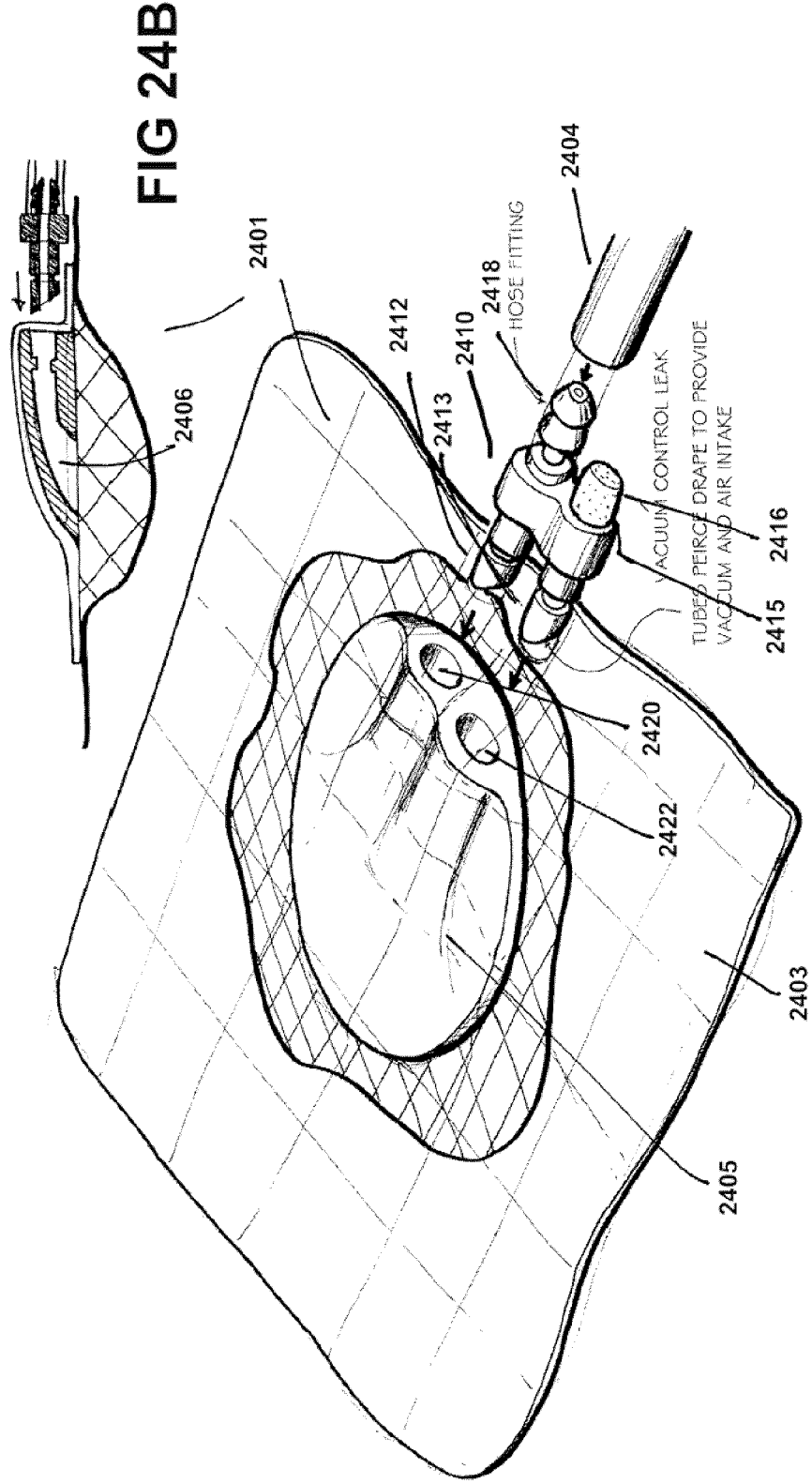

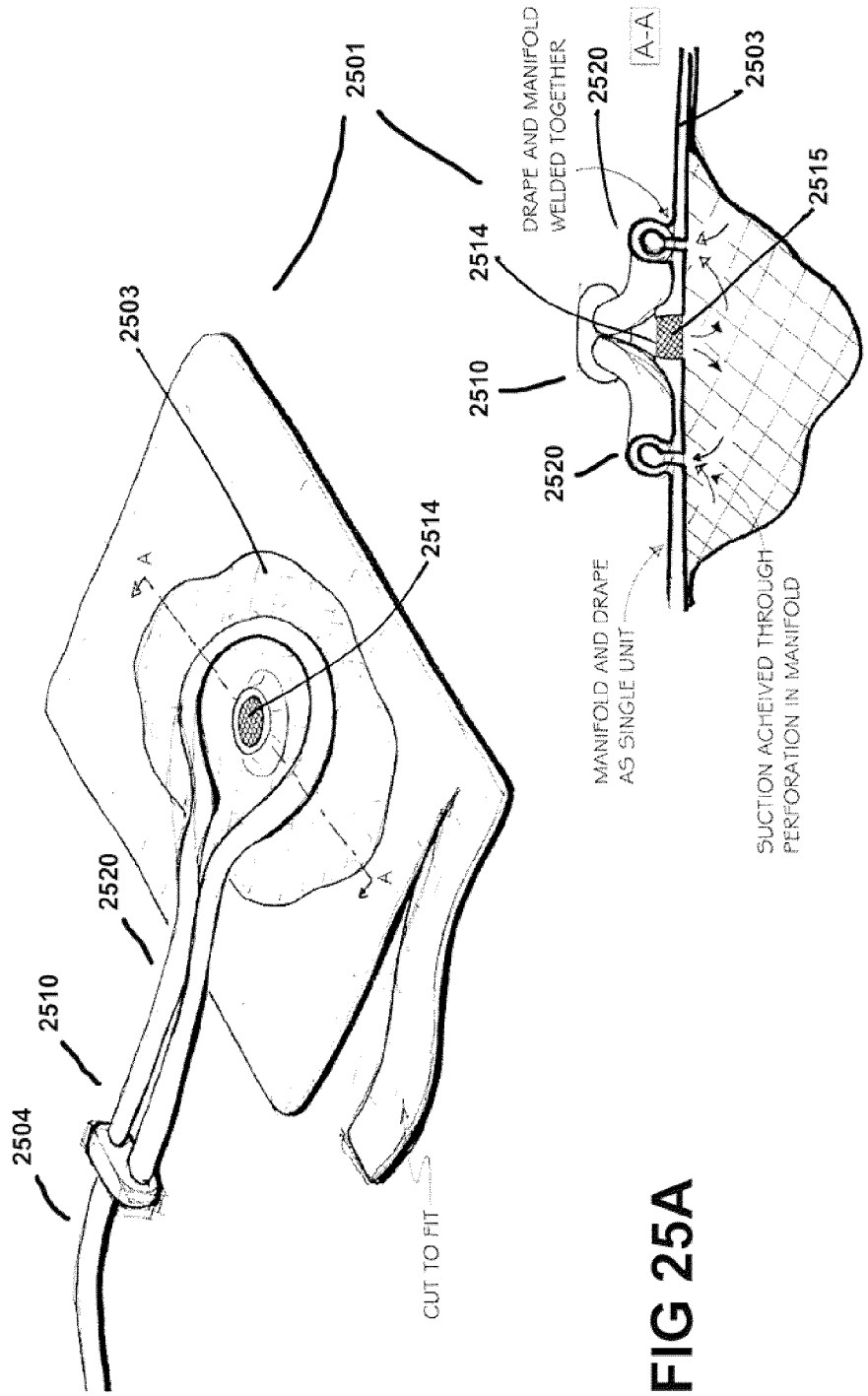

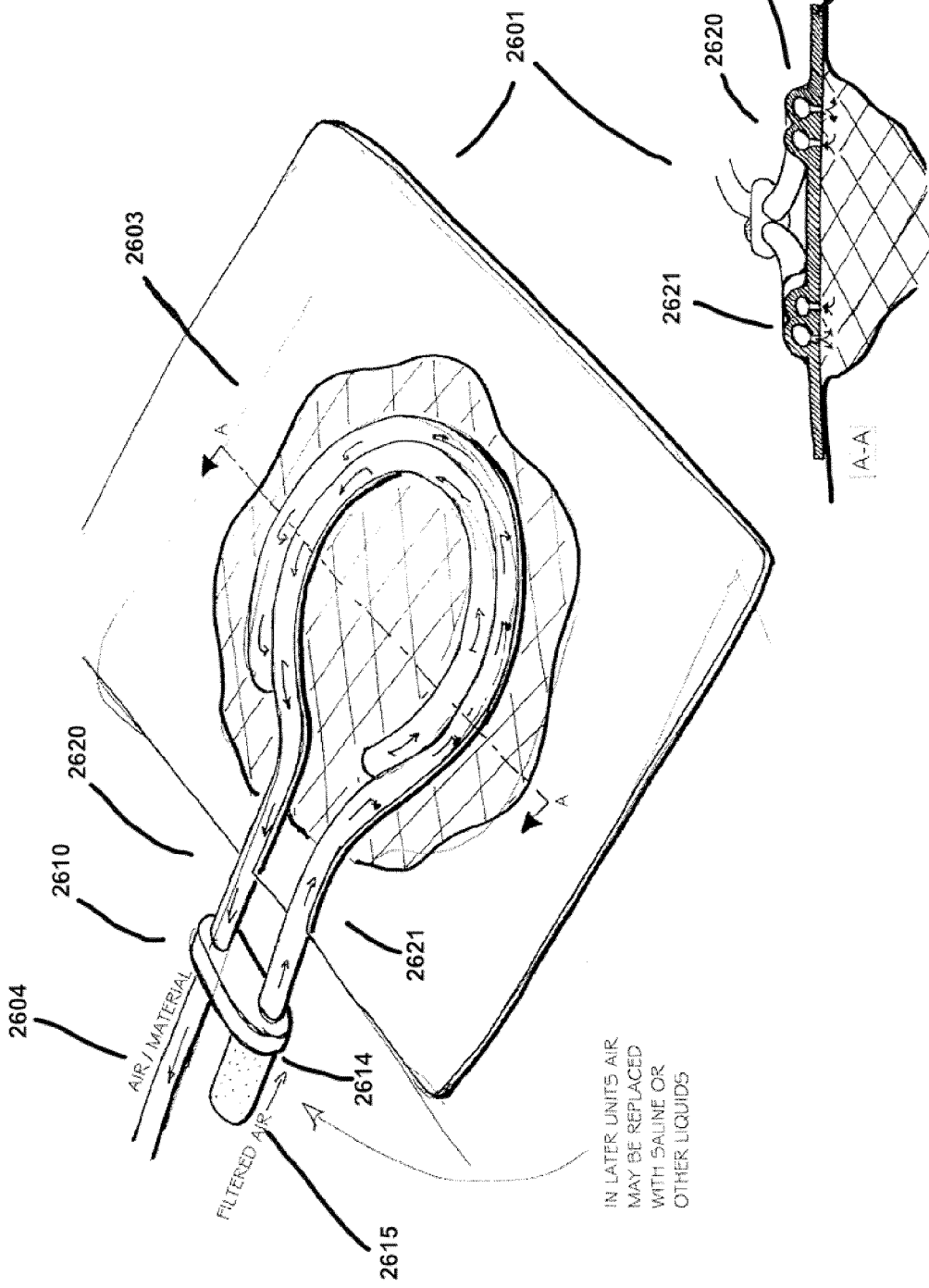
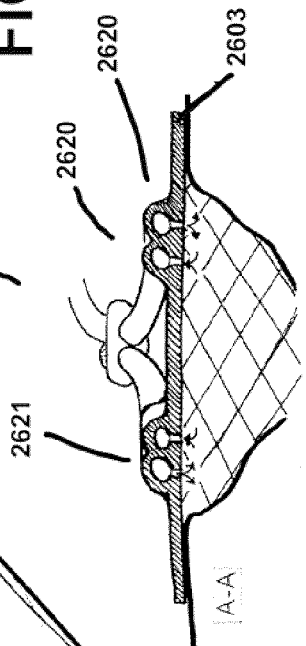

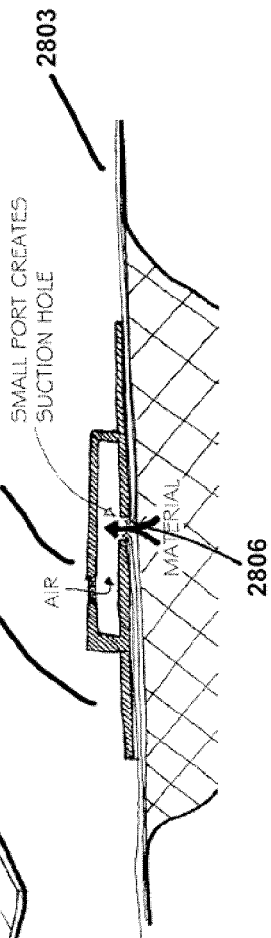
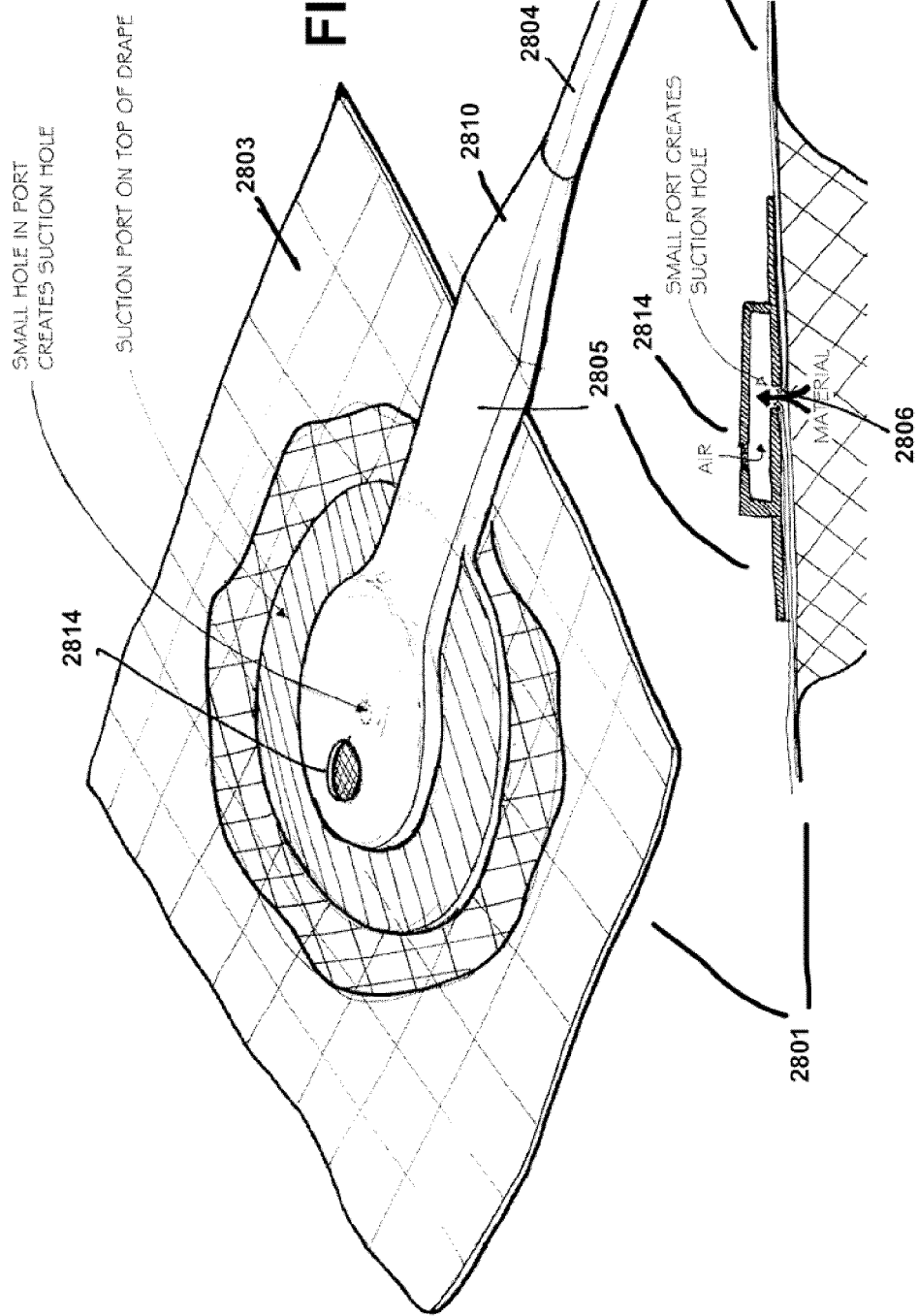

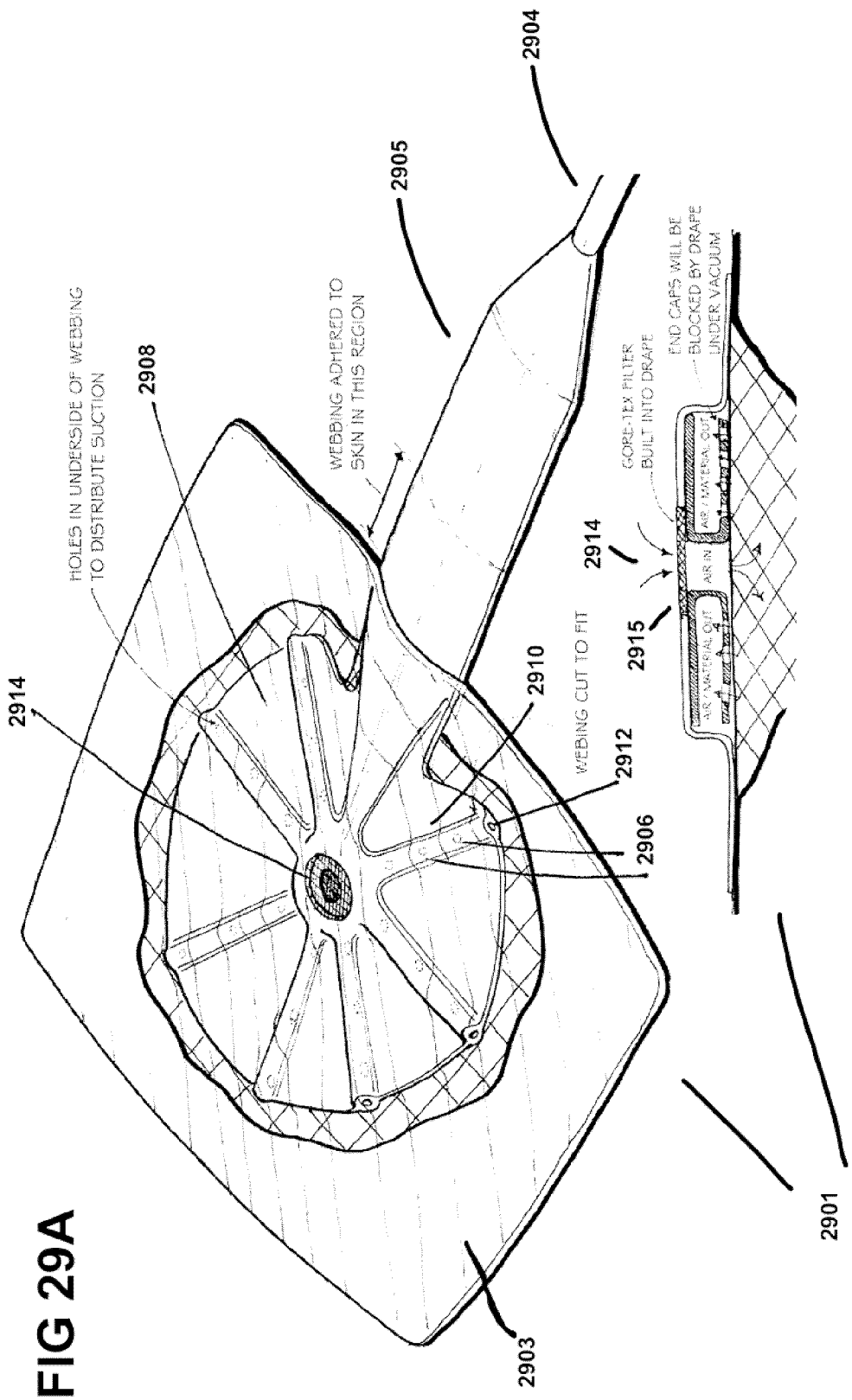

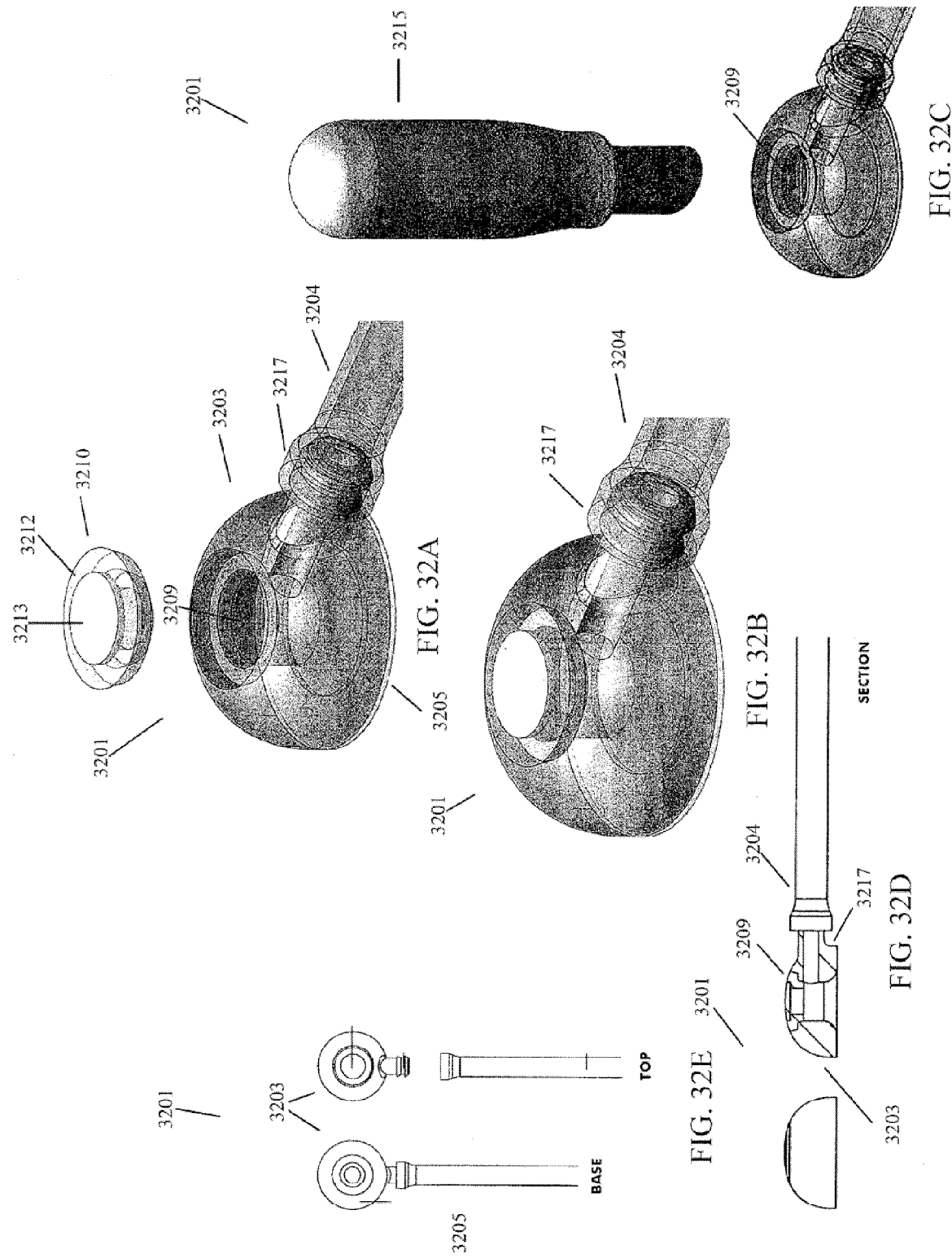

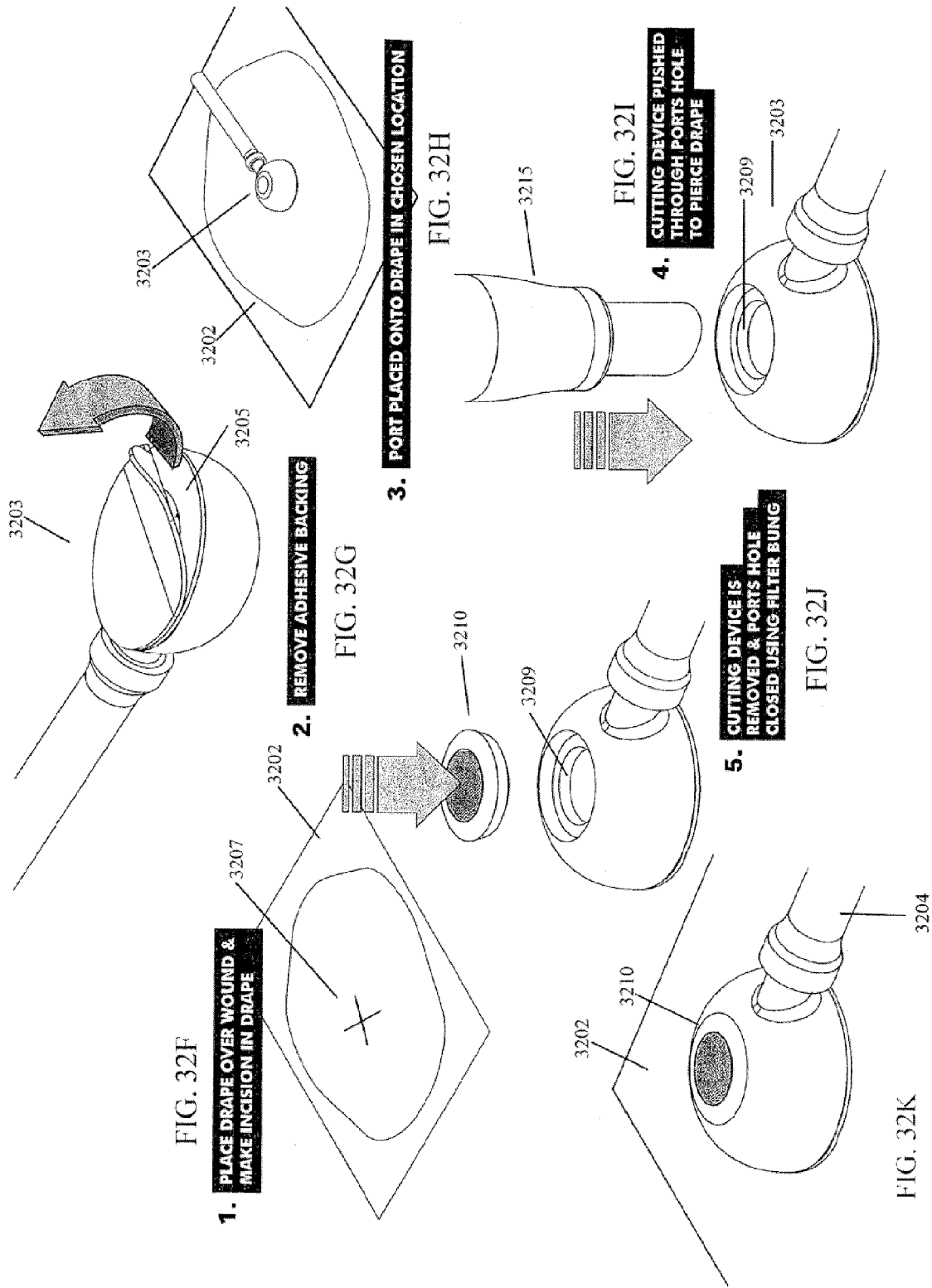

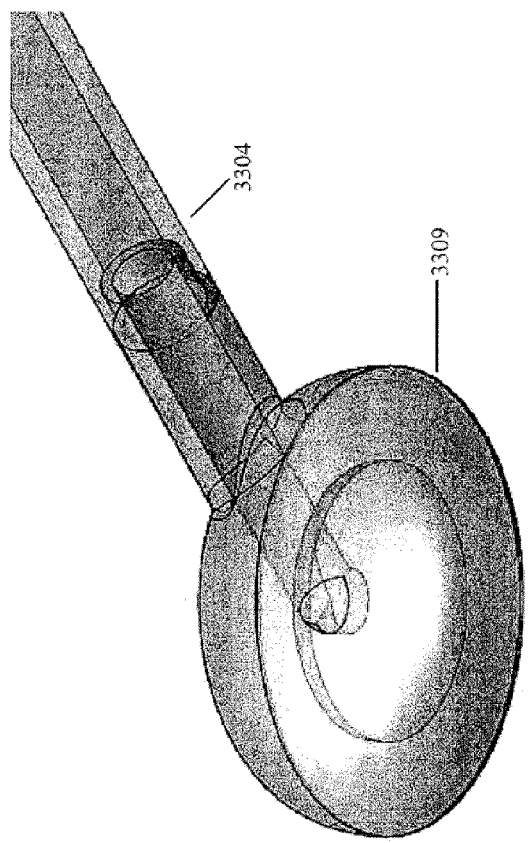
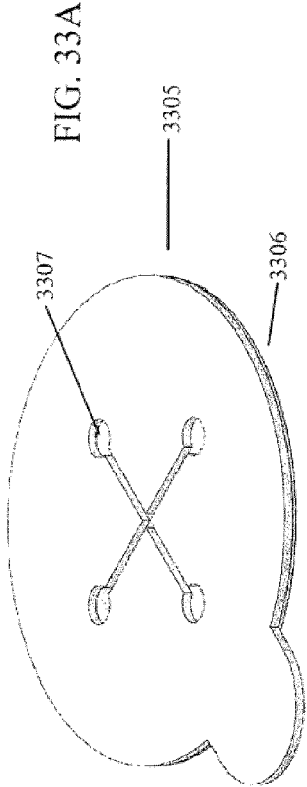
FIG. 33A
FIG. 33B
FIG. 33C

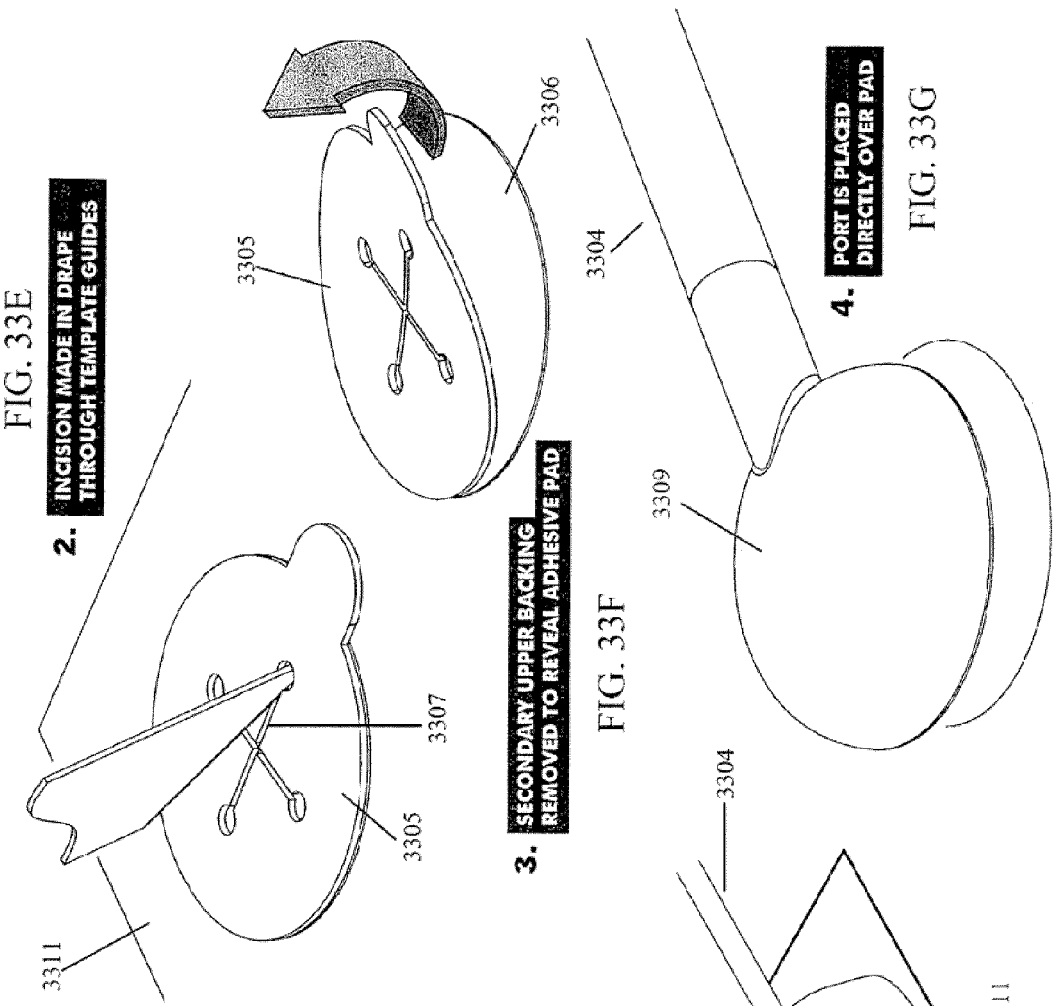
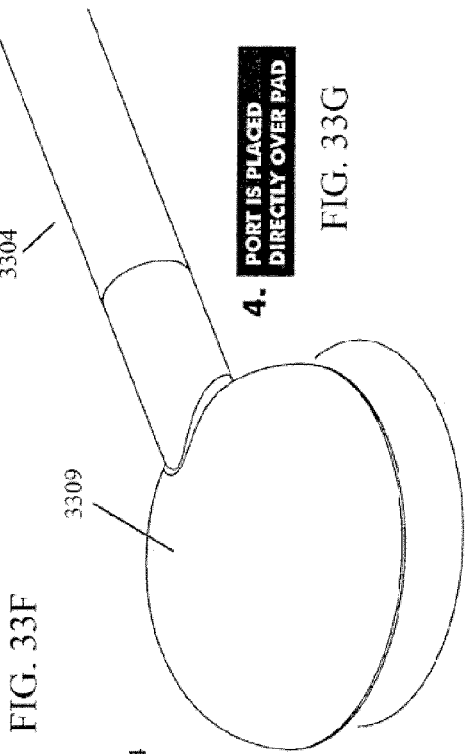
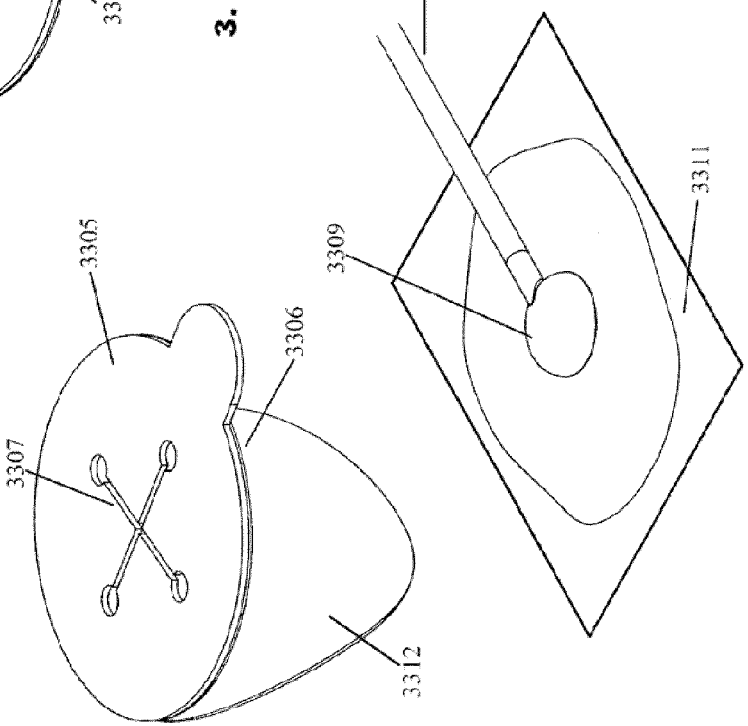

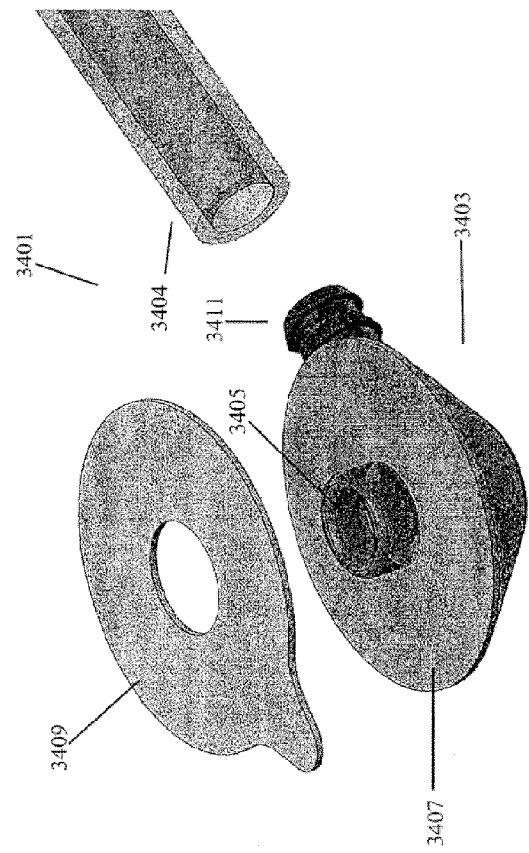
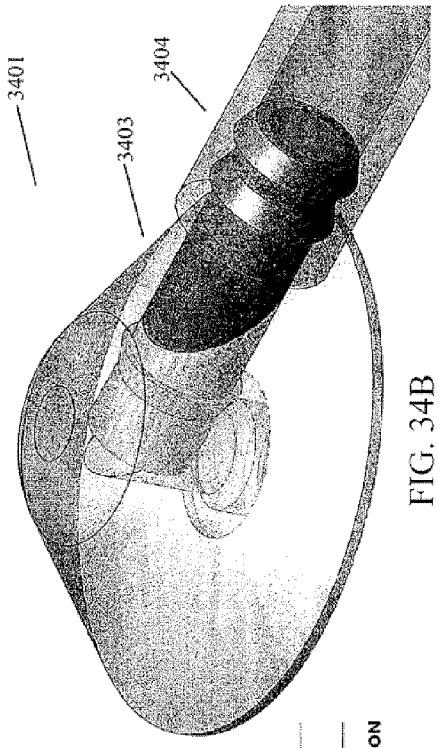
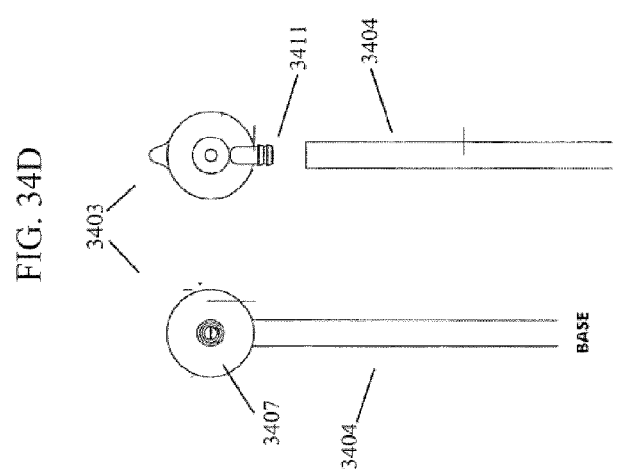
FIG. 34A
FIG. 34B
FIG. 34C
FIG. 34D

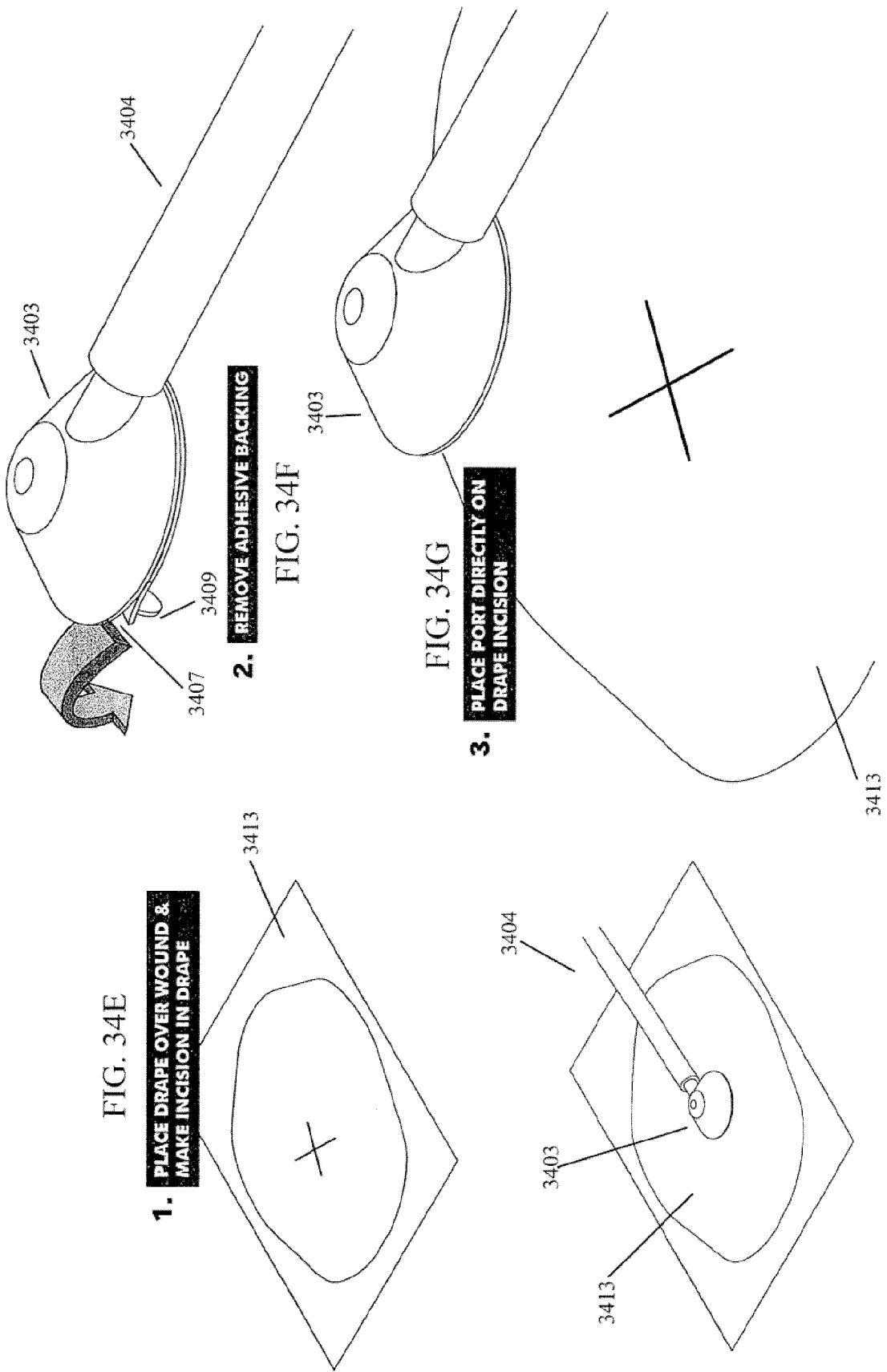

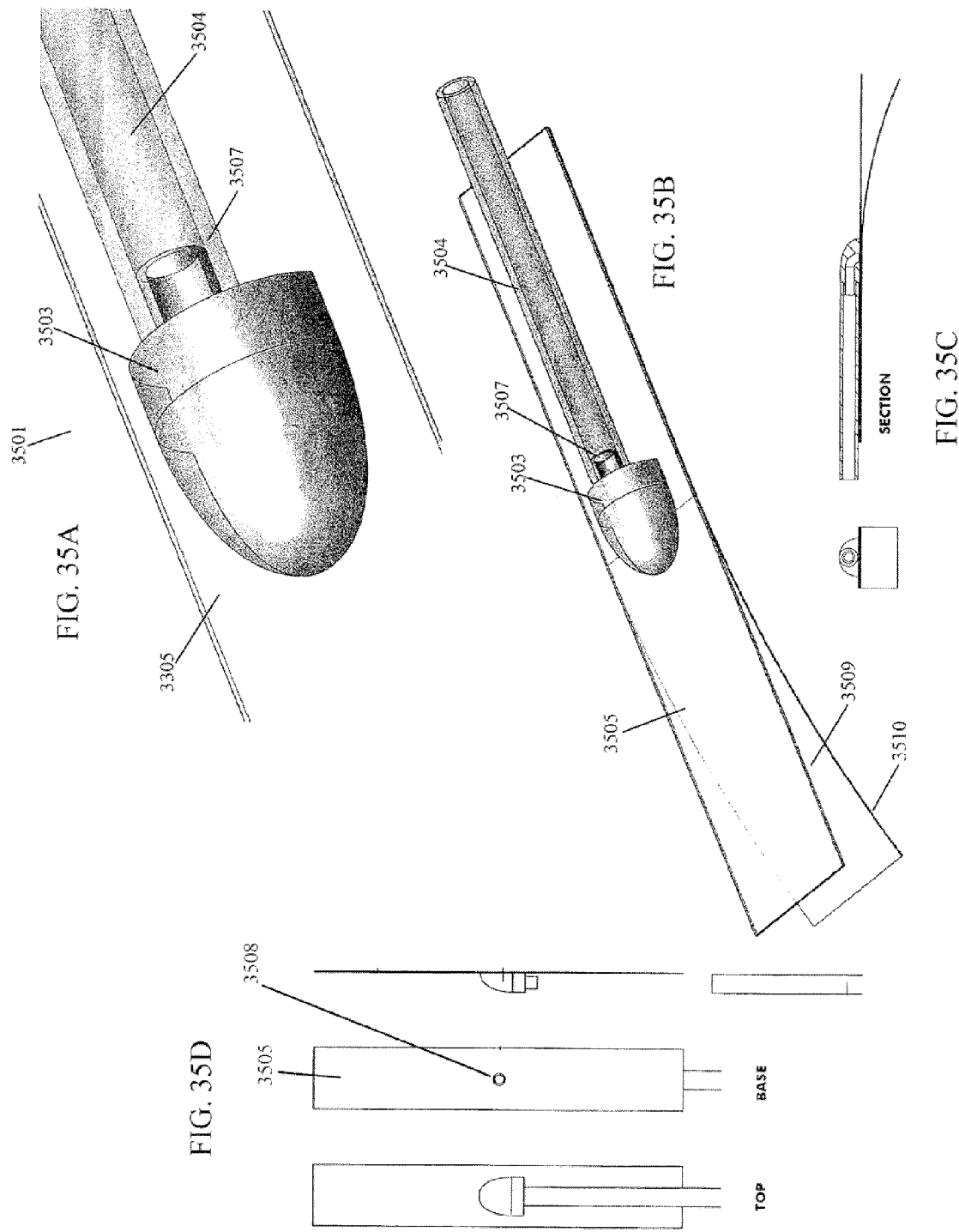

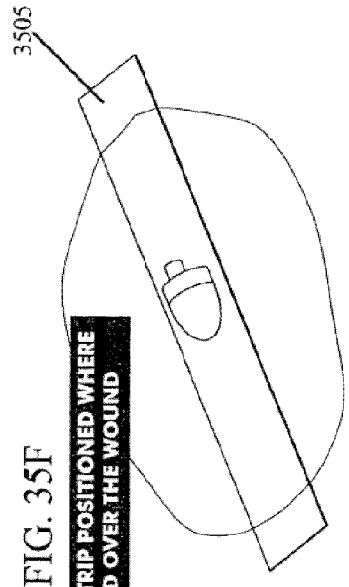
FIG. 35F
2. DRAIN STRIP POSITIONED WHERE REQUIRED OVER THE WOUND
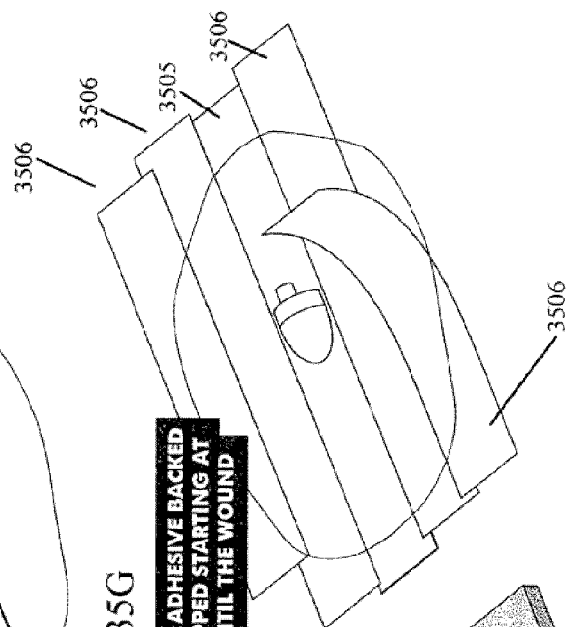
FIG. 35G
3. MULTIPLE STRIPS OF ADHESIVE BACKED DRAPE ARE OVERLAPPED STARTING AT THE DRAIN STRIP UNTIL THE WOUND IS COVERED
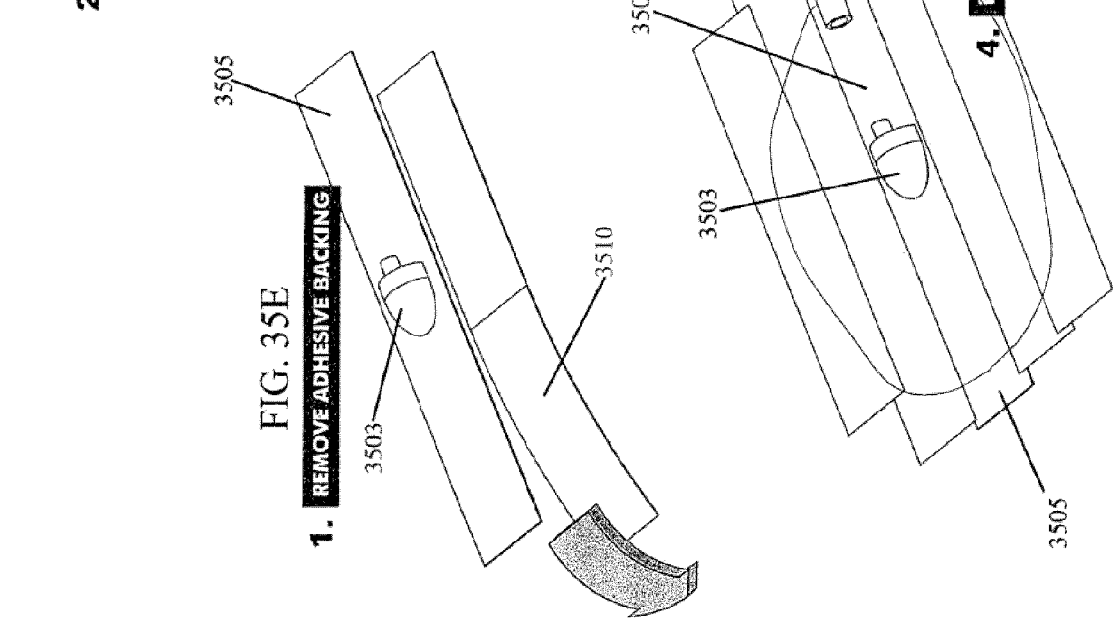
FIG. 35E
1. REMOVE ADHESIVE BACKING
FIG. 35H
4. INSERT DRAINAGE TUBE

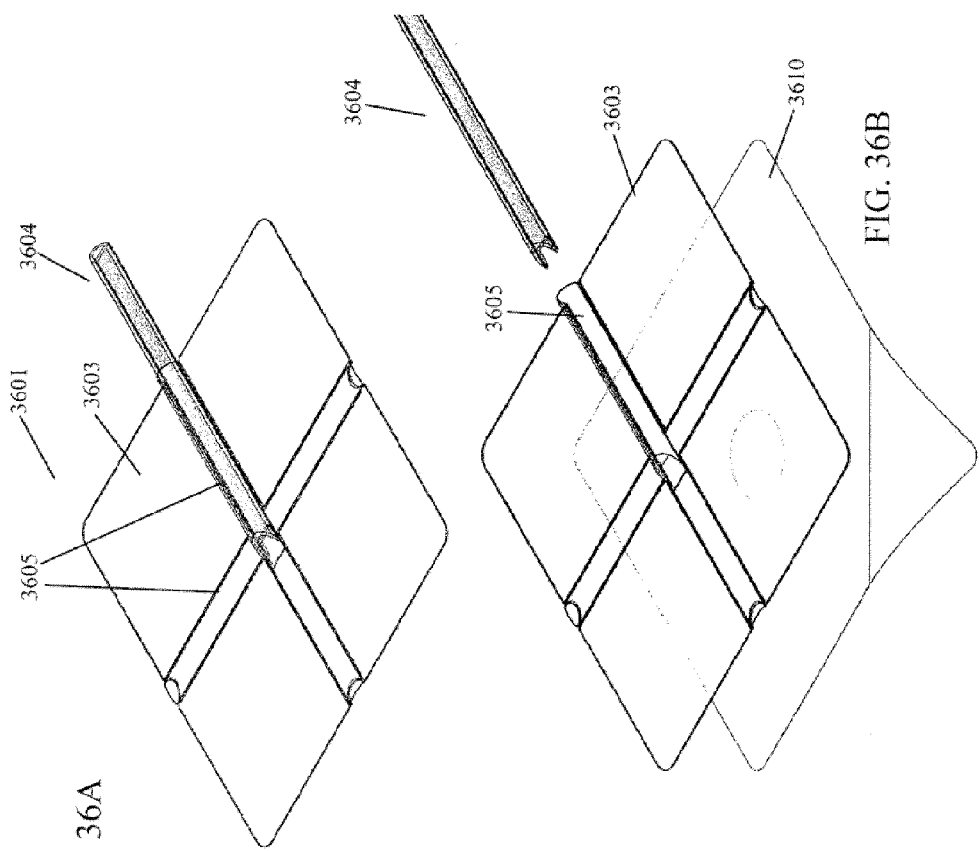
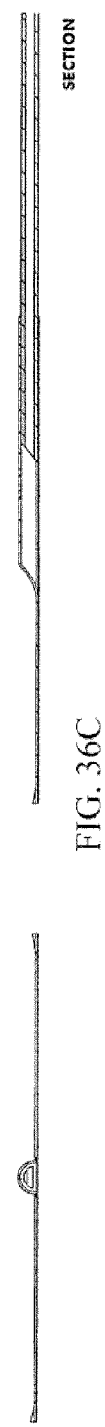
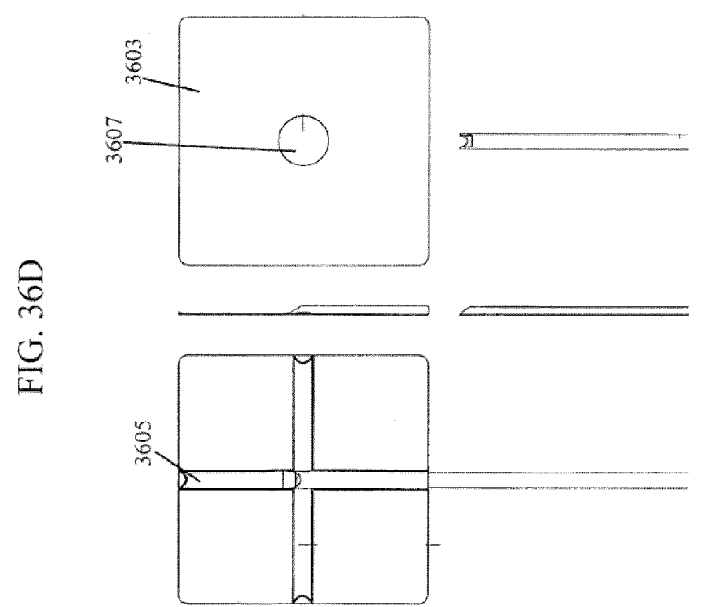

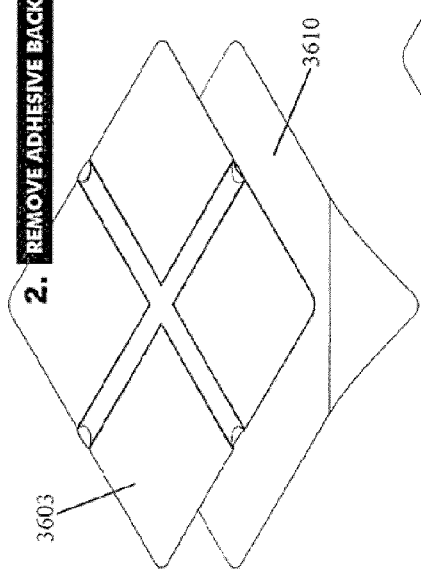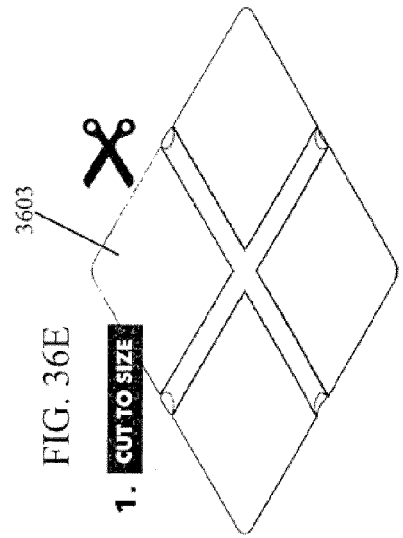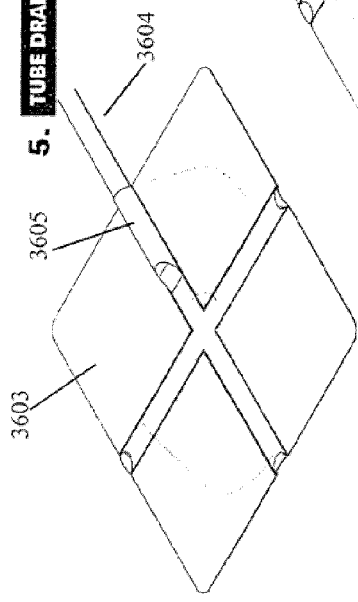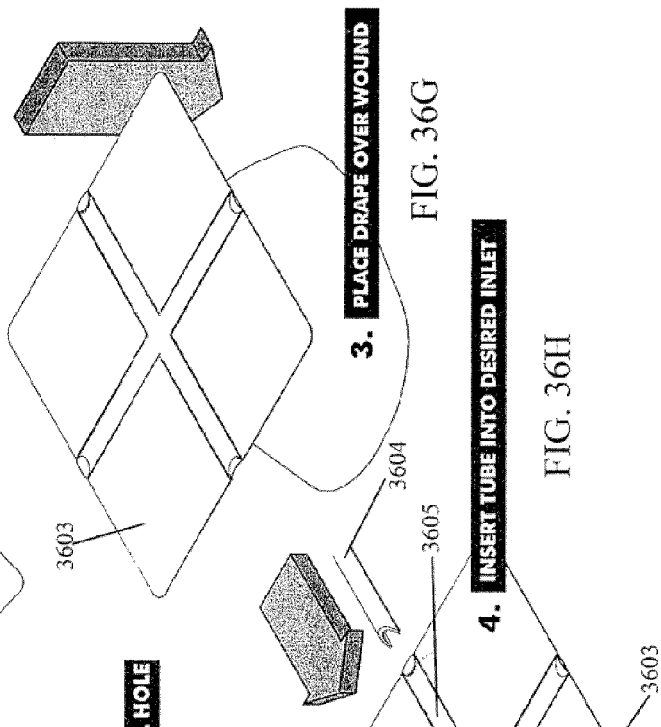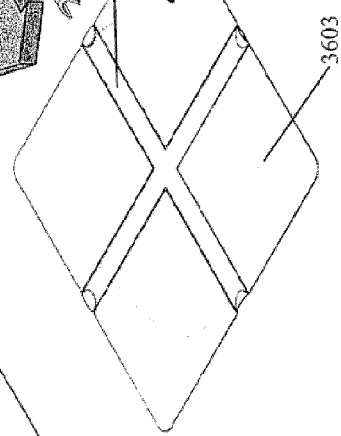

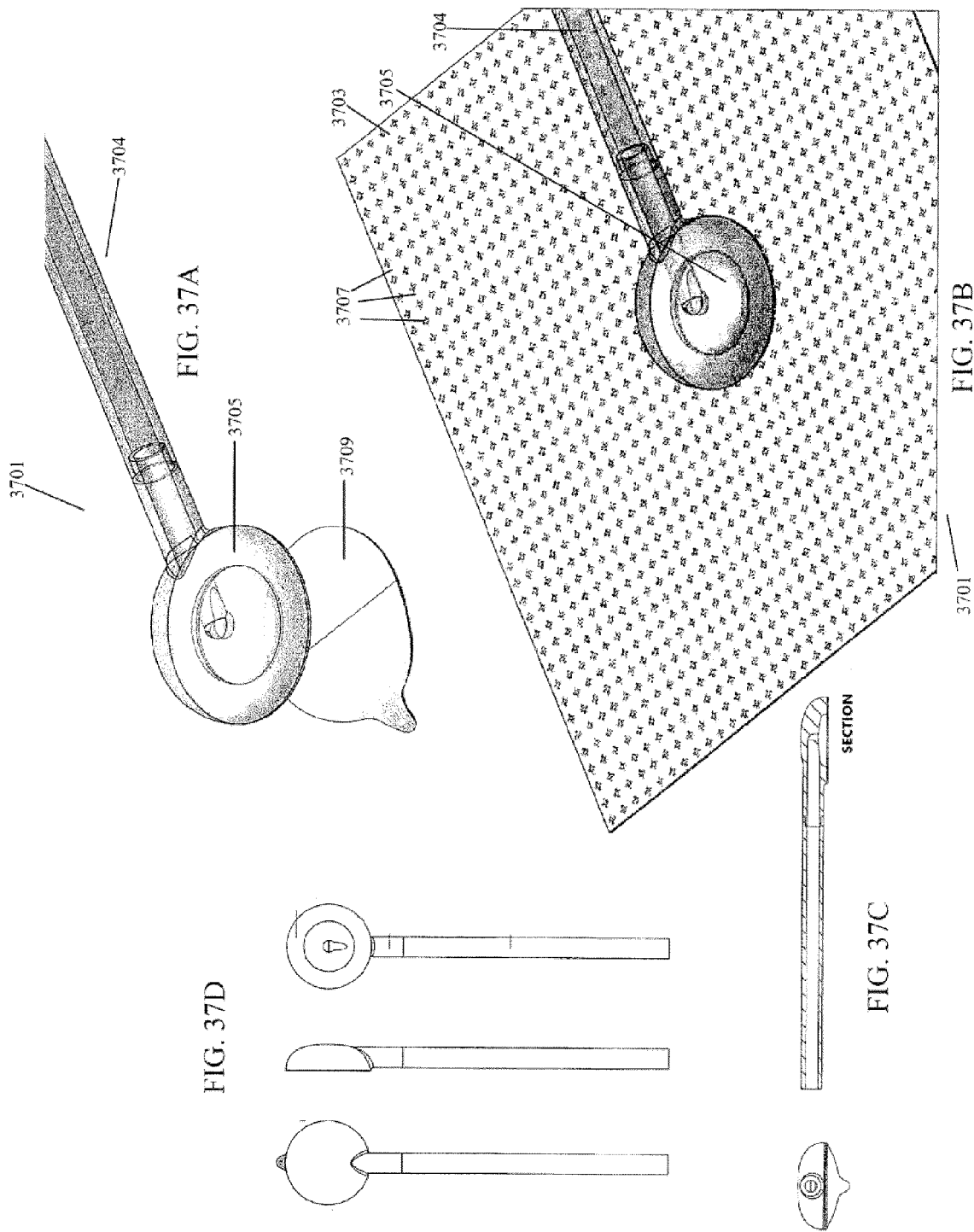

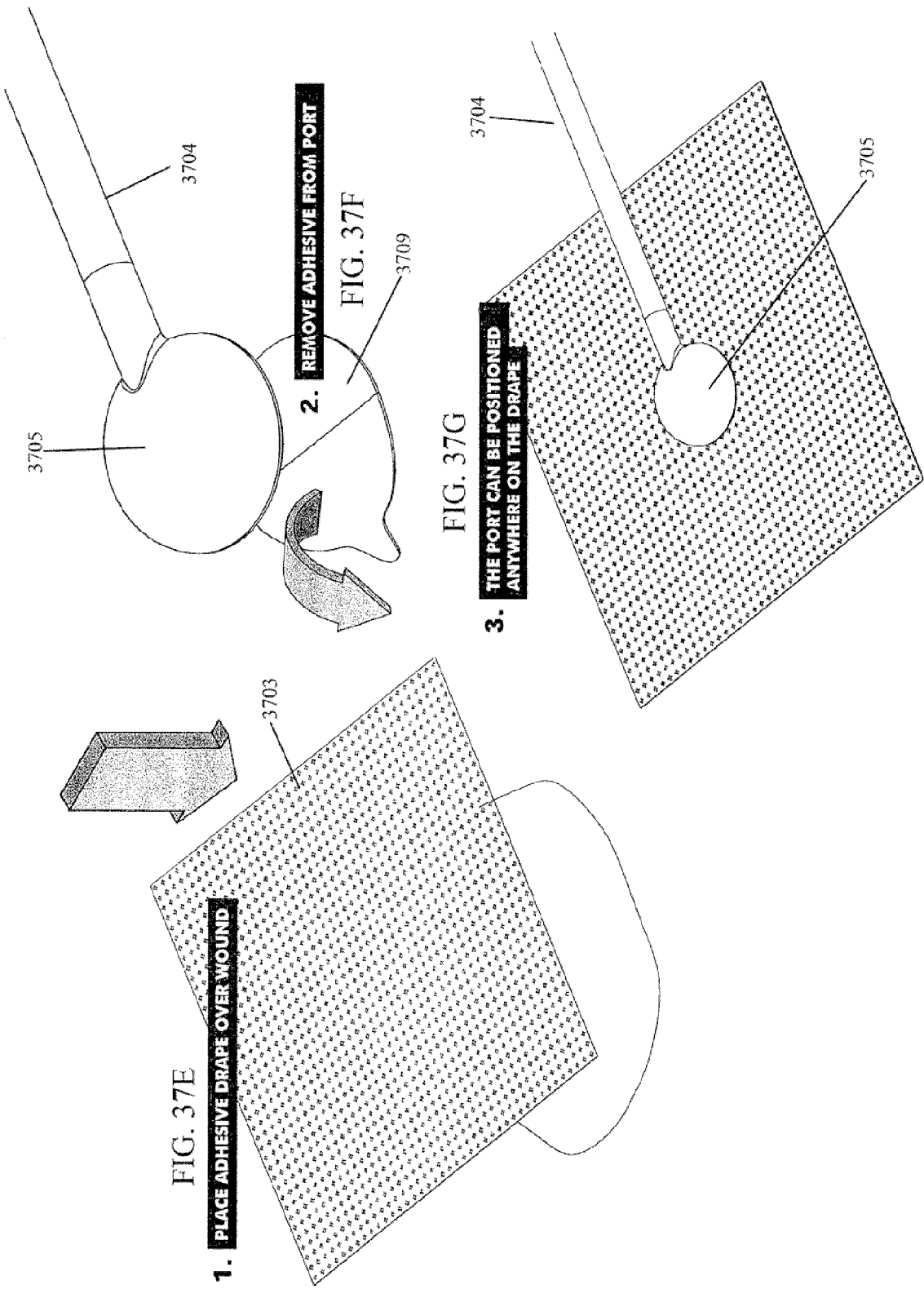

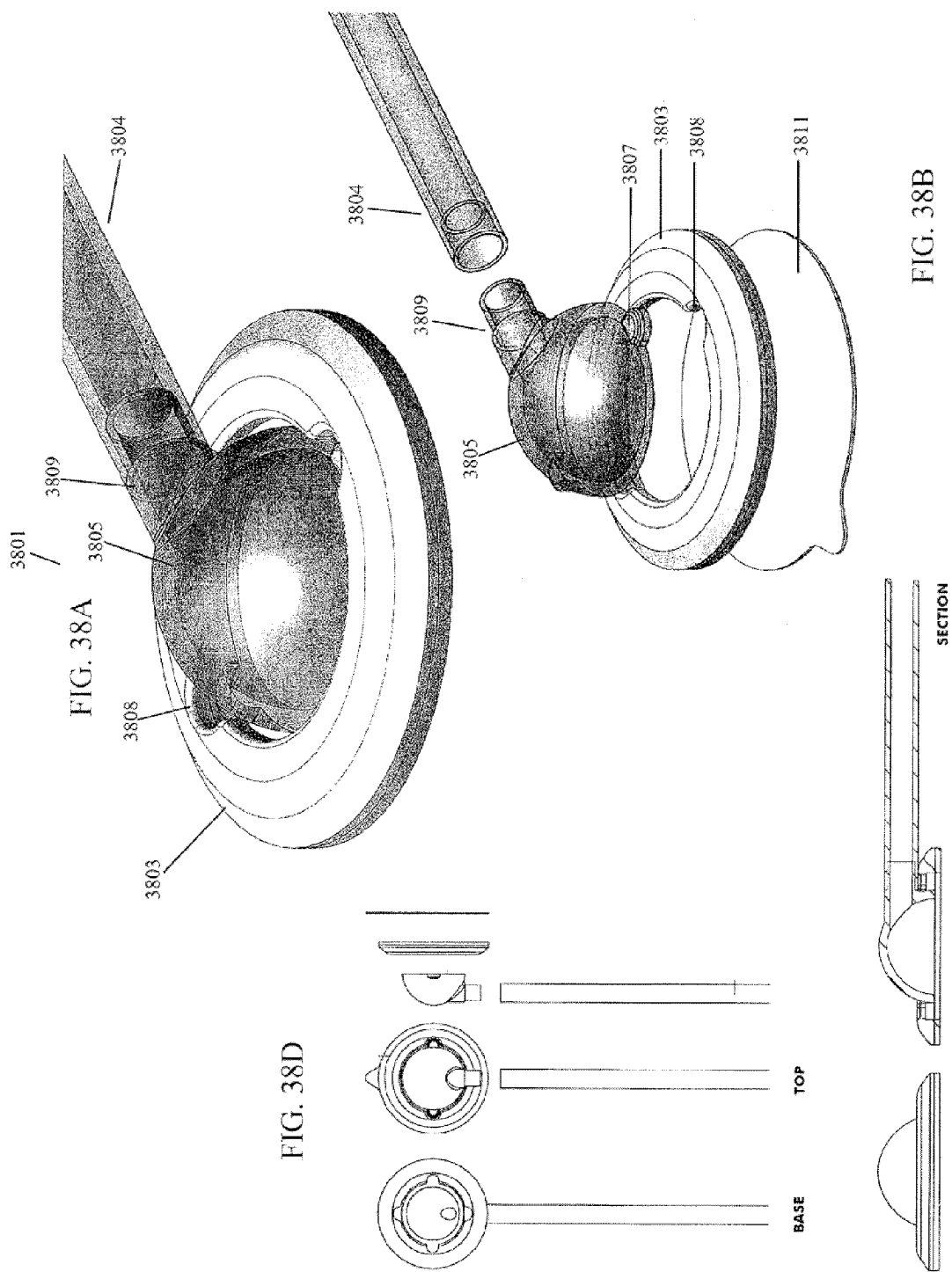

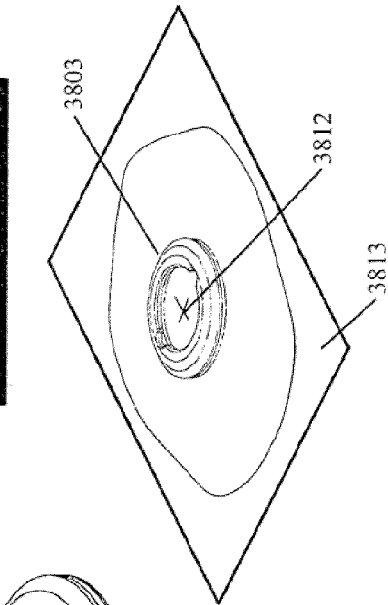
FIG. 38G
3. PLACE RING ON DRAPE AND MAKE INCISION IN DRAPE
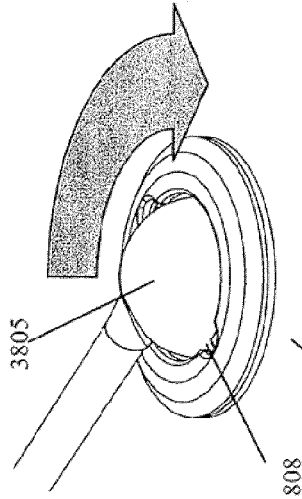
FIG. 38H
4. PUSH BAYONET PORT ONTO RING AND ROTATE 90°
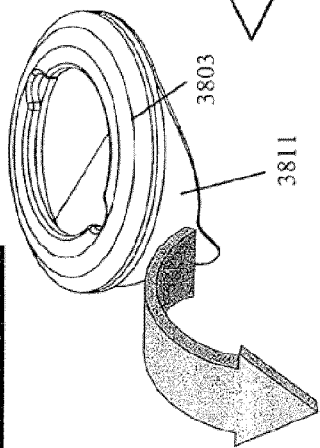
FIG. 38F
2. REMOVE ADHESIVE BACKING FROM BAYONET RING
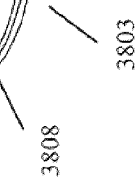
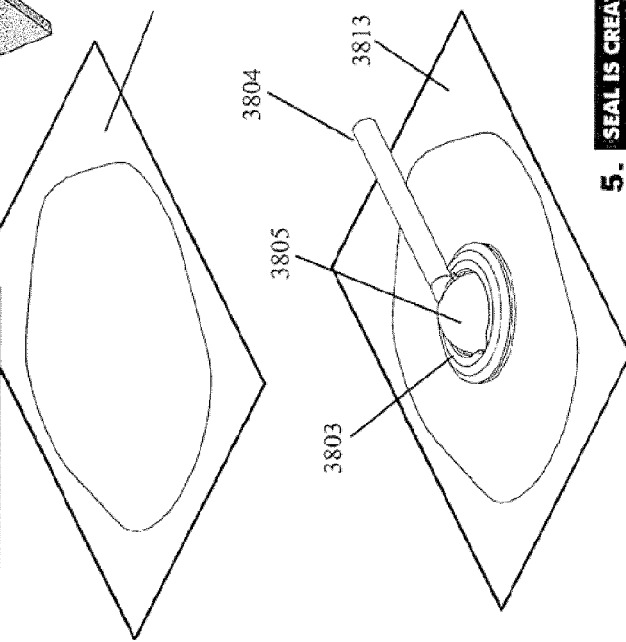
FIG. 38E
1. PLACE DRAPE ON WOUND
FIG. 38I
5. SEAL IS CREATED AROUND WOUND

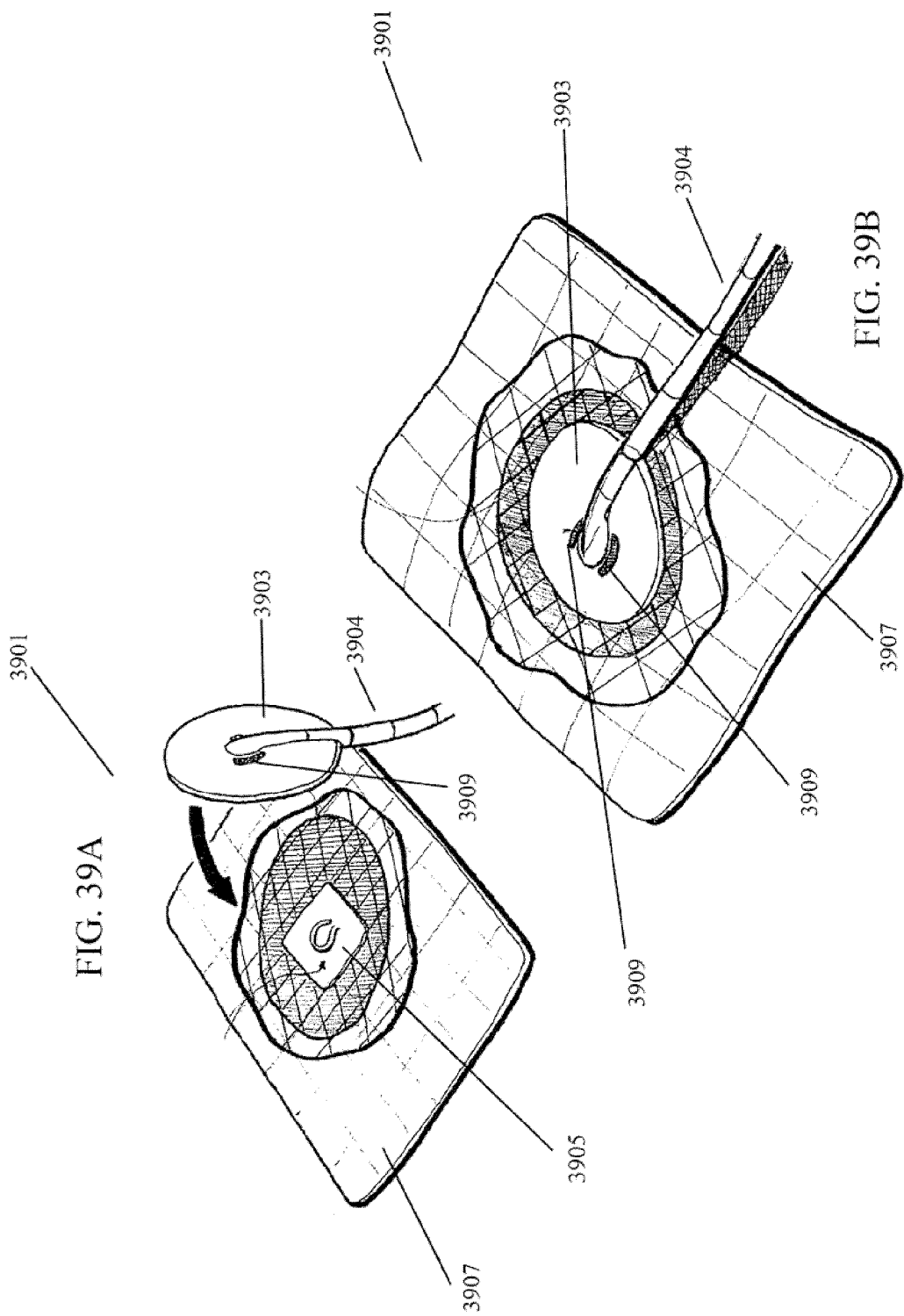

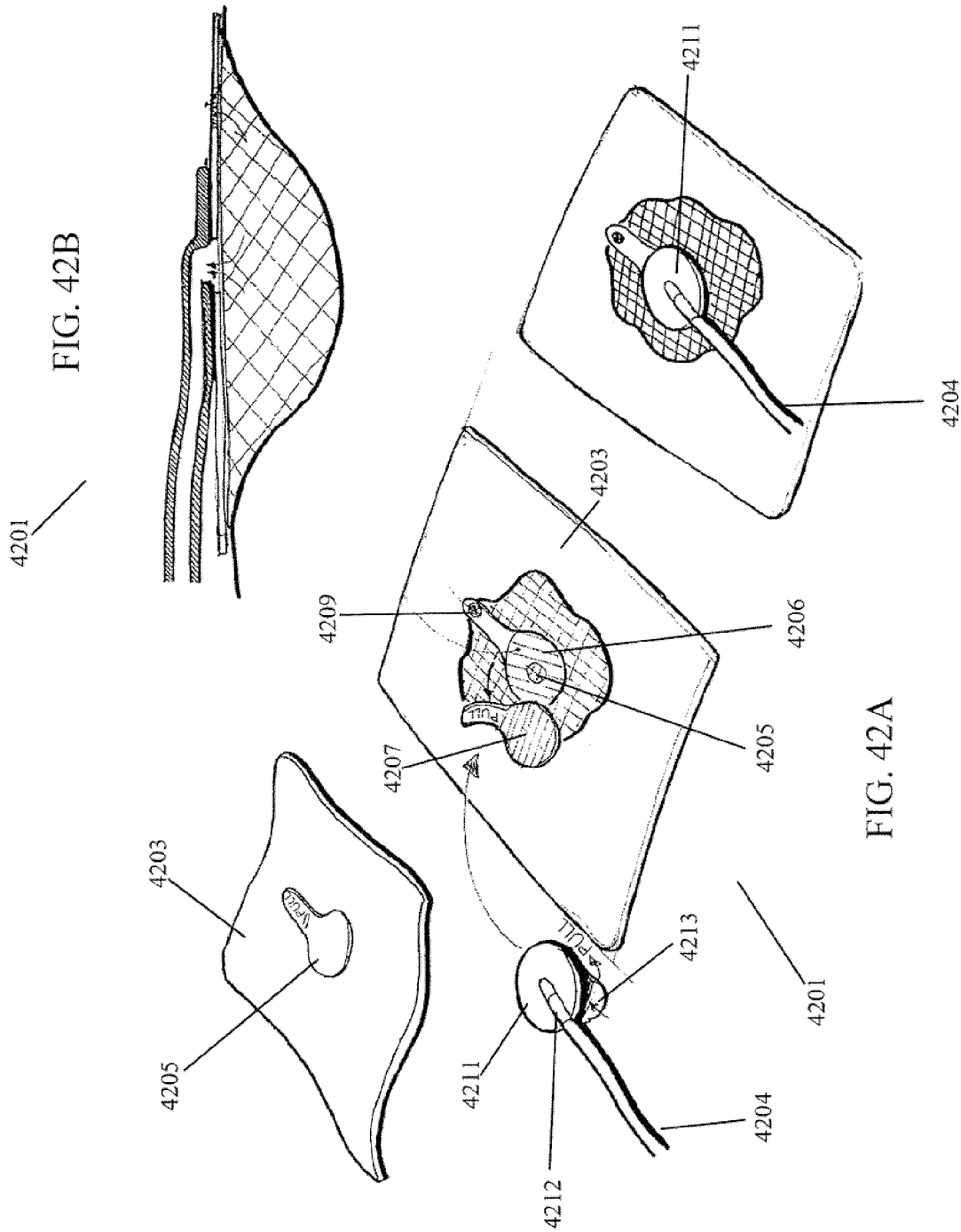

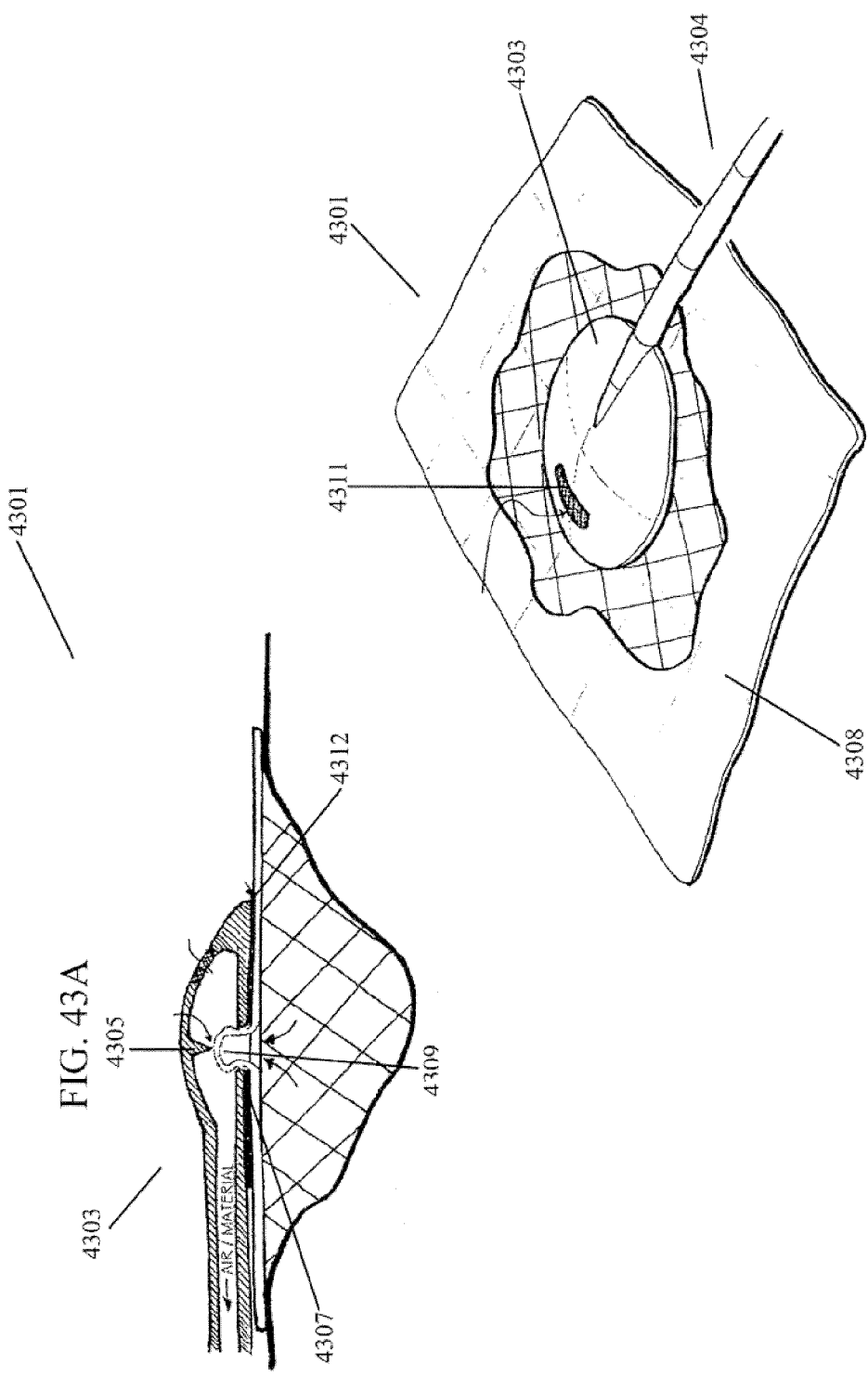

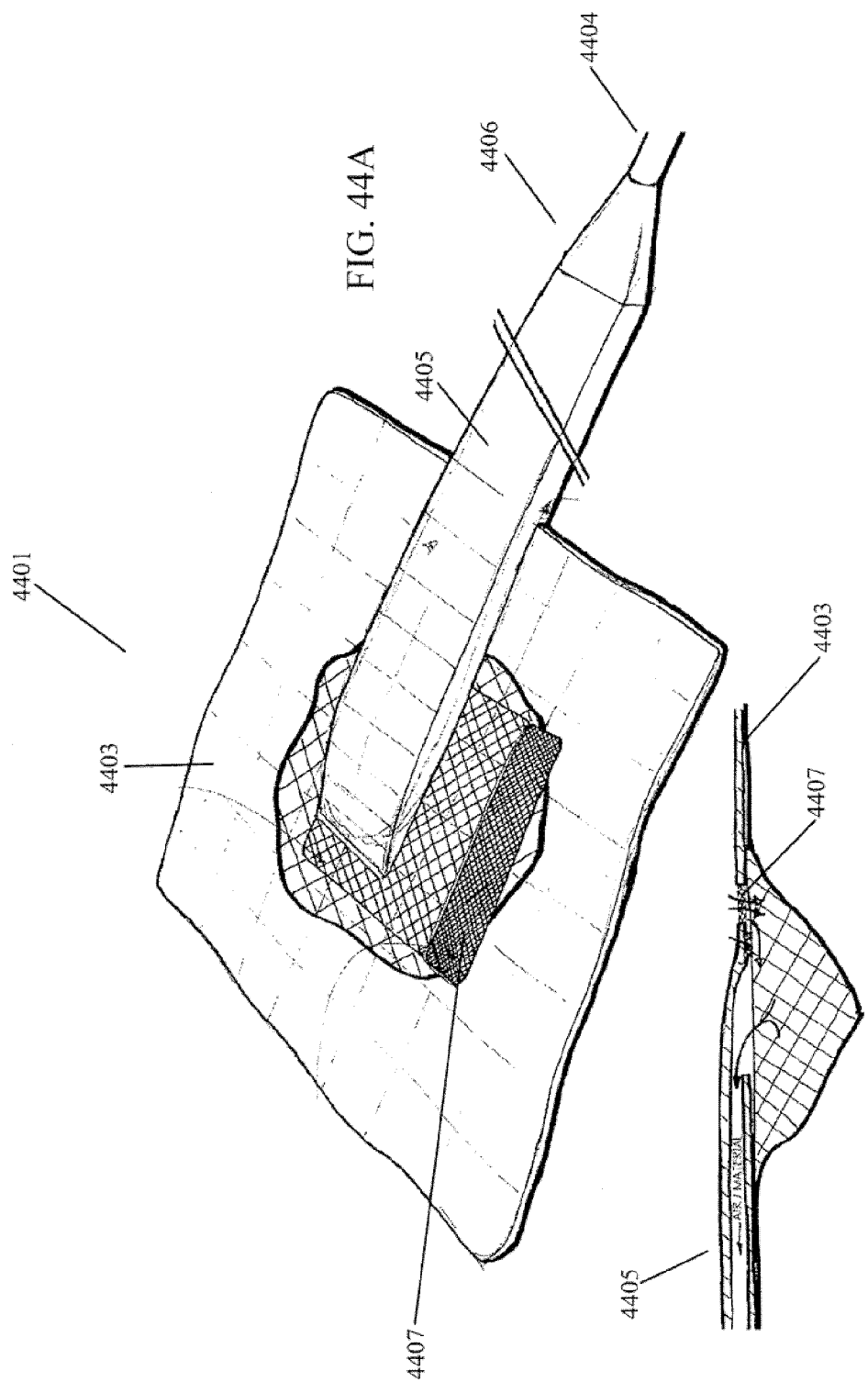

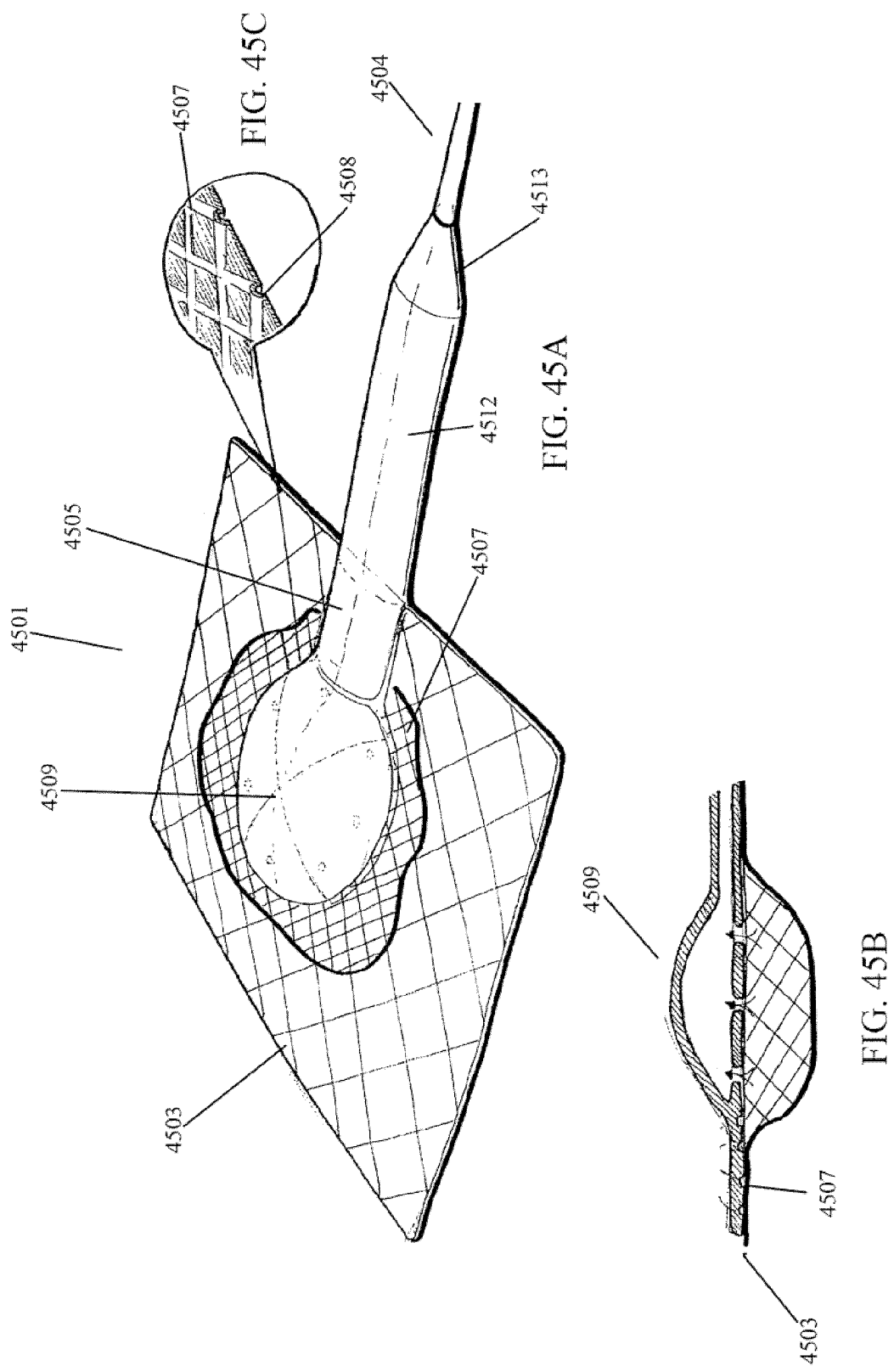

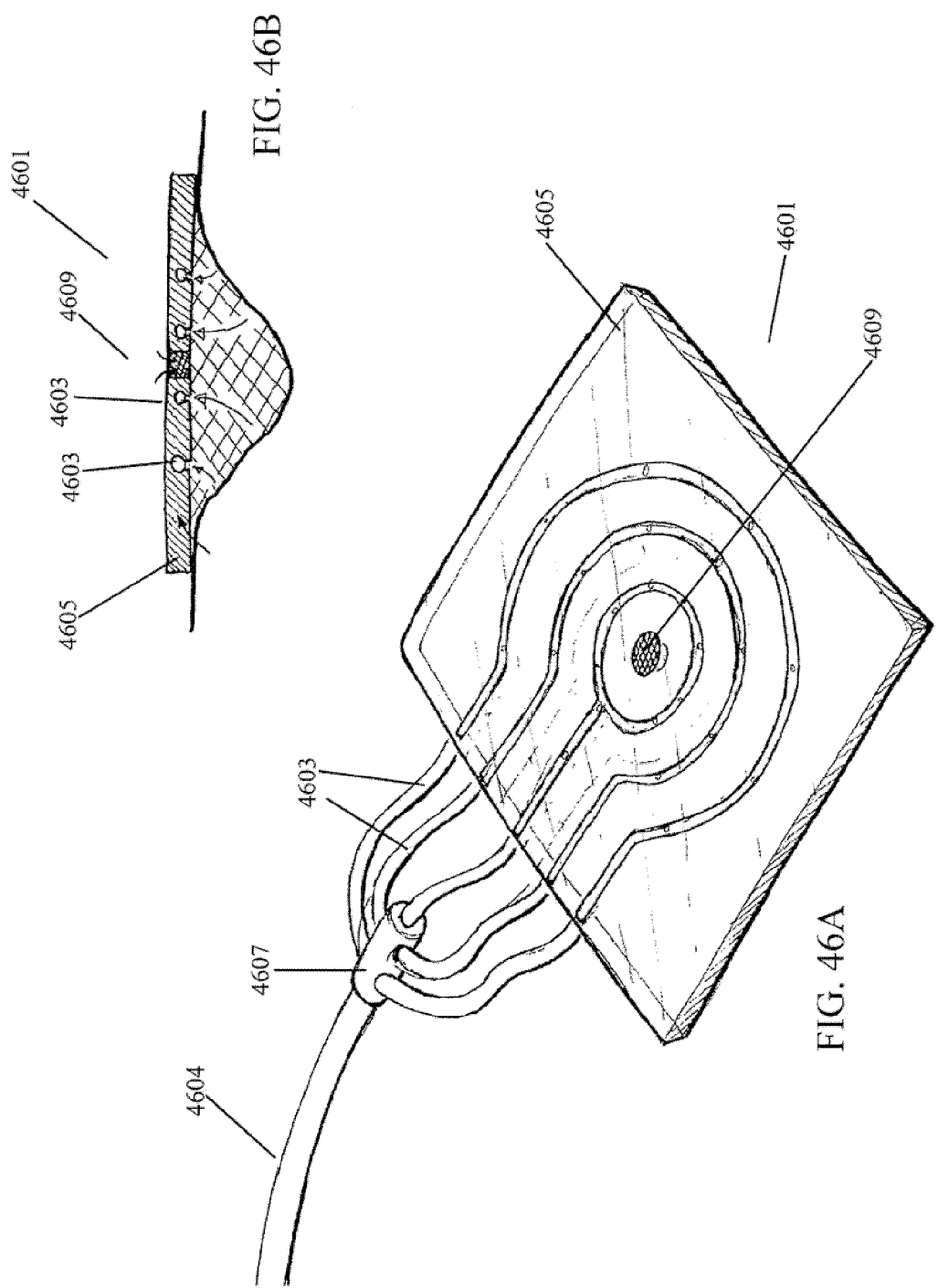

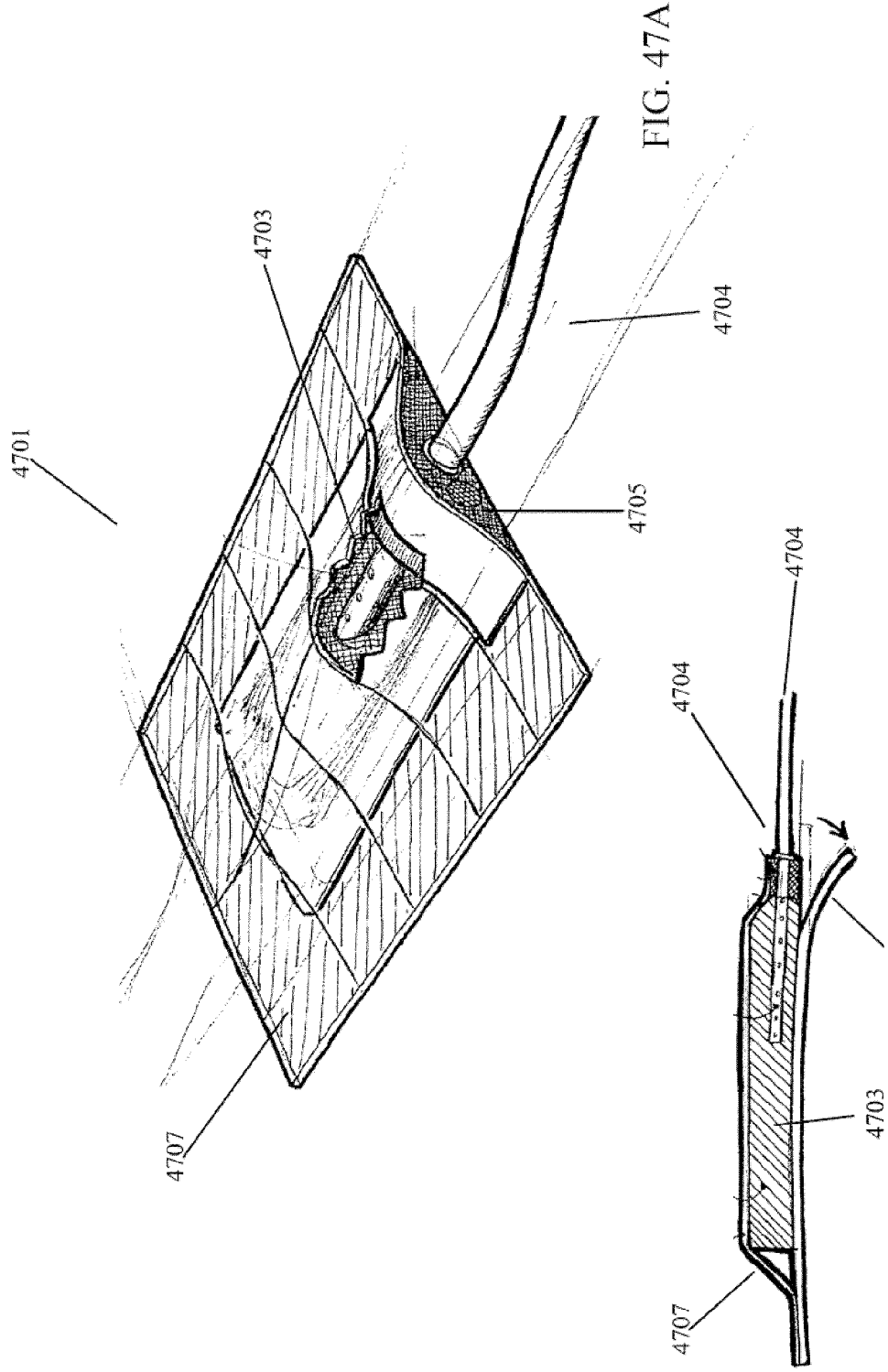

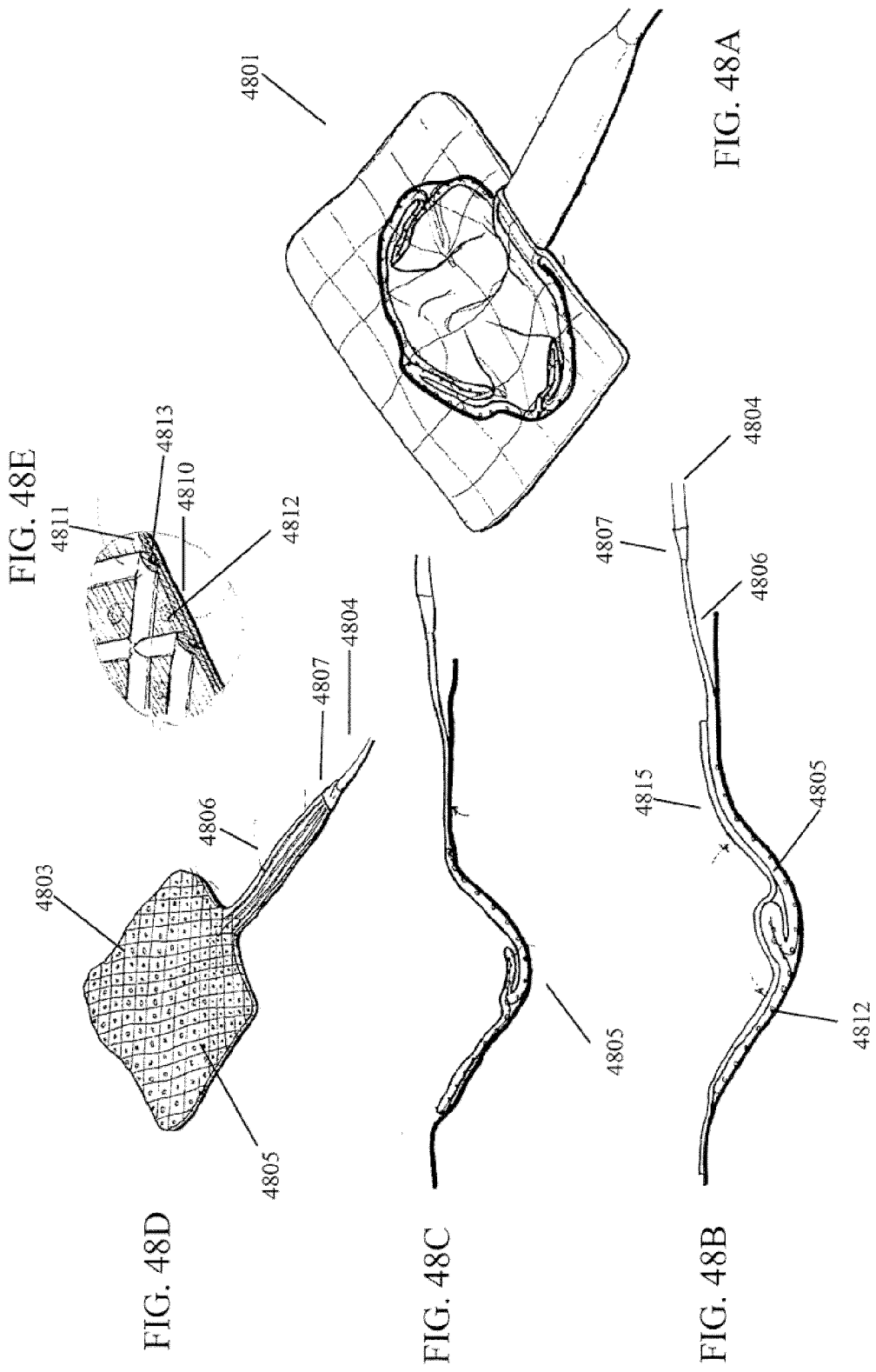

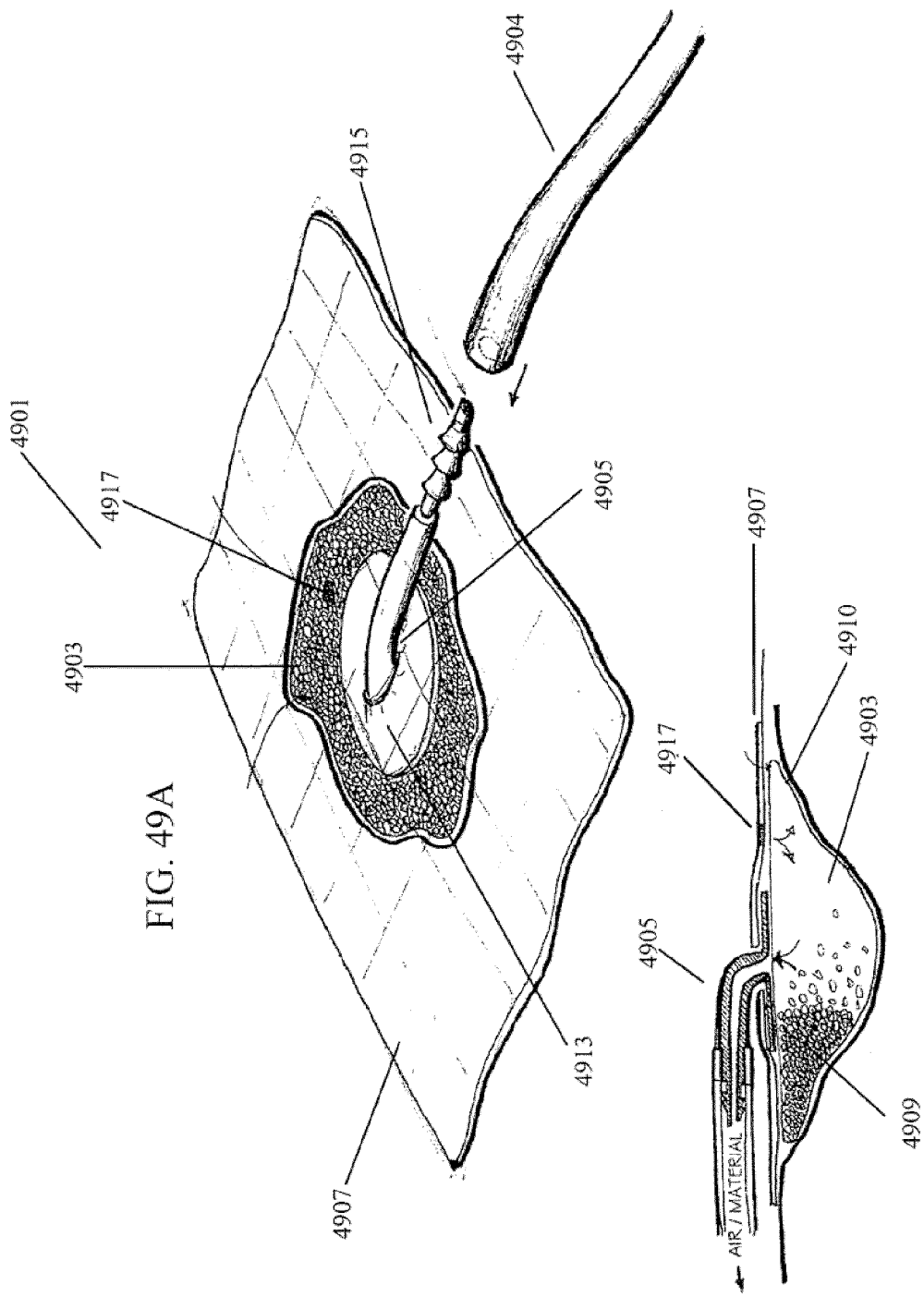

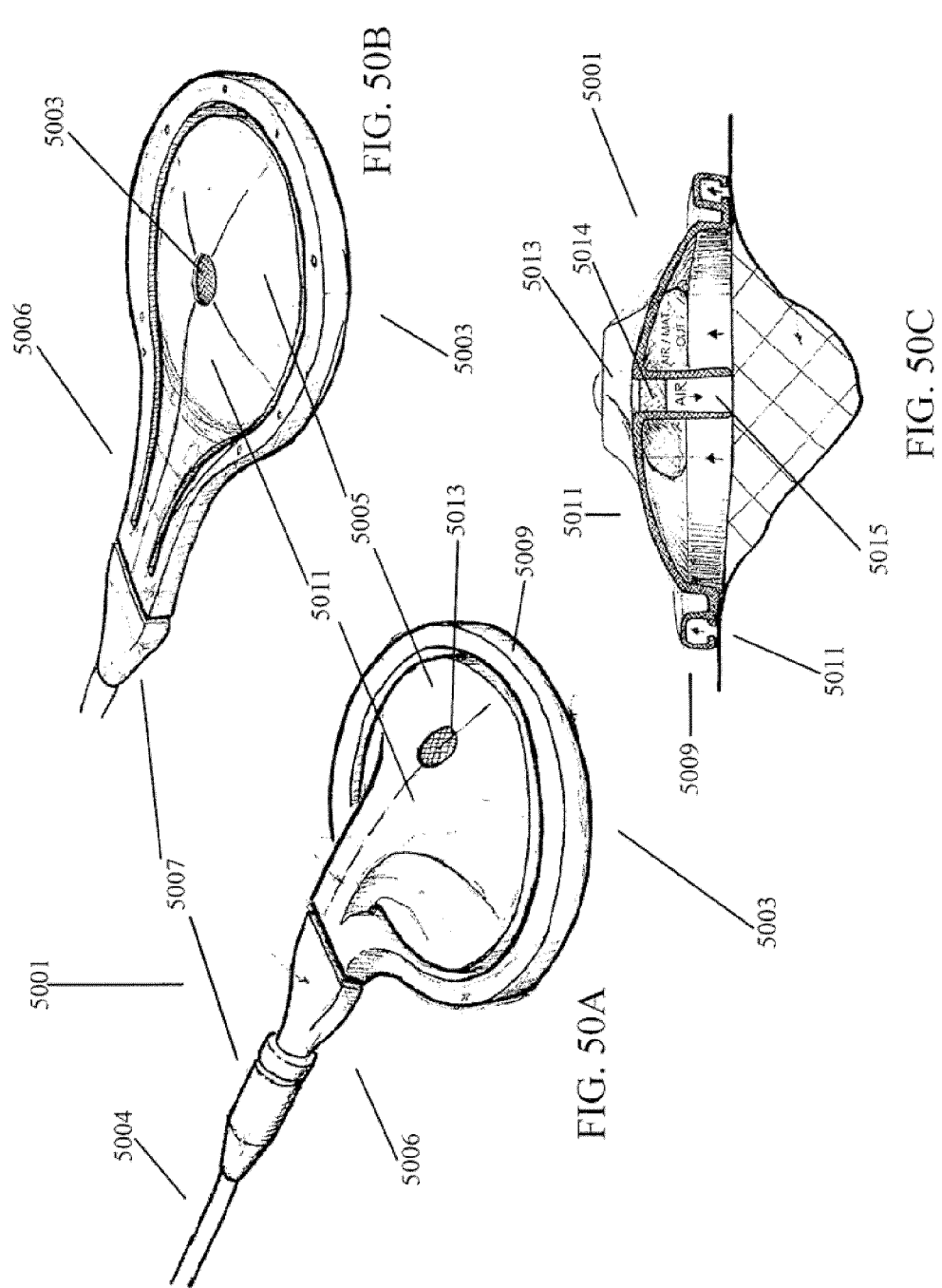

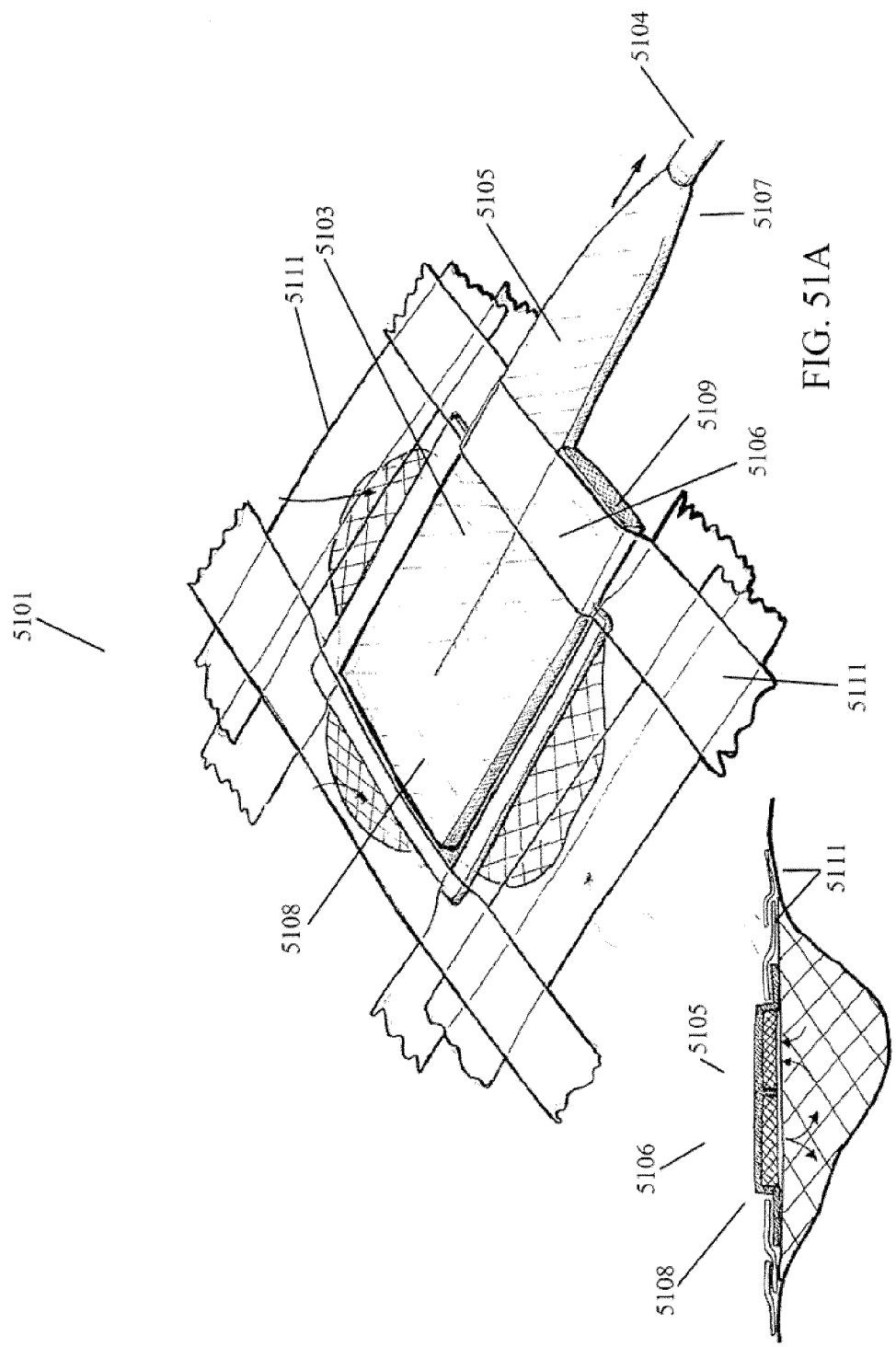

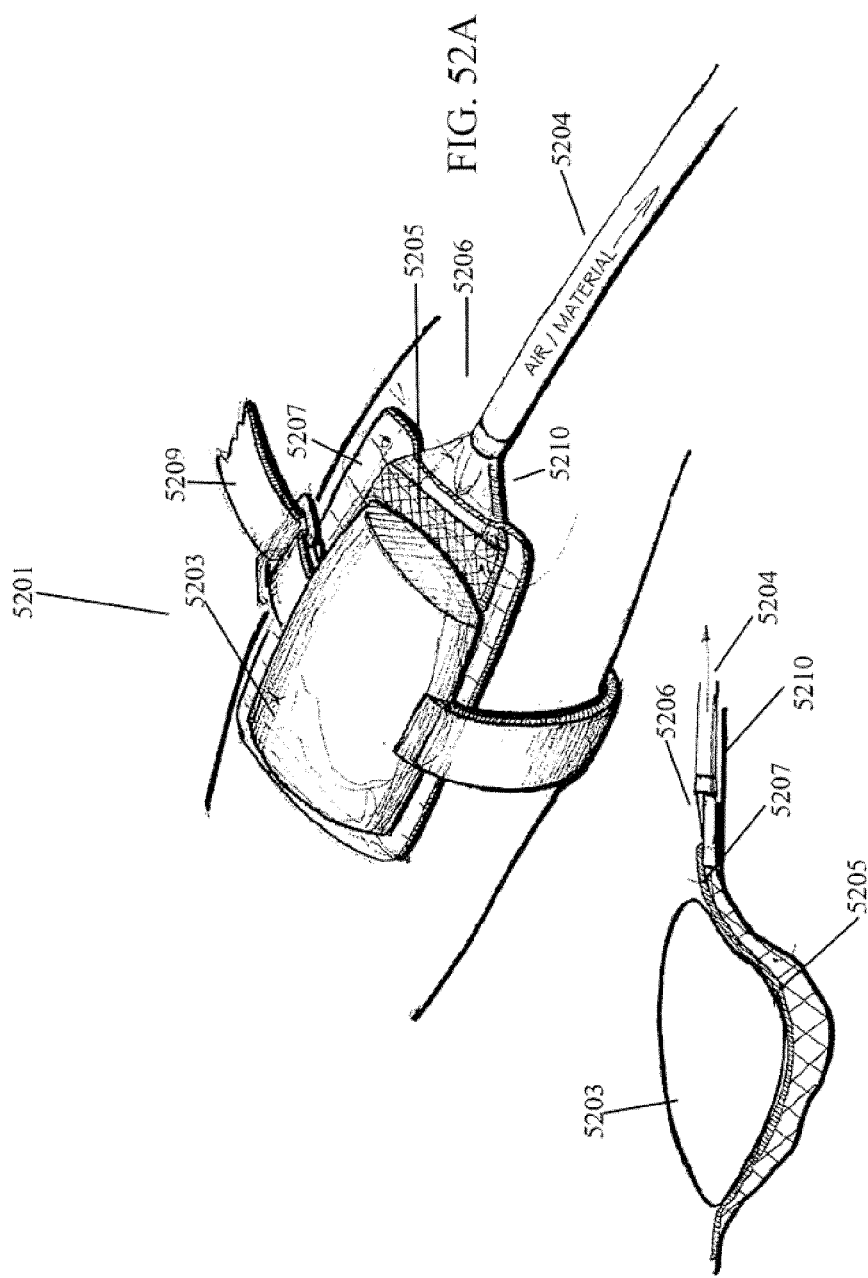

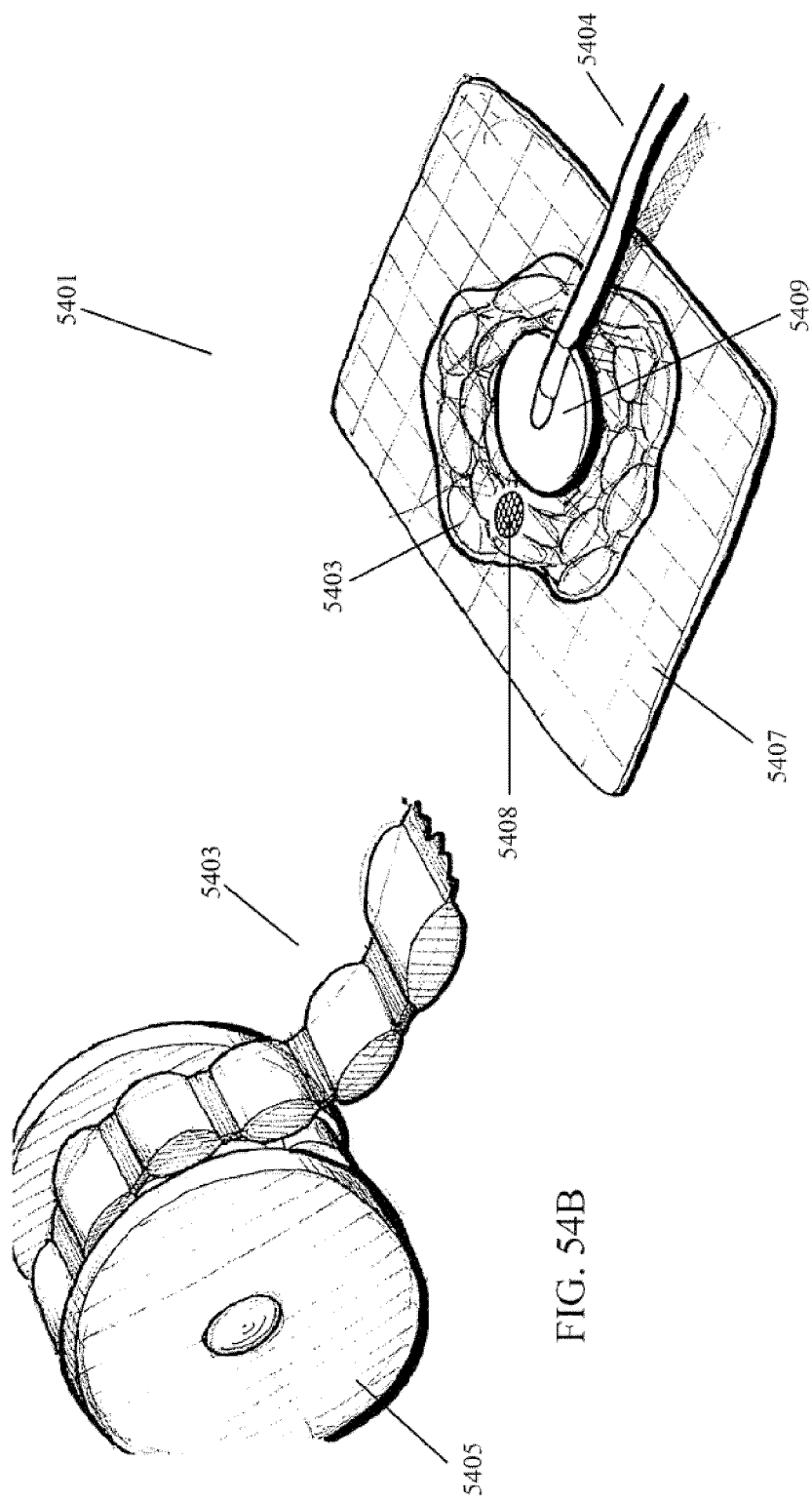

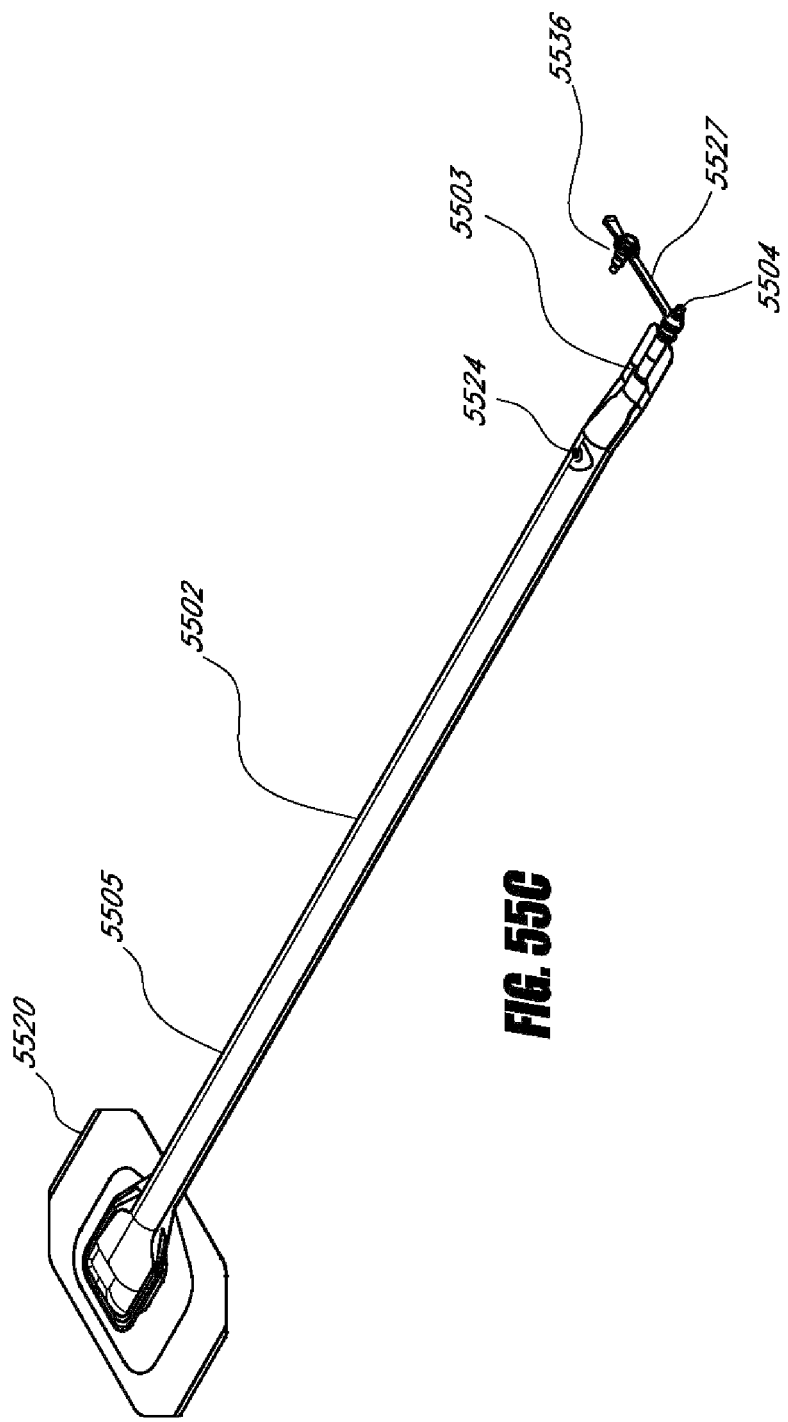

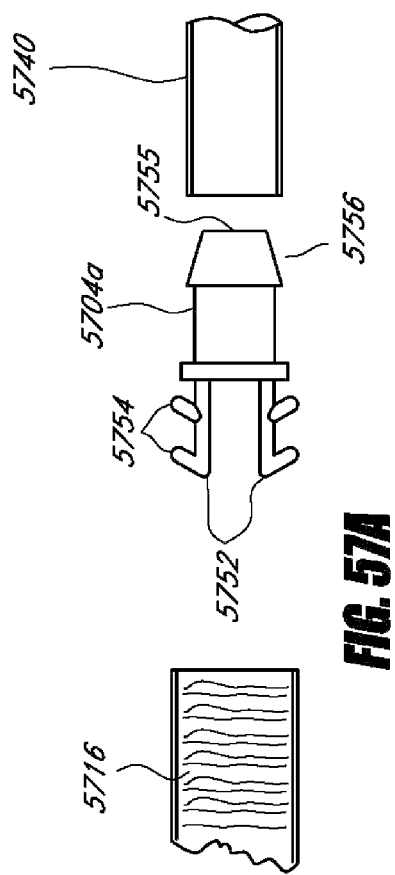
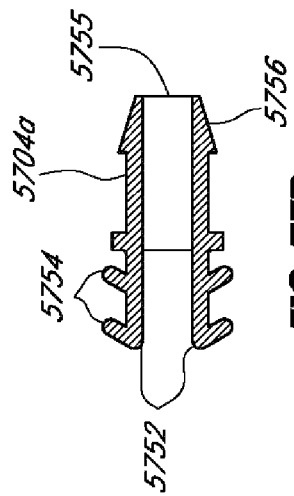

APPARATUSES AND METHODS FOR NEGATIVE PRESSURE WOUND THERAPY

CROSS-REFERENCE TO RELATED APPLICATIONS

This application is a U.S. National Phase of the PCT International Application No. PCT/US2010/061938 filed on Dec. 22, 2010, designating the United States and Published on Jul. 21, 2011, which claims the benefit of U.S. Provisional Application No. 61/289,358, filed Dec. 22, 2009, U.S. Provisional Application No. 61/332,440, filed May 7, 2010, and U.S. Provisional Application No. 61/369,008, filed Jul. 29, 2010, the entirety of each of which is hereby incorporated by reference.

FIELD OF THE INVENTION

Embodiments of the present invention relate generally to the treatment of wounds using negative pressure wound therapy, and more specifically to an improved apparatus and method thereof.

BACKGROUND OF THE INVENTION

The treatment of open or chronic wounds that are too large to spontaneously close or otherwise fail to heal by means of applying negative pressure to the site of the wound is well known in the art. Negative pressure wound treatment systems currently known in the art commonly involve placing a cover that is impermeable to liquids over the wound, using various means to seal the cover to the tissue of the patient surrounding the wound, and connecting a source of negative pressure (such as a vacuum pump) to the cover in a manner so that an area of negative pressure is created under the cover in the area of the wound.

SUMMARY OF THE INVENTION

Embodiments of the invention disclosed herein are directed to a negative pressure appliance and methods of treatment using a negative pressure appliance, and may be useful in the treatment of wounds using negative pressure.

Certain embodiments of the invention employ fluidic connectors and/or suction adapters for connecting a source of negative pressure to a dressing positioned over a wound site. These fluidic connectors and/or suction adapters offer advantages over the prior art. For example and for illustrative purposes only, some of the embodiments may offer a softer, kink-free fluidic connector for connecting a wound site to a source of negative pressure for treatment. Such a fluidic connector and/or suction adapter is faster to apply, requiring fewer steps compared to prior art connectors, and offers greater patient comfort and safety by being soft and conformable, thereby avoiding pressure ulcers and other complications caused by harder connectors.

Certain embodiments provide for a negative pressure wound treatment system comprising a wound packing material configured to be positioned at a wound, a flexible drape configured to be positioned over the wound and wound packing material and sealed to the skin surrounding the wound, and which further comprises a conduit configured to deliver negative pressure to the wound through an aperture in the drape and through the wound packing material to the wound. Such embodiments further comprise a flexible suction adapter configured to surround the aperture and connect the conduit to the flexible drape and for transmitting negative pressure from the conduit through the aperture.

In one embodiment, a negative pressure wound treatment system is provided comprising a flexible drape configured to be positioned over a wound and sealed to skin surrounding the wound. A conduit is configured to deliver negative pressure to the wound, wherein negative pressure is delivered through an aperture in the drape. A flexible suction adapter is configured to surround the aperture and connect the conduit to the flexible drape, the flexible suction adapter comprising upper and lower layers forming an elongate interior channel having a proximal end and a distal end, the proximal end configured for fluid communication with the conduit and the lower layer including at least one aperture for communicating with the aperture in the drape. An elongated foam spacer is within the interior channel extending between the proximal end and the distal end.

In another embodiment, a negative pressure wound treatment system comprises a flexible drape configured to be positioned over a wound and sealed to skin surrounding the wound. The flexible drape defines an elongate channel extending between upper and lower portions of the flexible drape, wherein the channel extends from an edge of the flexible drape to an interior portion thereof. The lower portion of the flexible drape includes at least one aperture in communication with the elongate channel for transmitting negative pressure through the channel and through the aperture. A conduit is configured to deliver negative pressure to the wound, wherein the conduit is connected to the channel to deliver negative pressure through the channel and the at least one aperture in the lower layer.

In yet another embodiment, a negative pressure wound treatment system comprises a bridge with top, bottom, and intermediate layers sandwiching top and bottom fluid channels, wherein the top channel comprises an air leak, and the bottom channel is connected to a source of negative pressure suitable for drawing exudates from a wound site. The bridge is attached to an applicator portion including at least one aperture and suitable for placement over a wound site, and may also include a visualization window for visualization of the wound site.

Methods of treating wounds with negative pressure are also described. A method of treating a wound with negative pressure may include applying a flexible drape over a wound site, applying a flexible suction adapter over the wound site, where the flexible adapter comprises an applicator and bridge portion provided with an air leak. The suction adapter is then connected to a source of negative pressure, and negative pressure is applied to the wound until it has reached a desired level of healing.

Also disclosed herein are embodiments of an apparatus for providing suction to a wound site comprising a top and bottom layer constructed from a liquid-impermeable material with a 3D knitted or 3D fabric material located between these top and bottom layers. An aperture in the bottom layer is in fluid communication with the 3D knitted or 3D fabric material. An elongate channel extends between the top and bottom layers containing the 3D knitted or 3D fabric material. The top layer, bottom layer, and 3D knitted or 3D fabric material include enlarged distal ends with the elongate channel extending in a proximal direction away from the enlarged distal ends.

In some embodiments, the elongate channel comprises a lower fluid passage, and the apparatus comprises an upper fluid passage disposed above and separate from the 3D knitted or 3D fabric material that is connected to an air leak. In some cases, the upper fluid passage may contain foam or another compliant spacer material. In other embodiments, an air leak communicates with a wound site through a conduit extending in a proximal direction away form the enlarged distal ends and may in some cases include a looped portion. The enlarged ends of the top and bottom layers may be rectangular or square, or may form a teardrop shape, and the 3D knitted or 3D fabric material may have a circular enlarged end. The 3D knitted or 3D fabric material may also be in fluid communication with a source of negative pressure, such as a pump. The bottom layer may be configured to be attached to a drape, or may be attached to an applicator. The bottom layer may also comprise an adhesive disposed on its wound-facing side, and can in some cases be provided with multiple apertures. In some embodiments, the 3D knitted or 3D fabric material may be in fluid communication with a dual lumen tube that incorporates an air leak at a proximal portion thereof. The air leak may in some cases comprise a plurality of discrete air channels, and may be located on the enlarged distal end of the top layer. The 3D knitted or 3D fabric material can be provided with a flattened distal end.

Embodiments of systems for the treatment of wounds using negative pressure using embodiments of the suction adapters disclosed above are also disclosed. These systems can comprise a suction adapter as described previously, a flexible drape configured to be positioned over a wound and sealed to the skin surrounding the wound, and where the suction adapter is configured to be attached to the drape so as to surround an aperture formed in the drape. A vacuum pump may be connected by at least one conduit to the suction adapter.

In another embodiment of a suction adapter, this adapter has an applicator with an upper and lower surface, with the upper surface connected to the distal end of a bridge. The bridge has a proximal end and a distal end, and has an upper fluid passage connected to an air leak and a lower fluid passage in fluid communication with a source of negative pressure, with the lower fluid passage comprising a 3D knitted or 3D fabric material.

In some embodiments of the suction adapter, the upper fluid passage may comprise foam. The bridge portion may further comprise a top layer, a bottom layer and an intermediate layer, each of the layers having proximal ends and distal ends and elongate portions extending therebetween, where the upper fluid passage extends between the top and intermediate layers, and the lower fluid passage extends between the intermediate and bottom layers. The distal end of the bridge may also have an enlarged shape. The air leak may be disposed at the proximal end of the bridge. The 3D knitted or 3D fabric material may include a top knitted layer, a bottom knitted layer, and a middle area with vertically extending fibers, and may be approximately 1.5 to 6 mm thick. The 3D knitted or 3D fabric material may be constructed so as to resist compression to less than half its original thickness when subjected to a load of 15 psi.

The suction adapter embodiments above may be used in embodiments of a negative pressure wound treatment system comprising a flexible drape configured to be positioned over a wound and sealed to the skin surrounding the wound, and where the suction adapter is configured to be attached to the drape so as to surround at least one aperture formed in the drape. A vacuum pump is preferably connected by at least one conduit to the suction adapter.

Further embodiments of negative pressure wound treatment systems described herein may comprise a flexible drape configured to be positioned over a wound and sealed to skin surrounding the wound, a conduit configured to deliver negative pressure to the wound, wherein negative pressure is delivered through an aperture in the drape, and a flexible suction adapter configured to surround the aperture on the drape and connect the conduit to the flexible drape. The flexible suction adapter can comprise upper and lower layers forming an elongate interior channel with proximal and distal ends, where the proximal end is configured to communicate fluidically with the conduit and wherein the lower layer has at least one aperture for communicating with the aperture in the drape. An elongated spacer extending between the proximal and distal ends may also be placed within the interior channel.

In some embodiments, the elongated spacer may become progressively larger toward the distal end. The interior channel may incorporate a looped portion that extends toward and away from the at least one aperture in the lower layer, and the spacer may be configured similarly. The channel in the suction adapter may also comprise an air leak, which may be disposed between the proximal and distal end of the channel, and may also incorporate a filter. The lower layer of the suction adapter may comprise more than one aperture, for example four apertures. The wound may also be packed with a wound packing material placed under the flexible drape.

Another embodiment of a negative pressure wound treatment system described herein includes a wound packing material configured to be positioned at a wound, a flexible drape configured to be positioned over the wound packing material and over the wound and sealed to skin surrounding the wound, a conduit configured to deliver negative pressure to the wound through an aperture in a drape and through the wound packing material placed in the wound, and a flexible suction adapter configured to surround the aperture and connect the conduit to the flexible drape and for transmitting negative pressure from the conduit through the aperture.

In some embodiments, the suction adapter may be a flexible shroud having a distal end configured to seal with the flexible drape around the aperture and a proximal end configured to seal about the conduit, where the conduit is configured to extend through the flexible shroud into the aperture. The suction adapter may also be a sealing disc sandwiched between annular upper and lower support discs, where the lower support disc is configured to be adhered to the flexible drape around the aperture, and the conduit is configured to extend through openings in the sealing disc and upper and lower support discs into the aperture. In other cases, the flexible suction adapter may be a sealing ring integrated with the aperture in the drape, with the conduit being sized and configured to make a sealing contact with the sealing ring. The flexible suction adapter may also comprise upper and lower support layers sandwiching a looped portion of the conduit, where the lower layer includes at least one aperture and the conduit includes a plurality of apertures so that negative pressure can be transmitted through the plurality of apertures in the conduit through the at least one aperture in the lower layer and through the aperture in the flexible drape. The flexible suction adapter can also have upper and lower support layers sandwiching an elongated foam spacer, where the lower layer includes at least one aperture for transmitting negative pressure from the foam spacer to the aperture in the flexible drape, and the elongated foam spacer includes a proximal end configured to connect to a distal end of the conduit. The suction adapter can also comprise a membrane with elongate parallel channels integrated onto it and configured to be positioned over the flexible drape around the aperture so as to channel wound exudate. In another embodiment, the flexible drape can define a lower layer and further comprises an upper layer that sandwiches the flexible suction adapter between the upper and lower layers; the flexible suction adapter can comprise a foam spacer.

Yet another embodiment of a negative pressure wound treatment system comprises a flexible drape configured to be positioned over a wound and sealed to skin surrounding the wound, with the flexible drape defining an elongate channel extending between upper and lower portions of the flexible drape, and where the channel extends from an edge of the flexible drape to an interior portion of the flexible drape, the lower portion of the flexible drape including at least one aperture in communication with the elongate channel for transmitting negative pressure through the channel and through the aperture. A conduit is configured to deliver negative pressure to the wound, where the conduit is connected to the channel to deliver negative pressure through the channel and the at least one aperture in the lower layer. In some embodiments, a foam spacer may extend into the channel, and spacer comprising bosses may also be present on in an interior portion of the channel.

Embodiments of a suction adapter described herein can include an applicator with an upper surface and a lower surface, a bridge with a proximal end and a distal end, where the distal end of the bridge is connected to the upper surface of the applicator, and where the bridge comprises a top layer, a bottom layer and an intermediate layer, each of the layers having proximal ends and distal ends and elongate portions extending therebetween. A first channel layer then extends between the top and intermediate layers, where the first channel layer has a proximal end and a distal end and an elongate portion extending therebetween. A second channel layer extends between the intermediate and bottom layers, where the channel layer has a proximal end and a distal end and an elongate portion extending therebetween. An air leak is disposed at the proximal end of the top layer that is configured to provide an air path into the first channel layer.

Another embodiment described herein includes a suction adapter suitable to treat a wound site with negative pressure that includes an applicator with an upper surface and a lower surface, a bridge having a proximal end and a distal end, where the distal end of the bridge is connected to the upper surface of the applicator. The bridge comprises a top layer, a bottom layer and an intermediate layer, with each layer having a proximal end and a distal end and an elongate portion extending therebetween, a first channel layer extending between the top and intermediate layers, the first channel layer having a proximal end and a distal end and an elongate portion extending therebetween and a second channel layer extending between the intermediate and bottom layers, the second channel layer having a proximal end and a distal end and an elongate portion extending therebetween. An air leak is disposed at the proximal end of the top layer, the air leak configured to provide an air path into the first channel layer. One of the first and second channel layers comprises foam and the other of the first and second channel layers comprising a fabric.

Methods of treating a wound with negative pressure are also disclosed herein. A method of treating a wound site with negative pressure comprises applying a flexible drape over a wound site, applying a flexible suction adapter over an opening in the flexible drape, where the flexible suction adapter comprises top and bottom layers constructed from a liquid-impermeable material, a 3D knitted or 3D fabric material located between the top and bottom layers, an aperture in the bottom layer in fluid communication with the wound site through the opening and the 3D knitted or 3D fabric material, and applying negative pressure to the wound, the negative pressure being transmitted to the wound through at least one conduit connected between the source of negative pressure and the flexible suction adapter and passing through the 3D knitted or 3D fabric material through the aperture in the bottom layer and into the opening in the flexible drape.

In some embodiments, the application of negative pressure to the wound may cause air to flow into the wound via an air leak disposed on the flexible suction adapter. The flow rate of air, may, in some embodiments be at least 0.08 liters/minute when negative pressure is applied to the suction adapter, and this flow rate may be maintained while a weight is placed on the suction adapter, for example a 4.75 kg weight. Adhesive may be placed on the suction adapter when adhering the adapter to the drape, or the adapter can be supplied pre-attached to a drape. Otherwise, the method above may comprise cutting an opening into the drape. Wound contact material can also be placed into the wound site prior to applying the drape. A similar method may transmit negative pressure to the wound through at least one conduit connected between the source of negative pressure and the flexible suction adapter and that passes through the 3D knitted material into the opening in the flexible drape.

Yet another method of treating a wound site with negative pressure is disclosed herein. This method comprises applying a flexible drape over a wound site, applying a flexible suction adapter over an opening made in the flexible drape, the flexible suction adapter comprising an applicator having an upper surface and a lower surface and a bridge having a proximal end and a distal end, and where the distal end of the bridge is connected to the upper surface of the applicator, and the bridge comprises a top layer, a bottom layer and an intermediate layer, each of the layers having proximal ends and distal ends and elongate portions extending therebetween, a first channel layer extending between the top and intermediate layers, where the first channel layer has a proximal end and a distal end and an elongate portion extending therebetween, a second channel layer extending between the intermediate and bottom layers, the channel layer having a proximal end and a distal end and an elongate portion extending therebetween, an air leak disposed at the proximal end of the top layer configured to provide an air path into the first channel layer. The flexible suction adapter is connected to a source of negative pressure, and negative pressure is applied to the wound, the negative pressure being transmitted through the second channel layer and drawing in air from the air leak through the first channel layer.

A further method for treating a wound with negative pressure is described herein. This method comprises applying a flexible drape over a wound site, applying a flexible suction adapter over an opening made in the flexible drape, connecting the flexible suction adapter to a source of negative pressure; and applying negative pressure to the wound, the negative pressure being transmitted through the second channel layer and drawing in air from the air leak through the first channel layer. The flexible suction adapter used comprises an applicator having an upper surface and a lower surface and a bridge having a proximal end and a distal end, the distal end of the bridge being connected to the upper surface of the applicator. The bridge comprises a top layer, a bottom layer and an intermediate layer, with each of the layers having proximal ends and distal ends and elongate portions extending therebetween, a first channel layer extending between the top and intermediate layers, the first channel layer having a proximal end and a distal end and an elongate portion extending therebetween, a second channel layer extending between the intermediate and bottom layers, the channel layer having a proximal end and a distal end and an elongate portion extending therebetween, an air leak disposed at the proximal end of the top layer configured to provide an air path into the first channel layer, and wherein one of the first and second channel layers comprises foam and the other of the first and second channel layers comprising a fabric.

BRIEF DESCRIPTION OF THE DRAWINGS

FIG. 1 illustrates a negative-pressure system that can be used in the treatment of wounds.

FIG. 2A illustrates an embodiment of a negative pressure wound treatment system with a flexible shroud being applied over a flexible drape.

FIG. 2B illustrates the system of FIG. 2A with the shroud applied to the flexible drape.

FIGS. 2C-2F illustrates a method of applying the negative pressure wound treatment system of FIGS. 2A and 2B to a patient.

FIG. 3A illustrates an embodiment of a negative pressure wound treatment system with a sealing disc being applied over a flexible drape.

FIG. 3B is an exploded view of the sealing disc of FIG. 3A.

FIG. 3C illustrates the system of FIG. 3A with the sealing disc applied to the flexible drape.

FIGS. 3D-3H illustrate a method of applying the negative pressure wound treatment system of FIGS. 3A-3C to a patient.

FIG. 4A illustrates an embodiment of negative pressure wound treatment system with a flexible drape having an integrated sealing ring.

FIG. 4B illustrates the system of FIG. 4A with a conduit inserted through the sealing ring.

FIG. 5A illustrates an embodiment of a negative pressure wound treatment system using a suction adapter with an air leak.

FIG. 5B is an exploded view of the suction adapter of FIG. 5A.

FIGS. 5C-5F illustrate a method of applying the negative pressure wound treatment system of FIGS. 5A-5B to a patient.

FIG. 6A illustrates an embodiment of a negative pressure wound treatment system with a flexible suction adapter.

FIG. 6B is an exploded view of the flexible suction adapter of FIG. 6A.

FIGS. 6C and 6D are alternative embodiments of the flexible suction adapter of FIGS. 6A-6B.

FIGS. 6E-6H illustrate a method of applying the negative pressure wound treatment system of FIGS. 6A-6D to a patient.

FIGS. 7A-7B illustrate other embodiments of a flexible suction adapter.

FIGS. 8A and 8B illustrate another embodiment of a negative pressure wound treatment system with a flexible suction adapter.

FIG. 9A illustrates an embodiment of a negative pressure wound treatment system with a flexible drape integrating a suction channel therein.

FIG. 9B is an exploded view of the flexible drape of FIG. 9A.

FIG. 9C-9D illustrate a method of applying the negative pressure wound treatment system of FIGS. 9A and 9B to a patient.

FIGS. 10A and 10B illustrate another embodiment of a negative pressure wound treatment system with a flexible drape integrating a suction channel therein.

FIGS. 11A and 11B illustrate another embodiment of a negative pressure wound treatment system with a flexible drape integrating a suction channel and spacers comprising bosses therein.

FIGS. 12A and 12B illustrate an embodiment of a flexible one-piece suction adapter.

FIGS. 13A and 13B illustrate an embodiment of a negative pressure wound treatment system with a drape-piercing suction adapter.

FIGS. 14A and 14B illustrate another embodiment of a negative pressure wound treatment system with an integrated drape and wound packing material.

FIGS. 15A-D illustrate another embodiment of a negative pressure wound treatment system with a flexible suction adapter.

FIGS. 17A-B illustrate an embodiment of a negative pressure wound treatment system with a low profile side drain.

FIGS. 19A-D illustrate embodiments of a negative pressure wound treatment system incorporating a flat drain portion.

FIGS. 20A-B illustrate an embodiment of a negative pressure wound treatment system incorporating a trimmable suction port.

FIGS. 21A-B illustrate another embodiment of a negative pressure wound treatment system incorporating a sealing ring.

FIGS. 22A-B illustrate an embodiment of a negative pressure wound treatment system incorporating a piercing attachment for use with a port.

FIGS. 23A-B illustrate a different embodiment of a negative pressure wound treatment system incorporating a piercing attachment for use with a port.

FIGS. 24A-B illustrate embodiments of a negative pressure wound treatment system incorporating a piercing connector and a controlled air leak.

FIGS. 25A-B illustrate embodiments of a negative pressure wound treatment system incorporating a manifold and a central controlled air leak.

FIGS. 26A-B illustrate embodiments of a negative pressure wound treatment system incorporating two manifolds.

FIGS. 28A-B illustrate an embodiment of a negative pressure wound treatment system incorporating a controlled air leak in a suction head.

FIGS. 29A-B illustrate an embodiment of a negative pressure wound treatment system incorporating a starburst negative pressure distribution manifold and a central controlled air leak.

FIGS. 32A-K illustrate embodiments of a negative pressure wound treatment system with a port and a piercing tool.

FIGS. 33A-H illustrate embodiments of a negative pressure wound treatment system incorporating a cutting template.

FIGS. 34A-H illustrate embodiments of a negative pressure wound treatment system comprising a soft port with a protruding channel.

FIGS. 35A-H illustrate an embodiment of a negative pressure wound treatment with drape strips provided with a port.

FIGS. 36A-I illustrate a negative pressure wound treatment system comprising a drape with integrated drainage channels.

FIGS. 37A-G illustrate a negative pressure wound treatment system incorporating a drape with miniature openings.

FIGS. 38A-I illustrate an embodiment of a negative pressure wound treatment system comprising a bayonet connector between a ring and a port.

FIGS. 39A-B illustrate a negative pressure wound treatment system comprising a low-profile port configured to attach to a valve attached to a drape.

FIGS. 42A-B illustrate an embodiment of a negative pressure wound treatment system incorporating a pre-made aperture onto a drape.

FIGS. 43A-B illustrate an embodiment of a negative pressure wound treatment system incorporating a piercing connector.

FIGS. 44A-B illustrate an embodiment of a negative pressure wound treatment system with a drape incorporating an integrated suction port.

FIGS. 45A-C illustrate an embodiment of a negative pressure wound treatment system incorporating a drape with cross-linked air channels and port integrated thereupon.

FIGS. 46A-B illustrate an embodiment of a negative pressure wound treatment system comprising suction channels integrated into a wound cover.

FIGS. 47A-B illustrate an embodiment of a negative pressure wound treatment system incorporating a low-profile suction unit.

FIGS. 48A-E illustrate an embodiment of a negative pressure wound treatment system comprising a flexible suction adapter sheet.

FIGS. 49A-B illustrate an embodiment of a negative pressure wound treatment system incorporating a wound packing pouch.

FIGS. 50A-C illustrate embodiments of a negative pressure wound treatment system comprising a port provided with a sealing ring.

FIGS. 51A-B illustrate another embodiment of a negative pressure wound treatment system incorporating a low-profile suction adapter.

FIGS. 52A-B illustrate an embodiment of a negative pressure wound treatment system provided with a bladder.

FIGS. 54A-B illustrate an embodiment of a negative pressure wound treatment system using discrete wound packing material portions.

FIG. 55C illustrates an isometric view of a flexible suction adapter that may be used in a negative pressure wound treatment system.

FIGS. 57A-B illustrate an embodiment of a connector with two or more projections and that may be connected to a suction adapter illustrated in FIG. 55.

DETAILED DESCRIPTION OF THE PREFERRED EMBODIMENTS

Figure 7B:
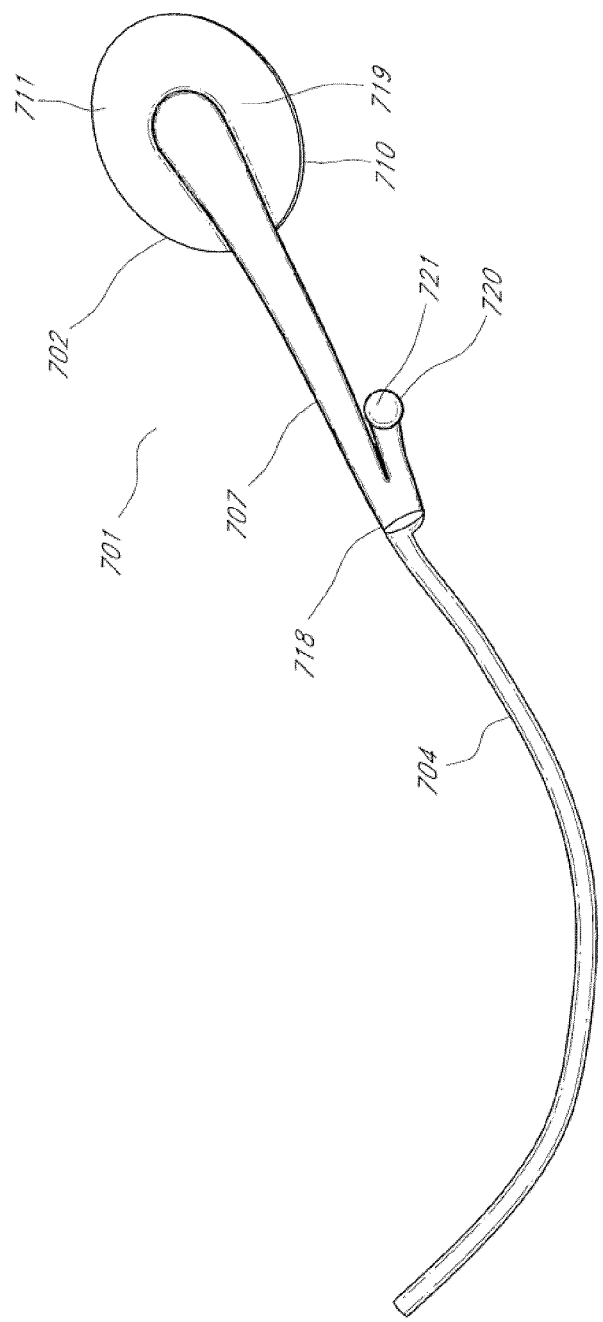

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. Wounds include, but are not limited to, open wounds, pressure sores, ulcers and burns. Treatment of such wounds can be performed using negative pressure wound therapy, wherein a reduced or negative pressure can be applied to the wound to facilitate and promote healing of the wound. It will also be appreciated that the negative pressure systems and methods as disclosed herein may be applied to other parts of the body, and are not necessarily limited to treatment of wounds.

With reference initially to FIG. 1, treatment of a wound with negative pressure in certain embodiments of the application uses a system as illustrated schematically. In one embodiment, a wound 101 may be partly or completely filled with a wound packing material 102, such as foam, gauze, or any other suitable material. Alternatively, no wound packing material may be utilized. A flexible drape 103 that is at least partially fluid impermeable, and preferably liquid impermeable, may then be laid over the wound packing material 102 and preferably onto at least part of the surrounding healthy skin surrounding a wound. The drape 103 may be connected via a conduit 104 such as a flexible tube to a source of negative pressure 106 such as a pump. This conduit 104 may, in some embodiments, comprise one or more tubes. Suitable sources for negative pressure include both powered negative pressure sources such as vacuum pumps, and manually powered negative pressure sources such as suction bulbs. Negative pressure is applied to the wound through the conduit 104 and through the wound packing material 102, and wound exudate and other secretions are drawn away from the wound, through the wound packing material, and into a canister or other collection unit 105. The collection unit 105 may be located along the conduit before the negative pressure source, or may be located elsewhere relative to the negative pressure source. In some embodiments, one or more filters 107 may be provided along the vacuum pathway, for example at the outlet of the pump. This filter 107 may be useful for absorbing odors or may be a bacterial filter. Suitable systems for treating wounds in the above manner include the RENASYS-F, RENASYS-G, RENASYS EZ and RENASYS GO systems available from Smith & Nephew.

The application of reduced or negative pressure to a wound in the above manner may be used to promote faster healing, increase blood flow, decrease bacterial burden, increase the rate of granulation tissue formation, remove exudate and slough from the wound, alleviate interstitial edema, stimulate the proliferation of fibroblasts, stimulate the proliferation of endothelial cells, close chronic open wounds, inhibit burn penetration, and enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached.

Suitable drapes such as those used in the embodiments described herein are preferably liquid tight, such that at least partial negative pressure may be maintained at the wound site. The drape may be constructed from, for example, transparent flexible plastics such as polyurethane. Other suitable materials include without limitation synthetic polymeric materials that do not absorb aqueous fluids, including polyolefins, such as polyethylene and polypropylene, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. Lastly, although several embodiments illustrated herein illustrate an operator cutting an aperture into a drape manually, drapes used in the embodiments disclosed here may also be provided with one or more pre-cut apertures.

The wound is optionally filled with a wound packing material. Preferably, this wound packing material is conformable to the wound bed. This material is preferably soft and resiliently flexible. Examples of suitable forms of such wound fillers are foams formed of a suitable material, e.g. a resilient thermoplastic. Preferred materials for the present wound dressing include reticulated polyurethane foams with small apertures or pores and open-celled foams. Other suitable materials may include gauze. Preferably, such wound packing material will be able to channel wound exudate and other fluids through itself when negative pressure is applied to the wound. Some wound packing materials may include pre-formed channels or openings for such purposes.

Typically, the negative pressure wound treatment system is operated until a wound has reached a level of healing acceptable to a physician. The treatment system is preferably operated using a negative or reduced pressure ranging from about 40 to 200 mm Hg, though the amount may be lower or higher depending on physician preference. The time period for use of the wound treatment apparatus on a wound is selected by the physician. During the time period that negative pressure is applied, dressing changes and other temporary interruptions to the treatment may occur. Preferably, the negative pressure wound treatment system is able to handle at least 1 L of wound exudate or other fluid per day, or 0.694 ml/min. Some embodiments may handle over 10 L of wound exudate per day.

In preparing a wound site for treatment with the embodiments described herein, the wound is typically cleaned, debrided, and dried in a medically-acceptable manner. Optionally, the wound site may be filled partly or completely with a wound packing material 102 as shown in FIG. 1, including for example but without limitation gauze or foam. This wound packing material may be trimmed to fit into the wound space. Next, a drape 103 is placed to cover the wound site while overlapping onto the healthy skin surrounding the wound; in some cases, the drape may need to be trimmed to size. Depending on the type of drape, a skin sealant may need to be applied to the skin surrounding the wound prior to placing the drape so that the drape may be adhered to the skin. Preferably, the drape 103 has an adhesive layer on its wound-facing side. Once adhered to the skin, the drape should form an air-tight seal against the skin. In order to treat the wound using negative pressure, some embodiments disclosed herein may require that the drape be pierced (for example to insert a conduit or to communicate with a suction adapter as described below) to create an aperture leading to the wound site. Obviously, some drapes may have an aperture or apertures already pre-cut or preformed into the drape, and some embodiments disclosed herein may not require an aperture to be made (as shown in FIG. 1). After application of negative pressure to the wound site, wound exudate and other fluids may be drawn away from the wound site and into a suitable receptacle 105, preferably interposed between the wound site and the source of negative pressure 106. Application of negative pressure is continued (with intervening dressing changes, if necessary) until the wound has reached a desired level of healing.

With reference to FIGS. 2A and 2B, one embodiment of a negative pressure wound treatment system 201 uses a flexible shroud 202 at the interface between a flexible drape 203 and a conduit 204. In dressing a wound to be treated using negative pressure, a wound packing material 205 as described above may be appropriately sized and placed into the wound cavity. As shown in FIG. 2A, the wound packing material 205 may be a foam having an elongate groove or channel 207 for receiving conduit 204. The drape 203 may be placed over the wound and over the wound packing material 205, with one or more apertures 206 formed through the drape that permit wound exudate to be evacuated from the wound through tube 204 leading to a negative pressure source. In order to effectively evacuate wound exudate from the wound, these drape apertures are preferably made fluid-tight. In the illustrated embodiment of FIGS. 2A and 2B, the flexible shroud 202 is placed over the aperture in the drape and around the tube 204, permitting a fluid-tight connection to be made without the use of cumbersome tape, paste, or other such sealing materials typically used.

As shown in FIG. 2A, the flexible shroud 202 has a distal end 210 facing toward the wound, and a proximal end 211 facing away from the wound. The distal end is enlarged relative to the proximal end to surround the aperture 206, giving the shroud in one embodiment the shape of a skirt. The distal end 210 preferably has a flat, distally facing surface, with a layer of adhesive 212 and a release layer 213 disposed on the distal end of the flexible shroud. The adhesive may be chosen from any adhesive able to create a fluid-tight seal, including pressure-sensitive adhesives such as silicone adhesives. In some embodiments, an adhesive layer is not necessary, and the flexible shroud 202 is self-sealing against the drape, for example when suction is applied. In order to seal the flexible shroud 202 against the conduit 204, a flexible grommet 214 may be provided at the proximal end 211, although some embodiments may have the flexible shroud be sealed or molded to the conduit 204 without the use of a grommet. The flexible shroud 202 may be fixed to a single location on the conduit 204, or it may slide freely along it. If the flexible shroud 202 is fixed to a single location on the conduit 204, it may be adhered to the conduit with any suitable means, including adhesives such as cyanoacrylates, light-activated adhesives, or welding.

In a preferred embodiment, the flexible shroud 202 is constructed from a pliable plastic material such as polyurethane. Preferably, the material chosen for the flexible shroud 202 is soft and at least partially conformable to the skin of a patient to avoid causing pressure ulcers or other complications due to prolonged pressure onto patient skin or the wound site.

One method for using the negative pressure treatment system of FIGS. 2A and 2B is illustrated in FIGS. 2C-2F. An operator may first debride and clean a wound in a typical manner known to a medical professional of ordinary skill in the art. As shown in FIG. 2C, a wound packing material 205, as previously described, may then be placed into the wound; in some cases, the wound packing material may extend above the level of the skin in the wound. As also illustrated in FIG. 2C, a drape 203 may be placed over the wound and the wound packing material 205, preferably overlapping onto the healthy skin adjacent the wound. Preferably, the drape is adhered to the skin and/or wound packing material. An aperture 206 is then made into the drape as shown in FIG. 2D, preferably in proximity to the wound packing material 205 and along the groove 207 formed in the wound packing material 205. Although FIG. 2D demonstrates an aperture 206 being made into the drape 203 with a pair of scissors, an aperture may be made by any suitable means, and in some embodiments, the drape 203 may be provided with an aperture pre-cut into the drape. As shown in FIG. 2E, a conduit 204 as described above is inserted through the aperture 206 and into the groove 207. In some cases, trimming or cutting of the tube may be necessary.

To apply the flexible shroud 202, as illustrated in FIG. 2F, release sheet 213 is removed to expose the adhesive layer 212 of the flexible shroud, and the flexible shroud is then adhered over and around the aperture 206 in order to create a fluid-tight seal. In certain embodiments, the shroud 202 may slide freely over the conduit 204; in such cases, the shroud 202 is slid down and adhered around the aperture 206. In other embodiments where the shroud 202 is attached to and does not slide freely over the conduit 204, the conduit 204 may need to be trimmed as needed to fit into the wound space under the drape 203. Preferably, the conduit 204 is slid into a groove 207 in the wound packing material 205. Subsequently, the conduit 204 may be connected to a negative pressure source. When activated, the negative pressure source will collapse the flexible shroud 202 (as shown in FIG. 2B) and draw wound exudate and other fluids from the wound area.

Turning to FIGS. 3A-3C, another embodiment of a negative pressure wound treatment system 301 uses a sealing disc 302 to seal the interface between the drape 303 and a conduit 304 in a fashion similar to what is described above. In this embodiment, the sealing disc 302 comprises an annular lower support disc 310 preferably constructed from an at least partly-flexible material, such as a polyurethane layer, with a hole through its center. On the bottom side of the lower support disc 310, an adhesive layer 312 may be disposed with an optional protective release layer 313 covering the adhesive layer, where the protective release layer may be removed prior to use. This adhesive layer 312 may be used to adhere the sealing disc 302 to the drape 303.

Preferably, the sealing disc 302 further comprises a seal 311 placed above the lower support disc 310, where the seal is able to create a fluid-tight seal between itself and a conduit 304. The seal 311 is preferably constructed from a flexible, conformable material such as silicone and comprises a central hole 316 that is preferably smaller than the central hole in the support disc. The exact size of the seal 311, and its relation in size to the support disc is not important, as long as the seal is able to create a fluid-tight seal between itself and the conduit 304. Some embodiments may comprise a lower support disc 310 with a central seal 311 integrated into the middle of sealing disc 310 (instead of above it), to create a one-piece unit construction.

Preferably, the sealing disc 302 also comprises an upper support disc 315 placed above the other components of the sealing disc, such that the seal 311 is sandwiched between the upper support disc 315 and lower support disc 310. The top disc may be constructed from the same material as the support disc, or it may be of a different material. Preferably, the top disc, the seal, and the support disc are secured together to form a single sealing disc 302, for example using means such as adhesives or welding.

To use the suction disc 302 described above, and with reference to FIG. 3D-3H, an operator will typically prepare the wound as described previously. Once the wound is prepared and a drape 303 placed over the wound (FIG. 3D), the drape 303 is pierced (FIG. 3E) and the sealing disc's adhesive protective layer 313 is removed (FIG. 3F) and placed over the resulting aperture 306 (FIG. 3G). Preferably, the sealing disc 302 is placed with its central hole 316 aligned with an aperture 306 made through the drape 303. Subsequently, as shown in FIG. 3H, the conduit 304, which may be cut to size, is inserted through the sealing disc 302 and into the drape 303, and connected to a source of negative pressure. In some embodiments, a channel 307 may be formed in the wound packing material 305, such that the conduit 304 may be slid into this channel 307. If necessary, a strip of tape or other adhesive 318 may be used to secure the conduit 304 to the drape 303 to prevent the conduit 304 from undesired movement. The wound is then treated until it has reached a desired level of healing.

FIGS. 4A-4B illustrate another embodiment of a negative pressure wound treatment system 401. As illustrated, a flexible drape 403 includes an integrated sealing ring 402 surrounding a pre-made aperture 406 in the flexible drape. The integrated sealing ring 402 (which may be similar to the embodiment discussed in FIGS. 3A-C) should be of a diameter large enough to permit passage of a conduit 404, but small enough so that a substantially fluid-tight seal is maintained once the conduit 404 is inserted therein. The sealing ring 402 is preferably constructed from a compliant material such a silicone or urethane. Here, rather than using an adhesive layer to attach the sealing disc to the drape as shown in FIGS. 3A-C, the sealing ring 402 is pre-attached to the drape 403, for example by molding the ring 402 onto the drape 403.

In use and after preparation of the wound as described previously, and with reference to FIG. 4B, a drape 403 is trimmed, if necessary, and sealed over a wound site optionally filled with a wound packing material 405. A conduit 404 is inserted through the aperture 406 of the integrated sealing ring 402. The tube 404, which may be cut to size, is connected to a source of negative pressure, and the wound is treated until it has reached a desired level of healing.

In FIGS. 5A and 5B, another embodiment of a negative pressure wound treatment system 501 is shown with a suction adapter 502 comprising an integrated air leak. The suction adapter 502 comprises upper and lower layers 511 and 510, which may be annular and/or disc shaped as shown, and formed of a flexible plastic material. As illustrated in FIG. 5B, the conduit 504 is preferably sandwiched between the upper and lower layers 511, 510 and forms a loop within the upper and lower layers 511, 510. The conduit 504 includes a plurality of apertures 515 in the looped portion, and the lower layer 510 is provided with an aperture or apertures 516 enabling it to serve as a conduit for removing wound exudate from the wound through the drape aperture or apertures 506 and into the apertures 515 of the conduit 504 sandwiched in the suction adapter 502. Preferably, a layer of adhesive 512 is placed on the lower portion 510 to provide for securing of the suction adapter to the drape. A protective release layer 513 removable by an operator may also be placed on the adhesive layer to protect it during handling.

In some embodiments, the conduit 504 may be secured to the upper and/or lower layers 511, 510 using, for example, a strip of adhesive, clip, or other fixative 517. In some embodiments, the fixative 517 may serve as a targeting or visual indicator to aid in the placement of the suction adapter 502 over the aperture 506. Preferably, the upper and lower layers 511, 510 of the suction adapter are sealed together with the conduit 504 to form a substantially fluid-tight suction adapter 502. The sealing may be accomplished through any appropriate means, such as adhesives or welding.

The conduit 504 has a proximal end 518 leading toward a source of negative pressure and a distal portion inserted into the suction adapter with its distal end 519 extending past the loop to form a controlled air leak 520. This air leak 520 provides a constant source of air entering into the suction adapter 502 and may aid in the removal of wound exudate. Additionally, this air leak 520, due to the constant rate at which air enters the negative pressure system, may be used in a feedback mechanism to the pump control circuitry and may be useful in detecting blockages occurring in the system, for example in the conduit 504. Preferably, a filter 521 is placed at the end of the air leak 520 to prevent outside contaminants, such as microorganisms, dust, or other foreign matter from entering the wound area. In some embodiments, the filter 521 may be designed so that a patient may use the system 501 in a shower or other similar environment without occluding the air leak 520. The filter may be hydrophobic and/or oleophobic. Preferably, the air leak 520 supports a flow rate of air of at least 0.08 L/min. Some embodiments may support an air leak of at least 0.16 L/min.

In use, and as illustrated in FIGS. 5C-5F, an operator would prepare a wound site in an acceptable manner as previously described. As shown in FIG. 5C, an optional wound packing material 505 may then be placed into the wound site, which would then be covered by a drape 503, appropriately sized and sealed. After piercing the drape 503 (FIG. 5D), the adhesive protective layer 513 is removed from the suction adapter 502 (FIG. 5E), placed over the drape aperture 506 (FIG. 5F), and connected to a source of negative pressure (not illustrated). The wound is then treated substantially as described previously. Note that in this embodiment, because the conduit 504 does not need to be inserted through the drape 503, no groove or channel in the wound packing material 505 (which was preferably included in certain other embodiments disclosed herein) is needed in using this suction adapter 502.

FIGS. 6A-6D show another embodiment of a negative pressure wound treatment system 601. The system comprises a wound packing material 605 and flexible drape 603 as described above. A flexible suction adapter 602 is further provided for connecting an aperture 606 in the drape to a conduit 604. Here, the suction adapter 602 is preferably formed of a relatively compliant and pliable material to avoid causing patient discomfort and injury, which may include pressure sores or ulcerations. The suction adapter 602 is connected via connectors 614, 615 to a source of negative pressure via the conduit 604. The connectors 614, 615 may be constructed from a semi-rigid material, including for example but without limitation plastics such as acrylonitrile butadiene styrene (ABS). In some embodiments, end caps (not illustrated) may be provided to seal off one or more of the connectors 614, 615 when they are disconnected from each other, so as to prevent wound exudate from leaking out of the system.

The flexible suction adapter 602 comprises an upper layer or sheet 611, a lower layer or sheet 610, and an elongate channel 608 extending between the upper and lower sheets having a proximal end 616 and a distal end 617. As illustrated, the channel preferably enlarges toward its distal end, and may form an elongated teardrop shape so as to permit negative pressure to be applied to a larger wound area at the distal end 617 while maintaining a smaller size at the proximal end 616 for connecting with the conduit 604. Additionally, the teardrop shape aids the suction adapter 602 in conforming to different wound sizes and shapes. The channel 608 as illustrated includes a spacer 609 extending between the proximal and distal ends, and at least one aperture 618 is formed on the lower sheet near the distal end 617 that permits fluid to be evacuated from a wound area (in a manner similar to what has been previously described). In some embodiments, there may be multiple apertures 618 to permit efficient transfer of fluid from the wound. For example, there may be four smaller apertures instead of one larger aperture. The spacer 609 is preferably constructed from a compliant material that is flexible and that also permits fluid to pass through it if the spacer is kinked or folded over. Preferably, the spacer 619 is sandwiched between the upper and lower layers 611 and 610, for example using adhesives or heat-sealing. In order to secure the suction adapter 602 over an aperture 606 on a drape, lower layer 610 may be provided with a layer of adhesive 612 disposed on its underside, and with an optional protective release sheet 613.

Suitable materials for the spacer 609 include without limitation foams, including open-cell foams such as polyethylene or polyurethane foam, meshes, 3D knitted fabrics, non-woven materials, and fluid channels. Advantageously, such materials used in the spacer 609 not only permit greater patient comfort, but may also provide greater kink resistance, such that the spacer 609 is still able to transfer fluid from the wound toward the source of negative pressure while being kinked or bent. In some embodiments, the fluid channels may simply comprise folds created when the upper sheet is wider than the lower sheet, or vice versa, such that application of negative pressure causes the wider sheet to collapse and form folds or wrinkles suitable to channel fluids from the wound to the source of negative pressure. An example of such an embodiment is illustrated in FIG. 8A described below, where a suction adapter may be constructed from a flexible and non-rigid material such as a film.

In other embodiments, and as illustrated in FIG. 6C, fluid channels may comprise one or more solid channels 619, and may not require the use of the spacer 609 described above. In some embodiments, these solid channels are molded into either or both the upper and lower sheets; alternatively, these may be constructed separately and inserted in the space between the upper and lower sheets. If possible, such channels are at least partly compliant and non-rigid, thereby avoiding patient discomfort and other complications. FIG. 6D illustrates another embodiment where the spacer 609 comprises a thin mesh 620.

FIGS. 6E-6H illustrate a method of using and applying the suction adapter 602 described above. The wound is prepared in an acceptable manner as described above, and a drape 603 is fitted and sealed over the wound site (which may contain an optional wound packing material 605) (FIG. 6E). An aperture 606 is then cut into the drape 603 (although some drapes may be provided with an aperture 606 already pre-cut) (FIG. 6F). The release layer 613, if present, is removed to expose the adhesive layer 612 on the underside of the suction adapter 602 (FIG. 6G). The suction adapter 602 is then placed such that the apertures 618 on its underside are substantially aligned with the aperture 606 on the drape 603. The suction adapter 602 is then connected to a source of negative pressure, and the treatment is applied until the wound has reached an acceptable level of healing.

FIGS. 7A-7B illustrate embodiments of the wound treatment system 701 with an air leak provided, where the conduit used in FIGS. 5A-H is replaced with a compliant material, for example foam. The compliant material aspect of these two embodiments will be described in further detail below. FIG. 7A demonstrates a suction adapter 702 similar in design to FIG. 5A, but which uses a compliant material. Here, the compliant spacer channel 707, preferably constructed from a compliant material such as foam able to transmit fluid through itself, is connected at its proximal end 718 to a conduit 704, which is then connected directly or indirectly to a source of negative pressure. At the distal end 719 an air leak 720 is provided, optionally with a filter 721. This air leak provides a constant source of air entering the suction adapter 702, and (as described previously in FIGS. 5 A-B) may be useful in detecting blockages in the system (for example the conduit 704) and may aid in the removal of wound exudate. Preferably, the filter 721 is constructed from a thin membrane, which may be hydrophobic or oleophobic. The filter 721 is preferably able to filter microorganisms and foreign particles from entering the wound site. In some embodiments, the filter 721 is able to be wetted, for example when a patient enters a shower. The filter 721 may be die-punched from a membrane stock and attached to the air leak 720 by any suitable means, such as welding or adhesives. This compliant spacer channel 707 is sandwiched between an upper layer 711 and a lower layer 710, with the lower layer 710 preferably being provided with a layer of adhesive optionally covered with a release layer in a similar fashion to the embodiments illustrated in FIGS. 5A-B. The lower layer 710 has one or more apertures permitting it to be fluidically connected to an aperture on a drape used to cover a wound (not illustrated). The apertures on the lower layer 710 are also fluidically connected to the compliant spacer channel 707, such that upon the application of negative pressure, wound exudate and other such fluids may be evacuated from the wound site through the aperture in the drape, through the aperture in the lower layer 710, and into the compliant spacer channel 707. Preferably, the section of the compliant spacer channel 707 situated over the apertures in the lower layer 710 is larger to permit more effective removal of wound exudate from the wound site, and may form an elongated teardrop shape.

Focusing on the air leak aspect of these embodiments, FIG. 7B illustrates an embodiment with a controlled air leak 720 on the suction adapter 702 that is provided at the proximal end 718 of the compliant spacer channel 707, instead of being provided at the distal end as described above. A filter 721 is optionally provided at the air leak site. The proximal end 718 is joined to a conduit 704. In a proximal air leak design, the air leak may be disposed at a "T"-junction between the apertures near the distal end and the proximal end of the spacer channel 707 connected to the negative pressure source. Of course, although FIG. 7B illustrates a proximal air leak using a foam fluid transfer material, such an embodiment could also be realized using other materials, for instance the conduit used in FIG. 5A.

Figure 7C:
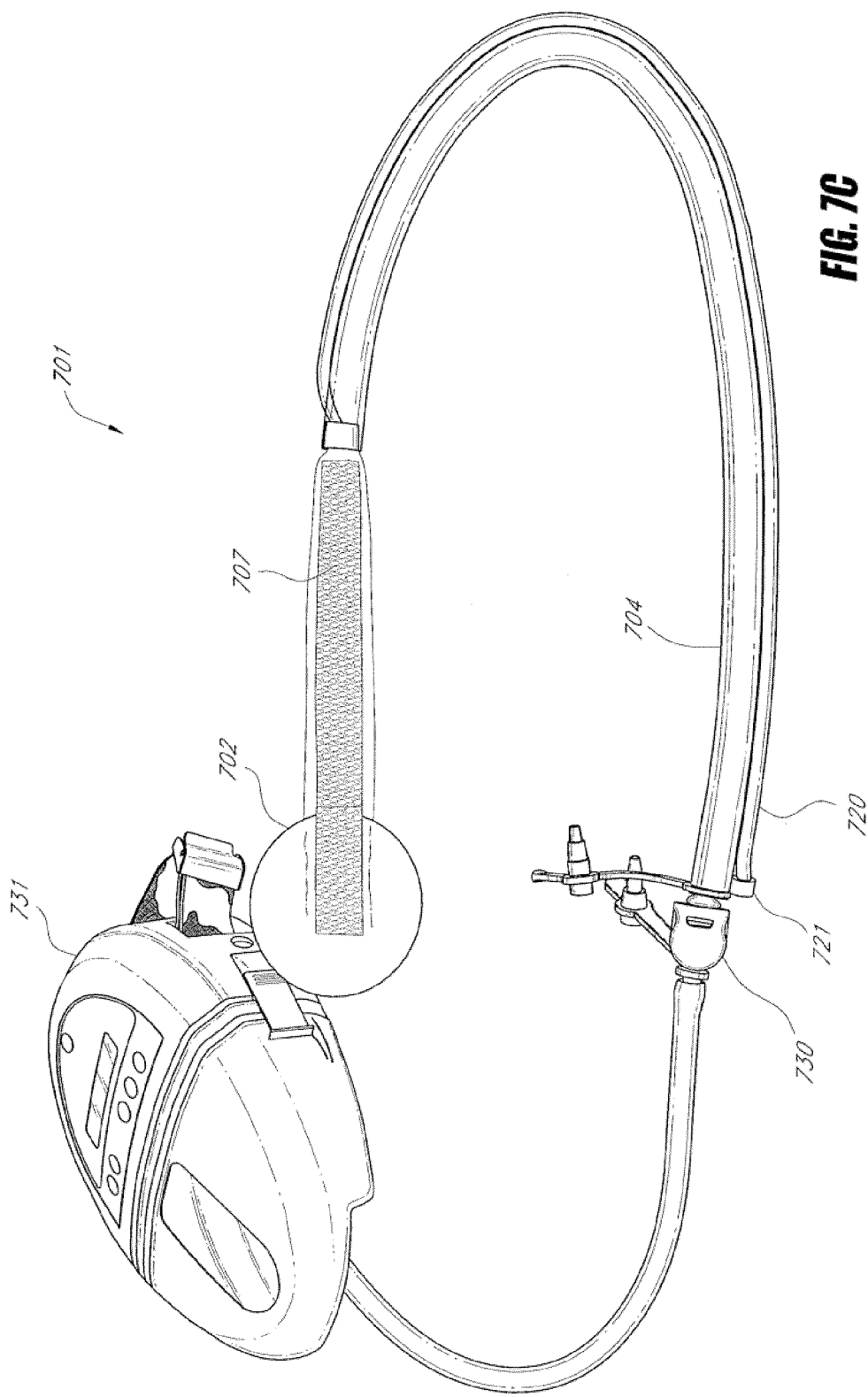
FIG. 7C illustrates a negative pressure wound treatment system using a flexible suction adapter.

FIG. 7C illustrates an embodiment joining a compliant suction adapter 702 and short compliant spacer channel 707 connected to a dual lumen tube 704 incorporating an air leak 720 at the proximal portion 718. Here, one lumen in the tube 704 is fluidically connected through connector 730 to a source of negative pressure 731 at its proximal end 718, and the other lumen is open at the proximal end 718 to form an air leak 720. This open end may optionally include an air filter 721. At the distal end of the dual lumen tube, both lumens are fluidically connected to the compliant spacer channel 707 to permit the application of negative pressure to the wound site through the suction head 702, in a manner similar to the other embodiments discussed above. In some embodiments, a compliant spacer channel 707 may not be necessary, and the dual lumen tube 704 may be directly connected to the suction head.

FIGS. 8A-B illustrate a suction adapter 802 of a similar design to the embodiments described in FIGS. 6A-H. Here, however, the suction adapter 802 is not filled with any material, and instead comprises a flat portion comprising elongate parallel channels 810 integrated onto the underside of suction adapter 802. These channels 810 may be molded integrally or attached separately onto the suction adapter 802. The suction adapter 802 preferably comprises one or more apertures 816 that would permit a fluidic connection to be made between an aperture 806 made in a drape 803, such that wound exudate from a wound site can be drawn through optional wound packing means 805, through the aperture 806, and into the suction adapter 802 through its aperture 816. The wound exudate is then drawn off through the conduit 804. An adhesive layer 812 is preferably provided on the underside of the suction adapter 802 to permit it to be secured to the drape 803, and preferably includes a release layer 813 that is removed prior to adhesion of the suction adapter 802.

FIGS. 9A and 9B illustrate an embodiment of the wound treatment system 901 using a drape 903 with a suction channel 902 integrated therein. In this embodiment, the drape 903 typically used to cover the wound and the optional wound packing material 905 that may be disposed in the wound also serves as a suction channel 902 to transfer fluids such as wound exudate away from the wound using a source of negative pressure, connected to the drape 903 through conduit 904. The drape 903 includes at least one aperture 916 suitable for the passage of wound exudate. A spacer 907 is preferably placed over the apertures 916, the spacer 907 being preferably composed of the same types of materials as the spacer 609 used in FIG. 6A, such as foam. The drape 903 comprises a top layer 911 and a bottom layer 910. In order to create a fluid-tight seal, the top layer 911 is attached to the bottom layer 910, sandwiching the spacer 907 between it. This top layer 911 should cover at least the spacer 907, and may be dimensioned to be as large or larger than the bottom layer 910 situated below it. The bottom and the top layers 910, 911 may be attached together using any suitable means, for example adhesives or welding.

An adhesive layer 912 with an optional release sheet 913 is preferably disposed on the wound-facing side of the bottom layer 910, as well as on the wound-facing side of the top sheet 911, if the top sheet is larger than the drape. The adhesive layer 912 preferably covers the entire wound-facing side of the drape 903, and may in some embodiments incorporate a multi-part release sheet 913 rather than a single release sheet 913. In this case, the release sheet 913 may be removable in several parts, for example to permit only a portion of the adhesive to be exposed for initial placement on the wound site, followed by removal of another portion of the release sheet 913 once the drape placement is finalized. The components of the assembled drape 903, including the drape itself, the spacer, and the top layer, may also comprise markings or other indicators, including visual or tactile indicators, to aid an operator in aligning, positioning, and deploying the drape.

In order to use the wound treatment system 901 described above and illustrated in FIGS. 9C-D, a medical professional would to prepare a wound site and optionally place wound packing material 905 inside the wound substantially in the manner described previously. Advantageously, instead of having to then place a drape over the wound site and create an aperture into the drape, a medical professional using a drape 903 with an integrated suction channel would only have to position the drape over the wound site, trim the drape 903 (if necessary), remove any adhesive release layer 913 (FIG. 9C), and seal the wound by attaching the drape 903 over the wound site (FIG. 9D). The drape 903 would then be connected to a conduit 904. This drape 903 would thus save time and avoid complications and difficulties in having to size and cut a hole in a drape that the prior art and some of the other embodiments presently employ.

In some embodiments, illustrated in FIGS. 10A and 10B (which is similar to the embodiment illustrated in FIG. 9A), the wound treatment system 1001 incorporates a drape without a separate spacer. Instead, the suction channel 1002 may comprise one or more ridges or folds 1010 present on the underside of the suction channel 1002, the ridges 1010 serving to maintain patency of the negative pressure connection from the wound to the source of negative pressure. In some cases, the ridges 1010 may be molded into either the top layer or the bottom layer of the drape 1003. Preferably, such ridges 1010 are substantially compliant and pliable to avoid causing patient discomfort and other complications.

FIGS. 11A-B demonstrate a variation of the embodiment illustrated in FIG. 9A, where wound treatment system 1101 uses a drape 1103 incorporating a spacer comprised of bosses 1107 serving to keep the top layer 1111 and bottom layer 1110 of the drape 1103 separate in order to form a suction channel 1102 for removal of wound exudate from a wound site at the aperture 1116. These bosses 1107 may be molded into the top or bottom layer of drape 1103, or else may be constructed separately and attached thereto. In some embodiments, the bosses 1107 are solid; in other embodiments they may be hollow. Preferably, the bosses 1107 are at least partially compliant and flexible, and may be formed from any suitable material, such as flexible plastics including polyurethane. The bottom layer 1110 optionally includes an adhesive layer and release sheet.

FIGS. 12A-B illustrate a wound treatment system 1201 comprising a flexible one-piece suction adapter. Here, the suction adapter 1202 may be manufactured from a compliant, flexible material such as plastic, including for example silicone, and comprises a proximal portion 1218 and a distal portion 1219, where the distal portion 1219 comprises a central aperture 1216 for placement around a wound site. The edges of the suction adapter may be chamfered (for example at chamfer 1206) to help seal the suction adapter against the edges of the wound site, and also minimize the risk of the suction adapter snagging or catching on other tubes, dressings, or other materials that may be in proximity to the wound site. Suction channels 1210 are also provided that serve to draw fluid away from the wound site through a conduit 1204 and toward a source of negative pressure connected thereto. In some embodiments, illustrated in FIG. 12B, the suction channels 1210 are formed through the proximal portion 1219 of the suction head, and are thus connected to a source of negative pressure. In other embodiments, illustrated in FIG. 12A, the suction channels 1210 may not be enclosed on all or part of the skin-facing portion. Optionally, a layer of adhesive 1212 is present on the wound-facing side of the suction head, although some embodiments may instead be self-sealing, for example if the suction head is constructed entirely or in part from silicone.

In use, once a wound site is cleaned, prepared in accordance with typical medical protocols, and optionally filled with a wound packing material, a first drape is placed over the wound and an aperture made thereon. Next, the suction adapter 1202 is placed over the drape aperture, with the central aperture 1216 being placed over the drape aperture. Subsequently, a second drape is placed over the wound site and suction adapter 1202. After connecting the suction adapter to a source of negative pressure through the conduit 1204, wound exudate is removed from the wound and the wound may then progress to a desired stage of healing.

FIGS. 13A and 13B illustrate another embodiment of a wound treatment system 1301 using a piercing cap 1302. Here, the piercing cap 1302 is provided with a bayonet or other piercing element 1310 suitable for perforating a drape 1303 placed over a wound site. On the wound-facing side of the drape is a suction base 1307 adapted to fit together with the piercing cap 1302, typically with a drape 1303 in between. The suction base 1307 is provided with a central aperture 1311 to be placed over the wound site. In order to fit together, the piercing cap 1302 and suction base 1307 are preferably each provided with portions that lock and fit together, for example locking tabs or screw-like engagement mechanisms 1308 and 1309. In certain preferred embodiments (illustrated in FIG. 13B), the piercing cap 1302 rotationally engages with the suction base 1307, thereby minimizing the force applied to the wound. Some embodiments may also include a sealing gasket to prevent air leaks between the interface of the piercing cap 1302 and the suction base 1307, although the drape 1303 may in some cases provide a sufficient seal.

In use, a wound site is prepared substantially in the manner that has been described previously above, but with a suction base 1307 being provided under the drape 1303 at the site over which a fluidic connection is to be made. After the drape 1303 has been sealed over the wound site (which may optionally include a wound packing material 1305), a piercing cap 1302 pierces the drape and attaches to the suction base 1307, thereby creating a fluidic connection enabling wound exudate to be conveyed from the wound site to the source of negative pressure through a conduit 1304. The wound site may then be maintained as such until it has reached a desired stage of healing.

FIGS. 14A-B illustrate an embodiment of a wound treatment system 1401 comprising a drape 1403 provided with a wound-packing material 1405 integrated thereon. In this embodiment, a drape 1403 substantially of same material used in the other embodiments described herein is provided with a wound packing material 1405, for example foam, attached to the wound-facing side of the drape 1403. Preferably, the adhesive does not attach the entire portion of the wound packing material to the wound-facing side of the drape, thus permitting a medical professional using the drape to easily trim the wound packing material to size. Optionally, precut or preformed detachable sections 1406 of wound packing material may be provided. The drape may be secured to the wound-facing material by a patch of adhesive 1412 disposed in the center of the drape 1403. In some embodiments, a channel 1407 may be provided through the wound packing material 1405, preferably through the center, so as to facilitate the placement of a conduit 1404 into the wound treatment system 1401. Optionally, the wound treatment system 1401 may be provided with such a conduit 1404 pre-attached or adhered into the channel 1407. Such an arrangement may be advantageous in providing optimal application of negative pressure to the wound site through the conduit 1404. Optionally, a seal bridge 1408 may be provided at the junction where the conduit 1404 exits the drape 1403, thereby sealing the wound site and preventing air leaks that may affect the application of negative pressure to the wound site. Preferably, the drape 1403 is provided with a further adhesive layer (not illustrated here) surrounding the adhesive patch 1412 and extending to the edges of the drape 1403, which is preferably covered with a release sheet (not illustrated here). Such a configuration permits an operator to accurately place the wound treatment system 1401 over a wound site and seal the drape 1403 against the skin surrounding the wound site by removing the release sheet once the drape 1403 and wound packing material 1405 have been positioned and sized appropriately. In some embodiments, additional adhesives, for example sealing tape, may be provided to aid in sealing the drape 1403 to the skin of a patient.

In order to use the wound treatment system 1401 described above, a wound site is cleaned and prepared in any suitable manner. Next, the wound packing material 1405 attached to the drape 1403 is fitted into the wound site, by trimming the wound packing material and/or by removing precut or preformed sections 1406 (if so provided) as necessary as well as by trimming the drape 1403 if necessary. A conduit 1404 is then inserted into a channel 1407, and after trimming (if necessary) and sealing the drape 1403 against the skin of the patient, the conduit 1404 is connected to a source of negative pressure and the wound is treated until it reaches a desired level of healing. In some embodiments, the conduit 1404 is provided pre-inserted into the channel 1407.

FIGS. 15A-D illustrate an embodiment of a negative pressure wound treatment system 1501 comprising a flexible suction adapter. This system may be combined with other components as described elsewhere in this application, for example the components illustrated in FIG. 7C, and particularly the source of negative pressure 731, tubing and a connector 730. Here, the system 1501 may comprise a bridge 1502 having a proximal end 1503 and a distal end 1505 and an applicator 1520 at the distal end 1505 of the bridge 1502. In some embodiments, the bridge 1502 may comprise an upper channel layer 1512 sandwiched between an upper layer 1510 and an intermediate layer 1514, with a lower channel layer 1516 sandwiched between the intermediate layer 1514 and a bottom layer 1518. Preferably, the layers 1510, 1514, and 1518 have elongate portions extending between proximal and distal ends and may be comprised of a material that is fluid-impermeable, for example polymers such as polyurethane. It will of course be appreciated that the layers 1510, 1514, and 1516 may each be constructed from different materials, including semi-permeable materials. Similarly to the embodiment described in FIG. 6 with regards to the spacer 609, the upper and lower channel layers 1512 and 1516 are preferably elongate layers extending from the proximal end 1503 to the distal end 1505 and may each preferably comprise a porous material, including for example open-celled foams such as polyethylene or polyurethane. In some embodiments, one or more of the upper and lower channel layers 1512 and 1516 may be comprised of a wicking fabric, for example a knitted or woven spacer fabric (such as a knitted polyester 3D fabric, Baltex 7970®, or Gehring 8790) or a nonwoven fabric. These materials selected are preferably suited to channeling wound exudate away from the wound and for transmitting negative pressure and/or vented air to the wound site, and may also confer a degree of kinking or occlusion resistance to the channel layers 1512 and 1516. In some embodiments, the wicking fabric may have a three-dimensional structure, which in some cases may aid in wicking fluid or transmitting negative pressure. To prevent the channels 1512 and/or 1516 from being displaced or twisted while encased in the system 1501—which may impair performance of the respective channels under negative pressure—it may in some embodiments be preferable to adhere or otherwise secure the channels 1512 and/or 1516 to one or more of the layers 1510, 1514, and 1518. In certain embodiments, including wicking fabrics, these materials remain open and capable of communicating negative pressure to a wound area under the typical pressures used in negative pressure therapy, for example between 80 to 150 mmHg. In some embodiments, the wicking fabric may comprise several layers of material stacked or layered over each other, which may in some cases be useful in preventing the channel 1516 from collapsing under the application of negative pressure. In other embodiments, the wicking fabric used in channel 1516 may be between 1.5 mm and 6 mm; more preferably, the wicking fabric may be between 3 mm and 6 mm thick, and may be comprised of either one or several individual layers of wicking fabric. In other embodiments, the channel 1512 may be between 1.2-3 mm thick, and preferably thicker than 1.5 mm. Additionally, and as described previously, the materials used in the system 1501 are preferably conformable and soft, which may help to avoid pressure ulcers and other complications which may result from a wound treatment system being pressed against the skin of a patient.

Figure 15C:
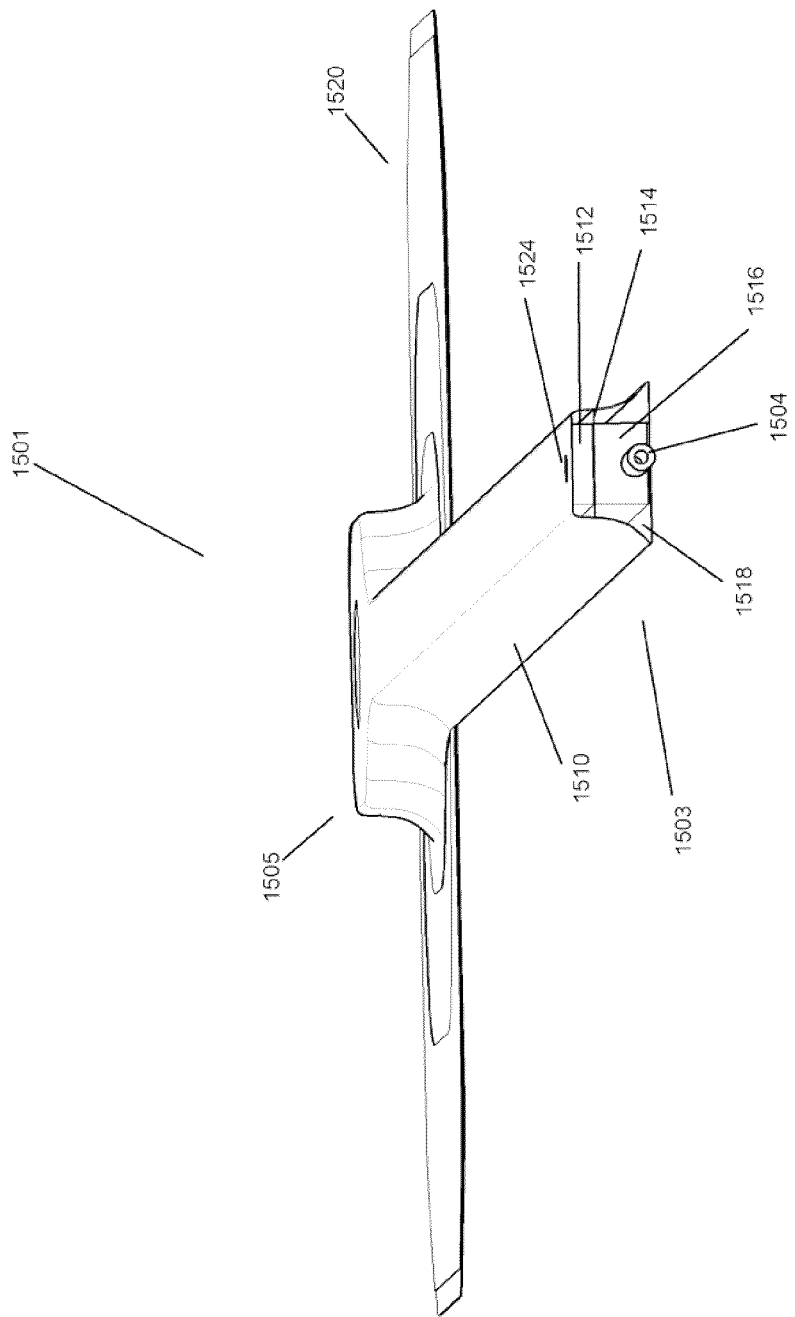

Preferably, the distal ends of the layers 1510, 1514, and 1518 and the channels 1512 and 1516 are enlarged at the distal end (to be placed over a wound site), and may form a "teardrop" or other enlarged shape. Preferably, and with additional reference to FIG. 15C, a connector 1504 is provided at the proximal end 1503 which may be used to connect the lower channel layer 1516 to a source of negative pressure. The connector 1504 may for example be embedded into the lower channel layer 1516, and preferably extends sufficiently away from the assembled bridge 1502 so as to permit a fluidic connector, for example a tube, to be connected to it so as to permit wound exudate to be suctioned away from the wound and for negative pressure to be applied to the wound site. The upper layer 1510 may comprise additional material extending downward, preferably at least of the thickness of the bridge 1502. During assembly, the upper layer 1510 is preferably attached, for example by melting, welding, or with adhesives, to the lower layer 1518 so as to form a fluid-tight seal (with the exception of the apertures at the distal and proximal ends). Preferably, the middle layer 1514 is attached to the top layer 1510 and the bottom layer 1518. Note that FIG. 15C is intended to illustrate the various materials and components at the proximal end 1503, and that a system 1501 constructed accordingly will preferably not have the proximal end 1503 open and unsealed. In some embodiments, it will be preferable to attach or bond the connector 1504 to at least one of the layers 1510, 1514, 1518 so as to create a fluid-tight connection.

In certain embodiments, a controlled air leak 1524 may be disposed on the bridge portion 1502, for example at the proximal end thereof. This air leak 1524 may comprise an opening or channel extending through upper layer 1510, such that the air leak 1524 is in fluidic communication with the upper channel 1512. Upon the application of suction to the system 1501, air will enter through the air leak 1524 and move from the proximal end 1503 to the distal end 1505 along the upper channel 1512. The air will then be suctioned into the lower channel 1516 by passing through the apertures through the distal ends of the layers 1512, 1514, 1516 and 1518. The air leak 1524 preferably comprises a filter (not illustrated), which may be similar in function to the filter 521 illustrated in FIG. 5A. Preferably, the air leak 1524 is located at the proximal end of the bridge portion 1502 so as to minimize the likelihood of wound exudate or other fluids coming into contact and possibly occluding or interfering with the air leak 1524 or its filter. In some embodiments, this filter is a microporous membrane capable of excluding microorganisms and bacteria, and which may be able to filter out particles larger than 45 μm.

Advantageously, some embodiments may provide for a filter that is at least partially chemically-resistant, for example to water, common household liquids such as shampoos, and other surfactants. In some embodiments, reapplication of vacuum to the system 1501 and/or wiping of the outside portion of the filter may be sufficient to clear any foreign substance occluding the filter. The filter may be composed of a suitably-resistant polymer such as acrylic, polyethersulfone, or polytetrafluoroethylene, and may be oleophobic and/or hydrophobic. In some embodiments, the filter may also comprise a supporting backing layer, for example a nonwoven polyester support. Preferably, the air leak 1524 will supply a relatively constant air flow that does not appreciably increase as additional negative pressure is applied to the system 1501. In embodiments of the system 1501 where the air flow through the air leak 1524 increases as additional negative pressure is applied, preferably this increased air flow will be minimized and not increase in proportion to the negative pressure applied thereto.

The system 1501 is preferably constructed so as to provide a consistent fluid flow even if the system 1501 is kinked or weighted down. For example, in use on a patient, the bridge portion 1502 may become folded over itself, or else the patient may roll over, thus placing his or her weight over at least a portion of the system 1501. Typically, prior art dressings and fluidic connectors become blocked or ineffective in such situations. Here, however, certain embodiments provide for improved blockage resistance if kinked or weighed down. Preferably, the system 1501 is able to maintain a flow rate through the air leak 1524 of at least 0.08 L/min, and preferably 0.12 L/min while negative pressure is applied through a source of negative pressure. Further embodiments also provide for the system 1501 to be able to handle fluid exudate drainage from the wound site through the lower channel 1516 of at least 10 L/day, or 6.9 ml/min. Certain embodiments provide for the system 1501 to maintain these flow rates with a weight, for example a 12 kg weight pressing down on the bridge portion through a rod with a 1 in. diameter. In some embodiments, these flow rates are also maintained while the bridge portion 1502 is kinked over itself with the same weight, or for example with a 4.75 kg weight placed directly on the folded region. It is preferable that the system 1501 be able to withstand being folded or kinked over even during an extended period of time, for example over 40 hours. Preferably, embodiments of the system 1501 are also able to transmit and maintain a negative pressure at the wound that is close to the negative pressure level at the source of negative pressure. For example, an acceptable level of pressure maintained at the wound may be within ±25 mmHg of the negative pressure set at the source of negative pressure, with this pressure being preferably maintained at this level within for example 95% of the time that the system 1501 has negative pressure applied to it. Acceptable pressure levels may include pressure ranges between 40-120 mmHg, although levels of 200 mmHg have successfully been used.

Figure 15D:
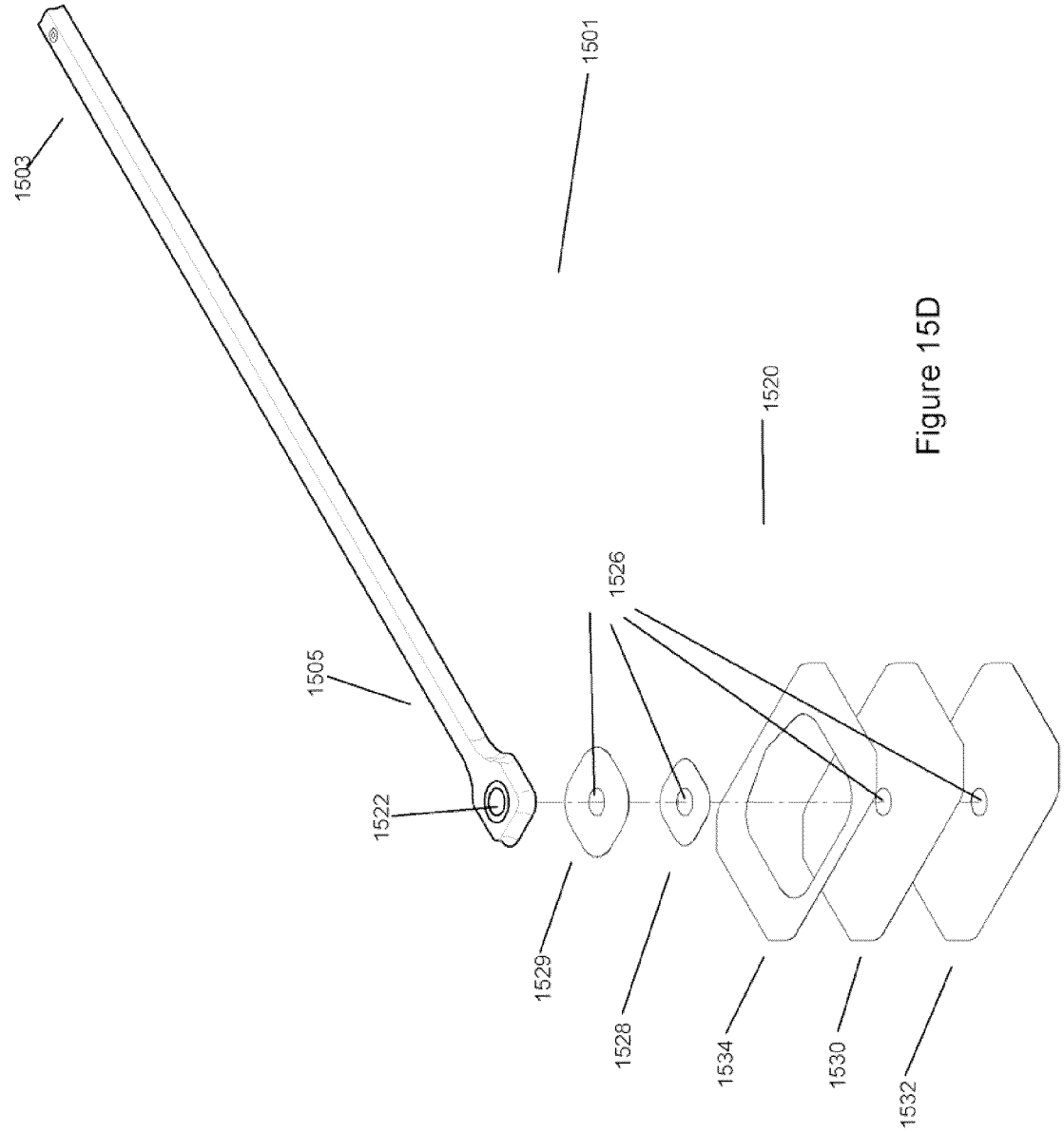

With additional reference to FIG. 15D, the system 1501 also comprises an applicator 1520 designed for placement over a wound site. Preferably, the applicator 1520 comprises a flexible layer 1530, for example polyethylene or polyurethane, with a layer of adhesive on its lower (wound-facing) side. Optionally, a protective release layer 1532 may be placed on the adhesive layer, which is removable before use. In some embodiments, a more rigid removable backing layer 1534 may be provided to facilitate handling of the applicator 1520 due to its flexible adhesive-backed layer 1530. The applicator 1520 preferably comprises an attachment point for the bridge 1502 at the distal end 1505, for example using a section of double-sided adhesive tape 1528. The double-sided adhesive tape 1528 may be protected by an additional protective release layer 1529, which is removed prior to adhering the bridge 1502 to the applicator 1520. It will be understood that different attachment methods are also contemplated, for example heat sealing, welding, or suitable adhesives. Some embodiments may also permit the manufacture of the bridge 1502 and the applicator 1520 as a single unit that does not require separate attachment means. The applicator 1520 preferably comprises at least one aperture 1526 through itself and designed to be placed over a wound site, and which can serve to fluidically connect the wound site to the source of negative pressure and to the air leak while also serving as a conduit to draw out wound exudate from the wound site. Additionally, certain embodiments may provide for the aperture 1526 to be used in a viewing window 1522 described below.

With continued reference to FIGS. 15A-B, certain embodiments may also provide for a viewing window 1522 that permits targeting and visualization of the wound site prior to placement of the system 1501 as well as ongoing monitoring of the wound site during the course of treatment. Preferably, a set of apertures are created or formed through the distal portions of layers 1510, 1512, 1514, 1516, and 1518 in alignment with aperture 1526 through the applicator 1520. Although FIG. 15B illustrates a set of apertures with a circular cross-section, other cross-sections are possible, for example with a polygonal or rectangular cross-section. Preferably, a viewing window 1522 which is at least partially transparent is provided to cover the first aperture through the top layer 1510 to shield the wound from contamination.

The filter provided in the controlled air leak 1524 in certain embodiments may be useful in a system 1501 for use with more ambulatory and active patients. For example, a chemically-resistant filter may permit a patient to bathe or shower without damaging the filter's functionality when reconnected to a source of negative pressure. Any occlusion or fluid blocking the air leak 1524 could then be cleared by, for example, wiping off the filter or re-applying negative pressure to the system 1501. Such a system would also have the advantage that the system 1501 and any assorted wound dressing materials, if present, would not need to be removed and then re-applied should a patient need to be disconnected from the source of negative pressure, for example incidental to bathing. This would entail significant advantages in improving the cost-effectiveness and ease of use of the present treatment system.

In use, the system 1501 may be used in a similar fashion to the other embodiments previously disclosed herein. A wound site is preferably cleaned and prepared in a suitable fashion, and a wound packing material, if necessary, placed into the wound site, followed by a drape. An opening through the drape to the wound site is then created, although some embodiments may have a pre-made aperture. Subsequently, an operator may situate the applicator portion 1520 over the aperture, optionally using the viewing window 1522 as a positioning aid. After removing the backing layer (if present) from the adhesive layer on the underside of the applicator portion 1520, the applicator is sealed to the drape, and the support layer (if present) is also removed from the applicator portion 1520. A fluidic conduit such as a tube may then be connected to the connector 1504. After the fluidic conduit is connected to a source of negative pressure, preferably with a container suitable for containing wound exudate interposed therebetween, the application of negative pressure may then be effectuated to the wound site until the wound site progresses to a desired level of healing.

During use of the system 1501, wound exudate is drawn by the negative pressure through the lower channel layer 1516. The air leak 1524 allows air to pass through the upper channel layer 1512 into the apertures through the distal ends of the layers 1512, 1514, 1516 and 1518. The negative pressure draws air passing through the upper channel layer into the lower channel layer 1516 back toward the source of negative pressure or pump. In some embodiments, the controlled air leak 1524 provides a constant flow of air through the system 1501, which then may be used to determine whether blockage or leakage is present. Causes of blockage can include, for example, situations where the lower channel 1516 becomes occluded with wound debris. Leakage causes can include, for example, improper sealing of the drape over the wound site, or physical damage to the system 1501 leading to excess air leaking into the system. The blockage or leakage may be determined, in certain embodiments, by measuring the speed of the pump while the pump works to maintain a constant negative pressure. Pump speed may also be measured indirectly by measuring the amount of voltage or signal sent to the pump.

Figure 16A:
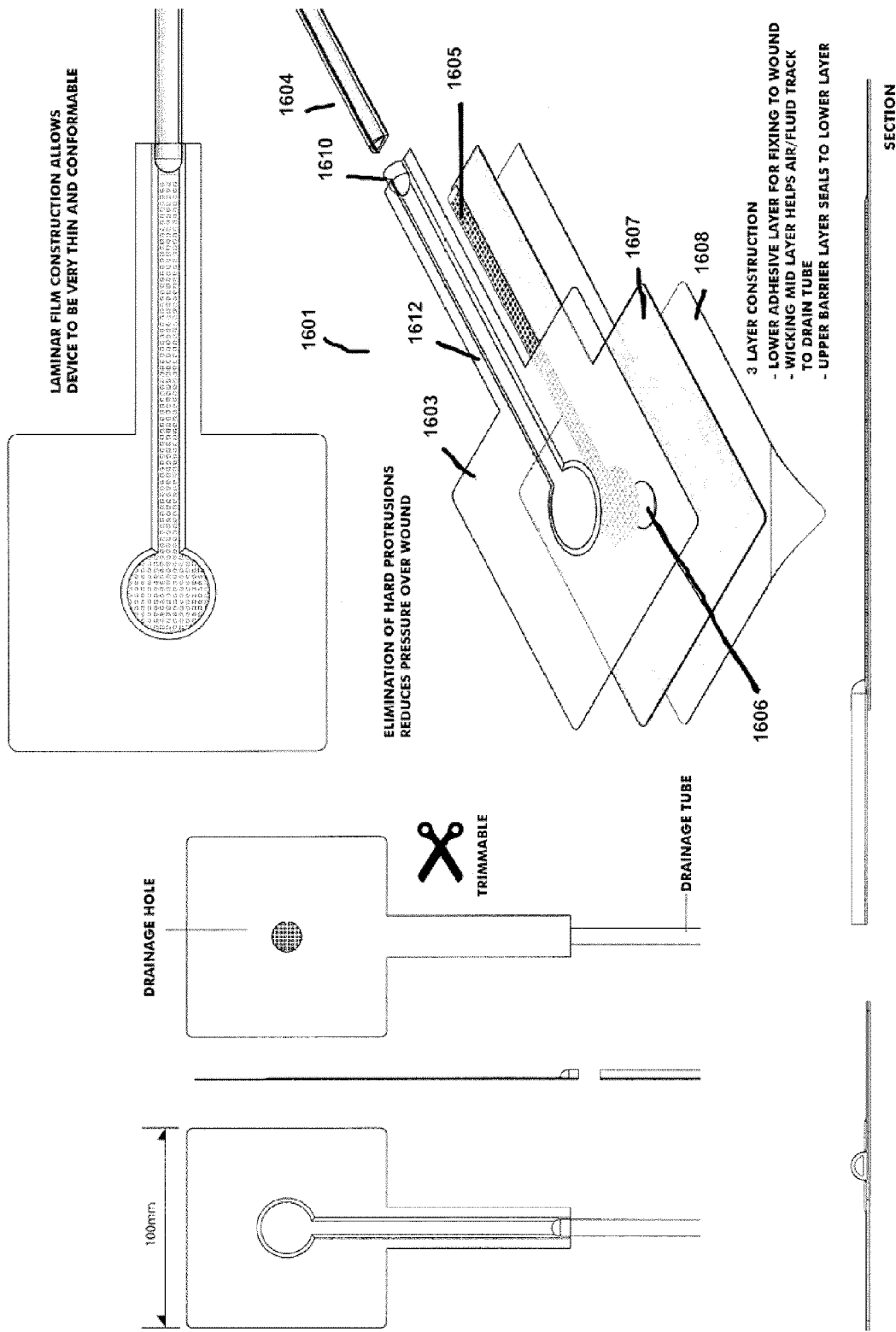
FIGS. 16A-B illustrate another embodiment of a negative pressure wound treatment system with a flexible drape integrating a suction channel therein.

FIG. 16A illustrates a wound treatment system 1601 similar to the embodiment described in FIG. 9. Here, a top layer 1603 (illustrated with a square or rectangular shape) is preferably constructed from a liquid-impermeable material, although it is preferably at least partially gas and water vapor permeable. A bottom layer 1607 (illustrated with a square or rectangular shape) may then be attached or bonded to the top layer 1603, for example using adhesives or welding, while sandwiching a wicking layer 1605 between these two layers. The bottom layer preferably has a layer of adhesive (not illustrated) disposed on at least part of the wound-facing side, which may be protected by an optional protective layer 1608 (illustrated in FIG. 16B). Preferably, at least the layers 1603, 1607, and 1608 are constructed of a material that is easily cut, for example with scissors, so that the system 1601 may be sized as appropriate for placement over a wound site.

The bottom layer 1607 preferably has at least one aperture 1606 capable of creating a fluidic connection between a wound site disposed under the aperture and the wicking layer 1605. This wicking layer 1605 is preferably an elongate layer placed between the layers 1603 and 1607, constructed from a material capable of wicking or transporting fluid from a wound site, especially while under suction. Suitable materials include but are not limited to foams as described above, woven materials, 3D knitted materials, materials constructed of from either or both hydrophilic materials (such as cotton), hydrophobic materials (such as polyethylene), or a mixtures of both. Either or both the top or bottom layers may have a channel 1612 suitable for containing the wicking layer 1605, and this channel and wicking layer are preferably enlarged at the distal end closest to the aperture 1606. As illustrated, the wicking layer 1605 has an enlarged end with a circular shape place over the aperture 1606. Preferably, a fluidic connector 1610 is attached to the top layer 1603 to permit a suction tube or other conduit 1604 to create a fluidic connection between the wound space, the wound treatment system 1601, and a source of negative pressure.

Figure 16B:
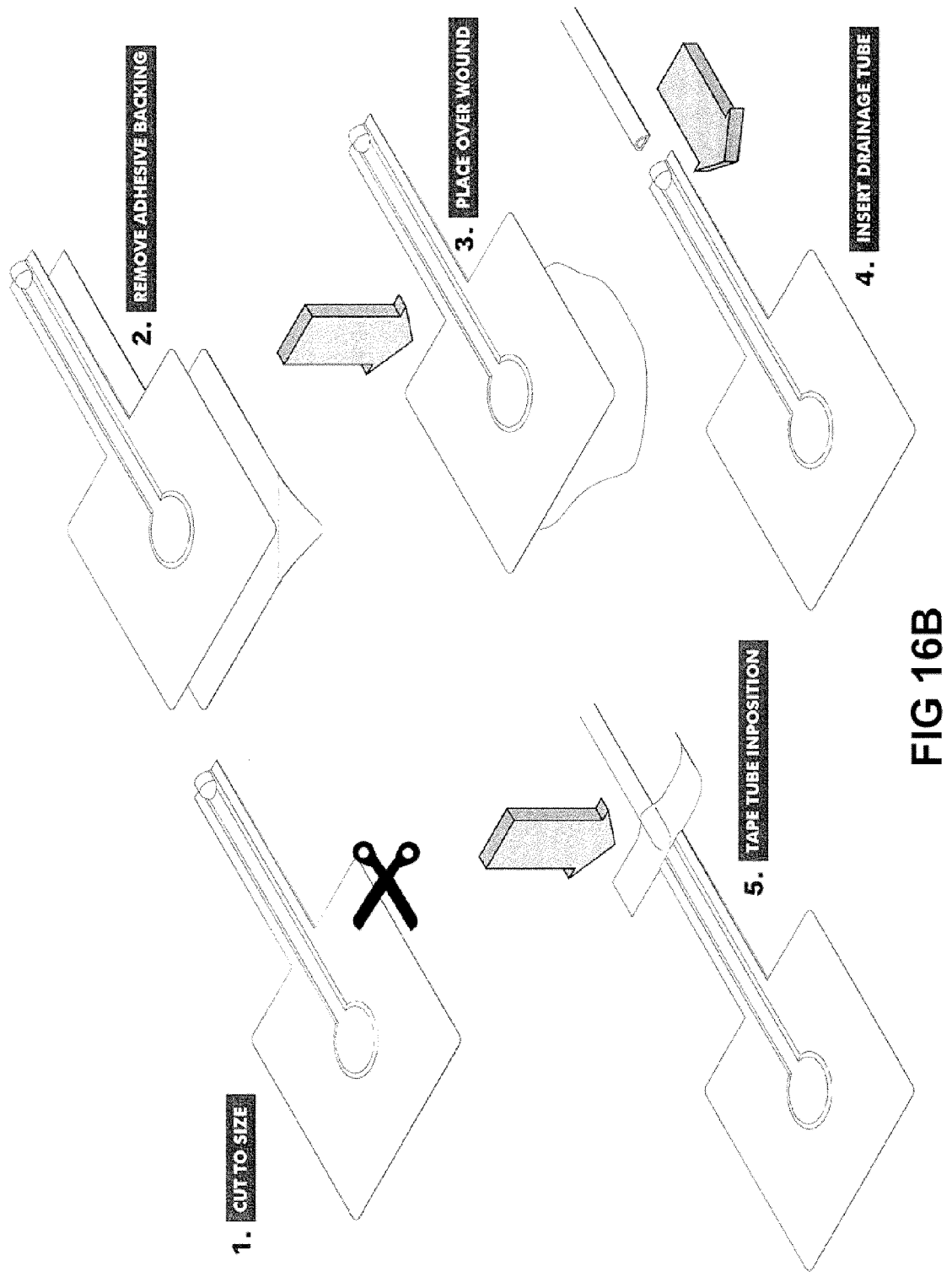

FIG. 16B illustrates a method of using the system 1601, where the system 1601 is cut to size and secured to the wound. In some embodiments, a strip of tape or other fixative may be used to secure the tube 1604 to the connector 1610.

Figure 17A:
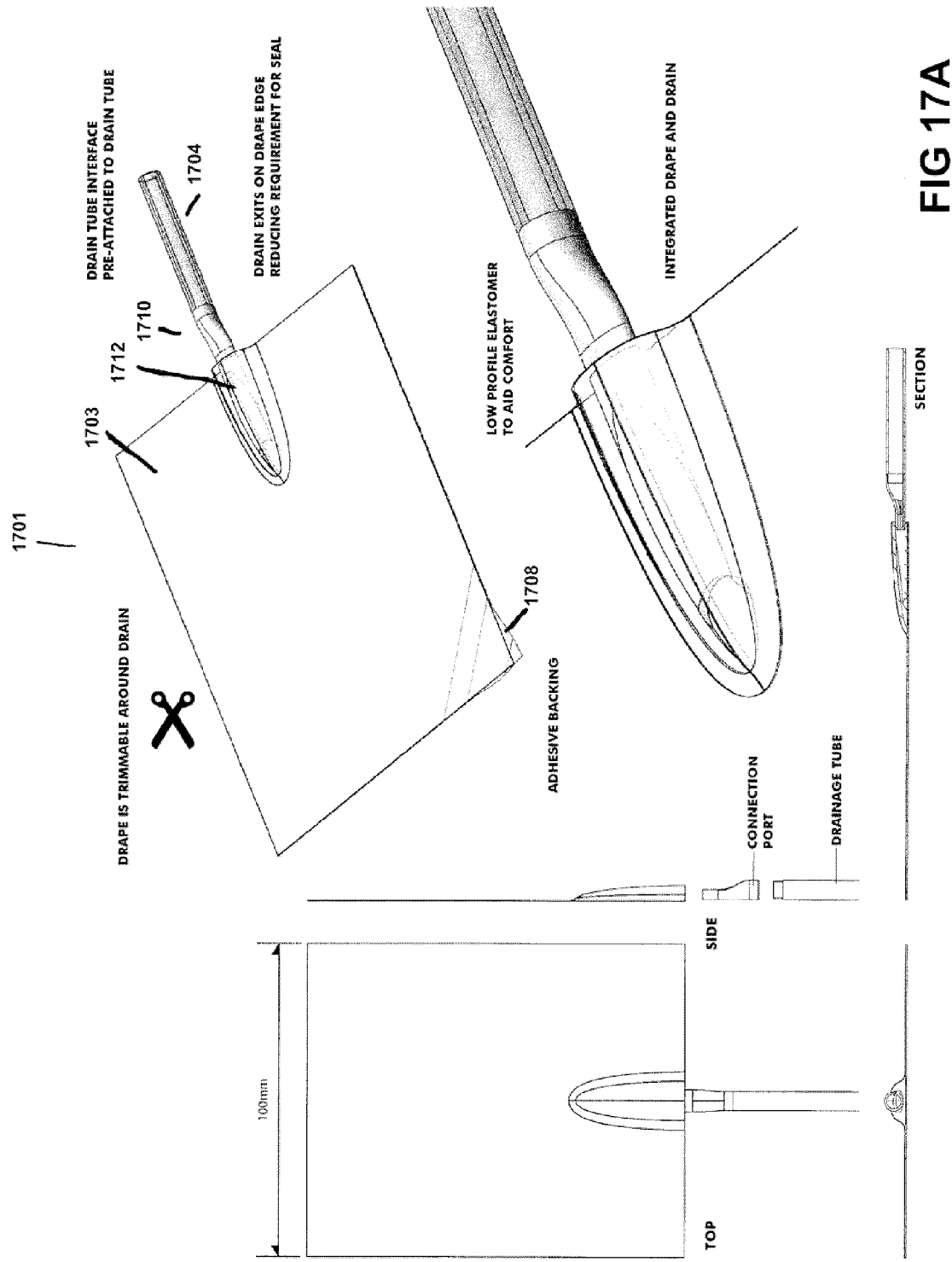

FIG. 17A illustrates an embodiment of a negative pressure wound treatment system 1701. The system 1701 preferably has a low-profile port 1712 integrated into a drape 1703 (illustrated with a square or rectangular shape), where the port 1712 preferably situated along one side of the drape 1703. The port 1712 is preferably sized to permit one side of a fluidic connector 1710 to be connected to it. The other side of the connector 1710 is preferably sized to permit a conduit or tube 1704 to be connected, although some embodiments may permit the conduit 1704 to be connected directly to the port 1712 without the use of a connector 1710. Preferably, the port 1712 is attached over an aperture through the drape 1703, permitting a fluidic connection to be made from the wound site through the port 1712, through the fluidic connector 1710, and into the conduit 1704, which is preferably connected to a source of negative pressure. A layer of adhesive may also be provided on all or some of the wound facing side of the drape 1703, and which may be protected by a release layer 1708.

FIG. 17B illustrates a method of using the system 1701 described above, where the drape 1703 is cut to size and applied to the wound.

Figure 18A:
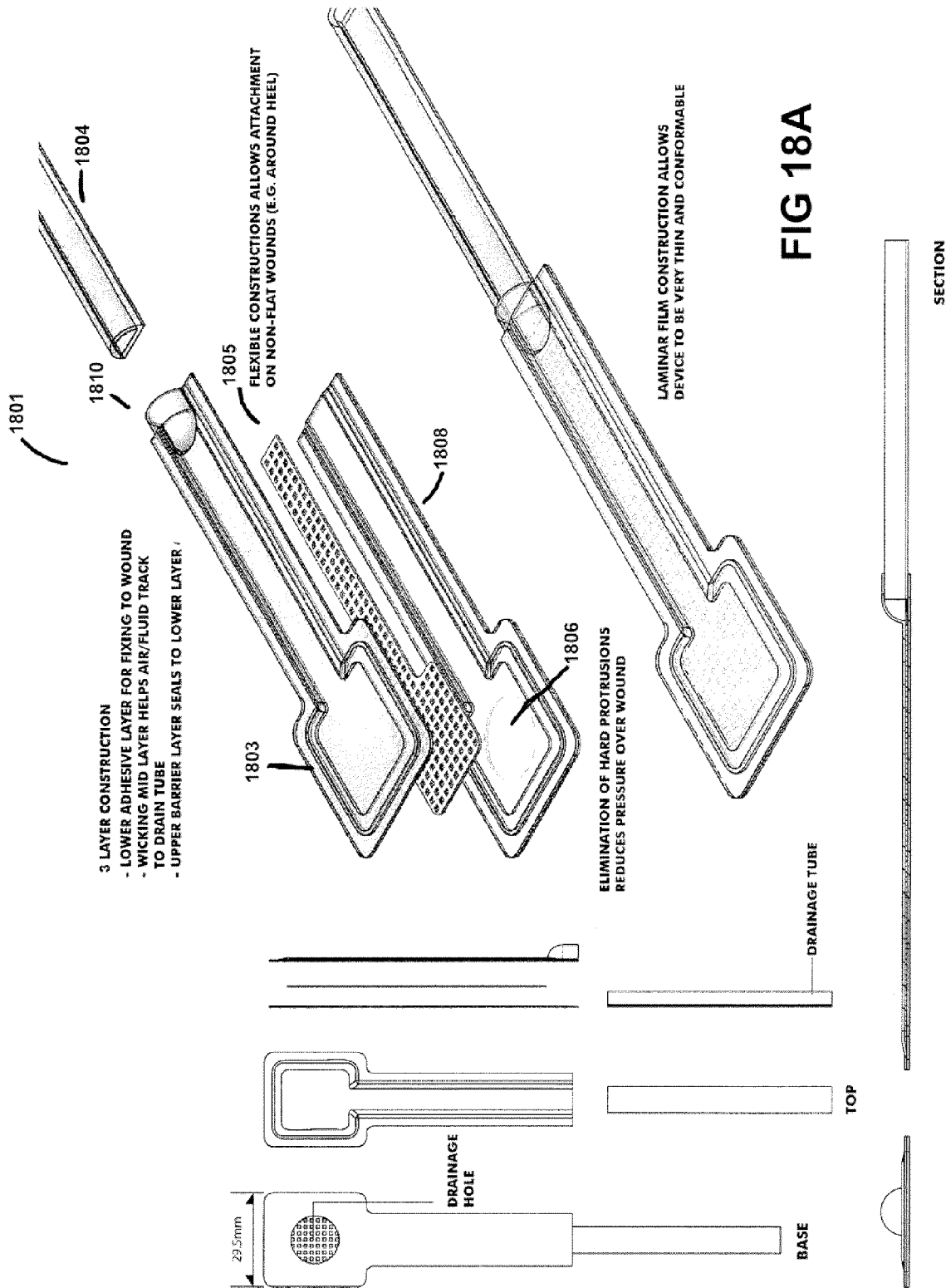
FIGS. 18A-B illustrate an embodiment of a negative pressure wound treatment system comprising a wicking layer.

FIG. 18A illustrates an embodiment of a negative pressure treatment system 1801 similar to FIG. 6A. In a preferred embodiment, a flexible wicking layer 1805 is sandwiched between a top layer 1803 and a bottom layer 1808, where the bottom layer 1808 is preferably provided with at least one aperture 1806 to expose the wicking layer to a wound site. Similarly to other embodiments, an adhesive layer and an optional protective layer may be disposed on the wound-facing side of the bottom layer 1808. A fluidic connector 1810 may be disposed at the proximal end of the system 1801 so as to create a fluidic connection between the wound site and a source of negative pressure through a conduit 1804. Preferably, the system 1801, and in particular the layers 1803, 1805, and 1808, are flexible and conformable to aid in the placement over a wound site located on, for example, a non-flat or difficult to access area of the body, such as a heel.

Figure 18B:
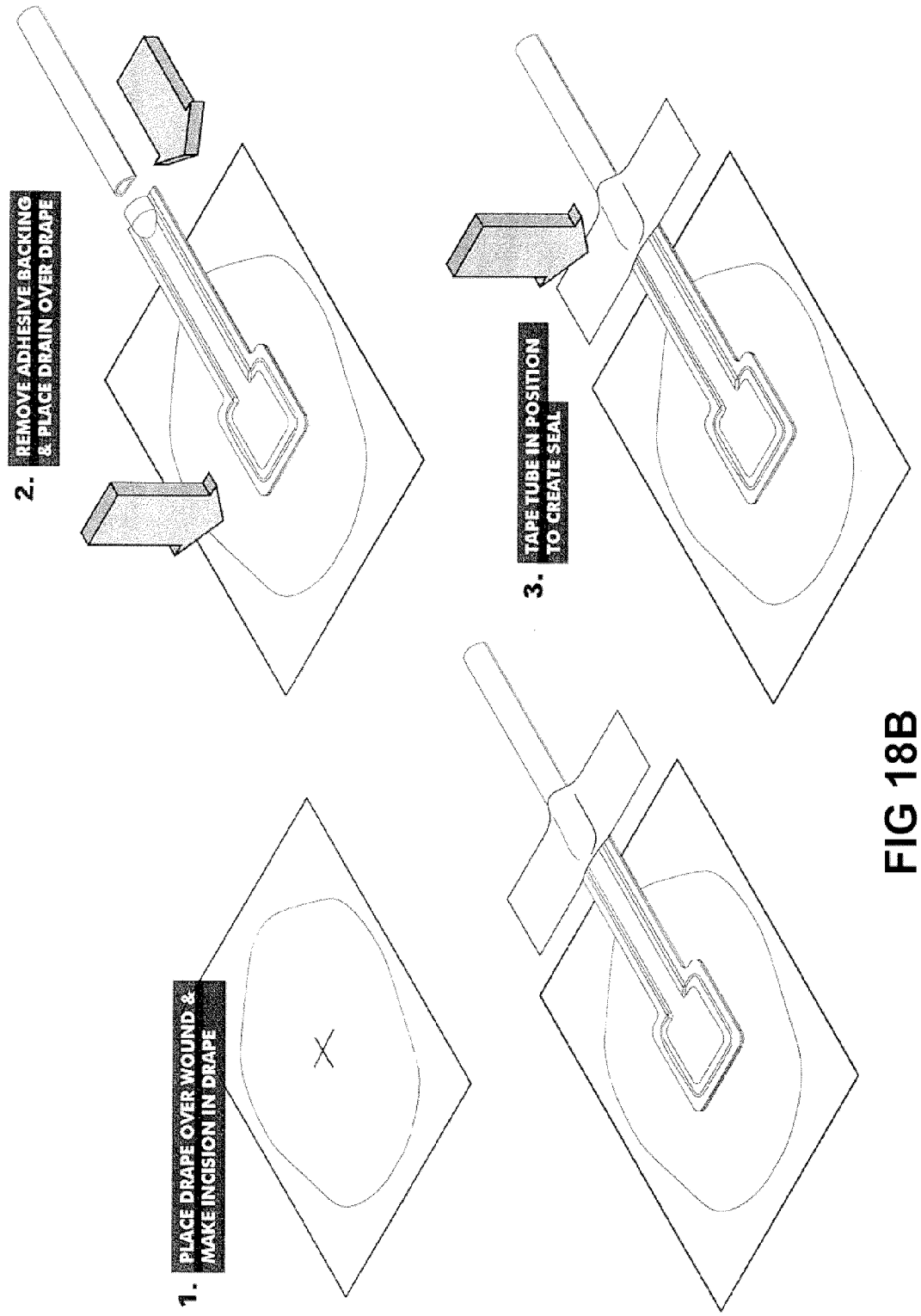

FIG. 18B illustrates a method of using the system 1801. As illustrated the system 1801 is applied to a drape having an incision or hole extending through the drape. In some embodiments, a strip of tape or other fixative may be used to secure the tube 1804 to the connector 1810.

Figure 19A:
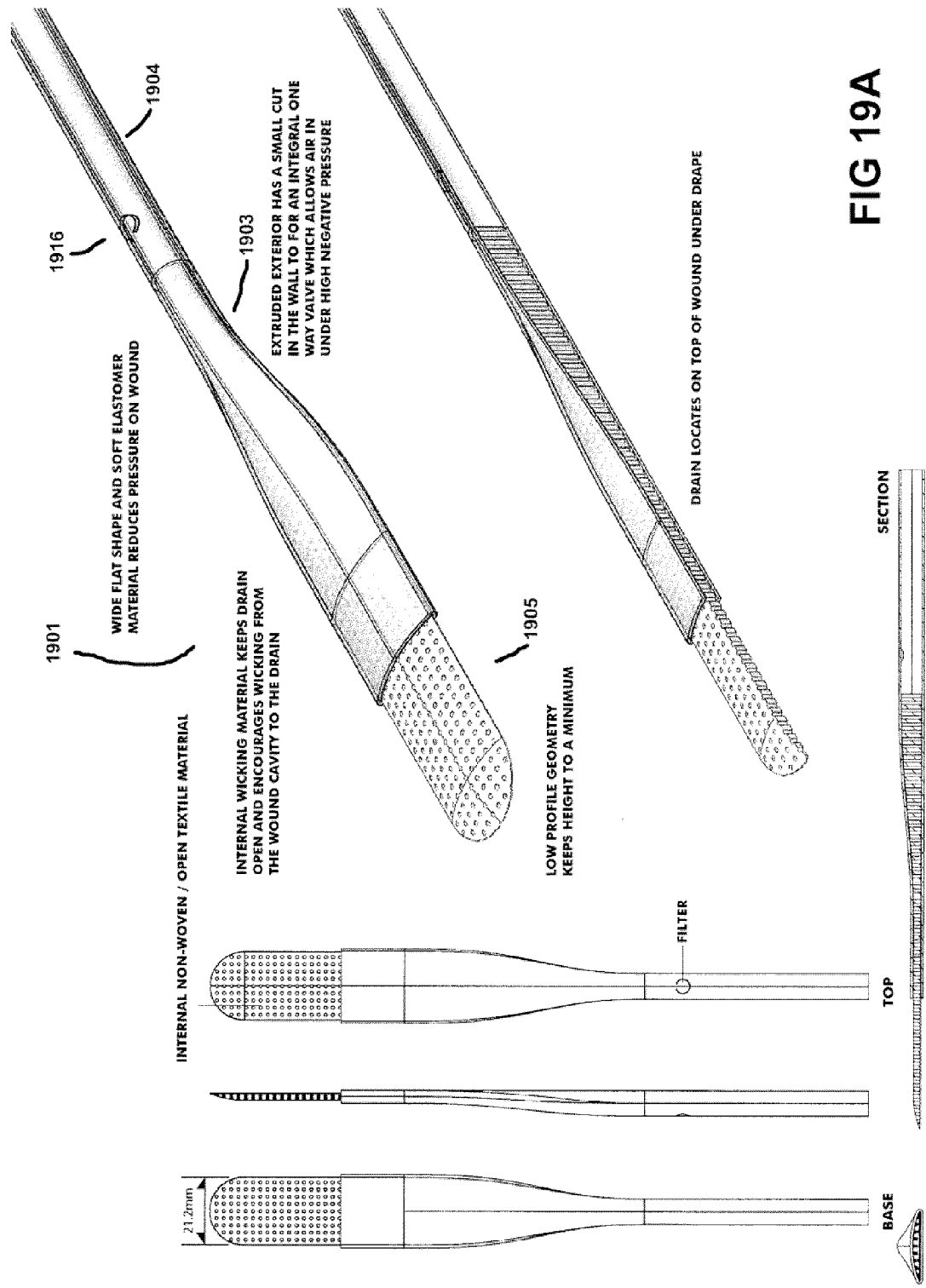
Figure 19B:
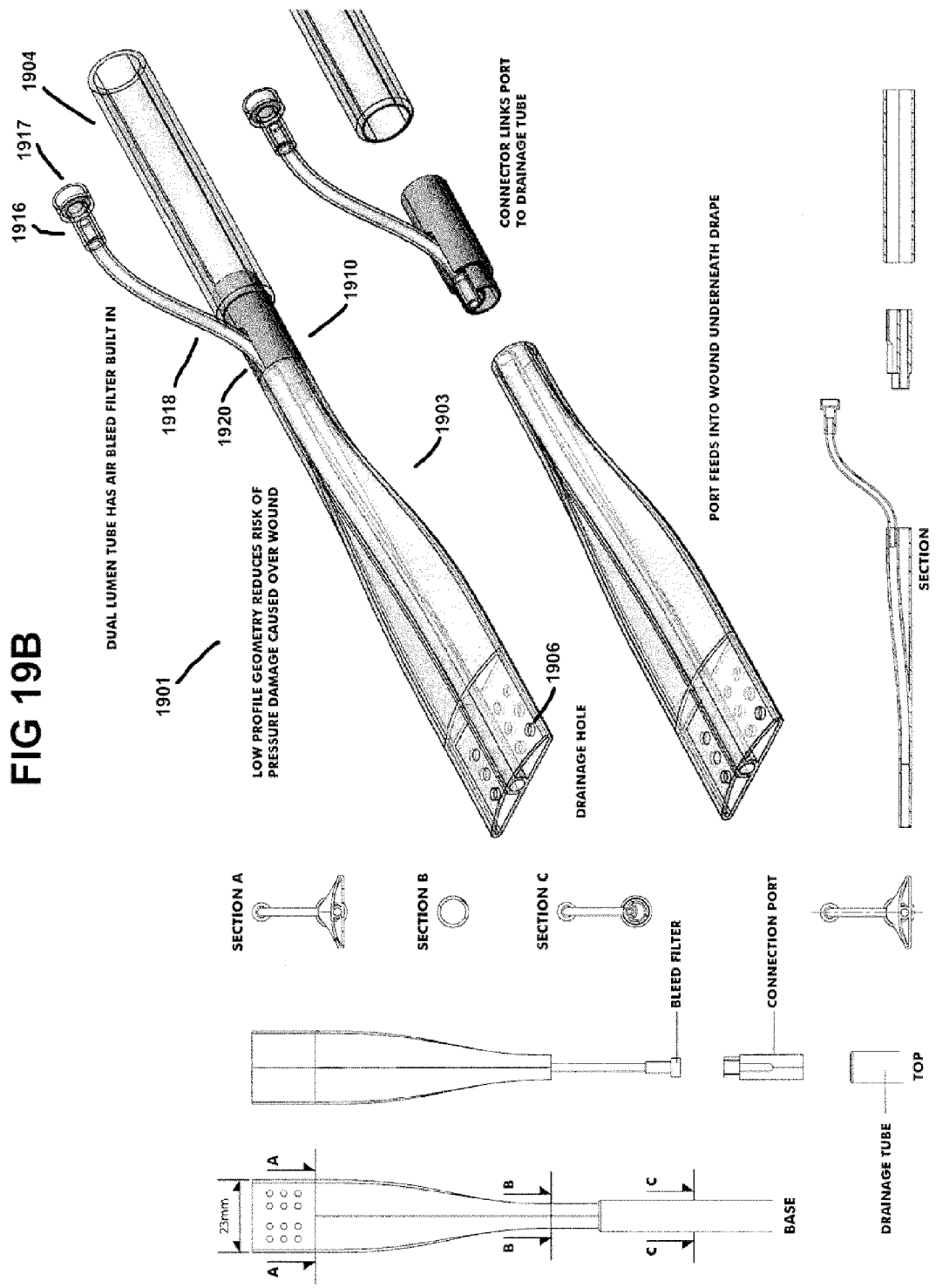

FIGS. 19A-B illustrate embodiments of a negative pressure treatment system 1901. With reference to FIG. 19A, the system 1901 comprises an exposed wicking layer 1905 extending from a flat drain portion 1903. The drain portion 1903 is preferably integrated with a tube or conduit 1904, and tapers down to become wider and flatter at its distal end. Preferably, the drain portion 1903 and the conduit 1904 are formed together as a single unit. The drain portion 1903 is also preferably constructed from a soft elastomeric material, including for example silicone, polyurethane, polyethylene, and/or polyvinylchloride, and which is able to conform to a wound site and spread out any pressure over a larger area. The wicking portion 1905 is preferably constructed from a soft material able to transmit fluid along itself, for example a nonwoven, open textile material (such as cotton gauze or XD spacer fabric (Baltex®)), thereby permitting it to be placed over or into a wound site so as to drain wound exudate and transmit negative pressure to the wound site. Some embodiments of the system 1901 may also provide for a controlled air leak 1916, similar to the air leak 1524 described in FIG. 15A. In certain embodiments, this air leak 1916 may be in the form of a one-way valve which opens and permits air to enter the system when high negative pressure is applied.

FIG. 19B illustrates another embodiment of the negative pressure treatment system 1901. Here, the drain portion 1903 may be partly bifurcated to permit a lumen 1918 attached to a controlled air leak 1916 to reach the area close to the wound site. This air leak 1916 preferably includes a filter element 1917 to prevent particulates and other contaminants from entering the wound site. The drain 1903 is preferably flat and tapered so as to present a low profile on the wound, and is preferably constructed of a soft elastomeric material of the type described above. To facilitate drainage of exudate from the wound, an aperture or apertures 1906 may be provided along the wound-facing portion of the drain. Turning back to the air leak 1916, certain embodiments provide for the proximal end of the air leak 1916 (closest to the air filter 1917) to be accommodated on a suction adapter 1910, for example in a notch 1920 made in the adapter 1910. The suction adapter 1910 is preferably designed to receive a tube or conduit 1904 and connect it to the drain 1903.

Figure 19D:
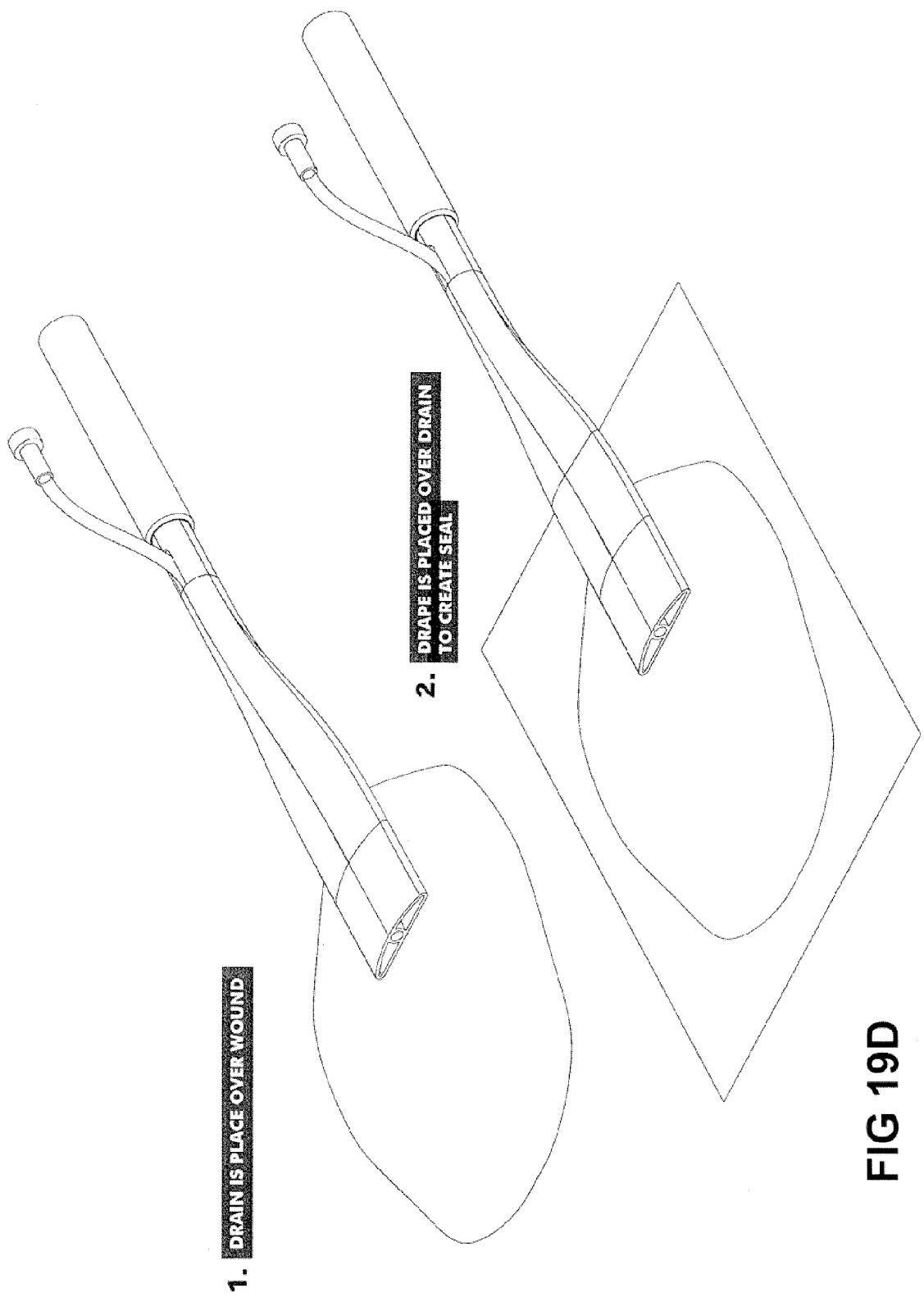

FIGS. 19C-D illustrate methods of using embodiments of the system 1901 described above.

FIG. 20A illustrates an embodiment of a negative pressure wound treatment 2001 comprising a trimmable suction port. A suction head 2006 is attached to a tail 2008 (although the head 2006 and tail 2008 may be formed as a single unit), where the tail 2008 comprises a channel 2009 disposed longitudinally inside to create a channel leading from the wound site, through at least one aperture 2012 disposed on the wound-facing side of the suction head 2006, and to a source of negative pressure. Preferably, this channel 2009 is sized to accommodate the insertion or attachment of a suction adapter 2010 and/or a conduit or tube 2004. The head 2006, although illustrated as being round, may be of any suitable shape, and preferably comprises a layer of adhesive disposed on its wound-facing side for attachment to a drape. Similar to previously-described embodiments, this adhesive layer is preferably protected by a removable backing layer.

The suction adapter 2010 may be sized to taper from a shorter, wider cross-section at its distal end inserted into the channel 2009 to a rounder profile at its proximal end to permit insertion or attachment of a tube 2004. Some embodiments may provide for a controlled air leak 2016 similar in design to other examples previously illustrated.

The tail 2008 is preferably constructed from a flexible, conformable material capable of being trimmed or cut, for example during sizing of the system 2001 for placement over a wound site. Accordingly, an operator may trim the tail 2008 as appropriate for the size and location of the wound site, followed by the insertion of, preferably, the suction adapter 2010 into the channel 2009, although some embodiments provide for the insertion of a tube 2004 directly into the channel 2009 without necessitating the use of a suction adapter 2010.

Figure 20B:
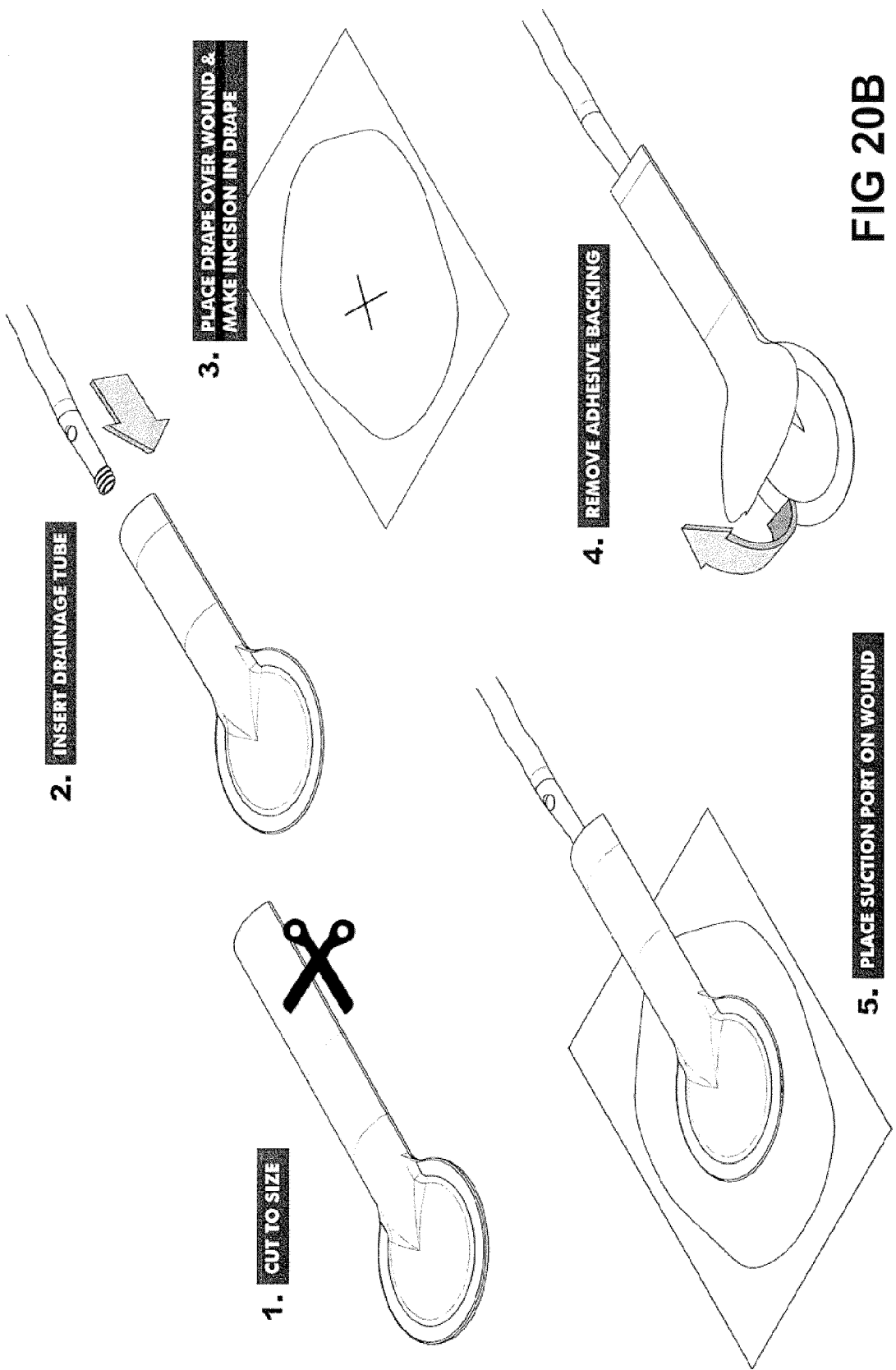

FIG. 20B illustrates a method of using the system 2001 described above.

FIG. 21A illustrates another embodiment of a negative pressure wound treatment system 2101 comprising a sealing ring similar to the system 301 illustrated in FIG. 3A. Here, a sealing disc 2103 is preferably constructed from a flexible, resilient material able to seal against a tube or conduit 2104 that is inserted through the sealing disc 2103's central aperture 2106 so as to create a fluid-tight seal. A preferred material may include silicone or polyurethane, although hydrogels may be used as well. Preferably, an adhesive layer 2108 is disposed on the wound-facing side of the disc 2103, optionally protected by a removable backing layer.

Figure 21B:
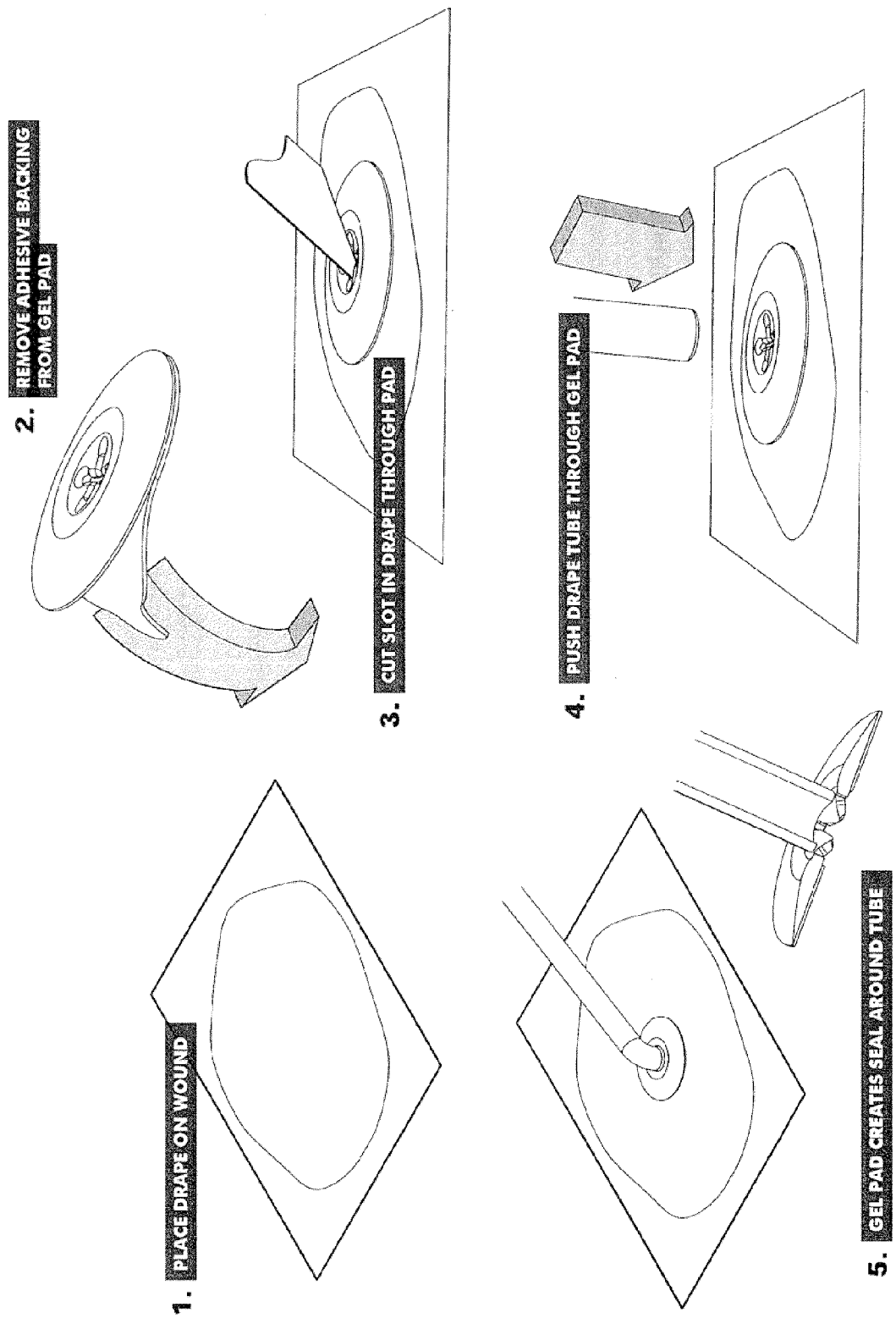

In use, and with further reference to FIG. 21B, the sealing disc 2103 is positioned over a drape covering a wound site, and the adhesive layer of the disc adhered to the drape. Flaps 2110 may also be provided to form a template or cutting guide for cutting a hole through the drape, in addition to serving as additional sealing means against the tube 2104. In some embodiments, the flaps 2110 may be arranged, for example, to form a cross or "X" shape, such that a cutting implement such as a scalpel can be used to form a correspondingly-sized aperture in the underlying drape. Subsequently, a conduit 2104 may be pushed through the aperture created through the drape. After verifying that the conduit 2104 has formed a fluid-tight seal against the disc 2103 and/or the flaps 2110, negative pressure therapy may be applied until the wound has reached a desired stage of healing.

Figure 22A:
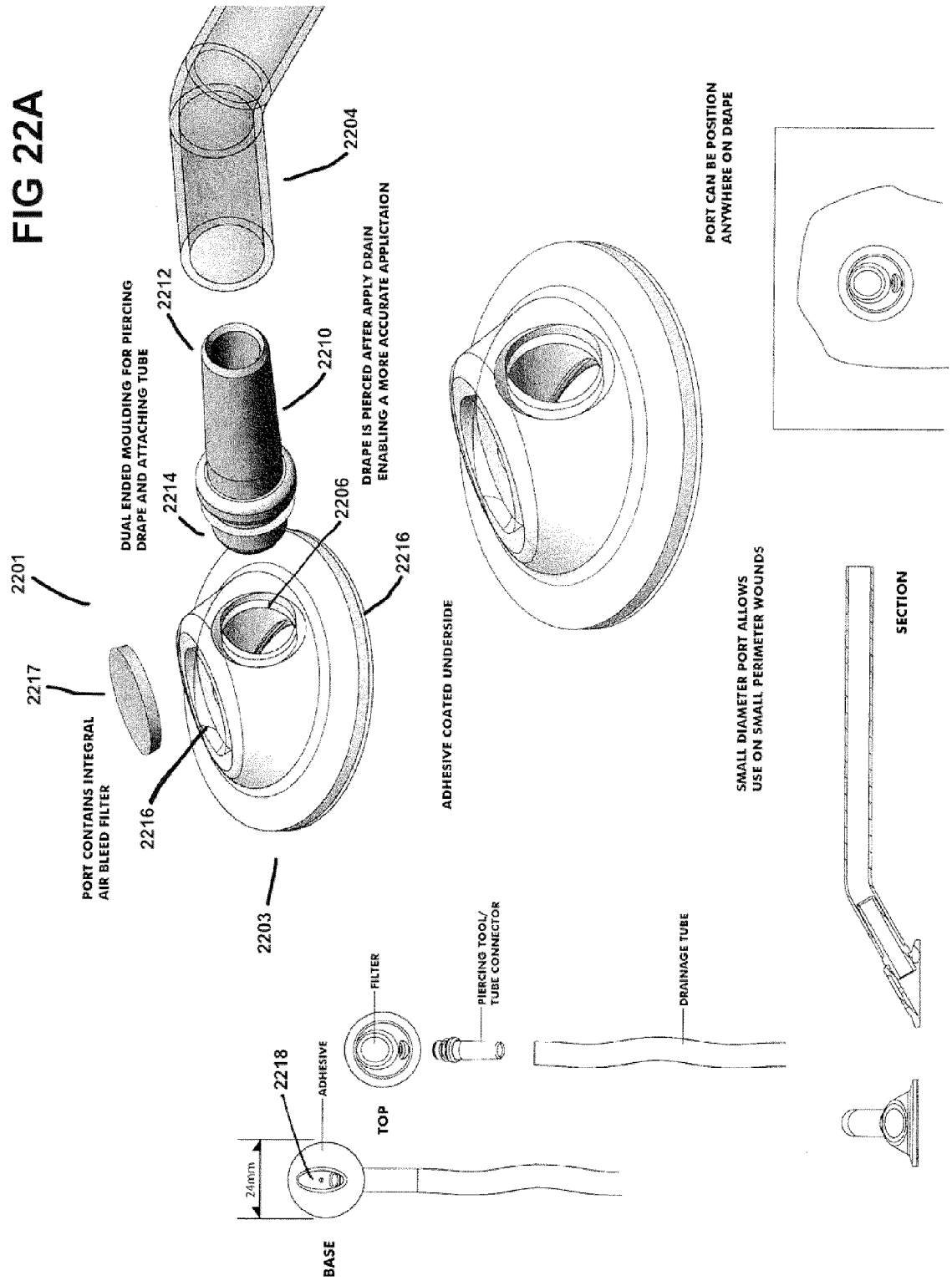

FIG. 22A illustrates an embodiment of a negative pressure wound treatment system 2201 incorporating a suction port with a piercing attachment. The system 2201 comprises a port 2203 adapted for placement over a wound site, and more preferably over a drape situated over a wound site prepared substantially in the same manner as previously described. The port 2203 preferably comprises an aperture 2218 for placement over a wound site, and this side of the port 2203 preferably comprises an adhesive layer 2216, optionally protected with a backing layer and adapted to adhere to a drape or to patient skin. The port 2203 preferably also comprises a side aperture 2206 sized to permit a fluidic connector 2210 to be connected to it. Advantageously, some embodiments permit for the port 2203 to be of a relatively small size, such that smaller wounds may be effectively treated. In some embodiments, the connector 2210 may comprise a piercing end 2212, where this piercing tip 2212 is sharpened or otherwise adapted to perforate a drape positioned over a wound site when pushed through the aperture 2206 so that the tip 2212 extends past the lower aperture 2218. This tip 2212 may also be adapted to create a fluidic connection between a tube or conduit 2204 connected to it. The other side of the fluidic connector 2210 is preferably a blunter and shorter end 2214. This end 2214 is preferably able to create a fluid-tight seal between the fluidic connector 2210 and the aperture 2206, and preferably does not extend past the aperture 2218 when inserted into the aperture 2206. Preferably, the port 2203 also comprises a controlled air leak 2216 similar to the embodiments previously described, and which may be provided with a filter 2217.

In use, and with further reference to FIG. 22B, a wound site may be prepared substantially in a manner previously described and sealed with a drape. The port 2203 may then be situated over an appropriate position over the drape, and then adhered to the drape. The piercing tip 2212 of the fluidic connector 2210 may then be pushed through the side aperture 2206 and past the bottom aperture 2218 so as to create an aperture in the drape positioned over the wound site. The connector 2210 may then be pulled out from the wound site and reversed so that the blunt end 2214 may then create a fluid-tight seal to the aperture 2206. The piercing tip 2212 may then be connected to a tube 2204, for example by slipping the end of the tube 2204 over the end 2212, although other connection means are possible. A suction source may then be activated, and negative pressure is applied to the wound and wound exudates and other materials suctioned from the wound site until the wound has reached a desired level of healing.

FIG. 23A illustrates a fluidic connector used in a negative pressure wound treatment system 2301. This system 2301 preferably comprises a port 2303, which may be shaped in a low-profile bridge shape with a flat side against a wound site. The port 2303 is preferably placed under a drape, with the drape sealed over it. Preferably, the port 2303 comprises at least one aperture 2306 on its wound-facing side, adapted to convey fluid away from a wound site and negative pressure to a wound site. The port 2303 may also be provided with a side aperture 2308 leading into a channel 2309, where the channel 2309 connects to the aperture 2306. The aperture 2308 and channel 2309 are preferably sized to receive a piercing fluidic connector 2310. This connector 2310 may be provided with a piercing tip 2312 at its distal end, where the piercing tip 2312 is sharpened or otherwise designed to create an aperture through a drape placed over the port 2303 to permit a fluidic connection to be made between the connector 2310 and the port 2303. Preferably, the port 2303 is constructed from a softer, more conformable material which may also serve to seal against the connector 2310 to aid in creating a fluid-tight seal. Some embodiments may provide for the connector 2310 to have a controlled air leak 2316, which may also be provided with a filter or a one-way valve. The one-way valve may be designed to open only under high negative pressure. The connector 2310 preferably comprises an aperture on its underside (not illustrated) so as to create a fluidic connection between itself and the aperture 2306. The proximal side 2314 of the fluidic connector is preferably constructed so as to be able to attach or connect a tube or conduit 2304 to it, where the tube 2304 is connected to a source of negative pressure.

FIG. 23B illustrates a method of using the system 2301 described above.

FIGS. 24A-B illustrate an embodiment of a negative pressure wound treatment system 2401 which comprises a port 2405 situated under a drape 2403 pierceable by a piercing fluidic connector 2410. The port 2405 is preferably situated over a wound site in need of treatment, and sealed under a drape 2403, although certain embodiments may instead provide for this port 2405 to be provided with adhesive means enabling it to be situated over an aperture made in a drape 2403. The port 2405 preferably contains at least one large aperture 2406 on its wound-facing side permitting the application of negative pressure to the wound and the removal of exudate from the wound site, in addition to two side ports 2420, 2422. The system 2401 preferably comprises a piercing fluidic connector 2410 provided with piercing tips 2412, 2413 able to pierce through the drape 2403 so as to fluidically connect to apertures 2420, 2422. One tip, illustrated for example here as tip 2412, may be used to create a fluidic connection from a tube or conduit 2404 through to the aperture 2420, where the tube 2404 is connected to the fluidic connector 2410 through hose fitting 2418. Another tip, illustrated for example as tip 2413, may serve as to create a conduit suitable for a controlled air leak 2415 through the aperture 2422 similar to those previously described. An air filter 2416 may optionally be provided.

FIGS. 25A-B illustrate an embodiment of a wound treatment system 2501 comprising a drape 2503 with a manifold 2520 integrated therein. In certain embodiments of the system 2501, a drape 2503 is provided which is trimmable and may be sealed over a wound site. A manifold 2520 may integrated or attached over a portion of the drape 2503 preferably the section of the drape 2503 which is to be placed over a wound site to be treated—and the manifold 2520 may contain multiple apertures or perforations suitable for channeling suction to the wound site and for suctioning away exudate and other fluids from the wound site. Preferably, a controlled air leak 2514 is provided that is in fluid communication with the wound site, and may for example be located in the middle of a loop that may be formed with the manifold 2520 around a wound site. This air leak preferably comprises a filter 2515. The manifold 2520 is preferably connected to a fluidic connector 2510, which may be used to connect to a tube or conduit 2504.

FIGS. 26A-B illustrate an embodiment of a negative pressure wound treatment system 2601 of a similar construction to the embodiments illustrated in FIGS. 25 A-B, but with an air leak 2614 provided on a fluidic connector 2610 rather than being formed in a central aperture. A manifold 2620 is preferably integrated or attached to the drape 2603, preferably in a semi-circular or looped configuration, with perforations or apertures suitable for conveying negative pressure and/or exudate from the wound site. This manifold 2620 is preferably connected to the fluidic connector 2610 so as to fluidically connect the wound site with a tube or conduit 2604 connected to a source of negative pressure. A second manifold 2621, connected to the air leak 2614, is preferably arranged in a similar semi-circular or looped arrangement around the manifold 2620, and permits air from the outside environment to enter into the wound site. Preferably, the air leak 2614 is protected with a filter 2615 to prevent outside contaminants from entering the wound site. In a similar fashion to the embodiment described in FIGS. 25 A-B, the drape 2603 may be trimmable for sizing purposes and may be sealed over a wound site.

Figures 27A, 27B, 27C:
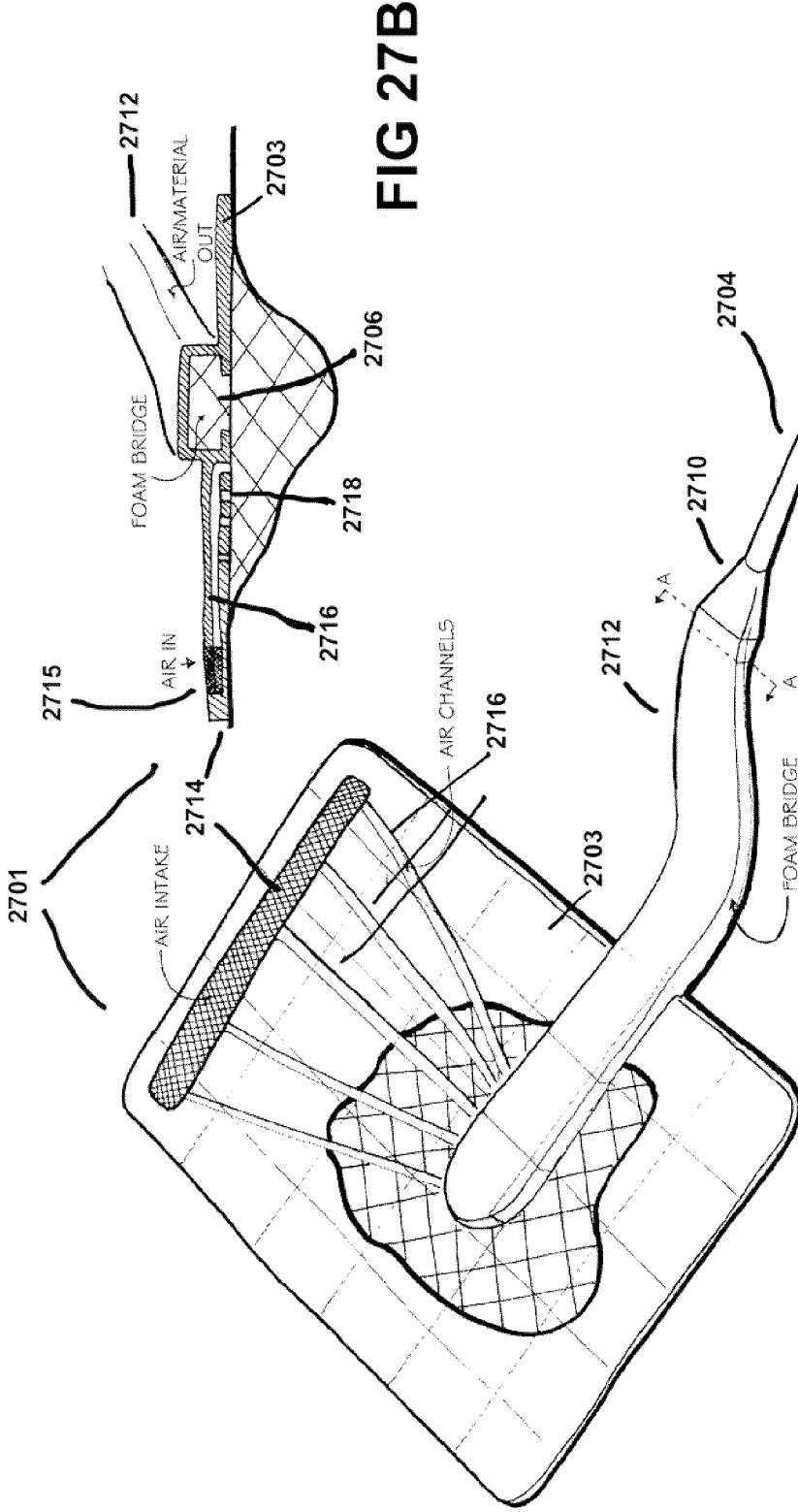
FIGS. 27A-C illustrate embodiments of a negative pressure wound treatment system comprising a flexible suction adapter with separate controlled air leak paths.

FIGS. 27A-C illustrate an embodiment of a negative pressure wound treatment system 2701 comprising a conformable wound drainage device with separate controlled air leak paths. In a preferred embodiment, a drape 2703 is provided with a conformable suction bridge 2712 preferably constructed from a fluid-impermeable material 2722. The bridge 22712 is preferably filled with a fluid-channeling material 2720, for example open-celled foam, that is at least partly resistant to occlusion due to pressure or kinking. The bridge 2712 may be bonded to or integrated with the drape 2703, or may be attached using any suitable means. The bridge 2712 is preferably provided with one or more apertures on its wound-facing side to permit wound exudate to be drawn away from the wound site using a source of negative pressure. The source of negative pressure is connected to the system 2701 through a conduit 2704 attached to a fluidic connector 2710 connected to the bridge 2712. A controlled air leak 2714 may also be provided at a location separate from the bridge 2712, with one or more air channels 2716 connecting to one or more apertures 2718 located near the wound site. Preferably, the air leak 2714 is provided with a filter 2715.

FIGS. 28A-B illustrate embodiments of a negative pressure wound treatment system 2801 comprising a controlled air leak 2814 integrated into a portion of a suction head 2805. The air leak 2814 causes air to be drawn into the suction head 2805, aiding in suctioning exudate from the wound site through the aperture or apertures 2806 disposed on the wound-facing side of the suction head 2805. Similarly to other embodiments, a fluidic connector 2810 provides a connection between a tube or conduit 2804 leading to a source of negative pressure and the suction head 2805. Preferably, the suction head 2805 has a layer of adhesive on its wound-facing side to permit attachment over an aperture made on a drape 2803 situated over a wound site. Other embodiments may instead provide for the drape 2803 to be integrated or attached to the suction head 2805 with a pre-formed aperture to be situated over the wound site.

FIGS. 29A-B illustrate embodiments of a negative pressure wound treatment system 2901 comprising a distributed negative pressure manifold. The system 2901 comprises a suction tail 2905 connected or attached to a suction head 2908, where the head 2908 comprises one or more projections 2910 extending outwardly from the center of the head 2908. As illustrated in this particular embodiment, several projections 2910 may form a web or starburst configuration, although other configurations are also possible, and may include further interlinking of the projections 2910. Each projection 2910 preferably comprises a central channel 2912 extending along the length of the projection 2910 and connected in the center of the suction head 2908. The channel 2912 is preferably connected to one or more apertures 2906 disposed along its length and suitable for suctioning wound exudate from a wound site. Preferably, a centrally-located controlled air leak 2914 communicating with the wound site is present, with a filter 2915 to keep particulates and other contaminants from entering the wound site. The filter 2915 may be constructed from any suitable material, for example Gore-Tex®. In some embodiments, at least a portion of the tail 2905 may be provided with a layer of adhesive on its wound-facing side, which can serve to better adhere to patient skin and seal the wound site.

In use, and with continued reference to FIGS. 29A-B, a wound site is prepared and cleaned in substantially the same way as described previously. The suction head 2908 is then trimmed as necessary to fit the wound site; the trimming may include cutting through the projections 2910. If so provided, an adhesive protective layer may be removed from the wound-facing side of the tail 2905 to adhere against the patient skin. Subsequently, a drape 2903 may be placed over the suction head 2908 and sealed to the skin surrounding the wound. A conduit 2904 connected to a source of negative pressure is then connected to the tail 2905, thus applying negative pressure to the wound site. When used, the head 2908 may be designed so that the drape 2903 seals against all or part of the open ends of the channels 2912 in the projections 2910 when the head 2908 is trimmed.

Figures 30A, 30B:
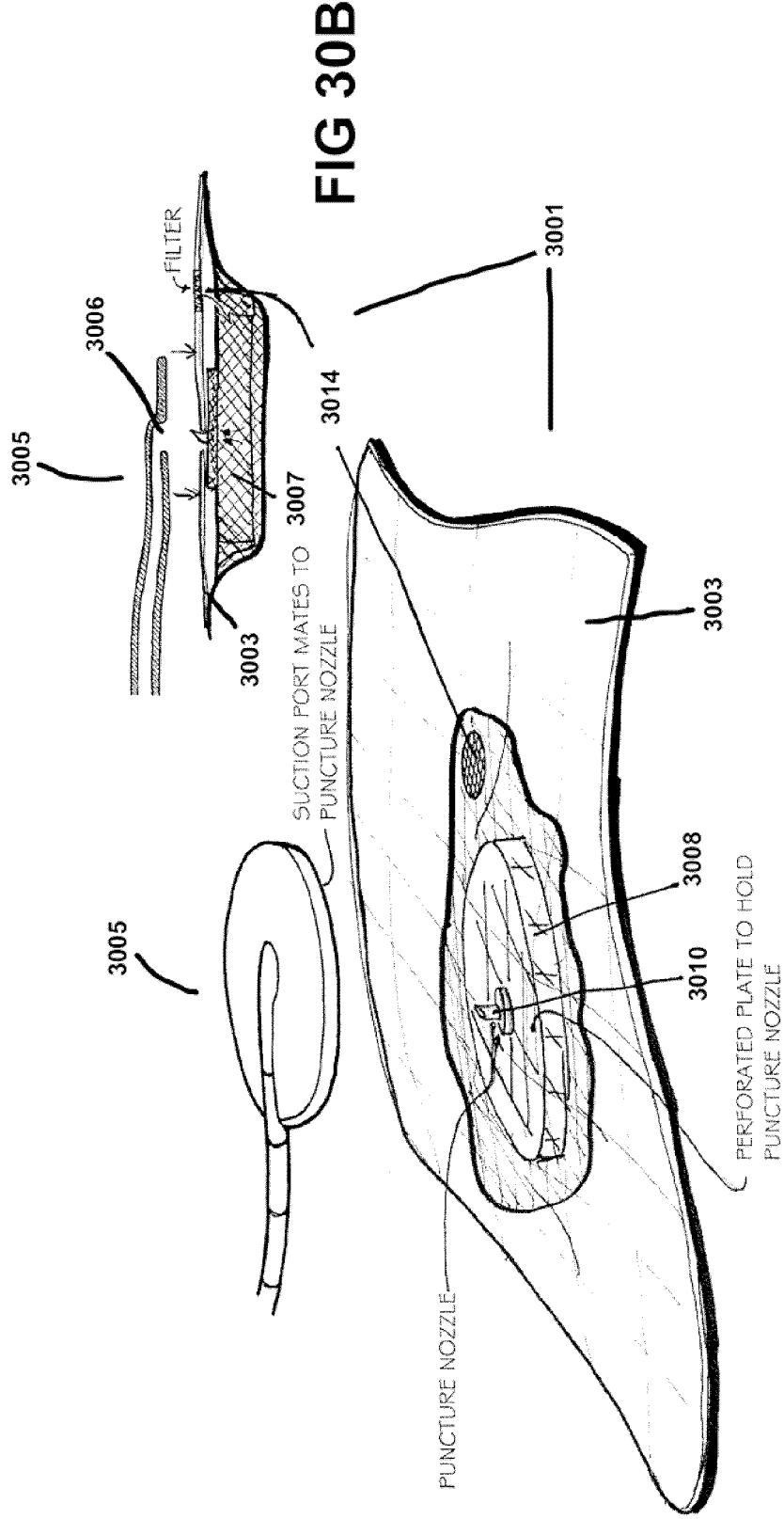
FIGS. 30A-B illustrate an embodiment of a negative pressure wound treatment system provided with a piercing nozzle.

FIGS. 30A-B illustrate an embodiment of a wound treatment system 3001 provided with a piercing nozzle 3010. Here, certain embodiments provide for the piercing nozzle 3010 to be mounted or attached to a plate 3008, where the plate 3008 is preferably perforated so as to effectively serve as a distribution manifold for negative pressure to the wound site and as a conduit to channel exudates away from the wound site. In certain embodiments, multiple piercing nozzles 3010 may be provided, and which may be distributed over the plate 3008. The piercing nozzle is preferably designed to have a sharp edge suitable for piercing a drape, for example a drape 3003 placed over a wound site and over the piercing nozzle 3010 and plate 3008, and the nozzle 3010 is also preferably comprises a conduit or channel therein suitable for conveying fluid and/or negative pressure. In a preferred embodiment, a suction head 3005 is provided with at least one aperture 3006 disposed on its wound-facing side. In some embodiments, an adhesive layer may be provided on the wound-facing side of the head 3005 suitable for securing the head 3005 to the drape 3003. In additional embodiments, the drape 3003 may be mechanically fastened to the head 3005 by means of features incorporated on the wound-facing side of the head 3005 suitable for mechanical fastening of the head 3005 to the drape 3003. The aperture 3006 may be designed so as to receive at least part of the piercing nozzle 3010, so as to create a fluidic connection between a wound site and a source of negative pressure connected to the head 3005 through the piercing nozzle 3010 and the aperture 3006. Some embodiments may also provide a controlled air leak 3014 optionally provided with a filter and integrated into the drape 3003; preferably, this air leak 3014 is located in a region in close proximity to the plate 3008.

With continued reference to FIGS. 30A-B, in use a wound site is prepared substantially as described previously. The plate 3008 is preferably placed over the wound site area, with the piercing nozzles 3010 facing upward. The drape 3003 is then placed over the wound site and over the plate 3008, and then sealed to the skin surrounding the wound site. Subsequently, the suction head 3005 is pressed over the nozzles 3010, causing the nozzles 3010 to pierce the drape 3003 and be received into the aperture 3006. The wound site is then connected to a source of negative pressure and treated until the wound has attained a selected stage of healing.

Figures 31A, 31B:
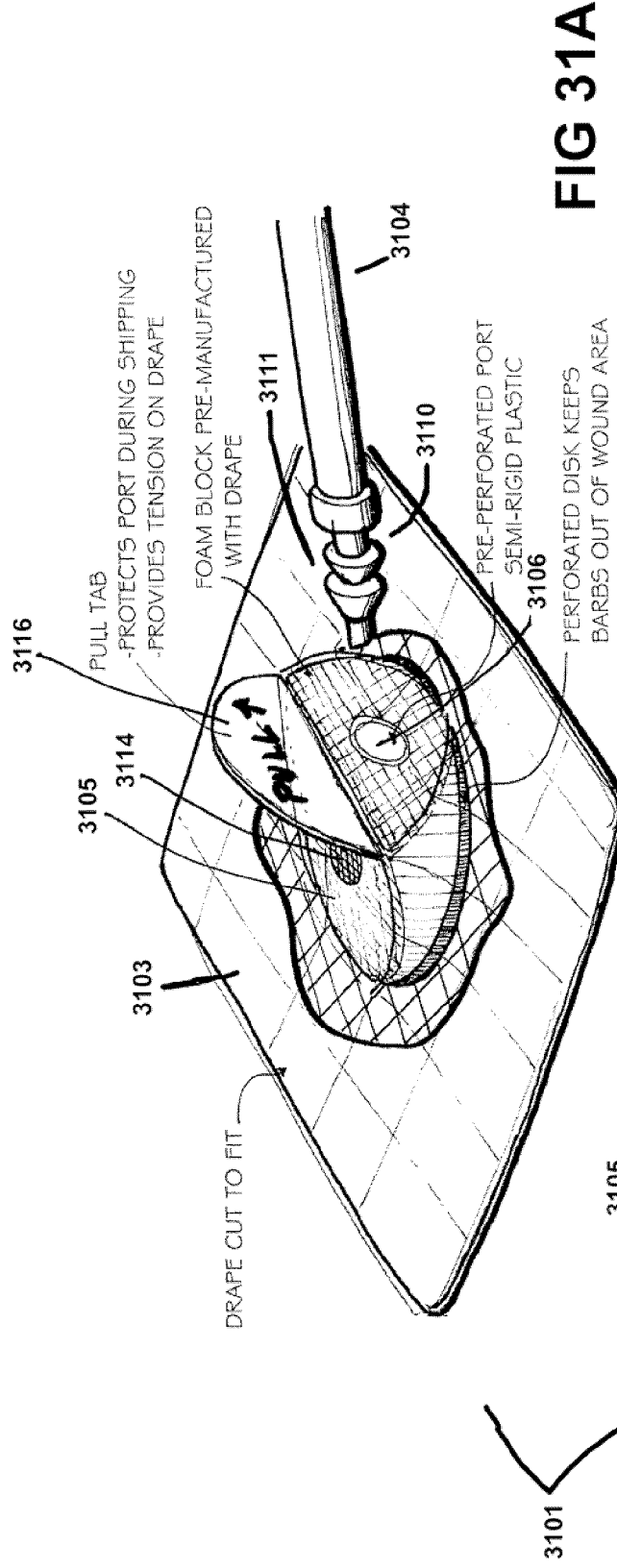
FIGS. 31A-B illustrate an embodiment of a negative pressure wound treatment system with a port, a piercing connector, and a controlled air leak.

FIGS. 31A-B illustrate an embodiment of a negative pressure treatment system 3101 comprising a suction port which shares some similarities with the embodiments described in FIG. 22. In a preferred embodiment, the system 3101 comprises a suction port 3105 integrated with a drape 3103. The port 3105 is preferably constructed from a section of foam or other porous material, with its outside surface surrounded by a semi-rigid plastic. In some embodiments, the drape 3103 may be provided pre-attached to the port 3105, for example by adhering the port 3105 onto the top side of the drape 3103, or by attaching the port 3105 to the around and to bottom side of the drape 3103. The port 3105 preferably comprises a controlled air leak 3114 which communicates to the interior of the port 3105. The port 3105 may also comprise an aperture 3106 able to receive a connector 3110 and/or a tube or conduit 3104. Preferably, this aperture 3106 is sealed with, for example, a thin layer of plastic that can be perforated with a connector 3110. The connector 3110 is preferably designed with a sharp tip able to pierce a layer of plastic disposed over the aperture 3106, and is able to create a fluid-tight seal between itself and the aperture 3106, for example by means of barbs 3111. A removable flap 3116 may also be attached to the port 3105 and made to overlay the aperture 3106 so as to protect the aperture 3106 from damage during handling. The flap 3116 may also be pulled during insertion of the connector 3110 to as to place the drape 3103 under tension and facilitate its perforation. To prevent the connector 3110 and/or tube 3104 from projecting past the port 3105 and possibly disturbing the wound site, a plate 3107 may be attached or formed with the port 3105. The plate 3107 is preferably constructed from a resilient, harder material such as a plastic and capable of resisting piercing when pushed by the connector 3110. In order to channel wound exudate from the wound site, the plate 3107 preferably comprises one or more apertures 3108.

FIGS. 32A-K illustrate embodiments of a negative pressure system 3201. Here, the system 3201 comprises a port 3203 with a layer of adhesive 3205 disposed on its underside. This adhesive layer 3205 may be placed over an aperture 3207 on a drape 3202 placed over a wound to secure the port 3203. Alternatively, the port 3203 may be adhered or welded to a smaller drape, optionally provided with a further adhesive layer. In some embodiments, this port 3203 may be relatively small, for example 17 mm across, although other sizes may also be appropriate. The port 3203 may be provided with a through opening 3209, preferably located on a vertical axis; this opening 3209 may also be provided with a removable cover 3210, which can in turn also function as a controlled air leak 3212. Preferably, the air leak 3212 comprises a filter 3213 to prevent contaminants from entering the wound. The opening 3209, preferably when in a vertical configuration, can be designed to accommodate a cutting tool 3215 designed to pierce an underlying drape. The port 3203 is also provided with a connection port 3217 to which a tube 3204 may be connected. In some embodiments, the tube 3204 is pre-assembled to the connection port 3217.

In use, after adhering the port 3203 over a drape placed over a wound, the removable cover 3210 is removed, and the cutting tool 3215 is pushed through the opening 3209 so as to pierce the drape. The cover 3210 is replaced and the tube 3204 is connected (if necessary) to the port 3203 and then connected at its downstream end to the source of negative pressure.

FIGS. 33A-H illustrate embodiments of a negative pressure treatment system 3301 provided with a template 3305. This template 3305 is preferably provided with a double-sided adhesive layer 3306 on its bottom-facing side, and comprises one or more cutting guides 3307. These guides 3307 may, for example, be in the shape of a cross as illustrated, or may take other forms. The system 3301 also comprises a port 3309 which is preferably of a similar size and shape to the template 3305, and which may have a tube 3304 pre-attached to itself. Obviously, some embodiments may instead provide for detachable tube 3304. In one non-limiting embodiment, the port 3309 measures approximately 25 mm across.

In use, the template 3305 is used to guide and control the size of the drape incision. It is placed over a drape 3311, preferably by adhering the bottom-facing side of the double-sided adhesive layer 3306 to the drape 3311 (an optional release layer 3312 may also be present). Subsequently, an incision is made through the cutting guides 3307 into the drape 3311 to create an aperture sufficient for a fluidic connection. Subsequently, the template 3305 is peeled away from the double-sided adhesive layer 3306 (optionally with the aid of a tab 3313) to reveal a top-facing layer of adhesive upon which the port 3309 may then be attached. Optionally, the double-sided adhesive layer 3306 may be pigmented to allow the user to easily align the port 3309 on the adhesive layer 3306. Alternatively, the port 3309 may be adhered or welded to a smaller drape, optionally provided with a further adhesive layer, and which may then be placed over the aperture formed under the adhesive 3306. Treatment of the wound then proceeds in a similar fashion as to the other embodiments previously described. An advantage of this cutting template 3303 is that the drape aperture size may be controlled so as to permit the use of a smaller port 3309, and which may be advantageous in treating smaller wounds.

FIGS. 34A-H illustrate embodiments of a negative pressure treatment system 3401 comprising a port 3403 including a protruding channel 3405 disposed on its underside. The channel 3405, and optionally part or the remainder of the port 3403 may be constructed from a soft and pliable material, including gels, foams, and combinations thereof such as silicone, polyurethane, polyethylene, polyvinyl chloride, and other plastics. The protruding channel 3405 may be useful in properly positioning the port 3403 over an aperture made into a drape 3413, and the preferably soft and conformable material used to construct it minimizes pressure damage caused by the port and/or channel pressing onto the wound. In some embodiments, the port 3403 measures approximately 17 mm across, although larger or smaller sizes may be used. A layer of adhesive 3407 with an optional release layer 3409 are preferably provided on the underside of the port for attachment to a drape, and the port 3403 should also comprise an opening 3411 so as to permit connection of a tube 3404. In an alternative embodiment, the port 3403 may be adhered or welded to a smaller drape, optionally provided with a further adhesive layer.

In FIGS. 35A-H, embodiments of a negative pressure system 3501 comprise a port 3503 attached to a drape strip 3505. The port 3503 is preferably constructed from a soft, conformable material, and includes an attachment port 3507 for a tube 3504 to be connected thereto. The underside of the drape strip 3505 has a layer of adhesive 3509, optionally covered by a release layer 3510. In use, the drape strip 3505 is adhered directly over a prepared wound, without the use of an additional drape, but with the wound preferably filled with a wound-packing material. If no wound packing material is used, then the adhesive 3509 is preferably chosen to be minimally adherent to wound tissue but sufficiently adherent to the skin surrounding the wound, for example a water-soluble acrylic adhesive, such that a fluid-tight seal may be made. After placing the initial drape strip 3505 over the wound, additional drape strips 3506 (typically not provided with a port) are placed in an overlapping fashion over the wound so as to create a fluid-tight seal over the entire wound. If necessary, the drape strips 3505 and 3506 are trimmed to fit. Subsequently, the tube 3504 is connected to a source of negative pressure and treated in a fashion as previously described, with wound exudate being carried through an aperture 3508 situated on the underside of the drape strip 3505 and communicating with the port 3503. In some embodiments, the drape strip 3505 and/or the additional drape strips 3506 measure approximately 20 mm across, although other sizes may be used.

FIGS. 36A-I illustrate embodiments of a negative pressure treatment 3601. Here, a drape 3603 is provided with one or more premade drainage channels 3605 leading to a drainage hole 3607 preferably centrally-located on and going through the drape 3603. The drape 3603 is provided with a layer of adhesive on its underside, optionally protected by a release layer 3610. In one non-limiting embodiment, the drape measures approximately 100 mm on one side. The drainage channels 3605 run from the edge of the drape 3603 to the drainage hole 3607, and are dimensioned so as to permit a tube 3604 to be slid into them so as to create a fluidic connection with the drainage hole 3607. Preferably, several drainage channels 3605 are provided, with these channels 3605 facing different directions on the drape 3603 so as to permit a tube 3604 to be connected from different directions. For example, four drainage channels 3605 may be provided at right angles to each other as illustrated. Of course, other arrangements are possible, such as a "starburst" configuration with more drainage channels 3605. Preferably, the drainage channels are constructed so as to remain sealed until a tube 3604 is inserted into them.

In FIGS. 37A-G, embodiments of a negative pressure treatment system 3701 are shown, the system 3701 comprising a drape 3703 and a port 3705 connected to a tube 3704. Here, the drape 3703 is preferably constructed from a material provided with miniature, self-sealing openings 3707. These openings 3707 may be molded or cut into the drape 3703, and are ordinarily fluid-tight. The underside of the drape 3703 as well as the underside of the port 3705 may be provided with a layer of adhesive covered by an optional release layer 3709. In an alternative embodiment, the port 3705 may be adhered or welded to a smaller drape, optionally provided with a further adhesive layer. Under the application of negative pressure, for example through the port 3705, these openings 3707 open so as to permit the transmission of negative pressure from the port to the wound space beneath the drape. In other embodiments, the openings 3707 may act as one-way valves. This drape 3703 has several advantages, such as not requiring a separate aperture to be cut into the drape 3703, while also permitting the port 3705 to be positioned at any appropriate location on the drape 3703. In some embodiments, the port 3705 measures approximately 25 mm across.

FIGS. 38A-I illustrate embodiments of a negative pressure treatment system 3801 which comprise a bayonet connection between a ring 3803 and a port 3805. The port 3805 has one or more tabs 3807 which mate into a corresponding recess 3808 located on the ring 3803, which in some embodiments may have a diameter of approximately 35 mm. The ring 3803 also includes a groove (not illustrated) adjoining the recess 3808 and configured to receive the tab(s) 3807 and thus create a fluid-tight connection. The ring 3803 preferably comprises an adhesive layer disposed on its underside (optionally protected by a release layer 3811), which may be used to secure it to a drape. In an alternative embodiment, the ring 3803 may be adhered or welded to a smaller drape, optionally provided with a further adhesive layer. The port 3805 has a connector 3809 configured to connect to a tube 3804. In use, the ring 3803 is placed and preferably adhered over an incision 3812 made on a drape 3813 placed over a wound. Subsequently, the port 3805 is positioned over the ring 3803 so that the tab 3807 may fit into the recess 3808. Once so positioned, the port is rotated, for example by from 30 to 90°, so that the tab 3807 slides into the groove adjoining the recess 3808 so as to create a fluidic seal. The user may therefore choose the orientation in which the tube connector 3809 points irrespective of the orientation of the ring 3803.

Turning now to FIGS. 39A-B, one embodiment of a negative pressure treatment system 3901 uses a low-profile port 3903 configured to attach to a one-way valve 3905 (which can for example be a reed or flap valve) attached to a drape 3907. In some embodiments, the one-way valve 3905 may be pre-attached to the drape 3907 prior to placing it over a wound. In other embodiments, the valve 3905 is attached onto the drape 3907 after the drape has been placed over the wound and an incision or aperture made into it, or else the valve 3905 in incorporated into a port that is provided pre-attached or welded to a drape. The port 3903 preferably comprises one or more air leaks 3909, which are of a similar design to those illustrated in other embodiments herein. A tube 3904 may be attached to the port 3903.

Figure 40:
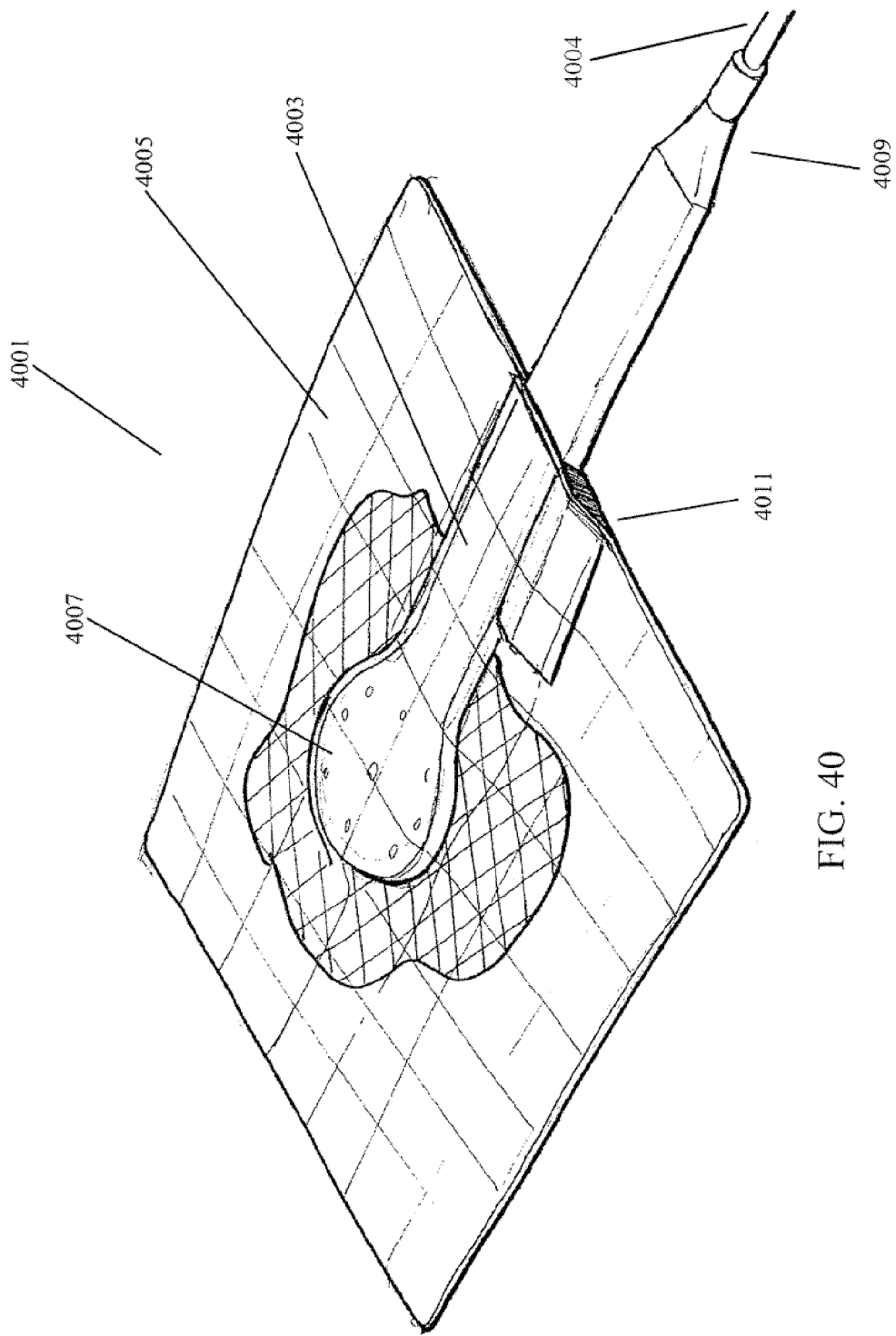
FIG. 40 illustrates an embodiment of a negative pressure wound treatment system provided with a low-profile fluidic connector.

FIG. 40 illustrates an embodiment of a negative pressure treatment system 4001 that is somewhat similar in operation to the embodiment illustrated in FIGS. 24A-B. Here, a low-profile fluidic connector 4003 may be slid under a drape 4005 situated over a wound. The connector 4003 comprises a suction head 4007 at its distal end, and has an adaptor 4009 at its proximal end configured to connect to a tube 4004. At the boundary of the drape an air leak filter 4011 may be placed next to the connector 4003 to permit for controlled air flow into the wound space. The filter 4011 may either be attached to the connector 4003 to allow for air flow into the interior channel of the connector 4003 or else may be configured to let air into the wound space without going through the connector 4003. In an alternative embodiment, the fluidic connector 4003 may be adhered or welded to the drape 4005 prior to use.

Figures 41A, 41B:
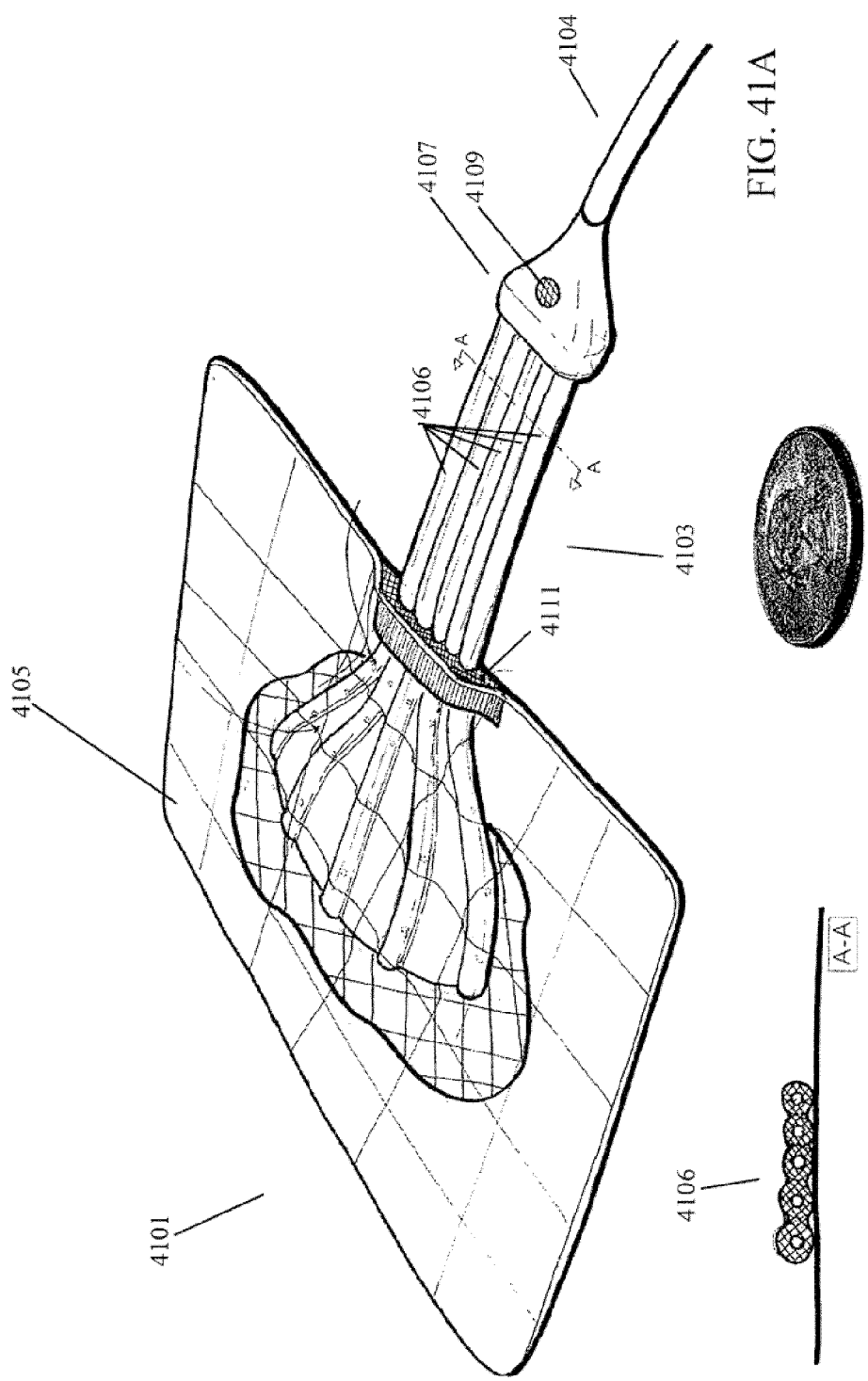
FIGS. 41A-B illustrate an embodiment of a negative pressure wound treatment system provided with a plurality of suction tubes.
Figure 53A:
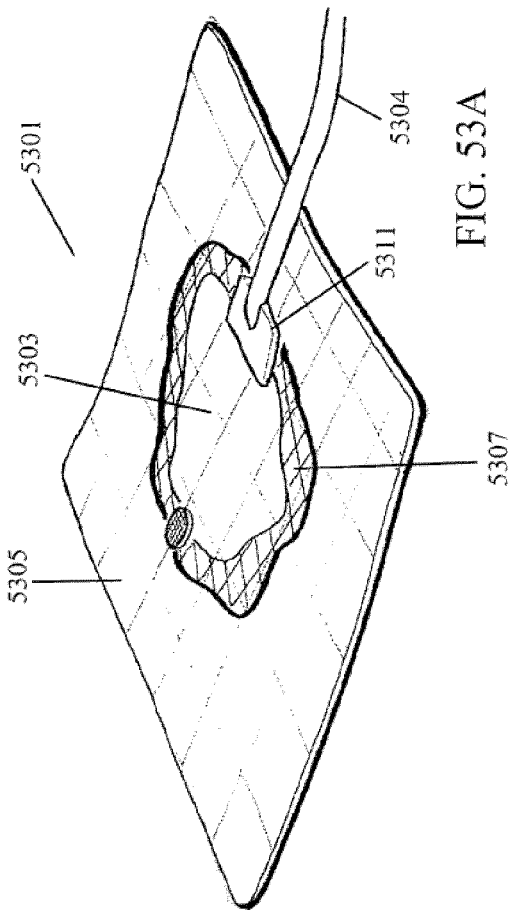
FIGS. 53A-D illustrate a different embodiment of a negative pressure wound treatment system provided with a bladder.
Figure 53B:
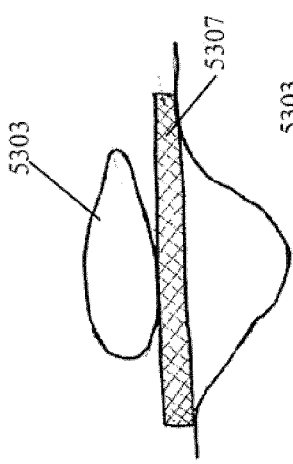
Figure 53C:
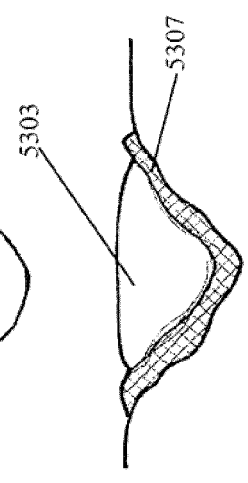
Figure 53D:
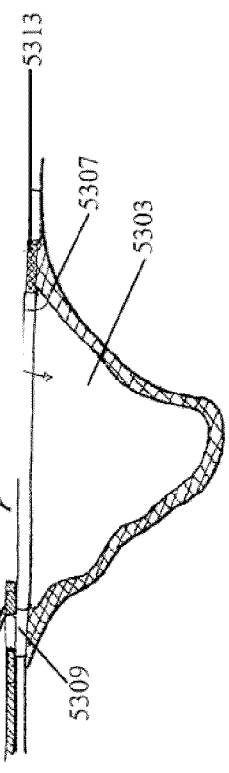

FIG. 41A illustrates an embodiment of a negative pressure treatment system 4101 comprising a suction adapter 4103 placed underneath a drape 4105. The suction adapter 4103 comprises a plurality of tubes 4106 so as to create a suction manifold that may be useful in distributing negative pressure while reducing the overall height of the adapter 4103, a useful aspect for low-profile conformable suction adapters. At the proximal end of the adapter 4103, a converging point 4107 connects to all of the tubes 4106 and connects to a single tube 4104 connected to a source of negative pressure. In some embodiments, an air leak 4109 may be provided on the adapter 4103, for example over the converging point 4107. Preferably, a seal 4111 can be provided at the junction where the tubes 4106 meet the drape 4105. Such a seal 4111 may be either integrated onto the tubes 4106, either in a fixed or slideable configuration, or else placed separately. The material used for the seal 4111 may be a closed-cell foam wedge, but any material capable of creating a fluid tight seal can be used. FIG. 41B illustrates a section taken along the line A-A illustrating how in some embodiments, the tubes 4106 can be of a very low height, which may be advantageous for example in minimizing patient discomfort. In some embodiments, the seal 4111 and the tubes 4106 are attached or welded to the drape 4105 to form a single unit.

In FIGS. 42A-B, an embodiment of a negative pressure treatment system 4201 comprises a drape 4203 with an aperture 4205 integrated into it. The aperture 4205 has an area 4206 coated with a layer of adhesive and may optionally be protected by a release layer 4207. The aperture 4205 may also comprise a controlled air leak 4209, preferably provided with a filter to prevent entry of pathogens and contaminants. A port 4211 is also part of the system 4201, and may comprise a connector 4212 to connect to a tube 4204. On the underside of port 4211, an adhesive layer optionally protected by a release layer 4213 may also be present. In use, the drape 4203 is placed over a wound with the aperture 4205 preferably located in a central position. Subsequently, the release layer 4207 is removed to expose an adhesive layer. Next, the port 4211, optionally following the removal of a release layer 4213, is adhered to the area 4206 so as to create a fluidic connection between the port 4211 and the aperture 4205.

FIGS. 43A-B illustrate an embodiment with a piercing point sharing some similarities to the embodiment described in FIGS. 13A-B. Here, an embodiment of a negative pressure treatment system 4301 comprises a port 4303 provided with one or more piercing tips 4305. Preferably, this piercing tip 4305 is located on the top inner surface of the port 4303 over an aperture 4307. In use, the application of vacuum through a tube 4304 to the port 4303 draws a portion 4309 of a drape 4308 placed over a wound into the aperture 4307. The piercing tip 4305 then pierces the drape portion 4309 so as to create a fluidic connection between the wound space and the source of negative pressure so as to permit wound exudate to be removed from the wound. Other aspects of the port 4303 are similar to embodiments described elsewhere herein, and the port may comprise a controlled air leak 4311 and a layer of adhesive 4312 disposed on the underside of the port 4303.

FIGS. 44A-B illustrate an embodiment of a negative pressure treatment system 4401 comprising a drape 4403 with an integrated suction port 4405. Here, the suction port 4405 is preferably constructed of a soft, conformable material which may in some embodiments be the same as the material used in the drape 4403. There is preferably a layer of adhesive disposed on the underside of the drape 4403 so as to permit adherence to the skin surrounding the wound. The port 4405 may be constructed separately and adhered or welded to the drape 4403, or in other embodiments the port 4405 may comprise a channel integrated onto the drape 4403 so as to form a single unit. At the proximal end of the port 4405, a connector 4406 is preferably provided so as to permit the connection of a tube 4404 to the system 4401. The drape 4403 may also comprise an air channel 4407 to permit air to enter the dressing, preferably at a controlled rate. This air channel 4407 can also comprise a filter to prevent contaminants from entering the wound.

In FIGS. 45A-C, an embodiment of a negative pressure treatment system 4501 comprises a drape 4503 with a port 4505 integrated thereto. The drape 4503 may also comprise cross-linked air channels 4507; such channels 4507 communicate with the wound space below the drape 4503 (for example via through holes 4508) so as to permit a controlled air flow rate to the wound. The edges of the drape 4503 provide openings for the cross-linked air channels 4507, and the drape 4503 may be cut to size without significantly interfering with the function of the air channels 4507. In some embodiments, however, it may be advantageous to use a filter or filtering element in conjunction with the air channels 4507 to prevent contaminants from entering the wound space. Preferably, an adhesive layer is disposed underneath the drape 4503. In one embodiment, the port 4505 comprises a domed portion 4509 approximately centered on the drape 4503. This domed portion 4509 forms a channel for the evacuation of wound exudate together with an elongated portion 4512, which communicates to a fluidic adapter portion 4513 connecting to a tube 4504. As with other embodiments described herein, the port 4505 is preferably constructed from a soft, conformable material (while being able to maintain patency sufficient to draw out fluid under negative pressure), and may be either integrated to the drape 4503 as a single unit (e.g., by molding) or constructed from multiple pieces later attached or joined together.

FIGS. 46A-B illustrate an embodiment of a negative pressure wound treatment system 4601 that comprises one or more suction channels 4603 integrated into an impermeable cover 4605. The one or more suction channels 4603 may enter into the cover 4605 to form a network of conduits surrounding a central air leak 4609, preferably provided with a filter. Of course, alternative configurations are possible, such as a fan- or net-shaped system of channels 4603, and the air leak 4609 may in some embodiments be omitted or placed in a different location. The channels 4603 converge onto a central collector 4607, which connects to a tube 4604 that may be connected to a source of negative pressure. The cover 4605 is preferably constructed of a fluid-impermeable material, and is preferably sufficiently thick so as to be able to integrate the channels 4603 within itself. Preferably, a layer of adhesive is disposed on its underside. An example of a suitable material for the cover 4605 may include a closed-cell foam. In some embodiments, spaces may be made into the cover 4605 into which the channels 4603 connect to. In other embodiments, the channels 4603 continue into the cover 4605 and the cover 4605 is, for example, molded around the channels 4603. In use, the system 4601's cover 4605 may be trimmed to size if necessary (while avoiding cutting through the channels 4603) and placed over a wound site, optionally filled with a wound packing material, and adhered to the skin surrounding the site. Subsequently, a source of suction may be applied to the wound and exudates removed through the channels 4603.

Turning now to FIGS. 47A-B, an embodiment of a negative pressure treatment system 4701 comprises a low-profile suction unit 4703 covered with a membrane 4707. In some embodiments, the suction unit 4703 may be constructed from open-cell foam. Embedded within the suction unit 4703 is a tube 4704. This tube 4704 may be fenestrated or perforated so as to help prevent clogging and apply suction over a larger area. The tube 4704 passes through an impermeable section 4705. This impermeable section 4705 may be constructed, for example, from a closed-cell foam, and is attached to the suction unit 4703. In some embodiments, the impermeable section 4705 may be molded around the tube 4704. Although the tube 4704 may be connected directly to a source of negative pressure, it may in some embodiments be advantageous to provide a connector situated proximally to the tube 4704 to permit connection of another tube in communication with a source of negative pressure. The membrane 4707 may be constructed in several parts, or may be one large sheet. Preferably, it is provided with a layer of adhesive on its underside, optionally protected by a release layer 4709 which covers the portions of adhesive not secured to the suction unit 4703 and/or the impermeable section 4705. In use, the system 4701 may be positioned over a wound, optionally filled with packing material. Then, the release layer 4709 is removed so as to permit the membrane 4707 to be adhered to the skin surrounding the wound. Negative pressure is then applied to the wound through the tube 4704.

FIGS. 48A-E illustrate an embodiment of a negative pressure treatment system 4801 comprising a flexible suction adapter sheet 4803 capable of being packed into a wound space. The sheet 4803 preferably comprises a larger, planar section 4805 at its distal end, connected to a tail portion 4806 at its proximal end. At the proximal end of the tail portion 4806, a connector 4807 may be provided to permit a tube 4804 to be connected thereto. The planar section 4805 may be comprised of two layers: a bottom layer 4810 and a top layer 4811. The bottom layer 4810 comprises one or more perforations 4812 that face toward the wound so as to collect wound exudate and distribute negative pressure to the wound. The top layer 4811 comprises a network of channels 4813 communicating with the perforations 4812, and fluidically link to the source of negative pressure so as to channel wound exudate to the source of negative pressure. In some embodiments, the channels 4813 form an interconnected network (such as in a grid configuration), which may be advantageous in preventing clogging and permitting negative pressure to be distributed to the entire bottom layer 4810 in spite of folding that may occur when the portion 4805 is placed within a wound. In some embodiments, the tail portion 4806 can comprise a layer of adhesive on its wound-facing side, which may be useful in forming a seal with the underlying skin. The sheet 4803 may also be covered with a flexible drape 4815 to provide an additional, substantially air-tight seal over the wound.

In use, a wound is cleaned, and the planar section 4805 is inserted into the wound so as to function as a wound packing material. Preferably, the bottom layer 4810 is placed facing into the wound. Subsequently, the tail portion 4806 may be adhered to the skin surrounding the wound. A drape 4815 is then placed and sealed over the entire wound, followed by connecting the tube 4804 to a source of negative pressure.

In FIGS. 49A-B, a negative pressure treatment system 4901 may comprise a wound packing pouch 4903 used with a port 4905 and a drape 4907. The pouch 4903 is a flexible pouch that may be filled with a conformable filler 4909, for example granular beads, and may be placed into the wound space as a filler. The pouch 4903 also comprises a semi-permeable or perforated membrane 4910 containing the filler 4909. In use, different size pouches 4903 may be supplied, or multiple pouches 4903 may be used to fill the wound space as desired. The port 4905 is similar to other ports described herein, and comprises a distal head portion 4913 designed to be placed in contact with the pouch 4903 so as to evacuate wound exudate and communicate negative pressure to the pouch 4903. In an alternative embodiment, this port 4905 may be adhered or welded to a smaller drape, optionally provided with a further adhesive layer. At the proximal end of the port 4905 is a connector 4915 configured to connect to a tube 4904. In some embodiments, this connector 4915 may comprise a piercing or chisel tip configured to pierce through the drape 4907, which may be advantageous in making an easier connection to the tube 4904. The drape 4907 may be provided with an adhesive layer on its wound-facing side, and provides an essentially fluid-tight seal over the wound space and over the pouch 4903. In some embodiments, the drape 4907 may be provided with a controlled air leak 4917, optionally protected with a filter, designed to permit a controlled amount of air into the wound.

FIGS. 50A-C illustrate embodiments of a negative pressure treatment system 5001 comprising a sealing port 5003. Here, the port 5003 comprises a distal head portion 5005 and a proximal tail portion 5006. The tail portion 5006 includes a connector 5007 configured to connect to a tube 5004. The head portion 5005 comprises an outer vacuum ring 5009; this ring 5009 may in some embodiments be used to seal the port 5003 against the skin surrounding a wound, and may be useful in smaller-sized wounds that the ring 5009 is able to circumscribe. In other embodiments and for larger wounds, a drape may be used in a manner similar to other embodiments described herein. In use, a slot 5011, or a series of apertures on the underside of the ring 5009 permits negative pressure transmitted into the ring 5009 to seal the ring 5009—and thus the entire port 5003—against the skin of a patient. The head portion 5005 also comprises a central region 5011 that applies a portion of the vacuum from the vacuum source to the wound and evacuates wound exudate (the remainder of the vacuum is applied to the skin surrounding the wound by the ring 5009). Here, the region 5011 may also comprise an air leak 5013, for example disposed centrally and with an optional air filter 5014. In some embodiments, a separate channel 5015 may be present to channel the air drawn into the wound and port 5003 downward and into the wound space. Preferably, such a channel 5015 is configured to make contact with any wound packing material placed into the wound.

FIGS. 51A-B illustrates an embodiment of a negative pressure wound treatment system 5101 comprising a low-profile suction adapter 5103 configured to be placed over a wound. The suction adapter 5103 preferably comprises a vacuum portion 5105 and a controlled air leak portion 5106, wherein both of these portions 5105, 5106 are preferably constructed of a flexible, soft material capable of transmitting air and fluid flow through themselves. Examples of such materials may include open-cell foams. The entire suction adapter 5103, including the portions 5105, 5106, is preferably covered on its upper portions with a liquid-impermeable membrane 5108. The vacuum portion comprises at its proximal end a connector 5107 for connecting to a tube 5104. The controlled air leak portion 5106 preferably comprises an open end 5109 not covered by membrane 5108 so as to permit a flow of air into the adapter 5103. Preferably, a filter is disposed over this end 5109 to prevent the entry of contaminants into the wound space. In this embodiment, strips of tape 5111 are used to seal the edges of the membrane 5108 against the skin of a patient. In other embodiments, some or all of the underside of the 5108 may be covered in a layer of adhesive. Preferably, the system 5101 is used on a wound that has been filled with a wound packing material such as foam or gauze.

In FIGS. 52A-B, a negative pressure treatment system 5201 comprises a bladder 5203 in combination with a suction adapter sheet 5205 and a drape 5207. The bladder 5203 may be filled with a fluid such as air or water, and may be secured to the wound for example by straps 5209, although other means sufficient to apply positive pressure on the wound may be used. Under the bladder 5203 is the drape 5207, which is preferably liquid-impermeable and coated with a layer of adhesive on its wound-facing side. The suction adapter sheet 5205 is below the drape, and may be of a type similar to the embodiment described in FIG. 48A. Preferably, this sheet 5205 comprises one or more conduits configured to channel wound exudate toward a source of negative pressure while distributing negative pressure over the entire wound area. The proximal portion 5206 of the sheet 5205 may comprise a connector 5210 suitable for connecting to a tube 5204. Optionally, the space below the suction adapter sheet 5205 is filled with a wound packing material such as an open-cell foam. Such a wound treatment system 5201 may be beneficial for use on wounds that require additional positive pressure upon the wound bed. Additionally, use of an embodiment with the straps 5209 may be beneficial for use in particular on the legs and arms of a patient.

FIGS. 53A-D show variations of the bladder system described in FIG. 52A. Here, the negative pressure wound treatment system 5301 comprises a bladder 5303 placed underneath a drape 5305. The bladder 5303 may be filled with a fluid such as saline solution, although other fluids such as air may be used. In some embodiments, a layer of wound contacting material 5307 may be placed in contact with the wound. This wound contacting material 5307 may be foam, gauze, or other suitable materials. Preferably, this material 5307 forms a thin layer and is pushed into contact with the wound. Subsequently, the bladder 5303 is placed into the wound so as to fill the remainder of the wound space. The drape 5305 is then placed over the bladder 5303 and wound contacting material 5307 and sealed to the skin surrounding the wound. An aperture 5309 may then be made into the drape 5305 (although the drape may be provided with an aperture already made into it) over a portion of the wound where the wound contacting material 5307 is in contact with the drape 5305, and a suction adapter 5311 placed over the aperture 5309. Alternatively, the suction adapter 5311 may be adhered or welded to the drape 5305 or a smaller drape, optionally provided with a further adhesive layer. The adapter 5311 may be connected to a source of negative pressure via a tube 5304 connected to its proximal end. In some embodiments, the drape 5305 may also be provided with a controlled air leak 5313, which is in some cases covered with a filtration element to prevent contaminants from entering the wound.

In FIG. 54A, an embodiment of a negative pressure wound treatment system 5401 is illustrated that uses a wound packing material 5403 provided in discrete portions. The wound packing material 5403 may be supplied in the form of a roll 5405, for example as illustrated in FIG. 54B, and dispensed as necessary to fill a wound space; individual sections may be detached, or long sections may be packed into the wound. The wound packing material 5403 may be comprised of a porous material such as open-cell foam, or any other material capable of transmitting negative pressure to the wound site. The form of the wound packing material 5403 may be achieved by molding or heat-forming the material. Alternatively, it may be fabricated using nets or films to join the individual sections. In a further embodiment, the wound packing material 5403 may be molded from solid polymers, and channels may be formed onto the surface to allow removal of fluids from the wound tissue. After a wound is filled with the wound packing material 5403, a drape 5407 (optionally provided with an integrated air leak 5408 similar to those previously described herein) is placed over the wound and sealed to the skin surrounding the wound. An aperture is then made into the drape 5407 sufficient to permit a port 5409 to be placed over it so that wound exudate may be removed from the wound site through a tube 5404 connected to the port 5409. Alternatively, the port 5409 may be adhered or welded to a smaller drape, optionally provided with a further adhesive layer or else the drape 5407.

Figure 55A:
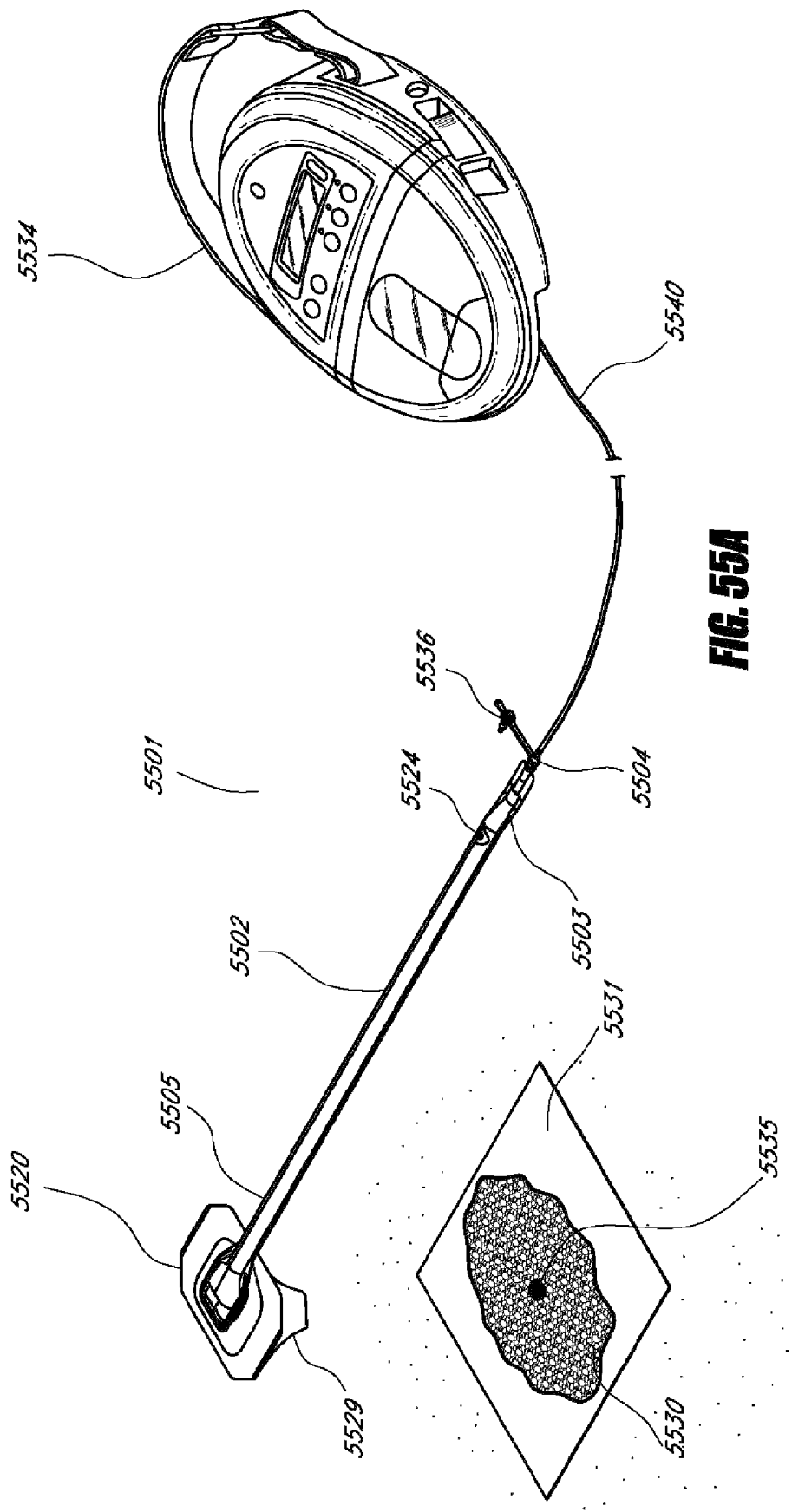
FIG. 55A illustrates an embodiment of a negative pressure wound treatment system comprising a pump, and illustrating a flexible suction adapter being applied to a wound.
Figure 55B:
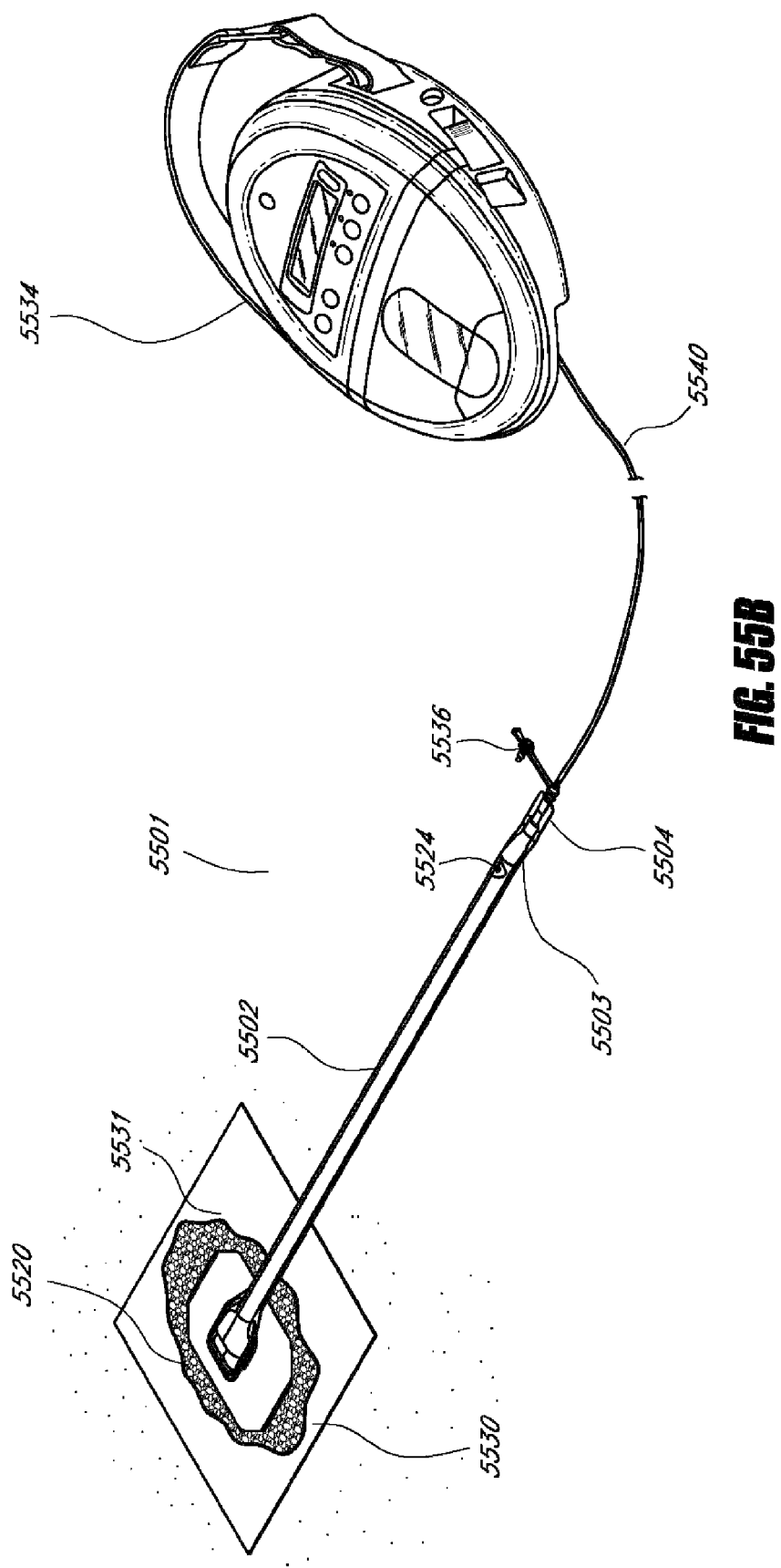
FIG. 55B illustrates the embodiment of FIG. 55A, with the flexible suction adapter having been placed over a wound.
Figure 55D:
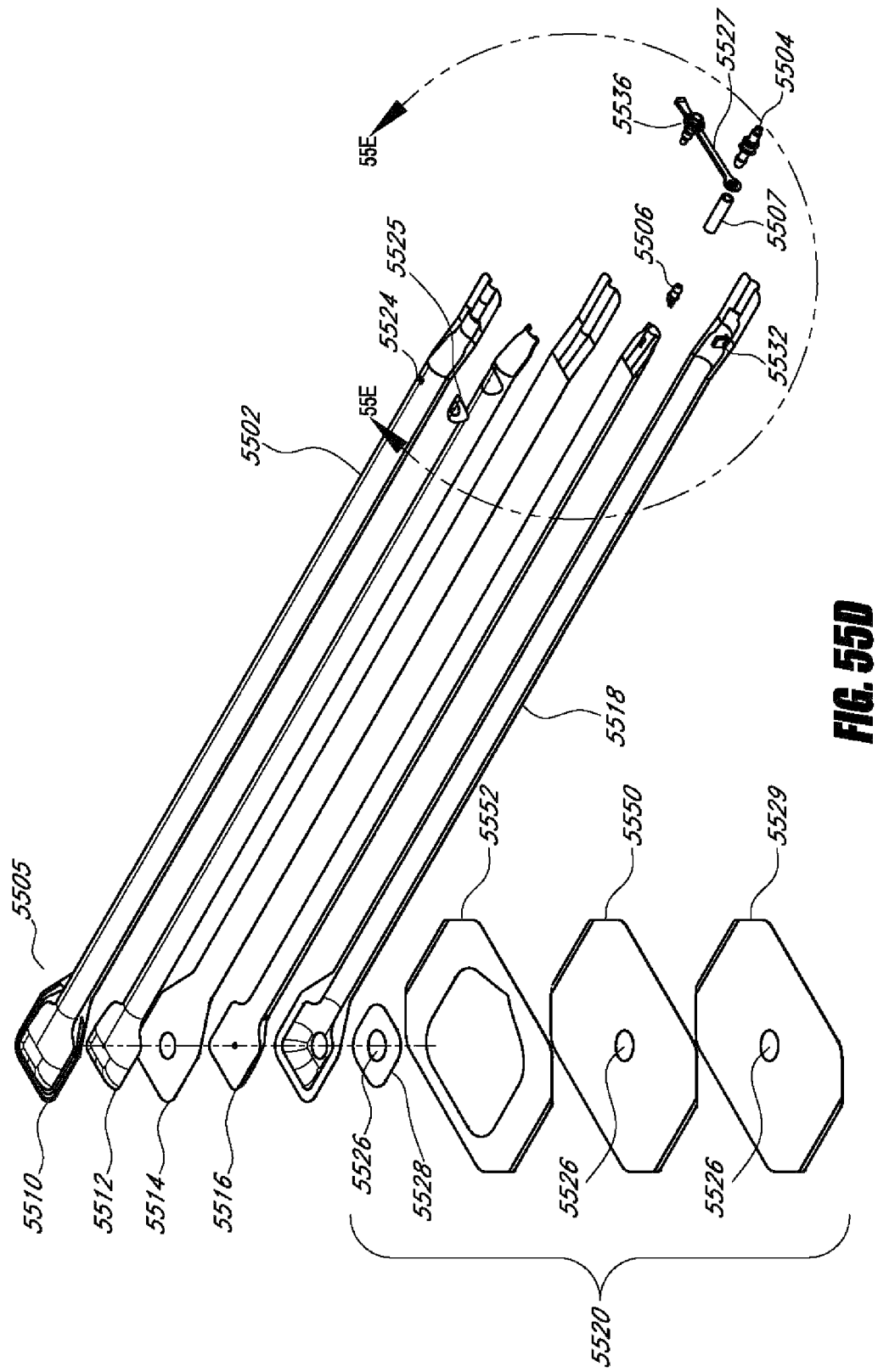
FIG. 55D illustrates an exploded view of the flexible suction adapter of FIG. 55C.

FIGS. 55A-J illustrate embodiments of a negative pressure wound treatment system 5501 similar to the embodiments illustrated in FIG. 15A. Here, the system 5501 may comprise a bridge 5502 having a proximal end 5503 and a distal end 5505 and an applicator 5520 at the distal end 5505 of the bridge 5502 forming a flexible suction adapter. Preferably, the system 5501 is constructed in a similar fashion to the system 1501, and may comprise a bridge 5502 constructed from a similar dual layer arrangement as previously described. A connector 5504 is preferably disposed at the proximal end 5503 of the bridge 5502, so as to connect to at least one of the channels 5512 and/or 5516, as shown in FIG. 55D. A cap 5536 may be provided with the system 5501 (and can in some cases, as illustrated, be attached to the connector 5504). The cap 5536 can be useful in preventing fluids from leaking out of the proximal end 5503. The system 5501 may include a source of negative pressure such as a pump or negative pressure unit 5534 capable of supplying negative pressure. The pump also preferably comprises a canister or other container for the storage of wound exudates and other fluids that may be removed from the wound. In some embodiments, this pump 5534 can be a RENASYS GO pump, as sold by Smith & Nephew. The pump 5534 may be connected to the connector 5504 via a tube 5540. In use, the applicator 5520 is placed over an aperture 5535 formed in a drape 5531 that is placed over a suitably-prepared wound 5530, which may in some cases be filled with a wound packing material such as foam or gauze. Subsequently, with the pump 5534 connected via the tube 5540 to the connector 5504, the pump is activated, thereby supplying negative pressure to the wound. Application of negative pressure may be applied until a desired level of healing of the wound 5530 is achieved.

Here, and with particular reference to FIGS. 55C-D, the system 5501 may comprise a bridge 5502 having a proximal end 5503 and a distal end 5505 and an applicator 5520 at the distal end 5505 of the bridge 5502. In some embodiments, the bridge 5502 may comprise an upper channel layer 5512 positioned between an upper layer 5510 and an intermediate layer 5514, with a lower channel layer 5516 positioned between the intermediate layer 5514 and a bottom layer 5518. Preferably, the layers 5510, 5514, and 5518 have elongate portions extending between proximal and distal ends and may be comprised of a material that is fluid-impermeable, for example polymers such as polyurethane. It will of course be appreciated that the layers 5510, 5514, and 5518 may each be constructed from different materials, including semi-permeable materials. As illustrated in FIG. 55D, the upper and lower layers 5510 and 5518 may be curved, rounded or outwardly convex over a majority of their lengths. During assembly, for example, the layers 5510, 5514, and 5518 may be pinched together to weld or adhere the layers together. In doing so, the proximal ends of the channels 5512 and 5516 may be sandwiched between these layers, thus partially compressing the proximal ends of the channels 5512, 5516 and stretching the layers 5510, 5514, 5518 over these aforementioned proximal ends. Of course, the proximal ends of the materials used in the bridge section 5502 may not necessarily be rounded or curved; as shown in FIG. 55J, they can remain substantially squared off and straight.

Similarly to the embodiment described in FIG. 6 with regards to the spacer 609, the upper and lower channel layers 5512 and 5516 are preferably elongate layers extending from the proximal end 5503 to the distal end 5505 and may each preferably comprise a porous material, including for example open-celled foams such as polyethylene or polyurethane. In some embodiments, one or more of the upper and lower channel layers 5512 and 5516 may be comprised of a fabric, for example a knitted or woven spacer fabric (such as a knitted polyester 3D fabric, Baltex 7970® , or Gehring 879®) or a nonwoven material. Suitable materials may also include terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure and/or vented air to the wound site, and may also confer a degree of kinking or occlusion resistance to the channel layers 5512 and 5516 as described below. In one embodiment, the upper channel layer 5512 may comprise an open-celled foam such as polyurethane, and the lower channel layer may comprise a fabric as described herein. In another embodiment, the upper channel layer is optional, and the system may instead be provided with an open upper channel. In the embodiment illustrated in FIG. 55D, the upper channel layer 5512 may have a curved, rounded or upwardly convex upper surface and a substantially flat lower surface, and the lower channel layer 5516 may have a curved, rounded or downwardly convex lower surface and a substantially flat upper surface.

In some embodiments, the fabric may have a three-dimensional (3D) structure, where one or more types of fibers form a structure where the fibers extend in all three dimensions. Such a fabric may in some cases aid in wicking, transporting fluid, and/or transmitting negative pressure. To prevent the channels 5512 and/or 5516 from being displaced or twisted while encased in the system 5501—which may impair performance of the respective channels under negative pressure—it may in some embodiments be preferable to adhere or otherwise secure the channels 5512 and/or 5516 to one or more of the layers 5510, 5514, and 5518. In certain embodiments, these materials remain open and capable of communicating negative pressure to a wound area under the typical pressures used in negative pressure therapy, for example between 40 to 150 mmHg, although higher and lower values are possible. In some embodiments, the fabric may comprise several layers of material stacked or layered over each other, which may in some cases be useful in preventing the channel 5516 from collapsing under the application of negative pressure. In other embodiments, the fabric used in channel 5516 may be between 1.5 mm and 6 mm; more preferably, the fabric may be between 3 mm and 6 mm thick, and may be comprised of either one or several individual layers of fabric. In other embodiments, the channel 5512 may be between 1.2-3 mm thick, and preferably thicker than 1.5 mm. Additionally, and as described previously, the materials used in the system 5501 are preferably conformable and soft, which may help to avoid pressure ulcers and other complications which may result from a wound treatment system being pressed against the skin of a patient. Further examples of 3D fabrics are discussed below in FIGS. 56A-C.

Preferably, the distal ends of the layers 5510, 5514, and 5518 and the channel layers 5512 and 5516 are enlarged at their distal ends (to be placed over a wound site), and may form a "teardrop" or other enlarged shape. The distal ends of at least the layers 5512, 5514, 5516, and 5518 may also be provided with at least one through aperture. This aperture may be useful not only for the drainage of wound exudate and for applying negative pressure to the wound, but also during manufacturing of the device, as these apertures may be used to align these respective layers appropriately.

Figure 55E:
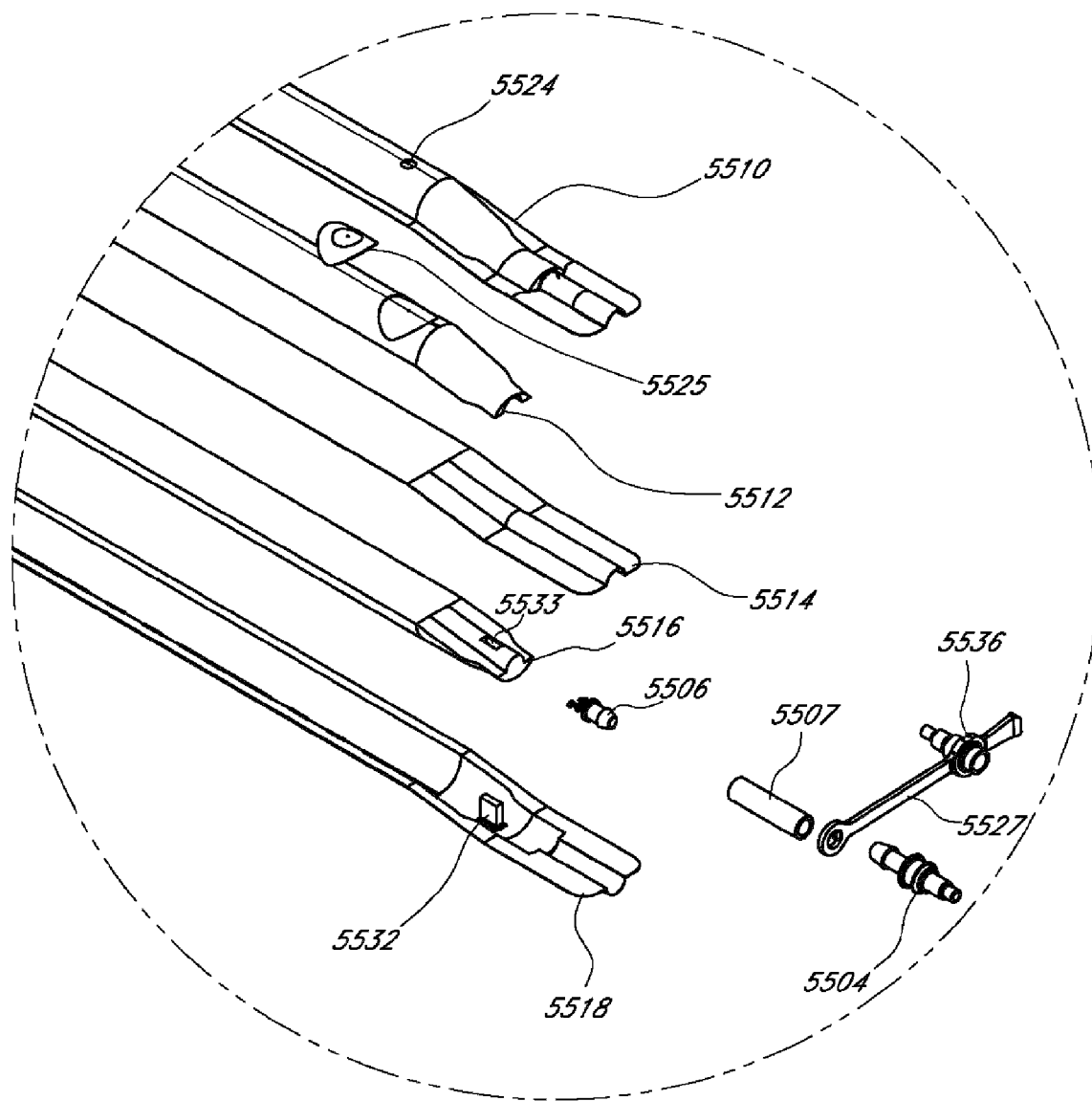
FIG. 55E illustrates a close-up view of the proximal end of the flexible suction adapter of FIG. 55D.
Figure 55F:
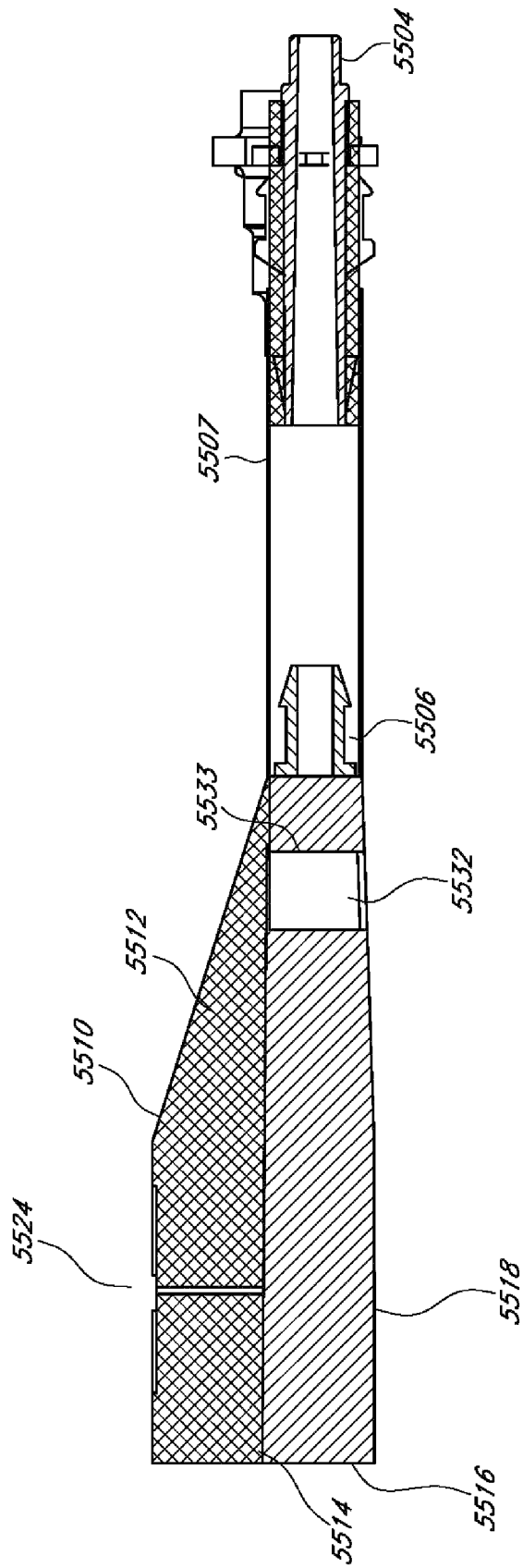
FIG. 55F illustrates a close-up cutaway view of the proximal end of the flexible suction adapter of FIG. 55C.
Figure 55G:
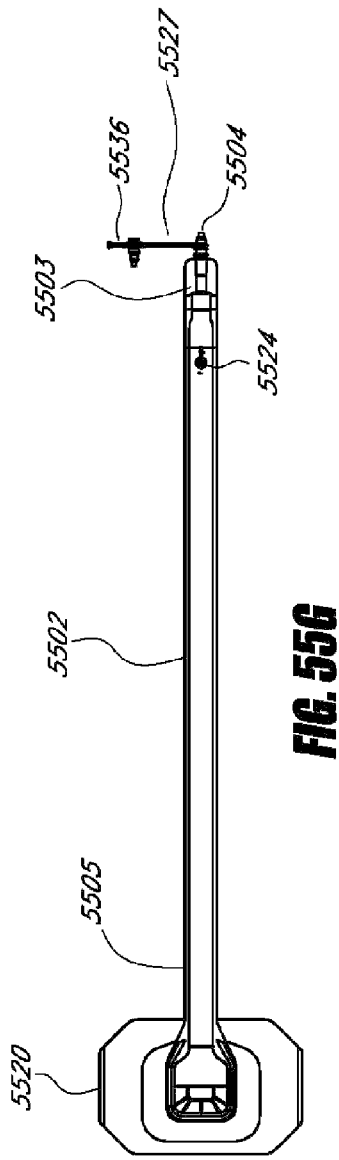
FIG. 55G illustrates a top view of the flexible suction adapter of FIG. 55C.
Figure 55H:
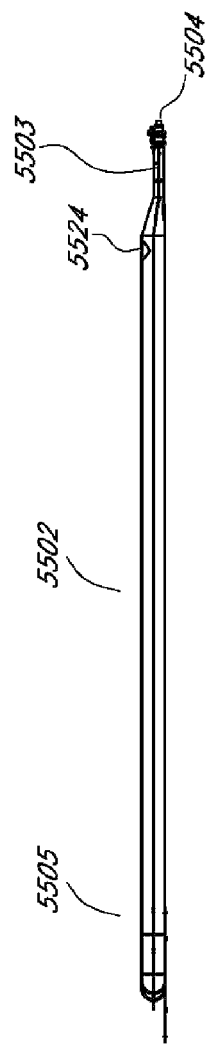
FIG. 55H illustrates a side view of the flexible suction adapter of FIG. 55C.
Figure 55I:
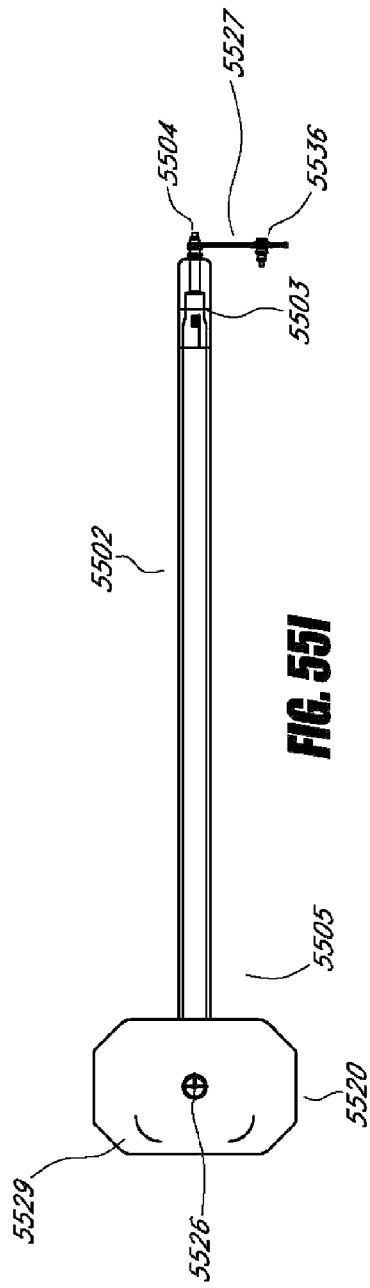
FIG. 55I illustrates a bottom view of the flexible suction adapter of FIG. 55C.
Figure 55J:
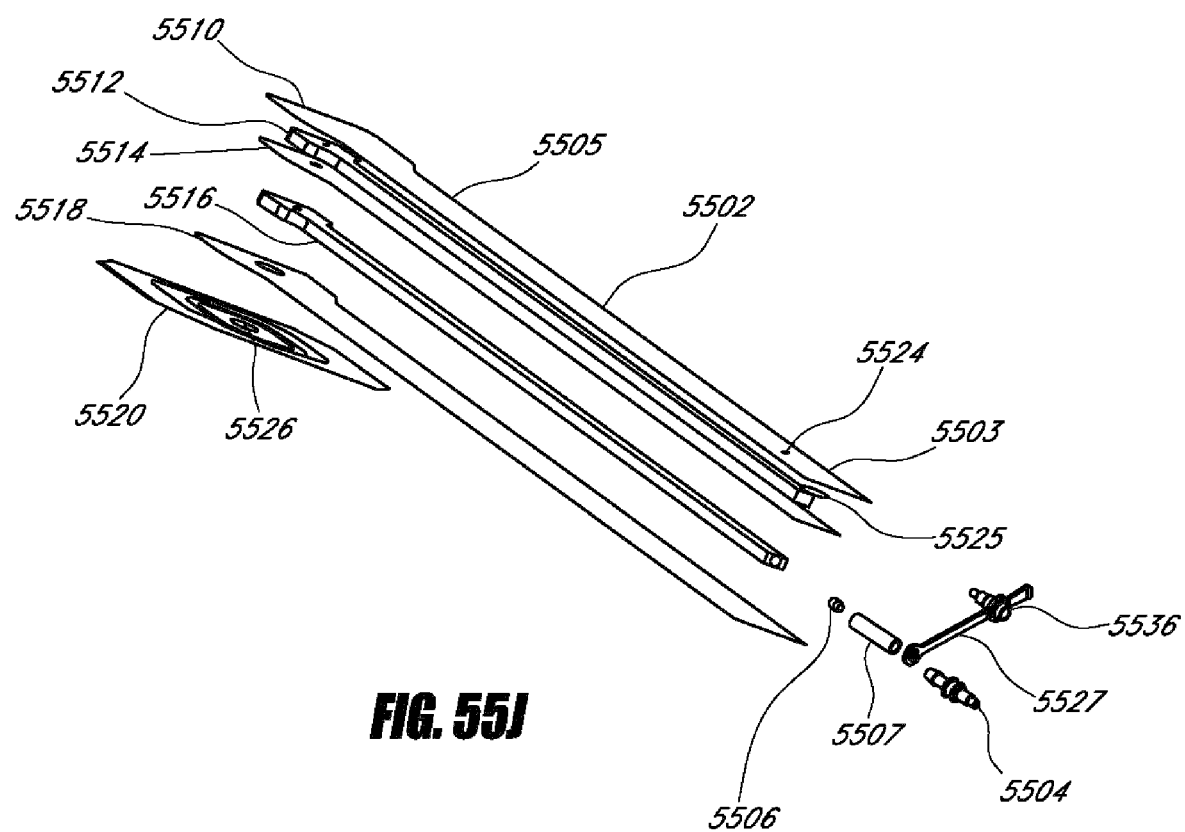
FIG. 55J illustrates an exploded view of an alternative flexible suction adapter.

With additional reference to FIGS. 55D-E and J, a channel connector 5506 is provided at the proximal end 5503 of the bridge 5502, the channel connector 5506 preferably being configured so as to be embedded into the lower channel layer 5516 so as to create a secure fluidic connection. The channel connector 5506 may in some embodiments be inserted into a pre-made cavity formed into the channel 5516; as illustrated in FIG. 55J, this cavity can be cut out or can be in the form of a rabbet joint. In some embodiments, the channel connector

5506 may be one of the connectors described in FIGS. 57A-B below. With one end of the channel connector 5506 being embedded into the lower channel layer 5516, the other end of the channel connector 5506 may be connected or in communication with, in one embodiment, a connector tube 5507, although in some embodiments the channel connector 5506 may be connected directly to the connector 5504, or else connected directly to a tube 5540 connected to a source of negative pressure. When using a connector tube 5507, the resulting assembly can permit a connector 5504 to be attached thereto. A cap 5536, which may be secured to the suction adapter for example via a cap leash 5527 secured with a ring disposed on the outer surface of the connector tube 5507. The cap 5536 may be used to cover the end of the suction adapter, for example at the connector 5504, so as to prevent exudate and other wound fluids from leaking out. The connector 5504 is preferably configured to connect with a tube 5540 connected to a source of negative pressure. The connector 5504 may for example comprise a lip or other such structure to aid in securing the connector 5504 to a tube 5540 and/or cap 5536, although it will be understood that other connector types are possible, including quick-disconnect couplings, luer locks, Christmas-tree, and other such connectors.

The upper layer 5510 may comprise additional material extending downward, preferably at least of the thickness of the bridge 5502; this material may then be used to bond or weld to the other layers so to form a fluid-tight seal. More specifically, during assembly, the upper layer 5510 may be attached, for example by melting, welding, or with adhesives, to the lower layer 5518 so as to form a fluid-tight seal (with the exception of the apertures at the distal and proximal ends). Preferably, the middle layer 5514 is attached to the top layer 5510 and the bottom layer 5518. In some embodiments, it may be preferable to attach or bond the connectors 5504 and/or 5506, as well as the tube 5507 to at least one of the layers 5510, 5514, 5518 so as to create a fluid-tight connection. To provide for a more secure connection, some embodiments may also be provided with a weld 5532 made onto the lower layer 5518. The lower channel 5516 may have a hole or aperture made through it, which may be used to weld it, via the weld 5532, to the lower layer 5518. This welding of the lower channel 5516 to the lower layer 5518 via the weld 5532 made through the hole 5533 may thus aid in preventing the various layers and channels from shifting or being displaced. Obviously, it will be understood that other securement means may be used, for example adhesives and the like, and that such arrangements may be also be used in the upper channel 5512.

In certain embodiments, for example as illustrated in FIGS. 55C-J, a controlled air leak 5524 may be disposed on the bridge portion 5502, for example at the proximal end thereof. This air leak 5524 may comprise an opening or channel extending through upper layer 5510, such that the air leak 5524 is in fluidic communication with the upper channel 5512. Upon the application of suction to the system 5501, air will enter through the air leak 5524 and move from the proximal end 5503 to the distal end 5505 along the upper channel 5512. The air will then be suctioned into the lower channel 5516 by passing through the apertures through the distal ends of the layers 5512, 5514, 5516 and 5518. The air leak 5524 preferably comprises a filter 5525, which may be similar in function to the filter 521 illustrated in FIG. 5A. Preferably, the air leak 5524 is located at the proximal end of the bridge portion 5502 so as to minimize the likelihood of wound exudate or other fluids coming into contact and possibly occluding or interfering with the air leak 5524 or its filter 5525. In some embodiments, this filter 5525 is a microporous membrane capable of excluding microorganisms and bacteria, and which may be able to filter out particles larger than 45 µm. Preferably, the filter 5525 can exclude particles larger than 1.0 µm, and more preferably, particles larger than 0.2 µm. Advantageously, some embodiments may provide for a filter 5525 that is at least partially chemically-resistant, for example to water, common household liquids such as shampoos, and other surfactants. In some embodiments, reapplication of vacuum to the system 5501 and/or wiping of the exposed outer portion of the filter 5525 may be sufficient to clear any foreign substance occluding the filter 5525. The filter 5525 may be composed of a suitably-resistant polymer such as acrylic, polyethersulfone, or polytetrafluoroethylene, and may be oleophobic and/or hydrophobic. In some embodiments, the filter 5525 may also comprise a supporting backing layer, for example a nonwoven polyester support. Preferably, the air leak 5524 will supply a relatively constant air flow that does not appreciably increase as additional negative pressure is applied to the system 5501. In embodiments of the system 5501 where the air flow through the air leak 5524 increases as additional negative pressure is applied, preferably this increased air flow will be minimized and not increase in proportion to the negative pressure applied thereto.

The filter 5525 provided in the controlled air leak 5524 in certain embodiments may be useful in a system 5501 for use with more ambulatory and active patients. For example, a chemically-resistant filter may permit a patient to bathe or shower without damaging the filter's functionality when reconnected to a source of negative pressure. Any occlusion or fluid blocking the air leak 5524 could then be cleared by, for example, wiping off the filter 5525 or re-applying negative pressure to the system 5501. Such a system would also have the advantage that the system 5501 and any assorted wound dressing materials, if present, would not need to be removed and then re-applied should a patient need to be disconnected from the source of negative pressure, for example incidental to bathing. This would entail significant advantages in improving the cost-effectiveness and ease of use of the present treatment system.

The system 5501 is preferably constructed so as to provide a consistent fluid flow even if the system 5501 is kinked or weighted down. For example, in use on a patient, the bridge portion 5502 may become folded over itself, or else the patient may roll over, thus placing his or her weight over at least a portion of the system 5501. Typically, prior art dressings and fluidic connectors become blocked or ineffective in such situations and in some cases may contribute to complications such as pressure ulcers. Here, however, certain embodiments provide for improved blockage resistance if kinked or weighed down. Preferably, by employing channel layers 5512 and 5516 as described above, and more preferably by employing a foam channel layer 5512 and a fabric channel layer 5516, the system 5501 is able to maintain a flow rate through the air leak 5524 of at least 0.08 L/min, and preferably 0.12 L/min while negative pressure is applied through a source of negative pressure. Further embodiments also provide for the system 5501 to be able to handle fluid exudate drainage from the wound site through the lower channel 5516 of at least 10 L/day, or 6.9 ml/min. Certain embodiments provide for the system 5501 to maintain these flow rates with a weight, for example a 12 kg weight, pressing down on the bridge portion through a rod with a 1 in. diameter. In some embodiments, these flow rates are also maintained while the bridge portion 5502 is kinked over itself with the same weight, or for example with a 4.75 kg weight placed directly on the folded region. It is preferable that the system 5501 be able to withstand being folded or kinked over even during an extended period of time, for example over 40 hours, and not show any degradation in performance (e.g., flow rates) compared to its performance prior to being folded or kinked over. Preferably, embodiments of the system 5501 are also able to transmit and maintain a negative pressure at the wound that is close to the negative pressure level at the source of negative pressure. For example, an acceptable level of pressure maintained at the wound may be within ±25 mmHg of the negative pressure set at the source of negative pressure, with this pressure being preferably maintained at this level within 95% of the time that the system 5501 has negative pressure applied to it. Acceptable pressure levels may include pressure ranges between 40-120 mmHg, although levels of 200 mmHg have successfully been used.

With additional reference to FIGS. 55A-D, G-J, the system 5501 also comprises an applicator 5520 designed for placement over a wound site. Preferably, the applicator 5520 comprises a flexible layer 5550, for example polyethylene or polyurethane, with a layer of adhesive on its lower (wound-facing) side. Optionally, a protective release layer 5529 may be placed on the adhesive layer, which is removable before use. In some embodiments, a more rigid removable backing layer 5552 may be provided on the upper side of the applicator 5520 to facilitate handling of the applicator 5520 due to the flexibility of the layer 5550. The applicator 5520 preferably comprises an attachment point for the bridge 5502 at the distal end 5505, for example using a section of double-sided adhesive tape 5528. The double-sided adhesive tape 5528 may be protected by an additional protective release layer, which is removed prior to adhering the bridge 5502 to the applicator 5520. It will be understood that different attachment methods are also contemplated, for example heat sealing, welding, or suitable adhesives. Some embodiments may also permit the manufacture of the bridge 5502 and the applicator 5520 as a single unit that does not require separate attachment means. The applicator 5520 preferably comprises at least one aperture 5526 through itself and designed to be placed over a wound site, and which can serve to fluidically connect the wound site to the source of negative pressure and to the air leak while also serving as a conduit to draw out wound exudate from the wound site.

In use, and with reference to FIGS. 55A-B, the system 5501 may be used in a similar fashion to the other embodiments previously disclosed herein. A wound site 5530 is preferably cleaned and prepared in a suitable fashion, and a wound packing material, if necessary, placed into the wound site, followed by a drape 5531. An aperture 5535 through the drape to the wound site is then created, although some embodiments may have a pre-made aperture 5535. Subsequently, an operator may situate the applicator portion 5520 over the aperture 5535. After removing the backing layer 5529 (if present) from the adhesive layer on the underside of the applicator portion 5520, the applicator is sealed to the drape 5531, and the backing layer 5552 (if present) is also removed from the applicator portion 5520. A fluidic conduit such as a tube 5540 may then be connected to the connector 5504. The tube 5540 may also be connected to connector 5504 prior to applying the applicator to the wound site. The fluidic conduit is connected to a source of negative pressure 5534, preferably with a container suitable for containing wound exudate interposed therebetween. The application of negative pressure may then be effectuated to the wound site 5530 until the wound site progresses to a desired level of healing.

During use of the system 5501, wound exudate from the wound site 5530 is drawn by the negative pressure through the lower channel layer 5516. The air leak 5524 allows air to pass through the upper channel layer 5512 into the apertures through the distal ends of the layers 5512, 5514, 5516 and 5518. The negative pressure draws air passing through the upper channel layer into the lower channel layer 5516 back toward the source of negative pressure or pump. In some embodiments, the controlled air leak 5524 provides a constant flow of air through the system 5501, which then may be used to determine whether blockage or leakage is present. Causes of blockage can include, for example, situations where the lower channel 5516 becomes occluded with wound debris. Leakage causes can include, for example, improper sealing of the drape over the wound site, or physical damage to the system 5501 leading to excess air leaking into the system. The blockage or leakage may be determined, in certain embodiments, by measuring the speed of the pump while the pump works to maintain a constant negative pressure. Pump speed may also be measured indirectly by measuring the amount of voltage or signal sent to the pump.

Figure 56A:
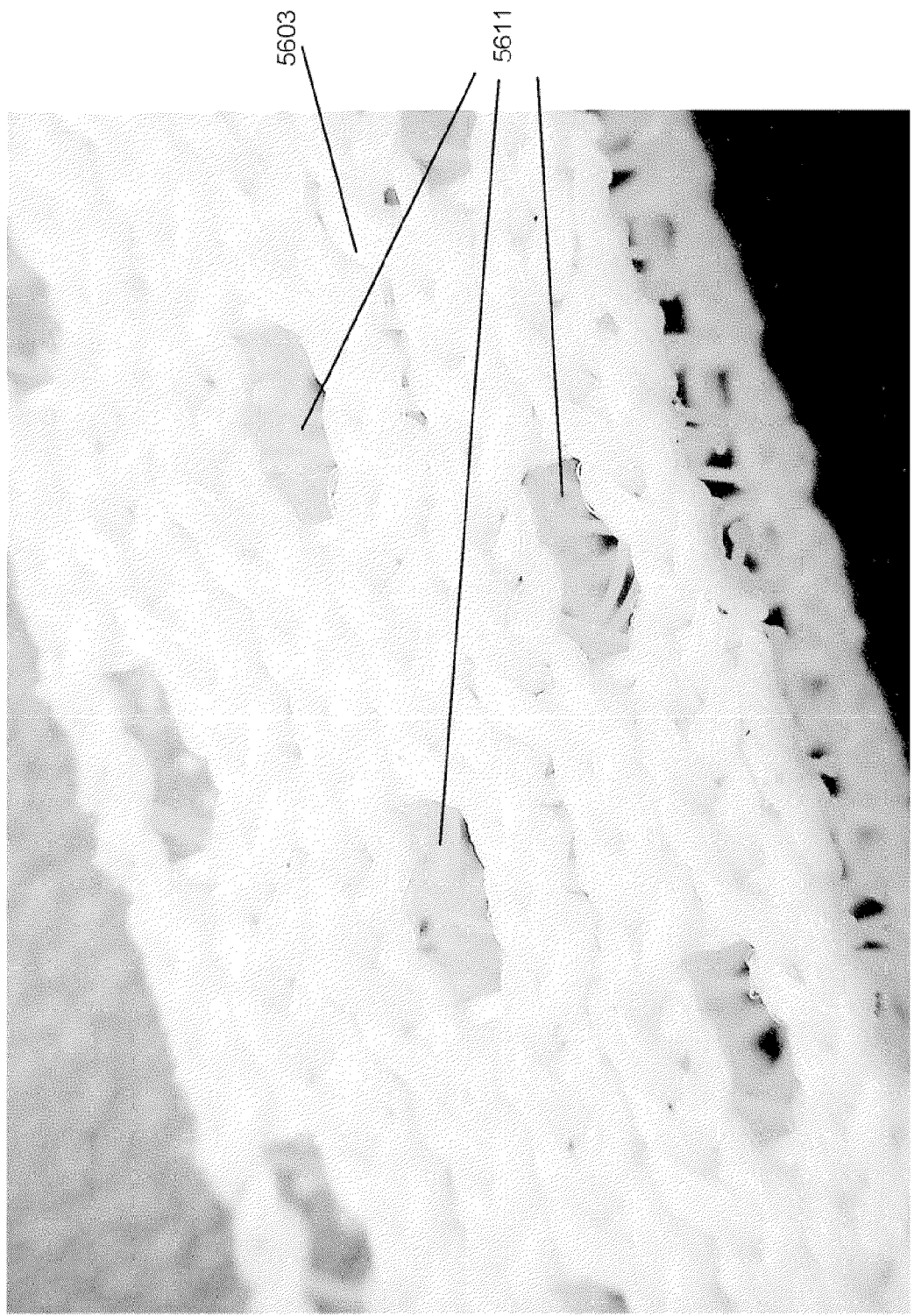
FIG. 56A illustrates a top view of a 3D fabric that may be used in a negative pressure wound treatment system.
Figure 56B:
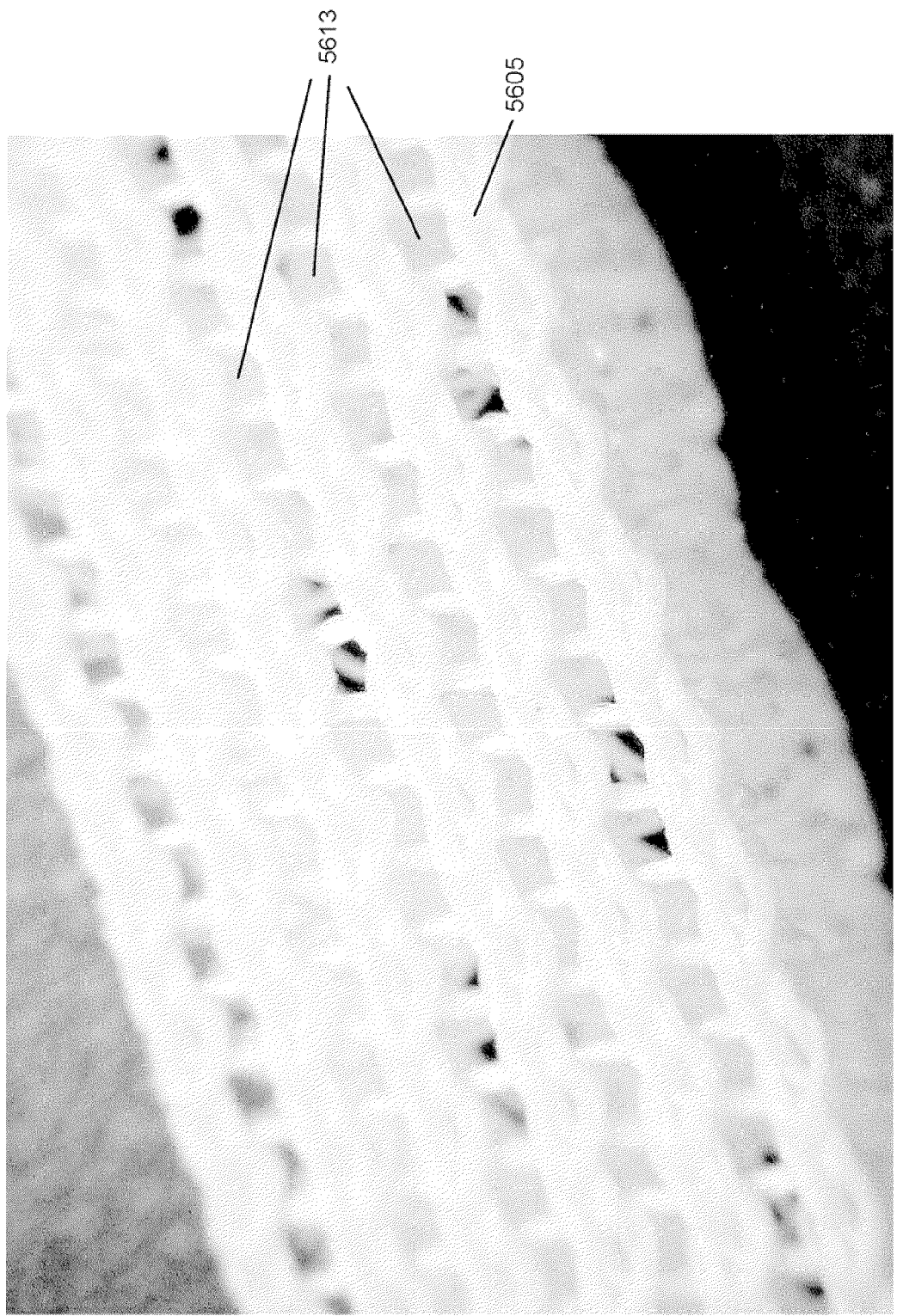
FIG. 56B illustrates a bottom view of the 3D fabric of FIG. 56A.
Figure 56C:
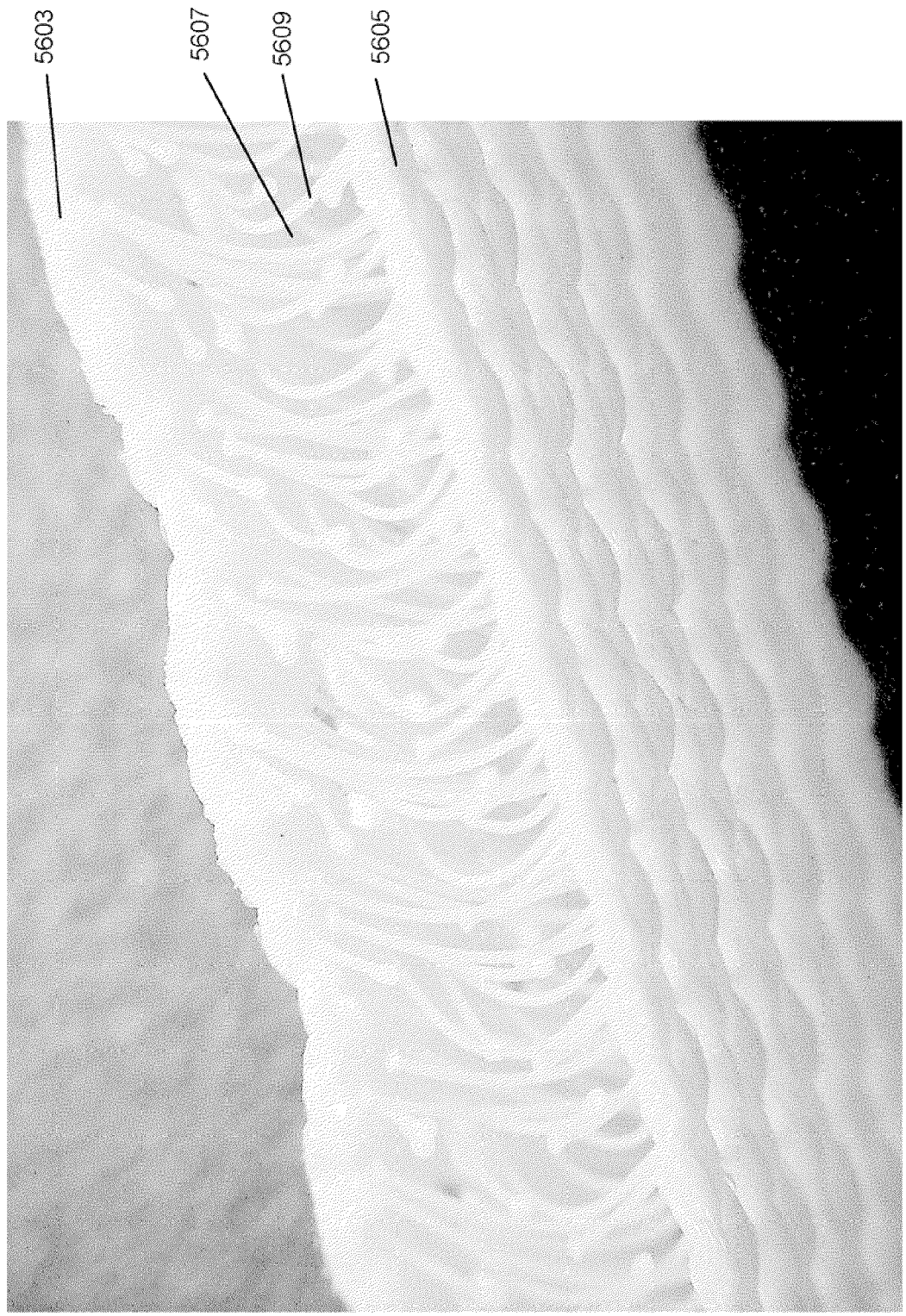
FIG. 56C illustrates a side cutaway view of the 3D fabric of FIG. 56A.

FIGS. 56A-C illustrate views of a 3D fabric that may be used in various embodiments described herein, for example the bridge 5502 of the suction adapter illustrated in FIGS. 55A-J. Although other porous materials such as foam may be used in the embodiments described herein, for example in the upper and lower channels 5512 and/or 5516 illustrated in FIGS. 55A-C, the use of 3D fabrics may be advantageous in some circumstances. Certain 3D fabrics have been found to perform well in conveying negative pressure to and wound exudate from a fluidic suction adapter, even while under compression—for example when a patient's weight is placed directly upon the suction adapter, or when negative pressure is applied and/or when the fluidic suction adapter is kinked or folded. Some 3D fabrics that have been found to perform acceptably include knitted polyester 3D fabric, Baltex 7970®, Gehring 879®, or Coolmax®. Of course, other fibers and fabric types may be used in part or in whole to make 3D fabrics, and include without limitation polyamides such as nylon, viscose, cotton, as well as other synthetic microfibers. 3D fabrics may also be constructed at least in part from fibers such as Nomex® and Kevlar®. Other types of fabrics and materials disclosed elsewhere herein may also be used.

In one embodiment, as illustrated in FIGS. 56A-C, the 3D fabric may comprise a bottom side 5603, a top side 5605, and an open middle area 5607. FIG. 56A illustrates the bottom (wound-facing) side 5603 of a 3D fabric, which may be woven so as to create oblong or ovoid openings 5611 extending lengthwise across the fabric. In one embodiment, the oblong or ovoid openings 5611 represent or provide an open area of between 10 and 45% (or about 10% to about 45%) of the surface area of the bottom layer, more preferably 10% to 30% (or about 10% to about 30%). Here, fibers are knitted (for example by warp knitting) so as to also include these larger openings or pores that permit bulk transport of wound fluids in addition to wound fluids carried along the fibers by capillary action of the fibers. Apertures that are optionally formed in the distal end of the 3D fabric (as illustrated in FIGS. 55D and J) may also aid in the bulk evacuation of wound debris and fluids.

FIG. 56B illustrates the top side 5605 of a 3D fabric that may be used as described herein. This top side 5605 in one embodiment does not have the larger ovoid apertures 5611 of the bottom side 5603, but may have openings 5613 defined by fibers extending lengthwise and generally transversely or at an angle across the width of the fabric. As illustrated, these openings are generally rhombus-shaped. In one embodiment, these openings 5613 may represent or provide an open area greater than that of the bottom layer, for example between 30% and 50% (or about 30% and about 50%). Of course, it will be understood that the fabric presented here is a non-limiting example, and different fabric configurations and orientations are possible, for example with the top side 5605 being placed downward so as to face the wound and with the bottom side 5603 facing upward.

FIG. 56C illustrates a cross-section of a 3D fabric (the bulb-like projections on the vertical fibers in the fabric are an artifact of the cutting process). The vertically extending fibers 5609 may be woven so as to extend through the middle open area 5607 while also being connected to the bottom and top layers 5603 and 5605. Preferably, the fibers 5609 present in the open middle layer 5607 will have sufficient stiffness so as to help prevent compression of the fabric. As illustrated in this figure, and without wishing to be bound by theory, 3D fabrics that have been found to perform well will often include a larger open area 5607 in the middle portion that may permit exudates and other fluids to be effectively transported away from a wound site while under the application of negative pressure, while more densely-woven outer layers 5603, 5605 may aid in providing additional tensile strength and capillary wicking action. For example, the middle layer may include an open volume of greater than 50% (or greater than about 50%). Obviously, the resulting fabric cannot be too thick or composed of fibers that are too stiff, as the resulting suction adapter and system may not remain sufficiently flexible for comfortable usage with a patient.

It will often be advantageous to tailor the performance characteristics of the 3D fabric while in use to account for various requirements of the suction adapter. In particular, the flow rate of exudate through the fabric, for example when under compression, may be simplified by considering the porosity of the fabric. In such situations, and again without wishing to be bound by theory, the porosity of the fabric, and thus the space that will be available for fluids to travel through, may be determined in part by the knit pattern of the fibers used in creating the 3D fabric, the thickness of the fibers used therein, and their respective stiffness and hardness (especially when under compression). Fibers may also be modified by surface properties (the fibers can be flat or textured) and the number of fibers or filaments used in the resulting fabric. Compression resistance may be affected by the choice of fiber or monofilament used in the vertical axis of the fabric, and generally, a stiffer material will improve compression resistance on this axis. Other materials properties, such as hydrophobicity, may play a role. In some cases, it may be beneficial to treat the fabric to be hydrophilic, for example with a hydrophilic polymer, so as to improve wicking of fluids. Preferred embodiments of the 3D fabric used with certain suction adapters have been found to work well when Baltex® fabric is treated in such a fashion. Other possible treatments may include lipophilic coatings to prevent proteins from adhering and building up during use, which may cause clogging and loss of pressure to the wound site.

The flow rate through the 3D fabric while under the application of negative pressure may be approximated by considering each opening as a separate orifice plate subject to Bernoulli's principle while under laminar flow. To simplify calculations, the area of openings for a given area of 3D fabric may be used. Thus, the 3D fabric may be optimized to achieve a good balance between factors such as the compression resistance required and the resulting flow rate under the application of negative pressure. Further optimization will also take place with the stiffness and flow rate of the 3D fabric being tailored to application in the embodiments described herein. Optimization of the properties and dimensions of the 3D fabric will also preferably take into account a balancing between the flow rate and stiffness required and the conformability of the fabric, as a fabric that is too stiff may not bend appropriately and may also be uncomfortable on the patient. The 3D fabric should preferably be designed so as to yield when compressed against tissue, thereby preventing tissue compression (for example against bony prominences in the patient) and the discomfort and damage, such as pressure ulcers, that may follow. For example, the dimensions of the fabric may be tailored for the ultimate use of the suction adapter—smaller in the case of distal extremities such as fingers, and larger for abdominal and burn wounds. A fabric that is too stiff may also cause pressure ulcers and other such complications, although it may function acceptably in larger dimensions.

In practice, and as also described previously herein, flow rates through embodiments of the suction adapter using 3D fabrics are at least 0.08 L/min, preferably up to 10 L/min during the application of negative pressure, and should be able to handle fluid exudate drainage of at least 10 L/day. Some embodiments of the suction adapter may be configured to handle much larger wounds, including abdominal wounds, and which in some cases may exude at least 0.5 L/hr, or 12 L/day. In more extreme cases, the pump used (for example, the RENASYS EZ) may be able to evacuate up to 16 L/min, thereby evacuating a large wound to a negative pressure level of 120 mmHg in less than a minute. The pressure drop calculated due to the 3D fabric should be minimal, and the level of negative pressure measured at a wound site is preferably within 25 mmHg of the pressure level measured at the source of negative pressure. Although the pressure drop increases as the negative pressure applied increases (thus rendering the 25 mmHg target more difficult to reach), embodiments of the wound treatment system are preferably able to maintain this target pressure to at least a negative pressure of 200 mmHg. The suction adapter and system are preferably able to function within pressure ranges required for negative pressure, which are estimated to be from around 40 mmHg to 200 mmHg. Pressure ranges greater than 200 mmHg are possible, but these may in some circumstances cause patient discomfort. The apparatus may also function at lower pressure ranges, such as 20 mmHg, although at such low pressure levels the therapeutic effects resulting from negative pressure may be diminished, with the device acting more as a drainage device. Preferably, embodiments of a negative pressure treatment system are able to maintain these target pressures at the wound site within 95% of the time that negative pressure is being applied to the wound. In some embodiments, the fabric may comprise several layers of material stacked or layered over each other, which may in some cases be useful in preventing the channel 5516 from collapsing under the application of negative pressure. In other embodiments, the fabric used in channel 5516 may be between 1.5 mm and 6 mm; more preferably, the fabric may be between 3 mm and 6 mm thick, and may be comprised of either one or several individual layers of fabric. In other embodiments, the channel 5512 may be between 1.2-3 mm thick, and preferably thicker than 1.5 mm. Preferably, the 3D fabric is able to withstand a load of at least 5.3 psi with a compression of not more than 10% of the fabric's original thickness. Further, the 3D fabric may also be able to resist compression to less than half of its original thickness when subjected to a load of 15 psi.

In a preferred embodiment, a 3D fabric may be woven from 100% polyester using yarns of 150 and 225 Denier, to yield a fabric weighing approximately 23 to 25 oz per square yard. In these cases, the fabric may be approximately 5.8-6.8 mm thick. The bottom portion of the fabric may also have several openings or pores 5611 similar to those illustrated in FIG. 56A, which may be elongated, rectangular or ovoid in shape and oriented with their long axis lengthwise along the fabric. The openings 5611 may be arranged in a plurality of rows extending lengthwise across the fabric, for example 2 to 5 rows, or more preferably 3 rows as illustrated in FIG. 56A. The openings 5611 may be spaced equidistantly from each other in each of the rows, and may form a staggered pattern from one row to another. In one embodiment, each row may have approximately 6-10 openings, more preferably 8 openings, per 2 inches (or about 50 mm). Along a given width or transverse dimension of the fabric, the transverse rows formed by the openings may have a spacing of approximately 6-10 openings, more preferably 8 openings, per 2⅛ inches (or about 54 mm). In one embodiment, the openings may have a length of between about 1/16" to about 1" lengthwise, and a width of between about 1/32" and ½ "widthwise. In one example, the openings measure approximately ⅛" (or about 3.2 mm) lengthwise and 1/32" (or about 0.79 mm) across. The 3D fabric in one embodiment may have an overall length of between about 50 and 100 mm, more preferably about 60 mm, a width between about 5 and 15 mm, more preferably about 9 mm, and a thickness of about 6 mm.

Embodiments of the systems described herein have been tested and found to perform satisfactorily. Such testing was performed by constructing suction adapters from embodiments described herein. The distal ends of the suction adapters were then placed over an aperture made onto a drape placed over a simulated wound cavity provided with a source of simulated wound fluid, which was controllable and which can vary the flow rate of the wound fluid. The simulated wound cavity was also in some cases packed with foam or some other wound packing material. In some tests, the simulated wound fluid was a 5:1 water to glycerol mix, and in others filtered horse serum (available from Oxoid, United Kingdom) was used. The proximal end of the suction adapter was then connected to a source of negative pressure, in this case a pump. Flow rate tests and other measurements were then conducted at various negative pressure ranges and simulated exudate flow rates and air leak rates.

FIGS. 57A-B illustrate embodiments of a connector 5704, similar to the connectors 1504 and 5506 described previously, and which may be used to securely connect a source of negative pressure to a channel 5716 of a suction adapter such as the ones described herein. For example, this channel 5716 may be the upper channel 1512 or, more preferably, the lower channel 1516 illustrated in FIGS. 15A-D, as well as the channels 5512 and 5516 in FIGS. 55-56. Generally, such connectors 5704 may be useful in providing a more secure connection from the source of negative pressure to a negative pressure treatment system. The use of these connectors 5704 is optional, and may not be necessary in all embodiments described herein. In use, a tube 5740 connected to the connector 5704 may pull, or other external forces may somehow disengage the connector 5704 away from the channel 5716 to which it is attached. In such situations, application of negative pressure to the wound may be reduced or stopped. Further means to secure the connector 5704 to the remainder of the system may, as described above, include bonding or attaching other layers of the treatment system, if present, to the connector 5704. For example, in the case of the embodiments described in FIGS. 15A-D, this may include bonding at least one of the layers 1510, 1514, 1518 to the connector 5704. The connectors 5704 may be designed so as to create a secure connection with a fabric or material used in a channel; when 3D fabrics or 3D knitted materials are used, some embodiments of the connector 5704 are configured to engage with or attach to a portion of the material or fibers of the material to create a more secure connection. Preferably, embodiments of the connector 5704 are able to withstand a pulling force of up to 20 kg before disconnection and/or failure of the connector occurs, preferably such that the connector disengages from the channel it is connected to. It will be understood that other embodiments may be configured to withstand a lower pulling force, and may be tailored to release so to prevent injury to a patient (for example, constriction of the suction adapter and/or drainage tubes around a limb).

FIGS. 57A-B illustrate an embodiment of the connector 5704a comprising two or more projections 5752 extending distally lengthwise from the preferably cylindrical main body of the connector 5704a. The main body also comprises a central channel 5755 extending lengthwise through the main body of the connector 5704a. The projections 5752 may additionally comprise one or more barbs 5754 attached thereto. Preferably, these barbs 5754 are angled proximally so as to act as anchors when pushed or inserted into the channel 5716. When the channel 5716 is a 3D fabric or knitted material, the barbs 5754 are configured to engage to the fibers therein, creating a more secure connection. At the proximal end of the connector 5704a, a lip 5756, which may be provided in a frustoconical form, may also be provided for connection to a tube 5740. The tube 5740 may be connected to the connector 5704a (as well as the other connectors described herein) for example by press-fitting, although other connections means are possible. The tube 5740 may be the same as tube 5507 in FIG. 55J, or it may be any other tube used to provide fluid communication with a source of negative pressure. It will also be appreciated that the features of these connectors, particularly at the distal ends, can be incorporated onto the ends of tubes used to communicate negative pressure, such that those tubes can be directly connected to the suction adapter system.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure. Many of the embodiments described above include similar components, and as such, these similar components can be interchanged in different embodiments.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A suction adapter suitable to treat a wound site with negative pressure, comprising:
  an applicator having an upper surface and a lower surface; and
  an elongate bridge having a proximal end and a distal end, the distal end of the bridge connected to the upper surface of the applicator, the bridge comprising:
  upper, intermediate, and lower flexible film layers;
  an upper fluid passage formed between the upper and intermediate film layers, the upper fluid passage connected to an air leak and comprising an elongate upper channel layer positioned between the upper and intermediate flexible film layers;
  a lower fluid passage formed between the intermediate and lower film layers, the lower fluid passage configured to be in fluid communication with a source of negative pressure, the lower fluid passage comprising a 3D knitted or 3D fabric material positioned between the intermediate and lower film layers.

2. The suction adapter of claim 1, wherein the upper channel layer comprises foam.

3. The suction adapter of claim 1, further comprising an air leak disposed at a proximal end of the upper layer of the bridge.

4. The suction adapter of claim 1, wherein the 3D fabric material comprises a fabric layer with a thickness between 1.5 mm and 6 mm.

5. The suction adapter of claim 1, wherein the 3D fabric material comprises a top knitted layer, a bottom knitted layer and a middle area comprising vertically extending fibers.

6. The suction adapter of claim 1, wherein the distal end of the bridge has an enlarged shape.

7. The suction adapter of claim 6, wherein the 3D knitted or 3D fabric material at the enlarged distal end of the bridge has a generally circular shape.

8. The suction adapter of claim 1, wherein the lower fluid passage comprising the 3D knitted or 3D fabric material is able to resist compression to less than half of its original thickness when subjected to a load of 15 psi.

9. A negative pressure wound treatment system, comprising:
  a suction adapter adapted to treat a wound site with negative pressure, comprising:
  an applicator having an upper surface and a lower surface, and
  a bridge having a proximal end and a distal end, the distal end of the bridge connected to the upper surface of the applicator, the bridge comprising:
  upper, intermediate, and lower flexible film layers;
  an upper fluid passage formed between the upper and intermediate film layers, the upper fluid passage connected to an air leak and comprising an elongate upper channel layer positioned between the upper and intermediate flexible film layers; and
  a lower fluid passage formed between the intermediate and lower film layers, the lower fluid passage configured to be in fluid communication with a source of negative pressure, the lower fluid passage comprising a 3D knitted or 3D fabric material positioned between the intermediate and lower film layers; and
  a flexible drape configured to be positioned over a wound and sealed to skin surrounding the wound,
  wherein the suction adapter is configured to attach to the drape and surround at least one aperture formed in the drape.

10. The system of claim 9, further comprising a vacuum pump connected by at least one conduit to the suction adapter.

11. The negative pressure wound treatment system of claim 9, wherein the upper channel layer comprises foam.

12. The negative pressure wound treatment system of claim 9, further comprising an air leak disposed at a proximal end of the upper layer of the bridge.

13. The negative pressure wound treatment system of claim 9, wherein the 3D knitted or 3D fabric material comprises a fabric layer with a thickness between 1.5 mm and 6 mm.

14. The negative pressure wound treatment system of claim 9, wherein the 3D knitted or 3D fabric material comprises a top knitted layer, a bottom knitted layer and a middle area comprising vertically extending fibers.

15. The negative pressure wound treatment system of claim 9, wherein the distal end of the bridge has an enlarged shape.

16. The negative pressure wound treatment system of claim 9, wherein the lower fluid passage comprising the 3D knitted or 3D fabric material is able to resist compression to less than half of its original thickness when subjected to a load of 15 psi.

* * * * *

UNITED STATES PATENT AND TRADEMARK OFFICE
CERTIFICATE OF CORRECTION

PATENT NO.        : 8,801,685 B2                               Page 1 of 1
APPLICATION NO.   : 13/381885
DATED             : August 12, 2014
INVENTOR(S)       : Ed Armstrong et al.

It is certified that error appears in the above-identified patent and that said Letters Patent is hereby corrected as shown below:

Title Page (Item 75) Inventors, line 3, change "Beverly" for Robert Emmerson to --Beverley--.

In the Specification
At column 3, line 3, change "form" to --from--.
At column 21, line 65, change "8790)" to --879®)--.
At column 23, line 13-31, delete "Advantageously, some ... thereto." and insert the same on Col. 23,
Line 12, after "45 μm." as a continuation of the same paragraph.
At column 29, line 62, change "2503" to --2503– --.
At column 46, line 31, change "applied" to --applied– --.
At column 49, line 15 (Approx.), change "1/2 "widthwise." to --1/2" widthwise.--.

Signed and Sealed this
Twenty-eighth Day of July, 2015

Michelle K. Lee
*Director of the United States Patent and Trademark Office*